(12) United States Patent
Olson et al.

(10) Patent No.: US 7,276,496 B2
(45) Date of Patent: Oct. 2, 2007

(54) CYCLIC MALONAMIDES AS INHIBITORS OF Aβ PROTEIN PROTECTION

(75) Inventors: Richard E. Olson, Wilmington, DE (US); Michael G. Yang, Wilmington, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 11/327,721

(22) Filed: Jan. 6, 2006

(65) Prior Publication Data

US 2006/0135762 A1  Jun. 22, 2006

Related U.S. Application Data

(63) Continuation of application No. 10/746,769, filed on Dec. 24, 2003, now Pat. No. 7,053,081, which is a continuation of application No. 09/825,211, filed on Apr. 3, 2001, now Pat. No. 6,759,404.

(51) Int. Cl.
C07D 243/24 (2006.01)
C07D 487/00 (2006.01)
A61K 31/55 (2006.01)

(52) U.S. Cl. ............... 514/212.07; 514/221; 540/509; 540/523

(58) Field of Classification Search .............. 540/509, 540/523; 514/212.07, 221
See application file for complete search history.

(56) References Cited

U.S. PATENT DOCUMENTS

| | | | |
|---|---|---|---|
| 4,666,829 A | 5/1987 | Glenner et al. |
| 4,897,489 A | 1/1990 | Yoshioko et al. |
| 4,929,614 A | 5/1990 | Calvet et al. |
| 5,175,159 A | 12/1992 | Bock et al. |
| 5,283,241 A | 2/1994 | Bochis et al. |
| 5,378,844 A | 1/1995 | Brufani et al. |
| 5,532,359 A | 7/1996 | Marsters et al. |
| 5,545,735 A | 8/1996 | Bochis et al. |
| 5,550,126 A | 8/1996 | Horwell et al. |
| 5,578,629 A | 11/1996 | Ciccarone et al. |
| 5,590,851 A | 1/1997 | Ackerman |
| 5,593,846 A | 1/1997 | Schenk et al. |
| 5,595,990 A | 1/1997 | Baldwin et al. |
| 5,602,145 A | 2/1997 | Samanen |
| 5,602,156 A | 2/1997 | Kohn et al. |
| 5,618,812 A | 4/1997 | Pineiro et al. |
| 5,639,746 A | 6/1997 | Yelm |
| 5,672,596 A | 9/1997 | Wyvratt et al. |
| 5,672,598 A | 9/1997 | De et al. |
| 5,703,129 A | 12/1997 | Felsenstein et al. |
| 5,710,153 A | 1/1998 | Ohmoto et al. |
| 5,710,171 A | 1/1998 | Dinsmore et al. |
| 5,756,528 A | 5/1998 | Anthony et al. |
| 5,763,437 A | 6/1998 | Sato et al. |
| 5,770,573 A | 6/1998 | Arrhenius et al. |
| 5,840,939 A | 11/1998 | Beckett et al. |
| 5,852,010 A | 12/1998 | Graham et al. |
| 5,856,326 A | 1/1999 | Anthony et al. |
| 5,859,012 A | 1/1999 | Dinsmore et al. |
| 5,869,682 A | 2/1999 | DeSolms |
| 5,872,135 A | 2/1999 | DeSolms |
| 5,885,995 A | 3/1999 | Dinsmore |
| 5,891,889 A | 4/1999 | Anthony et al. |
| 5,905,077 A | 5/1999 | Jungheim et al. |
| 5,919,785 A | 7/1999 | Dinsmore et al. |
| 5,936,089 A | 8/1999 | Carpino et al. |
| 5,965,578 A | 10/1999 | Graham et al. |
| 5,968,924 A | 10/1999 | Wyvratt et al. |
| 5,968,965 A | 10/1999 | Dinsmore et al. |

(Continued)

FOREIGN PATENT DOCUMENTS

EP  0421802  4/1991

(Continued)

OTHER PUBLICATIONS

Su San Mok et al, A Novel Metalloprotease in Rat rain cleaves.. Biochemistry, vol. 36, No. 1, 1997, pp. 156-163 XP002177252.

(Continued)

*Primary Examiner*—Bruck Kifle
(74) *Attorney, Agent, or Firm*—Aldo A. Algieri; Kelly Drye & Warren LLP

(57) ABSTRACT

This invention relates to novel cyclic malonamides having the formula (I):

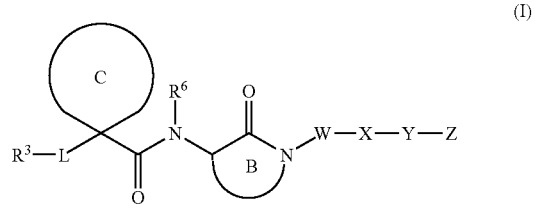

to their pharmaceutical compositions and to their methods of use. These novel compounds inhibit the processing of amyloid precursor protein and, more specifically, inhibit the production of Aβ-peptide, thereby acting to prevent the formation of neurological deposits of amyloid protein. More particularly, the present invention relates to the treatment of neurological disorders related to β-amyloid production such as Alzheimer's disease and Down's Syndrome.

20 Claims, No Drawings

U.S. PATENT DOCUMENTS

| | | | |
|---|---|---|---|
| 5,985,900 | A | 11/1999 | Abreo et al. |
| 5,998,447 | A | 12/1999 | Stilz et al. |
| 6,001,835 | A | 12/1999 | Dinsmore et al. |
| 6,057,660 | A | 5/2000 | Meier et al. |
| 6,060,038 | A | 5/2000 | Burns et al. |
| 6,066,738 | A | 5/2000 | Dinsmore et al. |
| 6,093,737 | A | 7/2000 | Anthony et al. |
| 6,117,910 | A | 9/2000 | Callahan et al. |
| 6,127,427 | A | 10/2000 | Martin et al. |
| 6,228,854 | B1 | 5/2001 | Scarborough et al. |
| 6,242,455 | B1 | 6/2001 | Grams et al. |
| 6,262,047 | B1 | 7/2001 | Zhu et al. |
| 6,271,262 | B1 | 8/2001 | Beckett et al. |
| 6,297,239 | B1 | 10/2001 | DeSolms et al. |
| 6,329,373 | B1 | 12/2001 | Martin et al. |
| 6,333,321 | B1 | 12/2001 | Scarborough |
| 6,358,987 | B1 | 3/2002 | Beckett et al. |
| 6,432,947 | B1 | 8/2002 | Arnaiz et al. |
| 6,440,965 | B1 | 8/2002 | Kelley et al. |
| 6,759,404 | B2 | 7/2004 | Olsen et al. |

FOREIGN PATENT DOCUMENTS

| | | |
|---|---|---|
| EP | 0434360 | 6/1991 |
| EP | 0652009 | 5/1995 |
| EP | 0842944 | 5/1998 |
| WO | WO92/16524 | 10/1992 |
| WO | WO9217460 | 10/1992 |
| WO | WO9403437 | 2/1994 |
| WO | WO9405634 | 3/1994 |
| WO | WO9414776 | 7/1994 |
| WO | WO9509633 | 4/1995 |
| WO | WO95/22966 | 8/1995 |
| WO | WO9617833 | 6/1996 |
| WO | WO9618602 | 6/1996 |
| WO | WO9620918 | 7/1996 |
| WO | WO9629313 | 9/1996 |
| WO | WO9633165 | 10/1996 |
| WO | WO9639137 | 12/1996 |
| WO | WO9942889 | 2/1997 |
| WO | WO9712861 | 4/1997 |
| WO | WO9719053 | 5/1997 |
| WO | WO9727852 | 8/1997 |
| WO | WO9736877 | 10/1997 |
| WO | WO9736879 | 10/1997 |
| WO | WO9736900 | 10/1997 |
| WO | WO9738664 | 10/1997 |
| WO | WO9745412 | 12/1997 |
| WO | WO 9745412 | 12/1997 |
| WO | WO9816523 | 4/1998 |
| WO | WO9822430 | 5/1998 |
| WO | WO9822433 | 5/1998 |
| WO | WO9822441 | 5/1998 |
| WO | WO9822493 | 5/1998 |
| WO | WO9827053 | 6/1998 |
| WO | WO9828268 | 7/1998 |
| WO | WO9828980 | 7/1998 |
| WO | WO9837079 | 8/1998 |
| WO | WO9841510 | 9/1998 |
| WO | WO9844797 | 10/1998 |
| WO | WO9858915 | 12/1998 |
| WO | WO9900654 | 1/1999 |
| WO | WO9903826 | 1/1999 |
| WO | WO9907730 | 2/1999 |
| WO | WO9907731 | 2/1999 |
| WO | WO9917777 | 4/1999 |
| WO | WO9918951 | 4/1999 |
| WO | WO9919305 | 4/1999 |
| WO | WO9932453 | 7/1999 |
| WO | WO9966934 | 12/1999 |
| WO | WO9967219 | 12/1999 |
| WO | WO9967220 | 12/1999 |
| WO | WO9967221 | 12/1999 |
| WO | WO 0002903 | 1/2000 |
| WO | WO 0007995 | 2/2000 |
| WO | WO 0028331 | 5/2000 |
| WO | WO 0038618 | 7/2000 |
| WO | WO 0160826 | 8/2001 |

OTHER PUBLICATIONS

PCT International Search Report for PCT/US01/10667;International filing date Apr. 3, 2001.

Bock et al., *J. Org. Chem 1987*, 52, pp. 3232-3239.

Brown et al., *Tetrahedron Letters*, 1971, 8, pp. 667-670.

Chung, S.K. Korean J.Med.Chem. 1995,5,pp. 94-111.

Glenner and Wong, *Biochem. Biophys. Res. Commun.*, 120: pp. 885-890, (1984).

T.W.Green and Wuts, Proptective Grups in organic Synthesis (Wiley 1991).

*J. Med. Chem 1999*, 42, pp. 3889-3898.

"Remington's Pharmeceutical Sciences," 17th ed. Mack Publishing Company, Easton, PA, 1985, p. 1418.

D. J. Selkoe, "Cell Biology of the amyloid (beta)-protein precursor and the mechanism of Alzheimer's disease," *Annu. Rev. Cell. Biol.*, 1994, 10: pp. 373-403.

Synthesis,1989,pp. 37-38 Bond-Forming Procedure.

Sherrill and Sugg, *J. Org. Chem. 1995*, 60, pp. 730-734.

D. A. Walsh, *Synthesis*, Sep. 1980, p. 677.

U.K Laemmli. Cleavage of Structural Proptains during the assembly of the head of bactreriophage T4, Nature 227,pp. 680-685, (1970).

CYCLIC MALONAMIDES AS INHIBITORS OF Aβ PROTEIN PROTECTION

This application is a continuation of U.S. patent application Ser. No. 10/746,769, filed Dec. 24, 2003 now U.S. Pat. No. 7,053,081, which is a continuation of U.S. patent application Ser. No. 09/825,211, filed Apr. 3, 2001 now U.S. Pat. No. 6,759,404, the contents of which are hereby incorporated by reference herein in their entirety.

FIELD OF THE INVENTION

This invention relates to novel cyclic malonamides having drug and bio-affecting properties, their pharmaceutical compositions and methods of use. These novel compounds inhibit the processing of amyloid precursor protein and, more specifically, inhibit the production of Aβ-peptide, thereby acting to prevent the formation of neurological deposits of amyloid protein. More particularly, the present invention relates to the treatment of neurological disorders related to β-amyloid production such as Alzheimer's disease and Down's Syndrome.

BACKGROUND OF THE INVENTION

Alzheimer's disease (AD) is a degenerative brain disorder characterized clinically by progressive loss of memory, temporal and local orientation, cognition, reasoning, judgment and emotionally stability. AD is a common cause of progressive dementia in humans and is one of the major causes of death in the United States. AD has been observed in all races and ethnic groups worldwide, and is a major present and future health problem. No treatment that effectively prevents AD or reverses the clinical symptoms and underlying pathophysiology is currently available (for review, Dennis J. Selkoe; Cell Biology of the amyloid (beta)-protein precursor and the mechanism of Alzheimer's disease, Annu Rev Cell Biol, 1994, 10: 373-403).

Histopathological examination of brain tissue derived upon autopsy or from neurosurgical specimens in effected individuals revealed the occurrence of amyloid plaques and neurofibrillar tangles in the cerebral cortex of such patients. Similar alternation s were observed in patients with Trisomy 21 (Down's syndrome), and hereditary cerebral hemorrhage with amyloidosis of the Dutch-type.

Neurofibrillar tangles are nonmembrane-bound bundles of abnormal proteinaceous filaments and biochemical and immunochemical studies led to the conclusion that their principle protein subunit is an altered phosphorylated form of the tau protein (reviewed in Selkoe, 1994).

Biochemical and immunological studies revealed that the dominant proteinaceous component of the amyloid plaque is an approximately 4.2 kilodalton (kD) protein of about 39 to 43 amino acids. This protein was designated Aβ, β-amyloid peptide, and sometimes β/A4; referred to herein as Aβ. In addition to its deposition in amyloid plaques, Aβ is also found in the walls of meningeal and parenchymal arterioles, small arteries, capillaries, and sometimes, venules. Aβ was first purified and a partial amino acid reported in 1984 (Glenner and Wong, Biochem. Biophys. Res. Commun. 120: 885-890). The isolation and sequence data for the first 28 amino acids are described in U.S. Pat. No. 4,666,829.

Compelling evidence accumulated during the last decade revealed that Aβ is an internal polypeptide derived from a type 1 integral membrane protein, termed β amyloid precursor protein (APP). β APP is normally produced by many cells both in vivo and in cultured cells, derived from various animals and humans. Aβ is derived from cleavage of β APP by as yet unknown enzyme (protease) system(s), collectively termed secretases.

The existence of at least four proteolytic activities has been postulated. They include β secretase(s), generating the N-terminus of Aβ, α secretase(s) cleaving around the 16/17 peptide bond in Aβ, and γ secretases, generating C-terminal Aβ fragments ending at position 38, 39, 40, 42, and 43 or generating C-terminal extended precursors which are subsequently truncated to the above polypeptides.

Several lines of evidence suggest that abnormal accumulation of Aβ plays a key role in the pathogenesis of AD. Firstly, Aβ is the major protein found in amyloid plaques. Secondly, Aβ is neurotoxic and may be causally related to neuronal death observed in AD patients. Thirdly, missense DNA mutations at position 717 in the 770 isoform of β APP can be found in effected members but not unaffected members of several families with a genetically determined (familiar) form of AD. In addition, several other β APP mutations have been described in familiar forms of AD. Fourthly, similar neuropathological changes have been observed in transgenic animals overexpressing mutant forms of human β APP. Fifthly, individuals with Down's syndrome have an increased gene dosage of β APP and develop early-onset AD. Taken together, these observations strongly suggest that Aβ depositions may be causally related to the AD.

It is hypothesized that inhibiting the production of Aβ will prevent and reduce neurological degeneration, by controlling the formation of amyloid plaques, reducing neurotoxicity and, generally, mediating the pathology associated with Aβ production. One method of treatment methods would therefore be based on drugs that inhibit the formation of Aβ in vivo.

Methods of treatment could target the formation of Aβ through the enzymes involved in the proteolytic processing of β amyloid precursor protein. Compounds that inhibit β or γ secretase activity, either directly or indirectly, could control the production of Aβ. Advantageously, compounds that specifically target γ secretases, could control the production of Aβ. Such inhibition of β or γ secretases could thereby reduce production of Aβ, which, thereby, could reduce or prevent the neurological disorders associated with Aβ protein.

PCT publication number WO 96/29313 discloses the general formula:

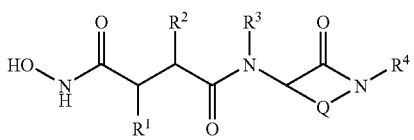

covering metalloprotease inhibiting compounds useful for the treatment of diseases associated with excess and/or unwanted matrix metalloprotease activity, particularly collagenase and or stromelysin activity.

Compounds of general formula:

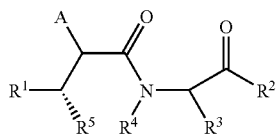

are disclosed in PCT publication number WO 95/22966 relating to matrix metalloprotease inhibitors. The compounds of the invention are useful for the treatment of conditions associated with the destruction of cartilage, including corneal ulceration, osteoporosis, periodontitis and cancer.

European Patent Application number EP 0652009A1 relates to the general formula:

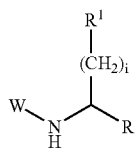

and discloses compounds that are protease inhibitors that inhibit Aβ production.

U.S. Pat. No. 5,703,129 discloses the general formula:

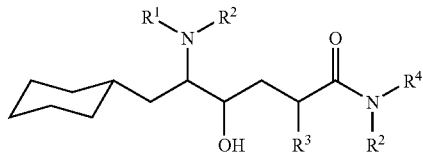

which covers 5-amino-6-cyclohexyl-4-hydroxy-hexanamide derivatives that inhibit Aβ production and are useful in the treatment of Alzheimer's disease.

Copending, commonly assigned U.S. patent application Ser. No. 09/370,089 filed Aug. 7, 1999 (equivalent to international application PCT US99/17717) discloses lactams of general formula:

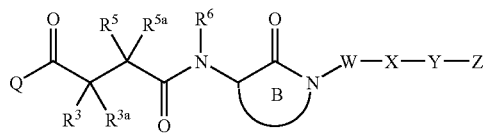

wherein the lactam ring B is substituted by succinamide and a carbocyclic, aryl, or heteroaryl group. These compounds inhibit the processing of amyloid precursor protein and, more specifically, inhibit the production of Aβ-peptide, thereby acting to prevent the formation of neurological deposits of amyloid protein.

None of the above references teaches or suggests the compounds of the present invention which are described in detail below.

SUMMARY OF THE INVENTION

One object of the present invention is to provide novel compounds which are useful as inhibitors of the production of Aβ protein or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating degenerative neurological disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors' discovery that compounds of Formula (I):

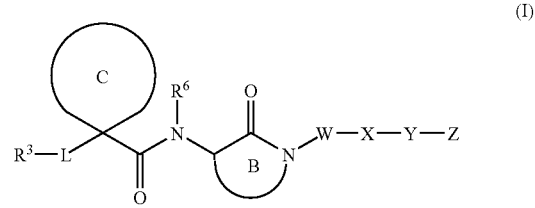

or a stereoisomer, pharmaceutically acceptable salt or prodrug forms thereof, wherein $R^3$, $R^6$, B, C, W, X, Y, and Z are defined below, are effective inhibitors of the production of Aβ.

DETAILED DESCRIPTION OF PREFERRED EMBODIMENTS

Thus, in a first embodiment, the present invention provides a novel compound of Formula (I):

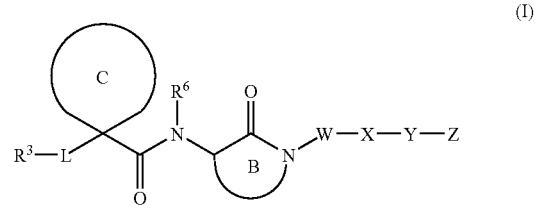

or a stereoisomer, pharmaceutically acceptable salt or prodrug thereof, wherein:

L is $-NR^{26}C(=O)-$, $-C(=O)NR^{26}-$, $-NR^{26}C(=O)O-$, $-OC(=O)NR^{26}$, or $-NR^{26}C(=O)NR^{26}-$;

$R^3$ is $(CR^7R^{7a})_n-R^4$,
$-(CR^7R^{7a})_l-S-(CR^7R^{7a})_m-R^4$,
$-(CR^7R^{7a})_l-O-(CR^7R^{7a})_m-R^4$,
$-(CR^7R^{7a})_l-N(R^{7b})-(CR^7R^{7a})_m-R^4$,
$-(CR^7R^{7a})_l-S(=O)-(CR^7R^{7a})_m-R^4$,
$-(CR^7R^{7a})_l-S(=O)_2-(CR^7R^{7a})_m-R^4$,
$-(CR^7R^{7a})_l-C(=O)-(CR^7R^{7a})_m-R^4$,
$-(CR^7R^{7a})_l-N(R^{7b})C(=O)-(CR^7R^{7a})_m-R^4$,
$-(CR^7R^{7a})_l-C(=O)N(R^{7b})-(CR^7R^{7a})_m-R^4$,
$-(CR^7R^{7a})_l-N(R^{7b})S(=O)_2-(CR^7R^{7a})_m-R^4$, or
$-(CR^7R^{7a})_l-S(=O)_2N(R^{7b})-(CR^7R^{7a})_m-R^4$;

n is 0, 1, 2, or 3;
m is 0, 1, 2, or 3;
l is 1, 2, or 3;
Ring C is a 3 to 8 membered carbocycle,
  wherein the carbocycle is saturated or partially saturated;
  optionally, the carbocycle contains a heteroatom selected from —O—, —S—, —S(=O)—, —S(=O)$_2$—, and —N($R^{20}$)—; and
  wherein the carbocycle is substituted with 0-4 $R^{21}$;
$R^4$ is H, OH, $OR^{14a}$,
  $C_1$-$C_8$ alkyl substituted with 0-3 $R^{4a}$,
  $C_2$-$C_8$ alkenyl substituted with 0-3 $R^{4a}$,
  $C_2$-$C_8$ alkynyl substituted with 0-3 $R^{4a}$,
  $C_3$-$C_{10}$ carbocycle substituted with 0-3 $R^{4b}$,
  $C_6$-$C_{10}$ aryl substituted with 0-3 $R^{4b}$, or
  5 to 10 membered heterocycle containing 1 to 4 heteroatoms selected from nitrogen, oxygen, and sulphur, wherein said 5 to 10 membered heterocycle is substituted with 0-3 $R^{4b}$;
$R^{4a}$, at each occurrence, is independently selected from H, OH, F, Cl, Br, I, $NR^{15}R^{16}$, $CF_3$,
  $C_3$-$C_{10}$ carbocycle substituted with 0-3 $R^{4b}$,
  $C_6$-$C_{10}$ aryl substituted with 0-3 $R^{4b}$, and
  5 to 10 membered heterocycle containing 1 to 4 heteroatoms selected from nitrogen, oxygen, and sulphur, wherein said 5 to 10 membered heterocycle is substituted with 0-3 $R^{4b}$;
$R^{4b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2$$CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;
$R^6$ is H;
  $C_1$-$C_6$ alkyl substituted with 0-3 $R^{6a}$;
  $C_3$-$C_{10}$ carbocycle substituted with 0-3 $R^{6b}$; or
  $C_6$-$C_{10}$ aryl substituted with 0-3 $R^{6b}$;
$R^{6a}$, at each occurrence, is independently selected from H, $C_1$-$C_6$ alkyl, $OR^{14}$, Cl, F, Br, I, =O, CN, $NO_2$, $NR^{15}R^{16}$, aryl and $CF_3$;
$R^{6b}$, at each occurrence, is independently selected from H, OH, Cl, F, Br, I, CN, $NO_2$, $NR^{15}R^{16}$, $CF_3$, $C_1$-$C_6$ alkyl, $C_1$-$C_4$ alkoxy, $C_1$-$C_4$ haloalkyl, and $C_1$-$C_4$ haloalkoxy;
$R^7$, at each occurrence, is independently selected from H, OH, Cl, F, Br, I, CN, $NO_2$, $CF_3$, $C_1$-$C_4$ alkyl, phenyl substituted with 0-5 $R^{7c}$;
$R^{7a}$, at each occurrence, is independently selected from H, Cl, F, Br, I, CN, $CF_3$, and $C_1$-$C_4$ alkyl;
$R^{7b}$ is independently selected from H and $C_1$-$C_4$ alkyl;
$R^{7c}$, at each occurrence, is independently selected from H, OH, Cl, F, Br, I, CN, $CF_3$, $C_1$-$C_4$ alkoxy, and $C_1$-$C_4$ alkyl;
B is a 5 to 10 membered lactam,
  wherein the lactam is saturated, partially saturated or unsaturated;
  wherein each additional lactam carbon is substituted with 0-2 $R^{11}$; and,
  optionally, the lactam contains an additional heteroatom selected from —O—, —S—, —S(=O)—, —S(=O)$_2$—, —N=, —NH—, and —N($R^{10}$)—;
$R^{10}$ is H, C(=O)$R^{17}$, C(=O)$OR^{17}$, C(=O)$NR^{18}R^{19}$, S(=O)$_2$$NR^{18}R^{19}$, S(=O)$_2$$R^{17}$;
  $C_1$-$C_6$ alkyl optionally substituted with 0-3 $R^{10a}$;
  $C_6$-$C_{10}$ aryl substituted with 0-4 $R^{10b}$;
  $C_3$-$C_{10}$ carbocycle substituted with 0-3 $R^{10b}$; or
  5 to 10 membered heterocycle containing 1 to 4 heteroatoms selected from nitrogen, oxygen, and sulphur, wherein said 5 to 10 membered heterocycle is substituted with 0-3 $R^{10b}$;
$R^{10a}$, at each occurrence, is independently selected from H, $C_1$-$C_6$ alkyl, $OR^{14}$, Cl, F, Br, I, =O, CN, $NO_2$, $NR^{15}R^{16}$, $CF_3$, aryl substituted with 0-4 $R^{10b}$; $C_3$-$C_{10}$ carbocycle substituted with 0-3 $R^{10b}$, and 5 to 10 membered heterocycle containing 1 to 4 heteroatoms selected from nitrogen, oxygen, and sulphur, wherein said 5 to 10 membered heterocycle is substituted with 0-3 $R^{10b}$;
$R^{10b}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, $CF_3$, acetyl, $SCH_3$, S(=O)$CH_3$, S(=O)$_2$$CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;
$R^{11}$, at each occurrence, is independently selected from H, $C_1$-$C_4$ alkoxy, Cl, F, Br, I, =O, CN, $NO_2$, $NR^{18}R^{19}$, C(=O)$R^{17}$, C(=O)$OR^{17}$, C(=O)$NR^{18}R^{19}$, S(=O)$_2$$NR^{18}R^{19}$, $CF_3$;
  $C_1$-$C_6$ alkyl optionally substituted with 0-3 $R^{11a}$;
  $C_6$-$C_{10}$ aryl substituted with 0-3 $R^{11b}$;
  $C_3$-$C_{10}$ carbocycle substituted with 0-3 $R^{11b}$; and
  5 to 10 membered heterocycle containing 1 to 4 heteroatoms selected from nitrogen, oxygen, and sulphur, wherein said 5 to 10 membered heterocycle is substituted with 0-3 $R^{11b}$;
$R^{11a}$, at each occurrence, is independently selected from H, $C_1$-$C_6$ alkyl, $OR^{14}$, Cl, F, Br, I, =O, CN, $NO_2$, $NR^{15}R^{16}$, $CF_3$;
  phenyl substituted with 0-3 $R^{11b}$;
  $C_3$-$C_6$ cycloalkyl substituted with 0-3 $R^{11b}$; and
  5 to 6 membered heterocycle containing 1 to 3 heteroatoms selected from nitrogen, oxygen, and sulphur, wherein said 5 to 6 membered heterocycle is substituted with 0-3 $R^{11b}$;
$R^{11b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2$$CH_3$,
  $C_1$-$C_6$ alkyl, $C_1$-$C_4$ alkoxy, $C_1$-$C_4$ haloalkyl,
  $C_1$-$C_4$ haloalkoxy, and $C_1$-$C_4$ haloalkyl-S—;
additionally, two $R^{11}$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0-3 $R^{13}$;
additionally, two $R^{11}$ substituents on the same or adjacent carbon atoms may be combined to form a $C_3$-$C_6$ carbocycle substituted with 0-3 $R^{13}$;
additionally, two $R^{11}$ substituents on adjacent atoms may be combined to form a benzo fused radical; wherein said benzo fused radical is substituted with 0-4 $R^{13}$;
W is —(CR$^8$R$^{8a}$)$_p$—;
p is 0, 1, 2, 3, or 4;
$R^8$ and $R^{8a}$, at each occurrence, are independently selected from H, F, $C_1$-$C_4$ alkyl, $C_2$-$C_4$ alkenyl, $C_2$-$C_4$ alkynyl and $C_3$-$C_8$ cycloalkyl;
X is a bond;
  $C_6$-$C_{10}$ aryl substituted with 0-3 $R^{Xb}$;
  $C_3$-$C_{10}$ carbocycle substituted with 0-3 $R^{Xb}$; or
  5 to 10 membered heterocycle substituted with 0-2 $R^{Xb}$;
$R^{Xb}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2$$CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ halothioalkoxy;

Y is a bond or —($CR^9R^{9a}$)$_t$—V—($CR^9R^{9a}$)$_u$—;
t is 0, 1, 2, or 3;
u is 0, 1, 2, or 3;
$R^9$ and $R^{9a}$, at each occurrence, are independently selected from H, F, $C_1$-$C_6$ alkyl and $C_3$-$C_8$ cycloalkyl;
V is a bond, —C(=O)—, —O—, —S—, —S(=O)—, —S(=O)$_2$—, —N($R^{19}$)—, —C(=O)$NR^{19b}$—, —$NR^{19b}$C(=O)—, —$NR^{19b}$S(=O)—S(=O)$_2$$NR^{19b}$—, —$NR^{19b}$S(=O)—, —S(=O)$NR^{19b}$—, —C(=O)O—, or —OC(=O)—;
Z is H;
  $C_1$-$C_8$ alkyl substituted with 1-3 $R^{12}$;
  $C_2$-$C_4$ alkenyl substituted with 1-3 $R^{12}$;
  $C_2$-$C_4$ alkynyl substituted with 1-3 $R^{12}$;
  $C_1$-$C_8$ alkyl substituted with 0-3 $R^{12a}$;
  $C_2$-$C_4$ alkenyl substituted with 0-3 $R^{12a}$;
  $C_2$-$C_4$ alkynyl substituted with 0-3 $R^{12a}$;
  $C_6$-$C_{10}$ aryl substituted with 0-4 $R^{12b}$;
  $C_3$-$C_{10}$ carbocycle substituted with 0-4 $R^{12b}$; or
  5 to 10 membered heterocycle containing 1 to 4 heteroatoms selected from nitrogen, oxygen, and sulphur, wherein said 5 to 10 membered heterocycle is substituted with 0-3 $R^{12b}$;
$R^{12}$, at each occurrence, is independently selected from
  $C_6$-$C_{10}$ aryl substituted with 0-4 $R^{12b}$;
  $C_3$-$C_{10}$ carbocycle substituted with 0-4 $R^{12b}$; and
  5 to 10 membered heterocycle containing 1 to 4 heteroatoms selected from nitrogen, oxygen, and sulphur, wherein said 5 to 10 membered heterocycle is substituted with 0-3 $R^{12b}$;
$R^{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, S(=O)$CH_3$, S(=O)$_2$$CH_3$,
  $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;
$R^{12b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2$$CH_3$,
  $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;
$R^{13}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, and $CF_3$;
$R^{14}$ is H, phenyl substituted with 0-4 $R^{14b}$, benzyl substituted with 0-4 $R^{14b}$, $C_1$-$C_6$ alkyl, $C_2$-$C_6$ alkoxyalkyl, or $C_3$-$C_6$ cycloalkyl;
$R^{14a}$ is H, $C_6$-$C_{10}$ aryl, benzyl, heterocycle, or $C_1$-$C_4$ alkyl;
$R^{14b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2$$CH_3$,
  $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;
$R^{15}$, at each occurrence, is independently selected from H, $C_1$-$C_6$ alkyl, aryl-($C_1$-$C_6$ alkyl)- wherein the aryl is substituted with 0-4 $R^{15b}$, ($C_1$-$C_6$ alkyl)-C(=O)—, and ($C_1$-$C_6$ alkyl)-S(=O)$_2$—;
$R^{15b}$, at each occurrence, is independently selected from H, OH, Cl, F, Br, I, CN, $NO_2$, $CF_3$, acetyl, $SCH_3$, S(=O)$CH_3$, S(=O)$_2$$CH_3$,
  $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;
$R^{16}$, at each occurrence, is independently selected from H, $C_1$-$C_6$ alkyl, benzyl, phenethyl, ($C_1$-$C_6$ alkyl)-C(=O)—, and ($C_1$-$C_6$ alkyl)-S(=O)$_2$—;
$R^{17}$ is H, $C_1$-$C_6$ alkyl, $C_2$-$C_6$ alkoxyalkyl, aryl substituted by 0-4 $R^{17a}$, or —$CH_2$-aryl substituted by 0-4 $R^{17a}$;
$R^{17a}$, is H, methyl, ethyl, propyl, butyl, methoxy, ethoxy, propoxy, butoxy, —OH, F, Cl, Br, I, $CF_3$, $OCF_3$, $SCH_3$, 'S(O)$CH_3$, $SO_2CH_3$, —$NH_2$, —N($CH_3$)$_2$, or $C_1$-$C_4$ haloalkyl;
$R^{18}$, at each occurrence, is independently selected from H, $C_1$-$C_6$ alkyl, phenyl, benzyl, phenethyl, ($C_1$-$C_6$ alkyl)-C(=O)—, and ($C_1$-$C_6$ alkyl)-S(=O)$_2$—;
$R^{19}$, at each occurrence, is independently selected from H, OH, $C_1$-$C_6$ alkyl, phenyl, benzyl, phenethyl, ($C_1$-$C_6$ alkyl)-C(=O)—, and ($C_1$-$C_6$ alkyl)-S(=O)$_2$—;
$R^{20}$ is H, C(=O)$R^{17}$, C(=O)$OR^{17}$, C(=O)$NR^{18}R^{19}$, S(=O)$_2$$NR^{18}R^{19}$, S(=O)$_2$$R^{17}$;
  $C_1$-$C_6$ alkyl optionally substituted with 0-2 $R^{20a}$;
  $C_6$-$C_{10}$ aryl substituted with 0-4 $R^{20b}$;
  $C_3$-$C_{10}$ carbocycle substituted with 0-3 $R^{20b}$; or
  5 to 10 membered heterocycle containing 1 to 4 heteroatoms selected from nitrogen, oxygen, and sulphur, wherein said 5 to 10 membered heterocycle is substituted with 0-3 $R^{20b}$;
$R^{20a}$, at each occurrence, is independently selected from H, $C_1$-$C_6$ alkyl, $OR^{14}$, F, =O, CN, $NO_2$, $NR^{15}R^{16}$, $CF_3$, aryl substituted with 0-4 $R^{20b}$, and heterocycle substituted with 0-4 $R^{20b}$;
$R^{20b}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, $CF_3$, acetyl, $SCH_3$, S(=O)$CH_3$, S(=O)$_2$$CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;
$R^{21}$, at each occurrence, is independently selected from H, $C_1$-$C_4$ alkoxy, Cl, F, Br, I, =O, CN, $NO_2$, $NR^{18}R^{19}$, C(=O)$R^{17}$, C(=O)$OR^{17}$, C(=O)$NR^{11}R^{19}$, S(=O)$_2$$NR^{18}R^{19}$, $CF_3$;
  $C_1$-$C_6$ alkyl optionally substituted with 0-3 $R^{21a}$;
  $C_6$-$C_{10}$ aryl substituted with 0-3 $R^{21b}$;
  $C_3$-$C_{10}$ carbocycle substituted with 0-3 $R^{21b}$; and
  5 to 10 membered heterocycle containing 1 to 4 heteroatoms selected from nitrogen, oxygen, and sulphur, wherein said 5 to 10 membered heterocycle is substituted with 0-3 $R^{21b}$;
$R^{21a}$, at each occurrence, is independently selected from H, $C_1$-$C_6$ alkyl, $OR^{14}$, Cl, F, Br, I, =O, CN, $NO_2$, $NR^{15}R^{16}$, $CF_3$;
  phenyl substituted with 0-3 $R^{21b}$;
  $C_3$-$C_6$ cycloalkyl substituted with 0-3 $R^{21b}$; and
  5 to 6 membered heterocycle containing 1 to 3 heteroatoms selected from nitrogen, oxygen, and sulphur, wherein said 5 to 6 membered heterocycle is substituted with 0-3 $R^{21b}$;
$R^{21b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2$$CH_3$,
  $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;
additionally, two $R^{21}$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0-3 $R^{23}$;
additionally, two $R^{21}$ substituents on the same or adjacent carbon atoms may be combined to form a $C_3$-$C_6$ carbocycle substituted with 0-3 $R^{23}$;
additionally, two $R^{21}$ substituents on adjacent atoms may be combined to form a benzo fused radical; wherein said benzo fused radical is substituted with 0-4 $R^{23}$;

$R^{23}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, and $CF_3$;

$R^{26}$ is H;
$C_1$-$C_6$ alkyl substituted with 0-3 $R^{26a}$;
$C_3$-$C_{10}$ carbocycle substituted with 0-3 $R^{26b}$; or
$C_6$-$C_{10}$ aryl substituted with 0-3 $R^{26b}$;

$R^{26a}$, at each occurrence, is independently selected from H, $C_1$-$C_6$ alkyl, $OR^{14}$, Cl, F, Br, I, =O, CN, $NO_2$, $NR^{15}R^{16}$, aryl and $CF_3$; and $R^{26b}$, at each occurrence, is independently selected from H, OH, Cl, F, Br, I, CN, $NO_2$, $NR^{15}R^{16}$, $CF_3$, $C_1$-$C_6$ alkyl, $C_1$-$C_4$ alkoxy, $C_1$-$C_4$ haloalkyl, and $C_1$-$C_4$ haloalkoxy.

[2] In a preferred embodiment the present invention provides a compound of Formula (I), wherein:

L is —$NR^{26}$C(=O)—, —C(=O)$NR^{26}$—, or —OC(=O)$NR^{26}$—;

$R^3$ is —(CHR$^7$)$_n$—$R^4$,
—(CHR$^7$)$_l$—N—(CR$^7$R$^{7a}$)$_m$—$R^4$, or
—(CHR$^7$)$_l$—O—(CR$^7$R$^{7a}$)$_m$—$R^4$;

n is 0, 1 or 2;
m is 0, 1 or 2;
l is 1;

Ring C is a 3 to 8 membered carbocycle substituted with 0-4 $R^{21}$; optionally, the carbocycle contains a heteroatom selected from —O— and —N($R^{20}$)—;

$R^4$ is H, OH, $OR^{14a}$,
$C_1$-$C_6$ alkyl substituted with 0-3 $R^{4a}$,
$C_2$-$C_6$ alkenyl substituted with 0-2 $R^{4a}$,
$C_2$-$C_6$ alkynyl substituted with 0-1 $R^{4a}$,
$C_3$-$C_6$ carbocycle substituted with 0-3 $R^{4b}$,
$C_6$-$C_{10}$ aryl substituted with 0-3 $R^{4b}$, or
5 to 6 membered heterocycle containing 1 to 4 heteroatoms selected from nitrogen, oxygen, and sulphur, wherein said 5 to 6 membered heterocycle is substituted with 0-3 $R^{4b}$;

$R^{4a}$, at each occurrence, is independently selected from H, OH, F, Cl, Br, I, $NR^{15}R^{16}$, $CF_3$,
$C_3$-$C_6$ carbocycle substituted with 0-3 $R^{4b}$,
phenyl substituted with 0-3 $R^{4b}$, and
5 to 6 membered heterocycle containing 1 to 4 heteroatoms selected from nitrogen, oxygen, and sulphur, wherein said 5 to 6 membered heterocycle is substituted with 0-3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$-$C_4$ alkyl, $C_1$-$C_3$ alkoxy, $C_1$-$C_2$ haloalkyl, and $C_1$-$C_2$ haloalkoxy;

$R^6$ is H;

$R^7$, at each occurrence, is independently selected from H, OH, F, $CF_3$, methyl, and ethyl;

Ring B is a 7 membered lactam,
wherein the lactam is saturated, partially saturated or unsaturated;
wherein each additional lactam carbon is substituted with 0-2 $R^{11}$; and,
optionally, the lactam contains a heteroatom selected from —O—, —S—, —S(=O)—, —S(=O)$_2$—, —N=, —NH—, and —N($R^{10}$)—;

$R^{10}$ is H, C(=O)$R^{17}$, C(=O)$OR^{17}$, C(=O)$NR^{18}R^{19}$, S(=O)$_2NR^{18}R^{19}$, S(=O)$_2R^{17}$;
$C_1$-$C_6$ alkyl optionally substituted with 0-2 $R^{10a}$;
$C_6$-$C_{10}$ aryl substituted with 0-4 $R^{10b}$;
$C_3$-$C_{10}$ carbocycle substituted with 0-3 $R^{10b}$; or
5 to 10 membered heterocycle containing 1 to 4 heteroatoms selected from nitrogen, oxygen, and sulphur, wherein said 5 to 10 membered heterocycle is substituted with 0-3 $R^{10b}$;

$R^{10a}$, at each occurrence, is independently selected from H, $C_1$-$C_6$ alkyl, $OR^{14}$, Cl, F, Br, I, =O, CN, $NO_2$, $NR^{15}R^{16}$, $CF_3$, phenyl substituted with 0-4 $R^{10b}$; and 5 to 10 membered heterocycle containing 1 to 4 heteroatoms selected from nitrogen, oxygen, and sulphur, wherein said 5 to 10 membered heterocycle is substituted with 0-3 $R^{10b}$;

$R^{10b}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, and $CF_3$;

$R^{11}$, at each occurrence, is independently selected from H, $C_1$-$C_4$ alkoxy, Cl, F, Br, I, =O, CN, $NO_2$, $NR^{18}R^{19}$, C(=O)$R^{17}$, C(=O)$OR^{17}$, C(=O)$NR^{18}R^{19}$, S(=O)$_2NR^{18}R^{19}$, $CF_3$;
$C_1$-$C_6$ alkyl optionally substituted with 0-3 $R^{11a}$;
$C_6$-$C_{10}$ aryl substituted with 0-3 $R^{11b}$;
$C_3$-$C_{10}$ carbocycle substituted with 0-3 $R^{11b}$; and
5 to 10 membered heterocycle containing 1 to 4 heteroatoms selected from nitrogen, oxygen, and sulphur, wherein said 5 to 10 membered heterocycle is substituted with 0-3 $R^{11b}$;

$R^{11a}$, at each occurrence, is independently selected from H, $C_1$-$C_6$ alkyl, $OR^{14}$, Cl, F, Br, I, =O, CN, $NO_2$, $NR^{15}R^{16}$, $CF_3$, or phenyl substituted with 0-3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$-$C_6$ alkyl, $C_1$-$C_4$ alkoxy, $C_1$-$C_4$ haloalkyl, and $C_1$-$C_4$ haloalkoxy;

additionally, two $R^{11}$ substituents on adjacent atoms may be combined to form a benzo fused radical; wherein said benzo fused radical is substituted with 0-2 $R^{13}$;

additionally, two $R^{11}$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0-2 $R^{13}$;

additionally, two $R^{11}$ substituents on the same or adjacent carbon atoms may be combined to form a $C_3$-$C_6$ carbocycle substituted with 0-2 $R^{13}$;

W is a bond, —$CH_2$—, —CH($CH_3$)—, —$CH_2CH_2$— or —CH($CH_3$)$CH_2$—;

X is a bond;
phenyl substituted with 0-2 $R^{Xb}$;
$C_3$-$C_6$ cycloalkyl substituted with 0-2 $R^{Xb}$; or
5 to 6 membered heterocycle substituted with 0-2 $R^{Xb}$;

$R^{Xb}$, at each occurrence, is independently selected from H, OH, Cl, F, $NR^{15}R^{16}$, $CF_3$, acetyl, $SCH_3$, S(=O)$CH_3$, S(=O)$_2CH_3$, $C_1$-$C_4$ alkyl, $C_1$-$C_3$ alkoxy, $C_1$-$C_2$ haloalkyl, and $C_1$-$C_2$ haloalkoxy;

Y is a bond, —$CH_2$—V—, —V—, or —V—$CH_2$—;

V is a bond, —C(=O)—, —O—, —S—, —S(=O)—, —S(=O)$_2$—, —NH—, —N($CH_3$)—, or —N($CH_2CH_3$)—;

Z is H; $C_1$-$C_6$ alkyl; $C_2$-$C_4$ alkenyl; $C_2$-$C_4$ alkynyl;
$C_1$-$C_3$ alkyl substituted with 1-2 $R^{12}$;
$C_2$-$C_3$ alkenyl substituted with 1-2 $R^{12}$;
$C_2$-$C_3$ alkynyl substituted with 1-2 $R^{12}$;
$C_6$-$C_{10}$ aryl substituted with 0-4 $R^{12b}$;
$C_3$-$C_6$ carbocycle substituted with 0-3 $R^{12b}$; or
5 to 10 membered heterocycle substituted with 0-3 $R^{12b}$;

$R^{12}$, at each occurrence, is independently selected from $C_6$-$C_{10}$ aryl substituted with 0-4 $R^{12b}$;

$C_3$-$C_{10}$ carbocycle substituted with 0-4 $R^{12b}$; and 5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
  $C_1$-$C_6$ alkyl, $C_1$-$C_4$ alkoxy, $C_1$-$C_4$ haloalkyl,
  $C_1$-$C_4$ haloalkoxy, and $C_1$-$C_4$ haloalkyl-S—;

$R^{13}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, and $CF_3$;

$R^{14}$ is H, phenyl, benzyl, $C_1$-$C_4$ alkyl, or $C_2$-$C_4$ alkoxyalkyl;

$R^{14a}$ is H, phenyl, benzyl, or $C_1$-$C_4$ alkyl;

$R^{15}$, at each occurrence, is independently selected from H, $C_1$-$C_4$ alkyl, benzyl, phenethyl, ($C_1$-$C_4$ alkyl)-C(=O)—, and ($C_1$-$C_4$ alkyl)-S(=O)$_2$—;

$R^{16}$, at each occurrence, is independently selected from H, OH, $C_1$-$C_4$ alkyl, benzyl, phenethyl, ($C_1$-$C_4$ alkyl)-C(=O)—, and ($C_1$-$C_4$ alkyl)-S(=O)$_2$—;

$R^{17}$ is H, methyl, ethyl, propyl, butyl, methoxymethyl, ethoxymethyl, methoxyethyl, ethoxyethyl, phenyl substituted by 0-3 $R^{17a}$, or —$CH_2$-phenyl substituted by 0-3 $R^{17a}$;

$R^{17a}$ is H, methyl, methoxy, —OH, F, Cl, $CF_3$, or $OCF_3$;

$R^{18}$, at each occurrence, is independently selected from H, methyl, ethyl, propyl, butyl, phenyl, benzyl, and phenethyl;

$R^{19}$, at each occurrence, is independently selected from H, methyl, and ethyl;

$R^{20}$ is H or C(=O)OR$^{17}$;

$R^{26}$ is H, methyl, or ethyl.

[3] In another preferred embodiment the present invention provides a compound of Formula (I), wherein:

Ring C is selected from:

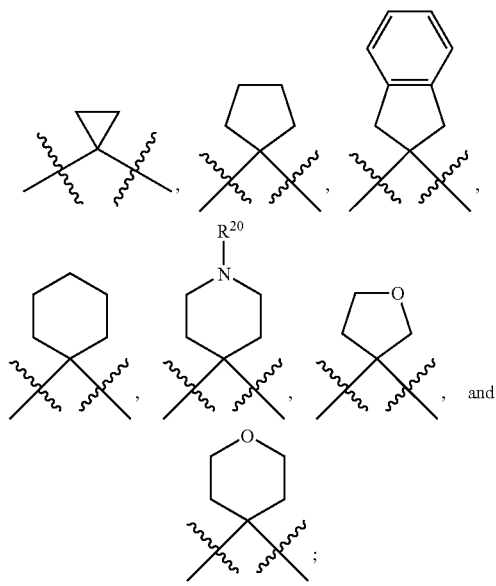

wherein Ring C is substituted with 0-2 $R^{21}$; and

Ring B is selected from:

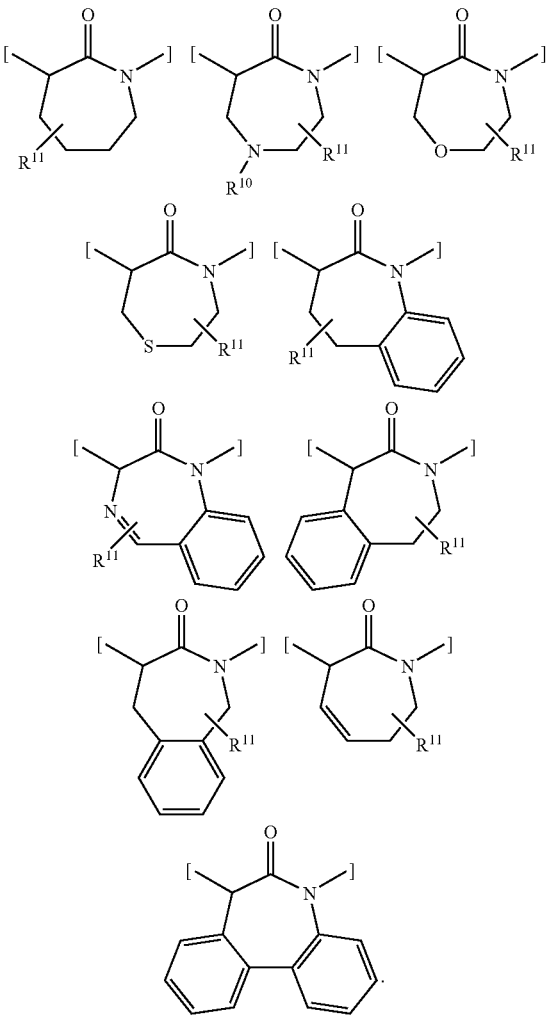

[4] In another more preferred embodiment the present invention provides a compound of Formula (I), wherein:

L is —NHC(=O)—, —C(=O)NH—, or —OC(=O)NH—;

$R^3$ is $R^4$, —$CH_2OR^4$, or —$CH_2CH_2OR^4$;

$R^4$ is $C_1$-$C_6$ alkyl substituted with 0-3 $R^{4a}$,
  $C_2$-$C_6$ alkenyl substituted with 0-1 $R^{4a}$, or
  $C_2$-$C_6$ alkynyl substituted with 0-1 $R^{4a}$;

$R^{4a}$, at each occurrence, is independently selected from H, OH, F, $NR^{15}R^{16}$, $CF_3$,
  $C_3$-$C_6$ carbocycle substituted with 0-3 $R^{4b}$,
  phenyl substituted with 0-3 $R^{4b}$, and
  5 to 6 membered heterocycle containing 1 to 4 heteroatoms selected from nitrogen, oxygen, and sulphur, wherein said 5 to 6 membered heterocycle is substituted with 0-3 $R^{4b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{4b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;

W is a bond, —$CH_2$—, —$CH(CH_3)$—, —$CH_2CH_2$— or —$CH(CH_3)CH_2$—;

X is a bond, phenyl, $C_3$-$C_6$ cycloalkyl, or 5 to 6 membered heterocycle;

Y is a bond, —C(=O)—, —O—, —S—, —S(=O)—, —S(=O)$_2$—, —NH—, —N($CH_3$)—, or —N($CH_2CH_3$)—;

Z is H; $C_1$-$C_6$ alkyl, $C_2$-$C_4$ alkenyl, $C_2$-$C_4$ alkynyl,
$C_1$-$C_3$ alkyl substituted with 1-2 $R^{12}$;
$C_2$-$C_3$ alkenyl substituted with 1-2 $R^{12}$;
$C_2$-$C_3$ alkynyl substituted with 1-2 $R^{12}$;
$C_6$-$C_{10}$ aryl substituted with 0-4 $R^{12b}$;
$C_3$-$C_6$ carbocycle substituted with 0-3 $R^{12b}$; or
5 to 6 membered heterocycle containing 1 to 4 heteroatoms selected from nitrogen, oxygen, and sulphur, wherein said 5 to 6 membered heterocycle is substituted with 0-3 $R^{12b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{12}$, at each occurrence, is independently selected from
$C_6$-$C_{10}$ aryl substituted with 0-4 $R^{12b}$;
$C_3$-$C_6$ carbocycle substituted with 0-3 $R^{12b}$; and
5 to 10 membered heterocycle containing 1 to 4 heteroatoms selected from nitrogen, oxygen, and sulphur, wherein said 5 to 10 membered heterocycle is substituted with 0-3 $R^{12b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{12b}$, at each occurrence, is independently selected from H, OH, Cl, F, $NR^{15}R^{16}$, $CF_3$, acetyl, $SCH_3$, S(=O)$CH_3$, S(=O)$_2CH_3$, methyl, ethyl, propyl, butyl, methoxy, ethoxy, propoxy, $C_1$-$C_2$ haloalkyl, and $C_1$-$C_2$ haloalkoxy;

$R^{13}$, at each occurrence, is independently selected from H, OH, methyl, ethyl, propyl, butyl, methoxy, ethoxy, Cl, F, Br, CN, $NR^{15}R^{16}$, and $CF^3$;

$R^{14}$ is H, phenyl, benzyl, methyl, ethyl, propyl, or butyl;

$R^{15}$, at each occurrence, is independently selected from H, methyl, ethyl, propyl, and butyl;

$R^{16}$, at each occurrence, is independently selected from H, OH, methyl, ethyl, propyl, butyl, benzyl, phenethyl, methyl-C(=O)—, ethyl-C(=O)—, methyl-S(=O)$_2$—, ethyl-S(=O)$_2$—, and propyl-S(=O)$_2$—;

$R^{18}$, at each occurrence, is independently selected from H, methyl, ethyl, propyl, butyl, phenyl, benzyl, and phenethyl;

$R^{19}$, at each occurrence, is independently selected from H, methyl, and ethyl;

$R^{20}$ is H.

[5] In another more preferred embodiment the present invention provides a compound of Formula (I), wherein:
L is —NHC(=O)—, —C(=O)NH—, or —OC(=O)NH—;

$R^3$ is —$CH_3$, —$CH_2CH_3$, —$CH_2CH_2CH_3$, —$CH_2CH_2CH_2CH_3$, —$CH_2CH_2CH(CH_3)_2$, —$CH_2(CH_3)_2$, —$CH(CH_3)CH_2CH_3$, —$CH_2CH(CH_3)_2$, —$CH_2C(CH_3)_3$, —$CF_3$, —$CH_2CF_3$, —$CH_2CH_2CF_3$, —$CH_2CH_2CH_2CF_3$, —CH(OH)$CH_2CH(CH_3)_2$, —CH(OH)CH($CH_3$)$_2$, —CH($NH_2$)$CH_2CH(CH_3)_2$, —$CH_2CH_2OCH_3$, —$CH_2OCH_2CH_3$, —$CF_2CH_2CH(CH_3)_2$, —CH(NHCH$_3$)$CH_2CH(CH_3)_2$, —CH(NHSO$_2CH_2CH_2CH_3$)$CH_2CH(CH_3)_2$, cyclohexyl-, cyclopentyl-, cyclopropyl-$CH_2$—, cyclobutyl-$CH_2$—, cyclopentyl-$CH_2$—, cyclohexyl-$CH_2$—, cyclopropyl-$CH_2CH_2$—, cyclobutyl-$CH_2CH_2$—, cyclopentyl-$CH_2CH_2$—, cyclohexyl-CH(OH)—, cyclohexyl-$CH_2CH_2$—, 1-$NH_2$-cyclopentyl, phenyl-$CH_2$—, (2-F-phenyl)$CH_2$—, (3-F-phenyl)$CH_2$—, (4-F-phenyl)$CH_2$—, (2-Cl-phenyl)$CH_2$—, (3-Cl-phenyl)$CH_2$—, (4-Cl-phenyl)$CH_2$—, (2,3-diF-phenyl)$CH_2$—, (2,4-diF-phenyl)$CH_2$—, (2,5-diF-phenyl)$CH_2$—, (2,6-diF-phenyl)$CH_2$—, (3,4-diF-phenyl)$CH_2$—, (3,5-diF-phenyl)$CH_2$—, (2,3-diCl-phenyl)$CH_2$—, (2,4-diCl-phenyl)$CH_2$—, (2,5-diCl-phenyl)$CH_2$—, (2,6-diCl-phenyl)$CH_2$—, (3,4-diCl-phenyl)$CH_2$—, (3,5-diCl-phenyl)$CH_2$—, (3-F-4-Cl-phenyl)$CH_2$—, (3-F-5-Cl-phenyl)$CH_2$—, (3-Cl-4-F-phenyl)$CH_2$—, phenyl-$CH_2CH_2$—, (2-F-phenyl)$CH_2CH_2$—, (3-F-phenyl)$CH_2CH_2$—, (4-F-phenyl)$CH_2CH_2$—, (2-Cl-phenyl)$CH_2CH_2$—, (3-Cl-phenyl)$CH_2CH_2$—, (4-Cl-phenyl)$CH_2CH_2$—, (2,3-diF-phenyl)$CH_2CH_2$—, (2,4-diF-phenyl)$CH_2CH_2$—, (2,5-diF-phenyl)$CH_2CH_2$—, (2,6-diF-phenyl)$CH_2CH_2$—, (3,4-diF-phenyl)$CH_2CH_2$—, (3,5-diF-phenyl)$CH_2CH_2$—, (2,3-diCl-phenyl)$CH_2CH_2$—, (2,4-diCl-phenyl)$CH_2CH_2$—, (2,5-diCl-phenyl)$CH_2CH_2$—, (2,6-diCl-phenyl)$CH_2CH_2$—, (3,4-diCl-phenyl)$CH_2CH_2$—, (3,5-diCl-phenyl)$CH_2CH_2$—, (3-F-4-Cl-phenyl)$CH_2CH_2$—, (3-F-5-Cl-phenyl)$CH_2CH_2$—, 4-piperidinyl-$CH_2CH_2$—, phenyl-$CH_2CH_2CF_2$—, phenyl-$CH_2$CH(OH)—, imidazolyl-$CH_2$CH(OH)—, or phenyl-$CH_2OCH_2$—;

Ring C is selected from:

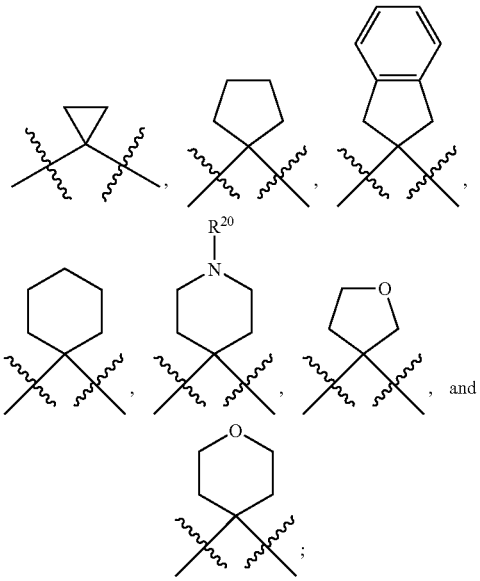

Ring B is selected from:

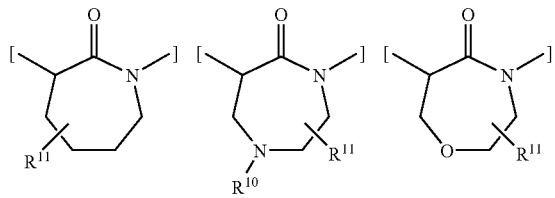

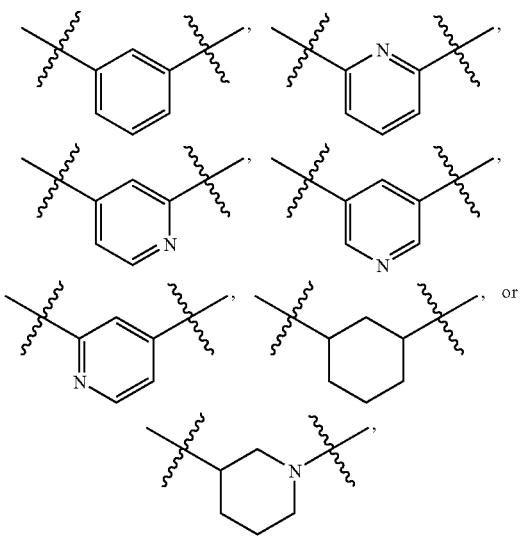

wherein each benzo fused ring is substituted with 0-1 $R^{13}$;
W is a bond or —$CH_2$—;
X is a bond;

Y is a bond, —C(=O)—, —O—, —S—, —S(=O)—, —S(=O)$_2$—, —NH—, or —N($CH_3$)—,
Z is phenyl, 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-$CF_3$O-phenyl, 3-$CF_3$O-phenyl, 4-$CF_3$O-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, cyclopropyl, cyclobutyl, cyclopentyl, cyclohexyl, morpholino, N-piperinyl, phenyl-$CH_2$—, (2-F-phenyl)$CH_2$—, (3-F-phenyl)$CH_2$—, (4-F-phenyl)$CH_2$—, (2-Cl-phenyl)$CH_2$—, (3-Cl-phenyl)$CH_2$, (4-Cl-phenyl)$CH_2$—, (2,3-diF-phenyl)$CH_2$—, (2,4-diF-phenyl)$CH_2$—, (2,5-diF-phenyl)$CH_2$—, (2,6-diF-phenyl)$CH_2$—, (3,4-diF-phenyl)$CH_2$—, (3,5-diF-phenyl)$CH_2$—, (2,3-diCl-phenyl)$CH_2$—, (2,4-diCl-phenyl)$CH_2$—, (2,5-diCl-phenyl)$CH_2$—, (2,6-diCl-phenyl)$CH_2$—, (3,4-diCl-phenyl)$CH_2$—, (3,5-diCl-phenyl)$CH_2$—, (3-F-4-Cl-phenyl)$CH_2$—, (3-F-5-Cl-phenyl)$CH_2$—, (3-Cl-4-F-phenyl)$CH_2$—, (2-MeO-phenyl)$CH_2$—, (3-MeO-phenyl)$CH_2$—, (4-MeO-phenyl)$CH_2$—, (2-Me-phenyl)$CH_2$—, (3-Me-phenyl)$CH_2$—, (4-Me-phenyl)$CH_2$—, (2-MeS-phenyl)$CH_2$—, (3-MeS-phenyl)$CH_2$—, 4-MeS-phenyl)$CH_2$—, (2-$CF_3$O-phenyl)$CH_2$—, (3-$CF_3$O-phenyl)$CH_2$—, (4-$CF_3$O-phenyl)$CH_2$—, (furanyl)$CH_2$—, (thienyl)$CH_2$—, (pyridyl)$CH_2$—, (2-Me-pyridyl)$CH_2$—, (3-Me-pyridyl)$CH_2$—, (4-Me-pyridyl)$CH_2$—, (1-imidazolyl)$CH_2$—, (oxazolyl)$CH_2$—, (isoxazolyl)$CH_2$—, (1-benzimidazolyl)$CH_2$—, (cyclopropyl)$CH_2$—, (cyclobutyl)$CH_2$—, (cyclopentyl)$CH_2$—, (cyclohexyl)$CH_2$—, (morpholino)$CH_2$—, (N-pipridinyl)$CH_2$—, phenyl-$CH_2CH_2$—, (phenyl)$_2$CH$CH_2$—, (2-F-phenyl)$CH_2CH_2$—, (3-F-phenyl)$CH_2CH_2$—, (4-F-phenyl)$CH_2CH_2$—, (2-Cl-phenyl)$CH_2CH_2$—, (3-Cl-phenyl)$CH_2CH_2$—, (4-Cl-phenyl)$CH_2CH_2$—, (2,3-diF-phenyl)$CH_2CH_2$—, (2,4-diF-phenyl)$CH_2CH_2$—, (2,5-diF-phenyl) $CH_2CH_2$—, (2,6-diF-phenyl)$CH_2CH_2$—, (3,4-diF-phenyl)$CH_2CH_2$—, (3,5-diF-phenyl)$CH_2CH_2$—, (2,3-diCl-phenyl)$CH_2CH_2$—, (2,4-diCl-phenyl)$CH_2CH_2$—, (2,5-diCl-phenyl)$CH_2CH_2$—, (2,6-diCl-phenyl)$CH_2CH_2$—, (3,4-diCl-phenyl)$CH_2CH_2$—, (3,25-diCl-phenyl)$CH_2CH_2$—, (3-F-4-Cl-phenyl)$CH_2CH_2$—, (3-F-5-Cl-phenyl)$CH_2CH_2$—, (3-CF-4-F-phenyl)$CH_2CH_2$—, (2-MeO-phenyl)$CH_2CH_2$—, (3C-MeO-phenyl)$CH_2CH_2$—, (4-MeO-phenyl)$CH_2CH_2$—, (2-Me-phenyl)$CH_2CH_2$—, (3-Me-phenyl)$CH_2CH_2$—, (4-Me-phenyl)$CH_2CH_2$—, (2-MeS-phenyl)$CH_2CH_2$—, (3-MeS-phenyl)$CH_2CH_2$—, (4-MeS-phenyl)$CH_2CH_2$—, (2-$CF_3$O-phenyl)$CH_2CH_2$—, (3-$CF_3$O-phenyl)$CH_2CH_2$—, (4-$CF_3$O-phenyl)$CH_2CH_2$—, (furanyl)$CH_2CH_2$—, (thienyl)$CH_2CH_2$—, (pyridyl)$CH_2CH_2$—, (2-Me-pyridyl)$CH_2CH_2$—, (3-Me-pyridyl)$CH_2CH_2$—, (4-Me-pyridyl)$CH_2CH_2$—, (imidazolyl)$CH_2CH_2$—, (oxazolyl)$CH_2CH_2$—, (isoxazolyl)$CH_2CH_2$—, (benzimidazolyl)$CH_2CH_2$—, (cyclopropyl)$CH_2CH_2$—, (cyclobutyl)$CH_2CH_2$—, (cyclopentyl)$CH_2CH_2$—, (cyclohexyl)$CH_2CH_2$—, (morpholino)$CH_2CH_2$—, or (N-pipridinyl)$CH_2CH_2$—;
$R^{10}$ is H, methyl, ethyl, phenyl, benzyl, phenethyl, 4-F-phenyl, (4-F-phenyl)$CH_2$—, (4-F-phenyl)$CH_2CH_2$—, 4-Cl-phenyl, (4-Cl-phenyl)$CH_2$—, (4-Cl-phenyl)$CH_2CH_2$—, 4-$CH_3$-phenyl, (4-$CH_3$-phenyl)$CH_2$—, (4-$CH_3$-phenyl)$CH_2CH_2$—, 4-$CF_3$-phenyl, (4-$CF_3$-phenyl)$CH_2$—, or (4-$CF_3$-phenyl)$CH_2CH_2$—;

$R^{11}$, at each occurrence, is independently selected from H, =O, methyl, ethyl, phenyl, benzyl, phenethyl, 4-F-phenyl, (4-F-phenyl)CH$_2$—, (4-F-phenyl)CH$_2$CH$_2$—, 3-F-phenyl, (3-F-phenyl)CH$_2$—, (3-F-phenyl)CH$_2$CH$_2$—, 2-F-phenyl, (2-F-phenyl)CH$_2$—, (2-F-phenyl)CH$_2$CH$_2$—, 4-Cl-phenyl, (4-Cl-phenyl)CH$_2$—, (4-Cl-phenyl)CH$_2$CH$_2$—, 3-Cl-phenyl, (3-Cl-phenyl)CH$_2$—, (3-Cl-phenyl)CH$_2$CH$_2$—, 4-CH$_3$-phenyl, (4-CH$_3$-phenyl)CH$_2$—, (4-CH$_3$-phenyl)CH$_2$CH$_2$—, 3-CH$_3$-phenyl, (3-CH$_3$-phenyl)CH$_2$—, (3-CH$_3$-phenyl)CH$_2$CH$_2$—, 4-CF$_3$-phenyl, (4-CF$_3$-phenyl)CH$_2$—, (4-CF$_3$-phenyl)CH$_2$CH$_2$—, cyclopentyl, pyrid-2-yl, pyrid-3-yl, and pyrid-4-yl;

$R^{13}$, at each occurrence, is independently selected from H, F, Cl, OH, —CH$_3$, —CH$_2$CH$_3$, —OCH$_3$, and —CF$_3$; and $R^{20}$ is H.

In another preferred embodiment the present invention provides a compound of Formula (I), wherein:

$R^3$ is —(CR$^7$R$^{7a}$)$_n$—R$^4$,
—(CR$^7$R$^{7a}$)$_l$—S—(CR$^7$R$^{7a}$)$_m$—R$^4$,
—(CR$^7$R$^{7a}$)$_l$—O—(CR$^7$R$^{7a}$)$_m$—R$^4$, or
—(CR$^7$R$^{7a}$)$_l$—N(R$^{7b}$)—(CR$^7$R$^{7a}$)$_m$—R$^4$;

n is 0, 1, or 2;
m is 0, 1, or 2;
l is 1 or 2;

Ring C is a 3 to 8 membered carbocycle substituted with 0-4 $R^{21}$; optionally, the carbocycle contains a heteroatom selected from —O—, and —N(R$^{20}$)—;

$R^4$ is H, OH, OR$^{14a}$,
C$_1$-C$_6$ alkyl substituted with 0-3 R$^{4a}$,
C$_2$-C$_6$ alkenyl substituted with 0-3 R$^{4a}$,
C$_2$-C$_6$ alkynyl substituted with 0-3 R$^{4a}$,
C$_3$-C$_{10}$ carbocycle substituted with 0-3 R$^{4b}$,
C$_6$-C$_{10}$ aryl substituted with 0-3 R$^{4b}$, or
5 to 10 membered heterocycle containing 1 to 4 heteroatoms selected from nitrogen, oxygen, and sulphur, wherein said 5 to 10 membered heterocycle is substituted with 0-3 R$^{4b}$;

$R^{4a}$, at each occurrence, is independently selected from is H, F, Cl, Br, I, CF$_3$,
C$_3$-C$_{10}$ carbocycle substituted with 0-3 R$^{4b}$,
C$_6$-C$_{10}$ aryl substituted with 0-3 R$^{4b}$, or
5 to 10 membered heterocycle containing 1 to 4 heteroatoms selected from nitrogen, oxygen, and sulphur, wherein said 5 to 10 membered heterocycle is substituted with 0-3 R$^{4b}$;

$R^{4b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$-C$_6$ alkyl, C$_1$-C$_4$ alkoxy, C$_1$-C$_4$ haloalkyl, and C$_1$-C$_4$ haloalkoxy;

$R^6$ is H, methyl, or ethyl;

$R^7$, at each occurrence, is independently selected from H, OH, Cl, F, Br, I, CN, NO$_2$, CF$_3$, phenyl and C$_1$-C$_4$ alkyl;

$R^{7a}$, at each occurrence, is independently selected from H, OH, Cl, F, Br, I, CN, NO$_2$, CF$_3$, and C$_1$-C$_4$ alkyl;

$R^{7b}$ is independently selected from H, methyl, ethyl, propyl, and butyl;

Ring B is a 7 membered lactam,
wherein the lactam is saturated, partially saturated or unsaturated;
wherein each additional lactam carbon is substituted with 0-2 R$^{11}$; and,
optionally, the lactam contains a heteroatom selected from, —O—, —S—, —S(=O)—, —S(=O)$_2$—, —N=, —NH—, and —N(R$^{10}$)—;

$R^{10}$ is H, C(=O)R$^{17}$, C(=O)OR$^{17}$, C(=O)NR$^{18}$R$^{19}$, S(=O)$_2$NR$^{18}$R$^{19}$, S(=O)$_2$R$^{17}$;
C$_1$-C$_6$ alkyl optionally substituted with 0-2 R$^{10a}$;
C$_6$-C$_{10}$ aryl substituted with 0-4 R$^{10b}$;
C$_3$-C$_{10}$ carbocycle substituted with 0-3 R$^{10b}$; or
5 to 10 membered heterocycle containing 1 to 4 heteroatoms selected from nitrogen, oxygen, and sulphur, wherein said 5 to 10 membered heterocycle is substituted with 0-3 R$^{10b}$;

$R^{10a}$, at each occurrence, is independently selected from H, C$_1$-C$_6$ alkyl, OR$^{14}$, Cl, F, Br, I, =O, CN, NO$_2$, NR$^{15}$R$^{16}$, CF$_3$, phenyl substituted with 0-4 R$^{10b}$; or 5 to 10 membered heterocycle containing 1 to 4 heteroatoms selected from nitrogen, oxygen, and sulphur, wherein said 5 to 10 membered heterocycle is substituted with 0-3 R$^{10b}$;

$R^{10b}$, at each occurrence, is independently selected from H, OH, C$_1$-C$_6$ alkyl, C$_1$-C$_4$ alkoxy, Cl, F, Br, I, CN, NO$_2$, NR$^{15}$R$^{16}$, or CF$_3$;

$R^{11}$, at each occurrence, is independently selected from H, C$_1$-C$_4$ alkoxy, Cl, F, Br, I, =O, CN, NO$_2$, NR$^{18}$R$^{19}$, C(=O)R$^{17}$, C(=O)OR$^{17}$, C(=O)NR$^{18}$R$^{19}$, S(=O)$_2$NR$^{18}$R$^{19}$, CF$_3$;
C$_1$-C$_6$ alkyl optionally substituted with 0-3 R$^{11a}$;
C$_6$-C$_{10}$ aryl substituted with 0-3 R$^{11b}$;
C$_3$-C$_{10}$ carbocycle substituted with 0-3 R$^{11b}$; or
5 to 10 membered heterocycle containing 1 to 4 heteroatoms selected from nitrogen, oxygen, and sulphur, wherein said 5 to 10 membered heterocycle is substituted with 0-3 R$^{11b}$;

$R^{11a}$, at each occurrence, is independently selected from H, C$_1$-C$_6$ alkyl, OR$^{14}$, Cl, F, Br, I, =O, CN, NO$_2$, NR$^{15}$R$^{16}$, CF$_3$, or phenyl substituted with 0-3 R$^{11b}$;

$R^{11b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$-C$_6$ alkyl, C$_1$-C$_4$ alkoxy, C$_1$-C$_4$ haloalkyl, and C$_1$-C$_4$ haloalkoxy;

additionally, two R$^{11}$ substituents on adjacent atoms may be combined to form a benzo fused radical; wherein said benzo fused radical is substituted with 0-3 R$^{13}$;

additionally, two R$^{11}$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0-3 R$^{13}$;

additionally, two R$^{11}$ substituents on the same or adjacent carbon atoms may be combined to form a C$_3$-C$_6$ carbocycle substituted with 0-3 R$^{13}$;

W is —(CR$^8$R$^{8a}$)$_p$—;

p is 0, 1, or 2;

$R^8$ and $R^{8a}$, at each occurrence, are independently selected from H, F, C$_1$-C$_3$ alkyl, C$_2$-C$_3$ alkenyl, C$_2$-C$_3$ alkynyl and C$_3$-C$_6$ cycloalkyl;

X is a bond;
C$_6$-C$_{10}$ aryl substituted with 0-3 R$^{Xb}$;
C$_3$-C$_{10}$ carbocycle substituted with 0-2 R$^{Xb}$; or
5 to 10 membered heterocycle substituted with 0-2 R$^{Xb}$;

$R^{Xb}$ at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$-C$_6$ alkyl, C$_1$-C$_4$ alkoxy, C$_1$-C$_4$ haloalkyl, and C$_1$-C$_4$ haloalkoxy;

Y is a bond or —(CR$^9$R$^{9a}$)$_t$—V—(CR$^9$R$^{9a}$)$_u$—;

t is 0, 1, or 2;

u is 0, 1, or 2;

$R^9$ and $R^{9a}$, at each occurrence, are independently selected from H, F, C$_1$-C$_4$ alkyl or C$_3$-C$_6$ cycloalkyl;

V is a bond, —C(=O)—, —O—, —S—, —S(=O)—, —S(=O)$_2$—, —N(R$^{19}$)—, —C(=O)NR$^{19b}$—, —NR$^{19b}$C(=O)—, —NR$^{19b}$S(=O)$_2$—, —S(=O)$_2$NR$^{19b}$—, —NR$^{19b}$S(=O)—, or —S(=O)NR$^{19b}$—;

Z is H;
C$_1$-C$_3$ alkyl substituted with 1-2 R$^{12}$;
C$_6$-C$_{10}$ aryl substituted with 0-4 R$^{12b}$;
C$_3$-C$_{10}$ carbocycle substituted with 0-4 R$^{12b}$; or
5 to 10 membered heterocycle substituted with 0-3 R$^{12b}$;

R$^{12a}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$-C$_6$ alkyl, C$_1$-C$_4$ alkoxy, C$_1$-C$_4$ haloalkyl, and C$_1$-C$_4$ haloalkoxy;

R$^{13}$, at each occurrence, is independently selected from H, OH, C$_1$-C$_6$ alkyl, C$_1$-C$_4$ alkoxy, Cl, F, Br, I, CN, NO$_2$, NR$^{15}$R$^{16}$, and CF$_3$;

R$^{14}$ is H, phenyl, benzyl, C$_1$-C$_6$ alkyl, or C$_2$-C$_6$ alkoxyalkyl;

R$^{14a}$ is H, phenyl, benzyl, methyl, ethyl, propyl, or butyl;

R$^{15}$, at each occurrence, is independently selected from H, C$_1$-C$_6$ alkyl, benzyl, phenethyl, (C$_1$-C$_6$ alkyl)-C(=O)—, and (C$_1$-C$_6$ alkyl)-S(=O)$_2$—;

R$^{16}$, at each occurrence, is independently selected from H, OH, C$_1$-C$_6$ alkyl, benzyl, phenethyl, (C$_1$-C$_6$ alkyl)-C(=O)—, and (C$_1$-C$_6$ alkyl)-S(=O)$_2$—;

R$^{17}$ is H, C$_1$-C$_6$ alkyl, C$_2$-C$_6$ alkoxyalkyl, aryl substituted by 0-4 R$^{17a}$, or —CH$_2$-aryl substituted by 0-4 R$^{17a}$;

R$^{17a}$ is H, methyl, ethyl, propyl, butyl, methoxy, ethoxy, propoxy, butoxy, —OH, F, Cl, Br, I, CF$_3$, OCF$_3$, SCH$_3$, S(O)CH$_3$, SO$_2$CH$_3$, —NH$_2$, —N(CH$_3$)$_2$, or C$_1$-C$_4$ haloalkyl;

R$^{18}$, at each occurrence, is independently selected from H, C$_1$-C$_6$ alkyl, phenyl, benzyl, phenethyl, (C$_1$-C$_6$ alkyl)-C(=O)—, and (C$_1$-C$_6$ alkyl)-S(=O)$_2$—; and R$^{19}$, at each occurrence, is independently selected from H, OH, C$_1$-C$_6$ alkyl, phenyl, benzyl, phenethyl, (C$_1$-C$_6$ alkyl)-C(=O)—, and (C$_1$-C$_6$ alkyl)-S(=O)$_2$—

R$^{20}$ is H or C(=O)R$^{17}$;

R$^{21}$, at each occurrence, is independently selected from H, C$_1$-C$_4$ alkoxy, Cl, F, Br, I, =O, CN, NO$_2$, NR$^{18}$R$^{19}$, C(=O)R$^{17}$, C(=O)OR$^{17}$, C(=O)NR$^{18}$R$^{19}$, S(=O)$_2$NR$^{18}$R$^{19}$, CF$_3$;
C$_1$-C$_6$ alkyl optionally substituted with 0-3 R$^{21a}$;
C$_6$-C$_{10}$ aryl substituted with 0-3 R$^{21b}$;
C$_3$-C$_{10}$ carbocycle substituted with 0-3 R$^{21b}$; or
5 to 10 membered heterocycle containing 1 to 4 heteroatoms selected from nitrogen, oxygen, and sulphur, wherein said 5 to 10 membered heterocycle is substituted with 0-3 R$^{21b}$;

R$^{21a}$, at each occurrence, is independently selected from H, C$_1$-C$_6$ alkyl, OR$^{14}$, Cl, F, Br, I, =O, CN, NO$_2$, NR$^{15}$R$^{16}$, CF$_3$;
phenyl substituted with 0-3 R$^{21b}$;
C$_3$-C$_6$ cycloalkyl substituted with 0-3 R$^{21b}$; and
5 to 6 membered heterocycle containing 1 to 3 heteroatoms selected from nitrogen, oxygen, and sulphur, wherein said 5 to 6 membered heterocycle is substituted with 0-3 R$^{21b}$;

R$^{21b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$,
C$_1$-C$_6$ alkyl, C$_1$-C$_4$ alkoxy, C$_1$-C$_4$ haloalkyl,
C$_1$-C$_4$ haloalkoxy, and C$_1$-C$_4$ haloalkyl-S—;

additionally, two R$^{21}$ substituents on the same or adjacent carbon atoms may be combined to form a C$_3$-C$_6$ carbocycle substituted with 0-3 R$^{23}$;

additionally, two R$^{21}$ substituents on adjacent atoms may be combined to form a benzo fused radical; wherein said benzo fused radical is substituted with 0-4 R$^{23}$; and R$^{23}$, at each occurrence, is independently selected from H, OH, C$_1$-C$_6$ alkyl, C$_1$-C$_4$ alkoxy, Cl, F, Br, I, CN, NO$_2$, NR$^{15}$R$^{16}$, and CF$_3$.

[6] In another preferred embodiment the present invention provides a compound of Formula (I):

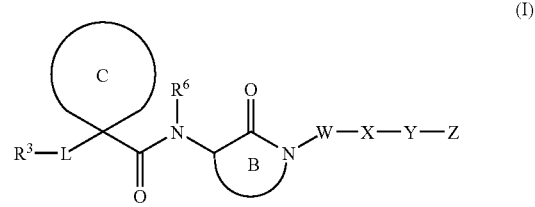

(I)

or a stereoisomer, pharmaceutically acceptable salt or prodrug thereof, wherein:

L is —NR$^{26}$C(=O)—, —C(=O)NR$^{26}$—, —NR$^{26}$C(=O)O—, —OC(=O)NR$^{26}$, or —NR$^{26}$C(=O)NR$^{26}$—;

R$^3$ is —(CR$^7$R$^{7a}$)$_n$—R$^4$,
—(CR$^7$R$^{7a}$)$_l$—S—R$^4$,
—(CR$^7$R$^{7a}$)$_l$—O—R$^4$;
—(CR$^7$R$^{7a}$)$_l$—N(R$^{7b}$)—R$^4$,
—(CR$^7$R$^{7a}$)$_l$—S(=O)—R$^4$, or
—(CR$^7$R$^{7a}$)$_l$—S(=O)$_2$—R$^4$;

n is 0, 1 or 2;
l is 1 or 2;
R$^4$ is H,
C$_1$-C$_8$ alkyl substituted with 0-3 R$^{4a}$,
C$_2$-C$_8$ alkenyl substituted with 0-3 R$^{4a}$,
C$_2$-C$_8$ alkynyl substituted with 0-3 R$^{4a}$,
C$_3$-C$_{10}$ carbocycle substituted with 0-3 R$^{4b}$,
C$_6$-C$_{10}$ aryl substituted with 0-3 R$^{4b}$, or
5 to 10 membered heterocycle containing 1 to 4 heteroatoms selected from nitrogen, oxygen, and sulphur, wherein said 5 to 10 membered heterocycle is substituted with 0-3 R$^{4b}$;

R$^{4a}$, at each occurrence, is independently selected from H, OH, F, Cl, Br, I, NR$^{15}$R$^{16}$, CF$_3$,
C$_3$-C$_{10}$ carbocycle substituted with 0-3 R$^{4b}$,
C$_6$-C$_{10}$ aryl substituted with 0-3 R$^{4b}$, and
5 to 10 membered heterocycle containing 1 to 4 heteroatoms selected from nitrogen, oxygen, and sulphur, wherein said 5 to 10 membered heterocycle is substituted with 0-3 R$^{4b}$;

R$^{4b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$,
C$_1$-C$_6$ alkyl, C$_1$-C$_4$ alkoxy, C$_1$-C$_4$ haloalkyl,
C$_1$-C$_4$ haloalkoxy, and C$_1$-C$_4$ haloalkyl-S—;

Ring C is a 3-8 membered carbocycle;
wherein said 3-8 membered carbocycle is saturated or partially unsaturated;
wherein said 3-8 membered carbocycle is substituted with 0-4 R$^{21}$; and
optionally, the carbocycle contains a heteroatom selected from —O— and —N(R$^{20}$)—;

additionally, two R$^{21}$ substituents on adjacent atoms may be combined to form a benzo fused radical; wherein said benzo fused radical is substituted with 0-4 R$^{23}$;

additionally, two $R^{21}$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0-3 $R^{23}$;

additionally, two $R^{21}$ substituents on the same or adjacent carbon atoms may be combined to form a $C_3$-$C_6$ carbocycle substituted with 0-3 $R^{23}$;

$R^{21}$, at each occurrence, is independently selected from H, OH, Cl, F, Br, I, CN, $NO_2$, $CF_3$, acetyl, $SCH_3$, S(=O)$CH_3$, S(=O)$_2CH_3$, $NR^{15}R^{16}$, $OR^{14a}$, $C_1$-$C_4$ alkyl, $C_2$-$C_6$ alkenyl, alkynyl, $C_1$-$C_4$ alkoxy, $C_1$-$C_4$ haloalkyl, $C_1$-$C_4$ haloalkoxy, and $C_1$-$C_4$ haloalkyl-S—, $C_3$-$C_6$ carbocycle, phenyl, and a 5 to 6 membered heterocycle containing 1 to 4 heteroatoms selected from nitrogen, oxygen, and sulphur;

$R^6$ is H, methyl, or ethyl;

$R^7$, at each occurrence, is independently H or $C_1$-$C_4$ alkyl;

$R^{7a}$, at each occurrence, is independently H or $C_1$-$C_4$ alkyl;

$R^{7b}$ is H or $C_1$-$C_4$ alkyl;

Ring B is selected from:

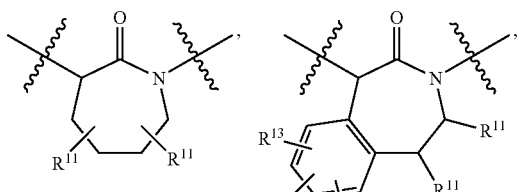

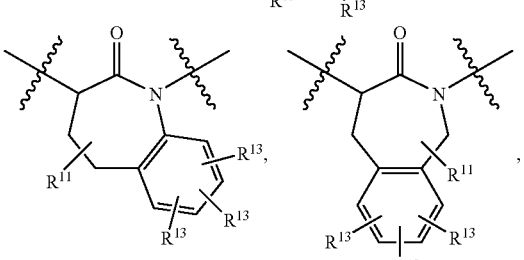

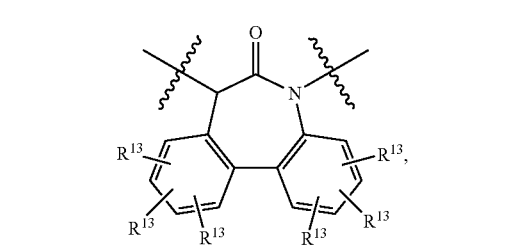

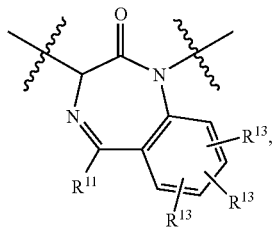

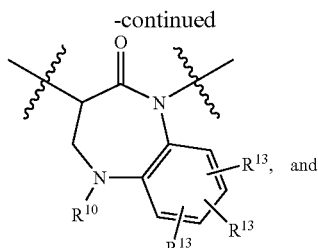, and

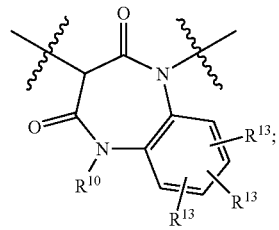;

$R^{10}$ is H, C(=O)$R^{17}$, C(=O)O$R^{17}$, C(=O)$NR^{18}R^{19}$, S(=O)$_2NR^{18}R^{19}$, S(=O)$_2R^{17}$;

$C_1$-$C_6$ alkyl optionally substituted with 0-3 $R^{10a}$;

$C_6$-$C_{10}$ aryl substituted with 0-4 $R^{10b}$;

$C_3$-$C_{10}$ carbocycle substituted with 0-3 $R^{10b}$; or 5 to 10 membered heterocycle containing 1 to 4 heteroatoms selected from nitrogen, oxygen, and sulphur, wherein said 5 to 10 membered heterocycle is substituted with 0-3 $R^{10b}$;

$R^{10a}$, at each occurrence, is independently selected from H, $C_1$-$C_6$ alkyl, $OR^{14}$, Cl, F, Br, I, =O, CN, $NO_2$, $NR^{15}R^{16}$, $CF_3$, or aryl substituted with 0-4 $R^{10b}$;

$R^{10b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

$R^{11}$, at each occurrence, is independently selected from H, $C_1$-$C_4$ alkoxy, Cl, F, Br, I, =O, CN, $NO_2$, $NR^{18}R^{19}$, C(=O)$R^{17}$, C(=O)O$R^{17}$, C(=O)$NR^{18}R^{19}$, S(=O)$_2NR^{18}R^{19}$, $CF_3$;

$C_1$-$C_6$ alkyl optionally substituted with 0-3 $R^{11a}$;

$C_6$-$C_{10}$ aryl substituted with 0-3 $R^{11b}$;

$C_3$-$C_{10}$ carbocycle substituted with 0-3 $R^{11b}$; and 5 to 10 membered heterocycle containing 1 to 4 heteroatoms selected from nitrogen, oxygen, and sulphur, wherein said 5 to 10 membered heterocycle is substituted with 0-3 $R^{11b}$;

$R^{11a}$, at each occurrence, is independently selected from H, $C_1$-$C_6$ alkyl, $OR^{14}$, Cl, F, Br, I, =O, CN, $NO_2$, $NR^{15}R^{16}$, $CF_3$;

phenyl substituted with 0-3 $R^{11b}$;

$C_3$-$C_6$ cycloalkyl substituted with 0-3 $R^{11b}$; and 5 to 6 membered heterocycle containing 1 to 4 heteroatoms selected from nitrogen, oxygen, and sulphur, wherein said 5 to 6 membered heterocycle is substituted with 0-3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

W is a bond or —$(CH_2)_p$—;

p is 1 or 2;

X is a bond;
 phenyl substituted with 0-2 $R^{Xb}$;
 $C_3$-$C_6$ carbocycle substituted with 0-2 $R^{Xb}$; or
 5 to 6 membered heterocycle substituted with 0-2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$-$C_4$ alkyl, $C_1$-$C_3$ alkoxy, $C_1$-$C_3$ haloalkyl, $C_1$-$C_3$ haloalkoxy, and $C_1$-$C_3$ halothioalkoxy;

Y is a bond, —C(=O)—, —O—, —S—, —S(=O)—, —S(=O)$_2$—, —N($R^{19}$)—, —C(=O)$NR^{19b}$—, —$NR^{19b}$C(=O)—, —$NR^{19b}$S(=O)$_2$—, —S(=O)$_2NR^{19b}$—, —$NR^{19b}$S(=O)—, —S(=O)$NR^{19b}$—, —C(=O)O—, or —OC(=O)—;

Z is H;
 $C_1$-$C_8$ alkyl substituted with 0-3 $R^{12a}$;
 $C_2$-$C_6$ alkenyl substituted with 0-3 $R^{12a}$;
 $C_2$-$C_6$ alkynyl substituted with 0-3 $R^{12a}$;
 $C_6$-$C_{10}$ aryl substituted with 0-4 $R^{12b}$;
 $C_3$-$C_{10}$ carbocycle substituted with 0-4 $R^{12b}$; or
 5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12a}$, at each occurrence, is independently selected from H, OH, Cl, F, Br, I, CN, $NO_2$, $NR^{15}R^{16}$, —C(=O)$NR^{15}R^{16}$,
 $CF_3$, acetyl, $SCH_3$, S(=O)$CH_3$, S(=O)$_2CH_3$,
 $C_1$-$C_6$ alkyl, $C_1$-$C_4$ alkoxy, $C_1$-$C_4$ haloalkyl,
 $C_1$-$C_4$ haloalkoxy, $C_1$-$C_4$ haloalkyl-S—,
 $C_6$-$C_{10}$ aryl substituted with 0-4 $R^{12b}$;
 $C_3$-$C_{10}$ carbocycle substituted with 0-4 $R^{12b}$; and
 5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$,
 $C_1$-$C_6$ alkyl, $C_1$-$C_4$ alkoxy, $C_1$-$C_4$ haloalkyl,
 $C_1$-$C_4$ haloalkoxy, and $C_1$-$C_4$ haloalkyl-S—;

$R^{13}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, and $CF_3$;

$R^{14}$ is H, phenyl, benzyl, $C_1$-$C_6$ alkyl, $C_2$-$C_6$ alkoxyalkyl, or $C_3$-$C_6$ cycloalkyl;

$R^{14a}$ is H, phenyl, benzyl, or $C_1$-$C_4$ alkyl;

$R^{15}$, at each occurrence, is independently selected from H, $C_1$-$C_6$ alkyl, benzyl, phenethyl, ($C_1$-$C_6$ alkyl)-C(=O)—, and ($C_1$-$C_6$ alkyl)-S(=O)$_2$—;

$R^{16}$, at each occurrence, is independently selected from H, OH, $C_1$-$C_6$ alkyl, benzyl, phenethyl, ($C_1$-$C_6$ alkyl)-C(=O)—, and ($C_1$-$C_6$ alkyl)-S(=O)$_2$—;

$R^{17}$ is H, $C_1$-$C_6$ alkyl, $C_2$-$C_6$ alkoxyalkyl, aryl substituted by 0-4 $R^{17a}$, or —$CH_2$-aryl substituted by 0-4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, S(O)$CH_3$, $SO_2CH_3$, —$NH_2$, —N($CH_3$)$_2$, or $C_1$-$C_4$ haloalkyl;

$R^{18}$, at each occurrence, is independently selected from H, $C_1$-$C_6$ alkyl, phenyl, benzyl, phenethyl, ($C_1$-$C_6$ alkyl)-C(=O)—, and ($C_1$-$C_6$ alkyl)-S(=O)$_2$—;

$R^{19}$, at each occurrence, is independently selected from H, OH, methyl, ethyl, propyl, butyl, phenyl, benzyl, and phenethyl;

$R^{19b}$, at each occurrence, is independently is H or $C_1$-$C_4$ alkyl;

$R^{20}$ is H, $C_1$-$C_4$ alkyl, or C(=O)$OR^{17}$;

$R^{23}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, and $CF_3$; and $R^{26}$ is H or $C_1$-$C_4$ alkyl.

[7] In another preferred embodiment the present invention provides a compound of Formula (Ia):

(Ia)

or a stereoisomer, pharmaceutically acceptable salt or prodrug thereof, wherein:

L is —$NR^{26}$C(=O)—, —C(=O)$NR^{26}$—, —$NR^{26}$C(=O)O—, —OC(=O)$NR^{26}$, or —$NR^{26}$C(=O)$NR^{26}$—;

$R^3$ is —(CHR$^7$)$_n$—$R^4$,
 —(CHR$^7$)$_l$—S—$R^4$,
 —(CHR$^7$)$_l$—O—$R^4$;
 —(CR$^7R^{7a}$)$_l$—N(R$^{7b}$)—$R^4$,
 —(CR$^7R^{7a}$)$_l$—S(=O)—$R^4$, or
 —(CR$^7R^{7a}$)$_l$—S(=O)$_2$—$R^4$;

n is 0, 1 or 2;

l is 1 or 2;

$R^4$ is H,
 $C_1$-$C_8$ alkyl substituted with 0-3 $R^{4a}$,
 $C_2$-$C_8$ alkenyl substituted with 0-3 $R^{4a}$,
 $C_2$-$C_8$ alkynyl substituted with 0-3 $R^{4a}$,
 $C_3$-$C_{10}$ carbocycle substituted with 0-3 $R^{4b}$,
 $C_6$-$C_{10}$ aryl substituted with 0-3 $R^{4b}$, or
 5 to 10 membered heterocycle containing 1 to 4 heteroatoms selected from nitrogen, oxygen, and sulphur, wherein said 5 to 10 membered heterocycle is substituted with 0-3 $R^{4b}$;

$R^{4a}$, at each occurrence, is independently selected from H, OH, F, Cl, Br, I, $NR^{15}R^{16}$, $CF_3$,
 $C_3$-$C_{10}$ carbocycle substituted with 0-3 $R^{4b}$,
 $C_6$-$C_{10}$ aryl substituted with 0-3 $R^{4b}$, and
 5 to 10 membered heterocycle containing 1 to 4 heteroatoms selected from nitrogen, oxygen, and sulphur, wherein said 5 to 10 membered heterocycle is substituted with 0-3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$,
 $C_1$-$C_6$ alkyl, $C_1$-$C_4$ alkoxy, $C_1$-$C_4$ haloalkyl,
 $C_1$-$C_4$ haloalkoxy, and $C_1$-$C_4$ haloalkyl-S—;

Ring C is a 3-8 membered carbocycle;
 wherein said 3-8 membered carbocycle is saturated or partially unsaturated;
 wherein said 3-8 membered carbocycle is substituted with 6-4 $R^{21}$;
 optionally, the carbocycle contains a heteroatom selected from —O—, and —N(R$^{20}$)—;
additionally, two $R^{21}$ substituents on adjacent atoms may be combined to form a benzo fused radical; wherein said benzo fused radical is substituted with 0-4 $R^{23}$;

additionally, two $R^{21}$ substituents on the same or adjacent carbon atoms may be combined to form a $C_3$-$C_6$ carbocycle substituted with 0-3 $R^{23}$;

$R^{21}$, at each occurrence, is independently selected from H, OH, Cl, F, Br, I, CN, $NO_2$, $CF_3$, acetyl, $SCH_3$, S(=O)$CH_3$, S(=O)$_2CH_3$, $NR^{15}R^{16}$, $OR^{14a}$, $C_1$-$C_4$ alkyl, $C_2$-$C_6$ alkenyl, alkynyl, $C_1$-$C_4$ alkoxy, $C_1$-$C_4$ haloalkyl, $C_1$-$C_4$ haloalkoxy, and $C_1$-$C_4$ haloalkyl-S—,
$C_3$-$C_6$ carbocycle, phenyl, and a
5 to 6 membered heterocycle containing 1 to 4 heteroatoms selected from nitrogen, oxygen, and sulphur;

$R^7$, at each occurrence, is independently H, methyl, or ethyl;

$R^{7b}$ is H, methyl, or ethyl;

Ring B is selected from:

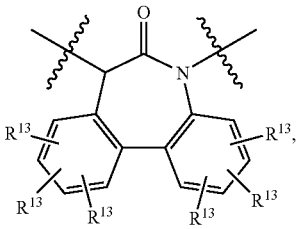

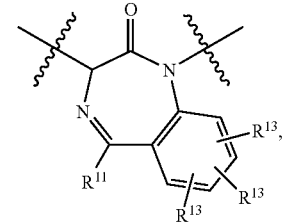

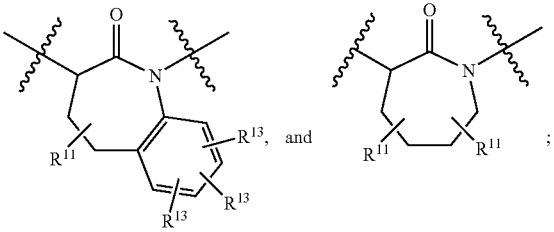

$R^{11}$, at each occurrence, is independently selected from H, $C_1$-$C_4$ alkoxy, Cl, F, Br, I, =O, CN, $NO_2$, $NR^{18}R^{19}$, C(=O)$R^{17}$, C(=O)$OR^{17}$, C(=O)$NR^{18}R^{19}$, S(=O)$_2NR^{18}R^{19}$, $CF_3$;
$C_1$-$C_6$ alkyl optionally substituted with 0-3 $R^{11a}$;
$C_6$-$C_{10}$ aryl substituted with 0-3 $R^{11b}$;
$C_3$-$C_{10}$ carbocycle substituted with 0-3 $R^{11b}$; and
5 to 10 membered heterocycle containing 1 to 4 heteroatoms selected from nitrogen, oxygen, and sulphur, wherein said 5 to 10 membered heterocycle is substituted with 0-3 $R^{11b}$;

$R^{11a}$, at each occurrence, is independently selected from H, $C_1$-$C_6$ alkyl, $OR^{14}$, Cl, F, Br, I, =O, CN, $NO_2$, $NR^{15}R^{16}$, $CF_3$;
phenyl substituted with 0-3 $R^{11b}$;
$C_3$-$C_6$ cycloalkyl substituted with 0-3 $R^{11b}$; and
5 to 6 membered heterocycle containing 1 to 4 heteroatoms selected from nitrogen, oxygen, and sulphur, wherein said 5 to 6 membered heterocycle is substituted with 0-3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$,
$C_1$-$C_6$ alkyl, $C_1$-$C_4$ alkoxy, $C_1$-$C_4$ haloalkyl,
$C_1$-$C_4$ haloalkoxy, and $C_1$-$C_4$ haloalkyl-S—;

W is a bond or —(CH$_2$)$_p$—;
p is 1 or 2;
X is a bond;
phenyl substituted with 0-2 $R^{Xb}$;
$C_3$-$C_6$ carbocycle substituted with 0-2 $R^{Xb}$; or
5 to 6 membered heterocycle substituted with 0-2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$-$C_4$ alkyl, $C_1$-$C_3$ alkoxy, $C_1$-$C_3$ haloalkyl, $C_1$-$C_3$ haloalkoxy, and $C_1$-$C_3$ halothioalkoxy;

Y is a bond, —C(=O)—, —O—, —S—, —S(=O)—, —S(=O)$_2$—, —N($R^{19}$)—, —C(=O)$NR^{19b}$—, —$NR^{19b}$C(=O)—, —$NR^{19b}$S(=O)$_2$—, —S(=O)$_2$$NR^{19b}$—, —$NR^{19b}$S(=O)—, —S(=O)$NR^{19b}$—, —C(=O)O—, or —OC(=O)—;

Z is H;
$C_1$-$C_8$ alkyl substituted with 0-3 $R^{12a}$;
$C_2$-$C_6$ alkenyl substituted with 0-3 $R^{12a}$;
$C_2$-$C_6$ alkynyl substituted with 0-3 $R^{12a}$;
$C_6$-$C_{10}$ aryl substituted with 0-4 $R^{12b}$;
$C_3$-$C_{10}$ carbocycle substituted with 0-4 $R^{12b}$; or
5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, S(=O)$CH_3$, S(=O)$_2CH_3$,
$C_1$-$C_6$ alkyl, $C_1$-$C_4$ alkoxy, $C_1$-$C_4$ haloalkyl,
$C_1$-$C_4$ haloalkoxy, $C_1$-$C_4$ haloalkyl-S—,
$C_6$-$C_{10}$ aryl substituted with 0-4 $R^{12b}$;
$C_3$-$C_{10}$ carbocycle substituted with 0-4 $R^{12b}$; and
5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$,
$C_1$-$C_6$ alkyl, $C_1$-$C_4$ alkoxy, $C_1$-$C_4$ haloalkyl,
$C_1$-$C_4$ haloalkoxy, and $C_1$-$C_4$ haloalkyl-S—;

$R^{13}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, and $CF_3$;

$R^{14}$ is H, phenyl, benzyl, $C_1$-$C_6$ alkyl, $C_2$-$C_6$ alkoxyalkyl, or $C_3$-$C_6$ cycloalkyl;

$R^{14a}$ is H, phenyl, benzyl, or $C_1$-$C_4$ alkyl;

$R^{15}$, at each occurrence, is independently selected from H, $C_1$-$C_6$ alkyl, benzyl, phenethyl, ($C_1$-$C_6$ alkyl)-C(=O)—, and ($C_1$-$C_6$ alkyl)-S(=O)$_2$—;

$R^{16}$, at each occurrence, is independently selected from H, OH, $C_1$-$C_6$ alkyl, benzyl, phenethyl, ($C_1$-$C_6$ alkyl)-C(=O)—, and ($C_1$-$C_6$ alkyl)-S(=O)$_2$—;

$R^{17}$ is H, $C_1$-$C_6$ alkyl, $C_2$-$C_6$ alkoxyalkyl, aryl substituted by 0-4 $R^{17a}$, or —CH$_2$-aryl substituted by 0-4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, S(O)$CH_3$, $SO_2CH_3$, —$NH_2$, —N(CH$_3$)$_2$, or $C_1$-$C_4$ haloalkyl;

$R^{18}$, at each occurrence, is independently selected from H, $C_1$-$C_6$ alkyl, phenyl, benzyl, phenethyl, ($C_1$-$C_6$ alkyl)-C(=O)—, and ($C_1$-$C_6$ alkyl)-S(=O)$_2$—;

$R^{19}$, at each occurrence, is independently selected from H, OH, methyl, ethyl, propyl, butyl, phenyl, benzyl, phenethyl;

$R^{20}$ is H, $C_1$-$C_4$ alkyl, or C(=O)OR$^{17}$;

$R^{23}$, at each occurrence, is independently selected from H, OH, $C_1$-$C_6$ alkyl, $C_1$-$C_4$ alkoxy, Cl, F, Br, I, CN, NO$_2$, NR$^{15}$R$^{16}$, and CF$_3$; and $R^{26}$ is H or $C_1$-$C_4$ alkyl.

[8] In another preferred embodiment the present invention provides a compound of Formula (Ic):

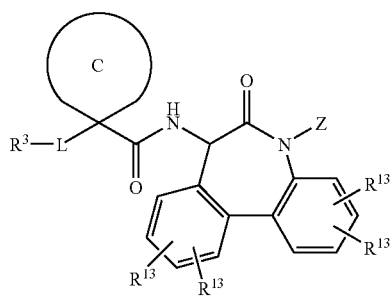

(Ic)

or a stereoisomer, pharmaceutically acceptable salt or prodrug thereof, wherein:

L is —NHC(=O)—, —C(=O)NH—, or —OC(=O)NH—;

$R^3$ is —(CH$_2$)$_n$—R$^4$,
—(CH$_2$)$_l$—S—R$^4$,
—(CH$_2$)$_l$—O—R$^4$, or
—(CH$_2$)$_l$—N(R$^{7b}$)—R$^4$;

n is 0, 1 or 2;

l is 1 or 2;

$R^4$ is $C_1$-$C_8$ alkyl substituted with 0-3 $R^{4a}$,
$C_2$-$C_8$ alkenyl substituted with 0-3 $R^{4a}$,
$C_2$-$C_8$ alkynyl substituted with 0-3 $R^{4a}$,
$C_3$-$C_{10}$ carbocycle substituted with 0-3 $R^{4b}$,
$C_6$-$C_{10}$ aryl substituted with 0-3 $R^{4b}$, or
5 to 10 membered heterocycle containing 1 to 4 heteroatoms selected from nitrogen, oxygen, and sulphur, wherein said 5 to 10 membered heterocycle is substituted with 0-3 $R^{4b}$;

$R^{4a}$, at each occurrence, is independently selected from H, OH, F, Cl, Br, I, NR$^{15}$R$^{16}$, CF$_3$,
$C_3$-$C_{10}$ carbocycle substituted with 0-3 $R^{4b}$,
$C_6$-$C_{10}$ aryl substituted with 0-3 $R^{4b}$, and
5 to 10 membered heterocycle containing 1 to 4 heteroatoms selected from nitrogen, oxygen, and sulphur, wherein said 5 to 10 membered heterocycle is substituted with 0-3 $R^{4b}$;

$R^{4b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$,
$C_1$-$C_6$ alkyl, $C_1$-$C_4$ alkoxy, $C_1$-$C_4$ haloalkyl,
$C_1$-$C_4$ haloalkoxy, and $C_1$-$C_4$ haloalkyl-S—;

$R^{7b}$ is H, methyl, or ethyl;

Ring C is a 3-8 membered carbocycle;
wherein said 3-8 membered carbocycle is saturated or partially unsaturated;
wherein said 3-8 membered carbocycle is substituted with 0-3 $R^{21}$;
optionally, the carbocycle contains a heteroatom selected from —O—, and —N(R$^{20}$)—;

$R^{21}$, at each occurrence, is independently selected from H, OH, Cl, F, Br, I, CN, NO$_2$, CF$_3$, acetyl, SCH$_3$, S(=O)CH$_3$, S(=O)$_2$CH$_3$, NR$^{15}$R$^{16}$, OR$^{14a}$, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, and $C_1$-$C_4$ haloalkyl-S—;

W is a bond, —CH$_2$—, —CH$_2$CH$_2$—;

X is a bond;
phenyl substituted with 0-2 $R^{Xb}$;
$C_3$-$C_6$ cycloalkyl substituted with 0-2 $R^{Xb}$; or
5 to 6 membered heterocycle substituted with 0-2 $R^{Xb}$;

$R^{Xb}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, $C_1$-$C_4$ alkyl, $C_1$-$C_3$ alkoxy, $C_1$-$C_2$ haloalkyl, and $C_1$-$C_2$ haloalkoxy;

Y is a bond, —C(=O)—, —O—, —S—, —S(=O)—, —S(=O)$_2$—, —N(R$^{19}$)—, —C(=O)NR$^{19b}$—, —NR$^{19b}$C(=O)—, —NR$^{19b}$S(=O)$_2$—, S(=O)$_2$NR$^{19b}$—, —NR$^{19b}$S(=O)—, —S(=O)NR$^{19b}$—, —C(=O)O—, or —OC(=O)—;

Z is H;
$C_1$-$C_8$ alkyl substituted with 0-3 $R^{12a}$;
$C_2$-$C_6$ alkenyl substituted with 0-3 $R^{12a}$;
$C_2$-$C_6$ alkynyl substituted with 0-3 $R^{12a}$;
$C_6$-$C_{10}$ aryl substituted with 0-4 $R^{12b}$;
$C_3$-$C_{10}$ carbocycle substituted with 0-4 $R^{12b}$; or
5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12a}$, at each occurrence, is independently selected from H, OH, Cl, F, Br, I, CN, NO$_2$, NR$^{15}$R$^{16}$, —C(=O)NR$^{15}$R$^{16}$, CF$_3$, acetyl, SCH$_3$, S(=O)CH$_3$, S(=O)$_2$CH$_3$,
$C_1$-$C_6$ alkyl, $C_1$-$C_4$ alkoxy, $C_1$-$C_4$ haloalkyl,
$C_1$-$C_4$ haloalkoxy, $C_1$-$C_4$ haloalkyl-S—,
$C_6$-$C_{10}$ aryl substituted with 0-4 $R^{12b}$;
$C_3$-$C_{10}$ carbocycle substituted with 0-4 $R^{12b}$; and
5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$,
$C_1$-$C_6$ alkyl, $C_1$-$C_4$ alkoxy, $C_1$-$C_4$ haloalkyl,
$C_1$-$C_4$ haloalkoxy, and $C_1$-$C_4$ haloalkyl-S—;

$R^{13}$, at each occurrence, is independently selected from H, OH, $C_1$-$C_6$ alkyl, $C_1$-$C_4$ alkoxy, Cl, F, Br, I, CN, NO$_2$, NR$^{15}$R$^{16}$, and CF$_3$;

$R^{14a}$ is H, phenyl, benzyl, or $C_1$-$C_4$ alkyl;

$R^{15}$, at each occurrence, is independently selected from H, $C_1$-$C_6$ alkyl, benzyl, phenethyl, ($C_1$-$C_4$ alkyl)-C(=O)—, and ($C_1$-$C_4$ alkyl)-S(=O)$_2$—;

$R^{16}$, at each occurrence, is independently selected from H, OH, $C_1$-$C_6$ alkyl, benzyl, phenethyl, ($C_1$-$C_4$ alkyl)-C(=O)—, and ($C_1$-$C_4$ alkyl)-S(=O)$_2$—; and $R^{20}$ is H or $C_1$-$C_4$ alkyl.

[9] In another preferred embodiment the present invention provides a compound of Formula (Ic) wherein:

L is —NHC(=O)—, —C(=O)NH—, or —OC(=O)NH—;

$R^3$ is —R$^4$, —CH$_2$R$^4$, —CH$_2$CH$_2$R$^4$, —CH$_2$OR$^4$, or —CH$_2$CH$_2$OR$^4$;

R⁴ is C₁-C₆ alkyl substituted with 0-3 R⁴ᵃ,
C₂-C₆ alkenyl substituted with 0-3 R⁴ᵃ,
C₂-C₆ alkynyl substituted with 0-3 R⁴ᵃ,
C₃-C₆ carbocycle substituted with 0-3 R⁴ᵇ,
phenyl substituted with 0-3 R⁴ᵇ, or
5 to 6 membered heterocycle containing 1 to 3 heteroatoms selected from nitrogen, oxygen, and sulphur, wherein said 5 to 6 membered heterocycle is substituted with 0-3 R⁴ᵇ;

R⁴ᵃ, at each occurrence, is independently selected from H, OH, F, Cl, Br, I, NR¹⁵R¹⁶, CF₃,
C₃-C₆ carbocycle substituted with 0-3 R⁴ᵇ,
phenyl substituted with 0-3 R⁴ᵇ, and
5 to 6 membered heterocycle containing 1 to 3 heteroatoms selected from nitrogen, oxygen, and sulphur, wherein said 5 to 6 membered heterocycle is substituted with 0-3 R⁴ᵇ;

R⁴ᵇ, at each occurrence, is independently selected from H, OH, Cl, F, Br, I, CN, NO₂, NR¹⁵R¹⁶, CF₃, acetyl, SCH₃, S(=O)CH₃, S(=O)₂CH₃,
C₁-C₆ alkyl, C₁-C₄ alkoxy, C₁-C₄ haloalkyl,
C₁-C₄ haloalkoxy, and C₁-C₄ haloalkyl-S—;

Ring C is a 3-6 membered carbocycle;
wherein said 3-6 membered carbocycle is saturated or partially unsaturated;
wherein said 3-6 membered carbocycle is substituted with 0-2 R²¹;
optionally, the carbocycle contains a heteroatom selected from —O—, and —N(R²⁰)—;

R²¹, at each occurrence, is independently selected from H, OH, Cl, F, Br, I, CN, NO₂, CF₃, acetyl, SCH₃, methyl, ethyl, methoxy, ethoxy, allyl, —OCF₃, and —SCF₃;

W is a bond, —CH₂—, —CH₂CH₂—;

X is a bond;
phenyl substituted with 0-1 R^{Xb};
C₃-C₆ cycloalkyl substituted with 0-1 R^{Xb}; or
5 to 6 membered heterocycle substituted with 0-1 R^{Xb};

R^{Xb} is selected from H, OH, Cl, F, NR¹⁵R¹⁶, CF₃, acetyl, SCH₃, S(=O)CH₃, S(=O)₂CH₃, methyl, ethyl, propyl, methoxy, ethoxy, propoxy, and —OCF₃;

Y is a bond, —C(=O)—, —O—, —S—, —S(=O)—, —S(=O)₂—, —NH—, —N(CH₃)—, or —N(CH₂CH₃)—;

Z is H;
C₁-C₈ alkyl substituted with 0-3 R¹²ᵃ;
C₂-C₆ alkenyl substituted with 0-3 R¹²ᵃ;
C₂-C₆ alkynyl substituted with 0-3 R¹²ᵃ;
C₆-C₁₀ aryl substituted with 0-4 R¹²ᵇ;
C₃-C₁₀ carbocycle substituted with 0-4 R¹²ᵇ; or
5 to 10 membered heterocycle containing 1 to 4 heteroatoms selected from nitrogen, oxygen, and sulphur, wherein said 5 to 10 membered heterocycle is substituted with 0-3 R¹²ᵇ;

R¹²ᵃ, at each occurrence, is independently selected from H, OH, Cl, F, Br, I, CN, NO₂, NR¹⁵R¹⁶, —C(=O)NR¹⁵R¹⁶, CF₃, acetyl, SCH₃, S(=O)CH₃, S(=O)₂CH₃,
C₁-C₆ alkyl, C₁-C₄ alkoxy, C₁-C₄ haloalkyl,
C₁-C₄ haloalkoxy, C₁-C₄ haloalkyl-S—,
C₆-C₁₀ aryl substituted with 0-4 R¹²ᵇ;
C₃-C₁₀ carbocycle substituted with 0-4 R¹²ᵇ; and
5 to 10 membered heterocycle containing 1 to 4 heteroatoms selected from nitrogen, oxygen, and sulphur, wherein said 5 to 10 membered heterocycle is substituted with 0-3 R¹²ᵇ;

R¹²ᵇ, at each occurrence, is independently selected from H, OH, Cl, F, Br, I, CN, NO₂, NR¹⁵R¹⁶, CF₃, acetyl, SCH₃, S(=O)CH₃, S(=O)₂CH₃,
C₁-C₆ alkyl, C₁-C₄ alkoxy, C₁-C₄ haloalkyl,
C₁-C₄ haloalkoxy, and C₁-C₄ haloalkyl-S—;

R¹³, at each occurrence, is independently selected from H, OH, C₁-C₆ alkyl, C₁-C₄ alkoxy, Cl, F, Br, I, CN, NO₂, NR¹⁵R¹⁶, and CF₃;

R¹⁵, at each occurrence, is independently selected from H, C₁-C₄ alkyl, and benzyl;

R¹⁶, at each occurrence, is independently selected from H, OH, methyl, ethyl, propyl, butyl, benzyl, phenethyl, methyl-C(=O)—, ethyl-C(=O)—, methyl-S(=O)₂—, ethyl-S(=O)₂—, and propyl-S(=O)₂—; and R²⁰ is H or C₁-C₄ alkyl.

[10] In another preferred embodiment the present invention provides a compound of Formula (Ic) wherein:

L is —NHC(=O)—, —C(=O)NH—, or —OC(=O)NH—;

R³ is —R⁴, —CH₂R⁴, —CH₂CH₂R⁴, —CH₂OR⁴, or —CH₂CH₂OR⁴;

R⁴ is C₁-C₆ alkyl substituted with 0-3 R⁴ᵃ,
C₂-C₆ alkenyl substituted with 0-3 R⁴ᵃ, or
C₂-C₆ alkynyl substituted with 0-3 R⁴ᵃ;

R⁴ᵃ, at each occurrence, is independently selected from is H, OH, F, Cl, Br, I, NR¹⁵R¹⁶, CF₃,
C₃-C₆ carbocycle substituted with 0-3 R⁴ᵇ, phenyl substituted with 0-3 R⁴ᵇ, and
5 to 6 membered heterocycle containing 1 to 3 heteroatoms selected from nitrogen, oxygen, and sulphur, wherein said 5 to 6 membered heterocycle is substituted with 0-3 R⁴ᵇ; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

R⁴ᵇ, at each occurrence, is independently selected from H, OH, Cl, F, Br, I, CN, NO₂, NR¹⁵R¹⁶, CF₃, acetyl, SCH₃, S(=O)CH₃, S(=O)₂CH₃,
C₁-C₆ alkyl, C₁-C₄ alkoxy, C₁-C₄ haloalkyl,
C₁-C₄ haloalkoxy, and C₁-C₄ haloalkyl-S—;

Ring C is a 3-6 membered carbocycle selected from:

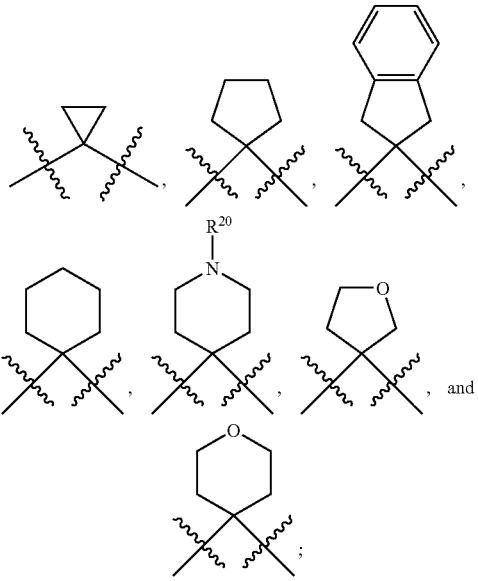

wherein said 3-6 membered carbocycle is substituted with 0-1 $R^{21}$;

$R^{21}$ is selected from H, OH, Cl, F, CN, $CF_3$, methyl, ethyl, methoxy, ethoxy, allyl, and $-OCF_3$;

W is a bond or $-CH_2-$;

X is a bond, phenyl, $C_3$-$C_6$ cycloalkyl or 5 to 6 membered heterocycle;

Y is a bond, $-C(=O)-$, $-O-$, $-S-$, $-S(=O)-$, $-S(=O)_2-$, $-NH-$, $-N(CH_3)-$, or $-N(CH_2CH_3)-$;

Z is H;

$C_1$-$C_8$ alkyl substituted with 0-3 $R^{12a}$;

$C_2$-$C_6$ alkenyl substituted with 0-3 $R^{12a}$;

$C_2$-$C_6$ alkynyl substituted with 0-3 $R^{12a}$;

$C_6$-$C_{10}$ aryl substituted with 0-4 $R^{12b}$;

$C_3$-$C_{10}$ carbocycle substituted with 0-4 $R^{12b}$; or 5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12a}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;

phenyl substituted with 0-4 $R^{12b}$;

$C_3$-6 carbocycle substituted with 0-4 $R^{12b}$; and 5 to 6 membered heterocycle containing 1 to 4 heteroatoms selected from nitrogen, oxygen, and sulphur, wherein said 5 to 6 membered heterocycle is substituted with 0-3 $R^{12b}$;

$R^{12b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;

$R^{13}$, at each occurrence, is independently selected from H, OH, methyl, ethyl, propyl, butyl, methoxy, ethoxy, Cl, F, Br, CN, $NR^{15}R^{16}$, and $CF_3$;

$R^{15}$, at each occurrence, is independently selected from H, methyl, ethyl, propyl, and butyl; and $R^{16}$, at each occurrence, is independently selected from H, OH, methyl, ethyl, propyl, butyl, benzyl, and phenethyl; and $R^{20}$ is H, methyl, or ethyl.

[11] In another preferred embodiment the present invention provides a compound of Formula (Ic) wherein:

L is $-NHC(=O)-$, $-C(=O)NH-$, or $-OC(=O)NH-$;

Ring C is selected from:

$R^3$ is $-CH_3$, $-CH_2CH_3$, $-CH_2CH_2CH_3$, $-CH_2CH_2CH_2CH_3$, $-CH_2CH_2CH(CH_3)_2$, $-CH_2(CH_3)_2$, $-CH(CH_3)CH_2CH_3$, $-CH_2CH(CH_3)_2$, $-CH_2C(CH_3)_3$, $-CF_3$, $-CH_2CF_3$, $-CH_2CH_2CF_3$, $-CH_2CH_2CH_2CF_3$, $-CH(OH)CH_2CH(CH_3)_2$, $-CH(OH)CH(CH_3)_2$, $-CH(NH_2)CH_2CH(CH_3)_2$, $-CH_2CH_2OCH_3$, $-CH_2OCH_2CH_3$, $-CF_2CH_2CH(CH_3)_2$, $-CH(NHCH_3)CH_2CH(CH_3)_2$, $-CH(NHSO_2CH_2CH_2CH_3)CH_2CH(CH_3)_2$, cyclohexyl-, cyclopentyl-, cyclopropyl-$CH_2-$, cyclobutyl-$CH_2-$, cyclopentyl-$CH_2-$, cyclohexyl-$CH_2-$, cyclopropyl-$CH_2CH_2-$, cyclobutyl-$CH_2CH_2-$, cyclopentyl-$CH_2CH_2-$, cyclohexyl-$CH(OH)-$, cyclohexyl-$CH_2CH_2-$, 1-$NH_2$-cyclopentyl, phenyl-$CH_2-$, (2-F-phenyl)$CH_2-$, (3-F-phenyl)$CH_2-$, (4-F-phenyl)$CH_2-$, (2-Cl-phenyl)$CH_2-$, (3-Cl-phenyl)$CH_2-$, (4-Cl-phenyl)$CH_2-$, (2,3-diF-phenyl)$CH_2-$, (2,4-diF-phenyl)$CH_2-$, (2,5-diF-phenyl)$CH_2-$, (2,6-diF-phenyl)$CH_2-$, (3,4-diF-phenyl)$CH_2-$, (3,5-diF-phenyl)$CH_2-$, (2,3-diCl-phenyl)$CH_2-$, (2,4-diCl-phenyl)$CH_2-$, (2,5-diCl-phenyl)$CH_2-$, (2,6-diCl-phenyl)$CH_2-$, (3,4-diCl-phenyl)$CH_2-$, (3,5-diCl-phenyl)$CH_2-$, (3-F-4-Cl-phenyl)$CH_2-$, (3-F-5-Cl-phenyl)$CH_2-$, (3-Cl-4-F-phenyl)$CH_2-$, phenyl-$CH_2CH_2-$, (2-F-phenyl)$CH_2CH_2-$, (3-F-phenyl)$CH_2CH_2-$, (4-F-phenyl)$CH_2CH_2-$, (2-Cl-phenyl)$CH_2CH_2-$, (3-Cl-phenyl)$CH_2CH_2-$, (4-Cl-phenyl)$CH_2CH_2-$, (2,3-diF-phenyl)$CH_2CH_2-$, (2,4-diF-phenyl)$CH_2CH_2-$, (2,5-diF-phenyl)$CH_2CH_2-$, (2,6-diF-phenyl)$CH_2CH_2-$, (3,4-diF-phenyl)$CH_2CH_2-$, (3,5-diF-phenyl)$CH_2CH_2-$, (2,3-diCl-phenyl)$CH_2CH_2-$, (2,4-diCl-phenyl)$CH_2CH_2-$, (2,5-diCl-phenyl)$CH_2CH_2-$, (2,6-diCl-phenyl)$CH_2CH_2-$, (3,4-diCl-phenyl)$CH_2CH_2-$, (3,5-diCl-phenyl)$CH_2CH_2-$, (3-F-4-Cl-phenyl)$CH_2CH_2-$, (3-F-5-Cl-phenyl)$CH_2CH_2-$, 4-piperidinyl-$CH_2CH_2-$, phenyl-$CH_2CH_2CF_2-$, phenyl-$CH_2CH(OH)-$, imidazolyl-$CH_2CH(OH)-$, or phenyl-$CH_2OCH_2-$;

W is a bond or $-CH_2-$;

X is a bond;

-continued

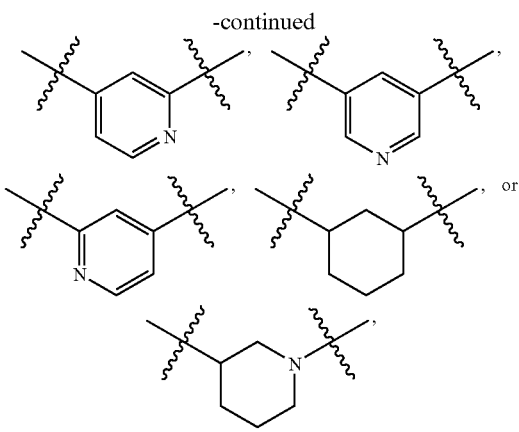

Y is a bond, —C(=O)—, —O—, —S—, —S(=O)—, —S(=O)$_2$—, —NH—, or —N(CH$_3$)—,

Z is methyl, ethyl, i-propyl, n-propyl, n-butyl, i-butyl, s-butyl, t-butyl, allyl, phenyl, 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF$_3$O-phenyl, 3-CF$_3$O-phenyl, 4-CF$_3$O-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, cyclopropyl, cyclobutyl, cyclopentyl, cyclohexyl, morpholino, N-piperinyl, phenyl-CH$_2$—, (2-F-phenyl)CH$_2$—, (3-F-phenyl)CH$_2$—, (4-F-phenyl)CH$_2$—, (2-Cl-phenyl)CH$_2$—, (3-Cl-phenyl)CH$_2$, (4-Cl-phenyl)CH$_2$—, (2,3-diF-phenyl)CH$_2$—, (2,4-diF-phenyl)CH$_2$—, (2,5-diF-phenyl)CH$_2$—, (2,6-diF-phenyl)CH$_2$—, (3,4-diF-phenyl)CH$_2$—, (3,5-diF-phenyl)CH$_2$—, (2,3-diCl-phenyl)CH$_2$—, (2,4-diCl-phenyl)CH$_2$—, (2,5-diCl-phenyl)CH$_2$—, (2,6-diCl-phenyl)CH$_2$—, (3,4-diCl-phenyl)CH$_2$—, (3,5-diCl-phenyl)CH$_2$—, (3-F-4-Cl-phenyl)CH$_2$—, (3-F-5-Cl-phenyl)CH$_2$—, (3-Cl-4-F-phenyl)CH$_2$—, (2-MeO-phenyl)CH$_2$—, (3-MeO-phenyl)CH$_2$—, (4-MeO-phenyl)CH$_2$—, (2-Me-phenyl)CH$_2$—, (3-Me-phenyl)CH$_2$—, (4-Me-phenyl)CH$_2$—, (2-MeS-phenyl)CH$_2$—, (3-MeS-phenyl)CH$_2$—, 4-MeS-phenyl)CH$_2$—, (2-CF$_3$O-phenyl)CH$_2$—, (3-CF$_3$O-phenyl)CH$_2$—, (4-CF$_3$O-phenyl)CH$_2$—, (furanyl)CH$_2$—, (thienyl)CH$_2$—, (pyridyl)CH$_2$—, (2-Me-pyridyl)CH$_2$—, (3-Me-pyridyl)CH$_2$—, (4-Me-pyridyl)CH$_2$—, (1-imidazolyl)CH$_2$—, (oxazolyl)CH$_2$—, (isoxazolyl)CH$_2$—, (1-benzimidazolyl)CH$_2$—, (cyclopropyl)CH$_2$—, (cyclobutyl)CH$_2$—, (cyclopentyl)CH$_2$—, (cyclohexyl)CH$_2$—, (morpholino)CH$_2$—, (N-pipridinyl)CH$_2$—, phenyl-CH$_2$CH$_2$—, (phenyl)$_2$CHCH$_2$—, (2-F-phenyl)CH$_2$CH$_2$—, (3-F-phenyl)CH$_2$CH$_2$—, (4-F-phenyl)CH$_2$CH$_2$—, (2-Cl-phenyl)CH$_2$CH$_2$—, (3-Cl-phenyl)CH$_2$CH$_2$—, (4-Cl-phenyl)CH$_2$CH$_2$—, (2,3-diF-phenyl)CH$_2$CH$_2$—, (2,4-diF-phenyl)CH$_2$CH$_2$—, (2,5-diF-phenyl)CH$_2$CH$_2$—, (2,6-diF-phenyl)CH$_2$CH$_2$—, (3,4-diF-phenyl)CH$_2$CH$_2$—, (3,5-diF-phenyl)CH$_2$CH$_2$—, (2,3-diCl-phenyl)CH$_2$CH$_2$—, (2,4-diCl-phenyl)CH$_2$CH$_2$—, (2,5-diCl-phenyl)CH$_2$CH$_2$—, (2,6-diCl-phenyl)CH$_2$CH$_2$—, (3,4-diCl-phenyl)CH$_2$CH$_2$—, (3,5-diCl-phenyl)CH$_2$CH$_2$—, (3-F-4-Cl-phenyl)CH$_2$CH$_2$—, (3-F-5-Cl-phenyl)CH$_2$CH$_2$—, (3-Cl-4-F-phenyl)CH$_2$CH$_2$—, (2-MeO-phenyl)CH$_2$CH$_2$—, (3-MeO-phenyl)CH$_2$CH$_2$—, (4-MeO-phenyl)CH$_2$CH$_2$—, (2-Me-phenyl)CH$_2$CH$_2$—, (3-Me-phenyl)CH$_2$CH$_2$—, (4-Me-phenyl)CH$_2$CH$_2$—, (2-MeS-phenyl)CH$_2$CH$_2$—, (3-MeS-phenyl)CH$_2$CH$_2$—, (4-MeS-phenyl)CH$_2$CH$_2$—, (2-CF$_3$O-phenyl)CH$_2$CH$_2$—, (3-CF$_3$O-phenyl)CH$_2$CH$_2$—, (4-CF$_3$O-phenyl)CH$_2$CH$_2$—, (furanyl)CH$_2$CH$_2$—, (thienyl)CH$_2$CH$_2$—, (pyridyl)CH$_2$CH$_2$—, (2-Me-pyridyl)CH$_2$CH$_2$—, (3-Me-pyridyl)CH$_2$CH$_2$—, (4-Me-pyridyl)CH$_2$CH$_2$—, (imidazolyl)CH$_2$CH$_2$—, (oxazolyl)CH$_2$CH$_2$—, (isoxazolyl)CH$_2$CH$_2$—, (benzimidazolyl)CH$_2$CH$_2$—, (cyclopropyl)CH$_2$CH$_2$—, (cyclobutyl)CH$_2$CH$_2$—, (cyclopentyl)CH$_2$CH$_2$—, (cyclohexyl)CH$_2$CH$_2$—, (morpholino)CH$_2$CH$_2$—, or (N-pipridinyl) CH$_2$CH$_2$—;

$R^{13}$, at each occurrence, is independently selected from H, F, Cl, OH, —CH$_3$, —CH$_2$CH$_3$, —OCH$_3$, or —CF$_3$.

$R^{20}$ is H, methyl, or ethyl.

[12] In another preferred embodiment the present invention provides a compound of Formula (Id) and (Ie)

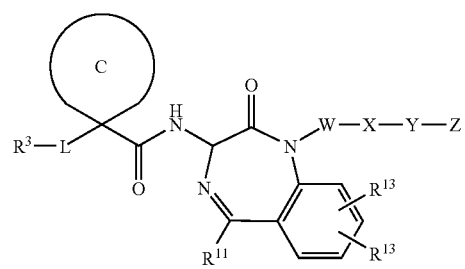

(Id)

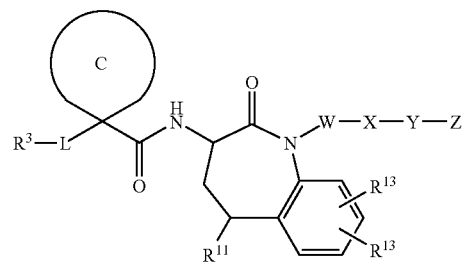

(Ie)

or a stereoisomer, pharmaceutically acceptable salt or prodrug thereof, wherein:

L is —NHC(=O)—, —C(=O)NH—, or —OC(=O)NH—;

$R^3$ is —(CH$_2$)$_n$—R$^4$,
—(CH$_2$)$_l$—S—R$^4$,
—(CH$_2$)$_l$—O—R$^4$, or
—(CH$_2$)$_l$—N(R$^{7b}$)—R$^4$;

n is 0, 1 or 2;

l is 1 or 2;

$R^4$ is C$_1$-C$_8$ alkyl substituted with 0-3 R$^{4a}$,
C$_2$-C$_8$ alkenyl substituted with 0-3 R$^{4a}$,
C$_2$-C$_8$ alkynyl substituted with 0-3 R$^{4a}$,
C$_3$-C$_{10}$ carbocycle substituted with 0-3 R$^{4b}$,
C$_6$-C$_{10}$ aryl substituted with 0-3 R$^{4b}$, or
5 to 10 membered heterocycle containing 1 to 4 heteroatoms selected from nitrogen, oxygen, and sulphur, wherein said 5 to 10 membered heterocycle is substituted with 0-3 R$^{4b}$;

$R^{4a}$, at each occurrence, is independently selected from H, OH, F, Cl, Br, I, $NR^{15}R^{16}$, $CF_3$,
  $C_3$-$C_{10}$ carbocycle substituted with 0-3 $R^{4b}$,
  $C_6$-$C_{10}$ aryl substituted with 0-3 $R^{4b}$, and
  5 to 10 membered heterocycle containing 1 to 4 heteroatoms selected from nitrogen, oxygen, and sulphur, wherein said 5 to 10 membered heterocycle is substituted with 0-3 $R^{4b}$;
$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
  $C_1$-$C_6$ alkyl, $C_1$-$C_4$ alkoxy, $C_1$-$C_4$ haloalkyl,
  $C_1$-$C_4$ haloalkoxy, and $C_1$-$C_4$ haloalkyl-S—;
$R^{7b}$ is H, methyl, or ethyl;
Ring C is a 3-8 membered carbocycle;
  wherein said 3-8 membered carbocyclic moiety is saturated or partially saturated;
  wherein said 3-8 membered carbocyclic moiety is substituted with 0-3 $R^{21}$;
  optionally, the carbocycle contains a heteroatom selected from —O— and —N($R^{20}$)—;
$R^{21}$, at each occurrence, is independently selected from H, OH, Cl, F, Br, I, CN, $NO_2$, $CF_3$, acetyl, $SCH_3$, $S(=O)CH_3$, $S(=O)_2CH_3$, $NR^{15}R^{16}$, $OR^{14a}$, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, and $C_1$-$C_4$ haloalkyl-S—;
$R^{11}$, at each occurrence, is independently selected from H, =O, $NR^{18}R^{19}$, $CF_3$;
  $C_1$-$C_4$ alkyl optionally substituted with 0-1 $R^{11a}$;
  phenyl substituted with 0-3 $R^{11b}$;
  $C_3$-$C_6$ carbocycle substituted with 0-3 $R^{11b}$; and
  5 to 7 membered heterocycle containing 1 to 4 heteroatoms selected from nitrogen, oxygen, and sulphur, wherein said 5 to 7 membered heterocycle is substituted with 0-3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, homopiperidinyl, and tetrazolyl;
$R^{11a}$, at each occurrence, is independently selected from H, $C_1$-$C_4$ alkyl, $OR^{14}$, F, Cl, =O, $NR^{15}R^{16}$, $CF_3$, or phenyl substituted with 0-3 $R^{11b}$;
$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$-$C_2$ haloalkyl, and $C_1$-$C_2$ haloalkoxy;
W is a bond, —$CH_2$—, —$CH_2CH_2$—;
X is a bond;
  phenyl substituted with 0-2 $R^{Xb}$;
  $C_3$-$C_6$ cycloalkyl substituted with 0-2 $R^{Xb}$; or
  5 to 6 membered heterocycle substituted with 0-2 $R^{Xb}$;
$R^{Xb}$, at each occurrence, is independently selected from H, OH, Cl, F, $NR^{15}R^{16}$, $CF_3$, acetyl, $SCH_3$, $S(=O)CH_3$, $S(=O)_2CH_3$, $C_1$-$C_4$ alkyl, $C_1$-$C_3$ alkoxy, $C_1$-$C_2$ haloalkyl, and $C_1$-$C_2$ haloalkoxy;
Y is a bond, —C(=O)—, —O—, —S—, —S(=O)—, —S(=O)_2—, —N($R^{19}$)—, —C(=O)$NR^{19b}$—, —$NR^{19b}$C(=O)—, —$NR^{19b}$S(=O)_2—, S(=O)_2$NR^{19b}$—, —$NR^{19b}$S(=O)—, —S(=O)$NR^{19b}$—, —C(=O)O—, or —OC(=O)—;
Z is H;
  $C_1$-$C_8$ alkyl substituted with 0-3 $R^{12a}$;
  $C_2$-$C_6$ alkenyl substituted with 0-3 $R^{12a}$;
  $C_2$-$C_6$ alkynyl substituted with 0-3 $R^{12a}$;
  $C_6$-$C_{10}$ aryl substituted with 0-4 $R^{12b}$;
  $C_3$-$C_{10}$ carbocycle substituted with 0-4 $R^{12b}$; or
  5 to 10 membered heterocycle containing 1 to 4 heteroatoms selected from nitrogen, oxygen, and sulphur, wherein said 5 to 10 membered heterocycle is substituted with 0-3 $R^{12b}$;
$R^{12a}$, at each occurrence, is independently selected from H, OH, Cl, F, Br, I, CN, $NO_2$, $NR^{15}R^{16}$, —C(=O) $NR^{15}R^{16}$, $CF_3$, acetyl, $SCH_3$, $S(=O)CH_3$, $S(=O)_2CH_3$,
  $C_1$-$C_6$ alkyl, $C_1$-$C_4$ alkoxy, $C_1$-$C_4$ haloalkyl,
  $C_1$-$C_4$ haloalkoxy, $C_1$-$C_4$ haloalkyl-S—,
  $C_6$-$C_{10}$ aryl substituted with 0-4 $R^{12b}$;
  $C_3$-$C_{10}$ carbocycle substituted with 0-4 $R^{12b}$; and
  5 to 10 membered heterocycle containing 1 to 4 heteroatoms selected from nitrogen, oxygen, and sulphur, wherein said 5 to 10 membered heterocycle is substituted with 0-3 $R^{12b}$;
$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
  $C_1$-$C_6$ alkyl, $C_1$-$C_4$ alkoxy, $C_1$-$C_4$ haloalkyl,
  $C_1$-$C_4$ haloalkoxy, and $C_1$-$C_4$ haloalkyl-S—;
$R^{13}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, and $CF_3$;
$R^{14}$ is H, phenyl, benzyl, $C_1$-$C_6$ alkyl, $C_2$-$C_6$ alkoxyalkyl, or $C_3$-$C_6$ cycloalkyl;
$R^{14a}$ is H, phenyl, benzyl, or $C_1$-$C_4$ alkyl;
$R^{15}$, at each occurrence, is independently selected from H, $C_1$-$C_6$ alkyl, benzyl, phenethyl, ($C_1$-$C_6$ alkyl)-C(=O)—, and ($C_1$-$C_6$ alkyl)-S(=O)_2—;
$R^{16}$, at each occurrence, is independently selected from H, OH, $C_1$-$C_6$ alkyl, benzyl, phenethyl, ($C_1$-$C_4$ alkyl)-C(=O)—, and ($C_1$-$C_4$ alkyl)-S(=O)_2—;
$R^{18}$, at each occurrence, is independently selected from H, $C_1$-$C_6$ alkyl, phenyl, benzyl, phenethyl, ($C_1$-$C_6$ alkyl)-C(=O)—, and ($C_1$-$C_6$ alkyl)-S(=O)_2—;
$R^{19}$, at each occurrence, is independently selected from H, OH, methyl, ethyl, propyl, butyl, phenyl, benzyl, phenethyl; and
$R^{20}$ is H or $C_1$-$C_4$ alkyl.

[13] In another preferred embodiment the present invention provides a compound of Formula (Id) and (Ie) wherein:
L is —NHC(=O)—, —C(=O)NH—, or —OC(=O)NH—;
$R^3$ is —$R^4$, —$CH_2R^4$, —$CH_2CH_2R^4$, —$CH_2OR^4$, or —$CH_2CH_2OR^4$;
$R^4$ is $C_1$-$C_6$ alkyl substituted with 0-3 $R^{4a}$,
  $C_2$-$C_6$ alkenyl substituted with 0-3 $R^{4a}$,
  $C_2$-$C_6$ alkynyl substituted with 0-3 $R^{4a}$,
  $C_3$-$C_6$ carbocycle substituted with 0-3 $R^{4b}$,
  phenyl substituted with 0-3 $R^{4b}$, or
  5 to 6 membered heterocycle containing 1 to 3 heteroatoms selected from nitrogen, oxygen, and sulphur, wherein said 5 to 6 membered heterocycle is substituted with 0-3 $R^{4b}$;
$R^{4a}$, at each occurrence, is independently selected from is H, OH, F, Cl, Br, I, $NR^{15}R^{16}$, $CF_3$,
  $C_3$-$C_6$ carbocycle substituted with 0-3 $R^{4b}$,
  phenyl substituted with 0-3 $R^{4b}$, or
  5 to 6 membered heterocycle containing 1 to 3 heteroatoms selected from nitrogen, oxygen, and sulphur, wherein said 5 to 6 membered heterocycle is substituted with 0-3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
$C_1$-$C_6$ alkyl, $C_1$-$C_4$ alkoxy, $C_1$-$C_4$ haloalkyl,
$C_1$-$C_4$ haloalkoxy, and $C_1$-$C_4$ haloalkyl-S—;

Ring C is a 3-6 membered carbocycle;
wherein said 3-6 membered carbocyclic moiety is saturated or partially unsaturated;
wherein said 3-6 membered carbocyclic moiety is substituted with 0-2 $R^{21}$;
optionally, the carbocycle contains a heteroatom selected from —O— and —N($R^{20}$)—;

$R^{21}$, at each occurrence, is independently selected from H, OH, Cl, F, Br, I, CN, $NO_2$, $CF_3$, acetyl, $SCH_3$, methyl, ethyl, methoxy, ethoxy, allyl, —$OCF_3$, and —$SCF_3$;

$R^{11}$, at each occurrence, is independently selected from H, =O, $NR^{18}R^{19}$, $CF_3$;
$C_1$-$C_4$ alkyl optionally substituted with 0-1 $R^{11a}$;
phenyl substituted with 0-3 $R^{11b}$;
$C_3$-$C_6$ carbocycle substituted with 0-3 $R^{11b}$; and
5 to 7 membered heterocycle containing 1 to 4 heteroatoms selected from nitrogen, oxygen, and sulphur, wherein said 5 to 7 membered heterocycle is substituted with 0-3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, homopiperidinyl, and tetrazolyl;

$R^{11a}$, at each occurrence, is independently selected from H, methyl, ethyl, propyl, butyl, methoxy, ethoxy, propoxy, phenoxy, F, Cl, =O, $NR^{15}R^{16}$, $CF_3$, or phenyl substituted with 0-3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$-$C_2$ haloalkyl, and $C_1$-$C_2$ haloalkoxy;

W is a bond, —$CH_2$—, —$CH_2CH_2$—;

X is a bond;
phenyl substituted with 0-1 $R^{Xb}$;
$C_3$-$C_6$ cycloalkyl substituted with 0-1 $R^{Xb}$; or
5 to 6 membered heterocycle substituted with 0-1 $R^{Xb}$;

$R^{Xb}$ is selected from H, OH, Cl, F, $NR^{15}R^{16}$, $CF_3$, acetyl, $SCH_3$, $S(=O)CH_3$, $S(=O)_2CH_3$, methyl, ethyl, propyl, methoxy, ethoxy, propoxy, and —$OCF_3$;

Y is a bond, —C(=O)—, —O—, —S—, —S(=O)—, —S(=O)$_2$—, —NH—, —N($CH_3$)—, or —N($CH_2CH_3$)—;

Z is H;
$C_1$-$C_8$ alkyl substituted with 0-3 $R^{12a}$;
$C_2$-$C_6$ alkenyl substituted with 0-3 $R^{12a}$;
$C_2$-$C_6$ alkynyl substituted with 0-3 $R^{12a}$;
$C_6$-$C_{10}$ aryl substituted with 0-4 $R^{12b}$;
$C_3$-$C_{10}$ carbocycle substituted with 0-4 $R^{12b}$; or
5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, $S(=O)CH_3$, $S(=O)_2CH_3$,
$C_1$-$C_6$ alkyl, $C_1$-$C_4$ alkoxy, $C_1$-$C_4$ haloalkyl,
$C_1$-$C_4$ haloalkoxy, $C_1$-$C_4$ haloalkyl-S—,
$C_6$-$C_{10}$ aryl substituted with 0-4 $R^{12b}$;
$C_3$-$C_{10}$ carbocycle substituted with 0-4 $R^{12b}$; or
5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
$C_1$-$C_6$ alkyl, $C_1$-$C_4$ alkoxy, $C_1$-$C_4$ haloalkyl,
$C_1$-$C_4$ haloalkoxy, and $C_1$-$C_4$ haloalkyl-S—;

$R^{13}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, and $CF_3$;

$R^{14}$ is H, phenyl, benzyl, $C_1$-$C_4$ alkyl, or $C_2$-$C_4$ alkoxyalkyl;

$R^{15}$, at each occurrence, is independently selected from H, methyl, ethyl, propyl, butyl, benzyl, and phenethyl;

$R^{16}$, at each occurrence, is independently selected from H, OH, methyl, ethyl, propyl, butyl, benzyl, phenethyl, methyl-C(=O)—, ethyl-C(=O)—, methyl-S(=O)$_2$—, and ethyl-S(=O)$_2$—;

$R^{18}$, at each occurrence, is independently selected from H, methyl, ethyl, propyl, butyl, phenyl, benzyl, and phenethyl;

$R^{19}$, at each occurrence, is independently selected from H, methyl, ethyl, propyl, and butyl;

$R^{20}$ is H or $C_1$-$C_4$ alkyl.

[14] In another preferred embodiment the present invention provides a compound of Formula (Id) and (Ie) wherein:

L is —NHC(=O)—, —C(=O)NH—, or —OC(=O)NH—;

$R^3$ is —$R^4$, —$CH_2R^4$, —$CH_2CH_2R^4$, —$CH_2OR^4$, or —$CH_2CH_2OR^4$;

$R^4$ is $C_1$-$C_6$ alkyl substituted with 0-3 $R^{4a}$,
$C_2$-$C_6$ alkenyl substituted with 0-3 $R^{4a}$, or
$C_2$-$C_6$ alkynyl substituted with 0-3 $R^{4a}$;

$R^{4a}$, at each occurrence, is independently selected from is H, OH, F, Cl, Br, I, $NR^{15}R^{16}$, $CF_3$,
$C_3$-$C_6$ carbocycle substituted with 0-3 $R^{4b}$,
phenyl substituted with 0-3 $R^{4b}$, or
5 to 6 membered heterocycle containing 1 to 3 heteroatoms selected from nitrogen, oxygen, and sulphur, wherein said 5 to 6 membered heterocycle is substituted with 0-3 $R^{4b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
$C_1$-$C_6$ alkyl, $C_1$-$C_4$ alkoxy, $C_1$-$C_4$ haloalkyl,
$C_1$-$C_4$ haloalkoxy, and $C_1$-$C_4$ haloalkyl-S—;

Ring C is a 3-6 membered carbocycle selected from:

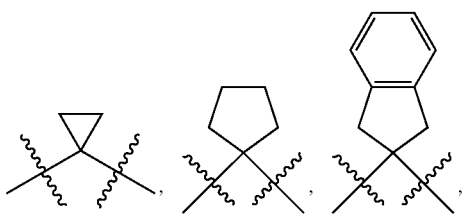

-continued

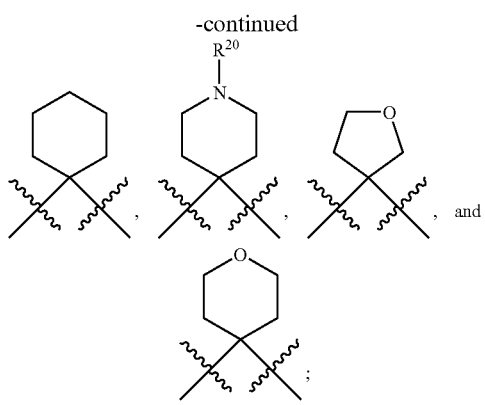

wherein said 3-6 membered carbocycle is substituted with 0-1 $R^{21}$;

$R^{21}$ is selected from H, OH, Cl, F, CN, $CF_3$, methyl, ethyl, methoxy, ethoxy, allyl, and —$OCF_3$;

$R^{11}$, at each occurrence, is independently selected from H, =O, $NR^{18}R^{19}$;

$C_1$-$C_4$ alkyl optionally substituted with 0-1 $R^{11a}$;
phenyl substituted with 0-3 $R^{11b}$;
5 to 7 membered heterocycle containing 1 to 4 heteroatoms selected from nitrogen, oxygen, and sulphur, wherein said 5 to 7 membered heterocycle is substituted with 0-3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, homopiperidinyl, and tetrazolyl;

$R^{11a}$, at each occurrence, is independently selected from H, methyl, ethyl, propyl, methoxy, ethoxy, propoxy, phenoxy, F, Cl, =O, $NR^{15}R^{16}$, $CF_3$, or phenyl substituted with 0-3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$-$C_2$ haloalkyl, and $C_1$-$C_2$ haloalkoxy;

W is a bond or —$CH_2$—;

X is a bond, phenyl, $C_3$-$C_6$ cycloalkyl or 5 to 6 membered heterocycle;

Y is a bond, —C(=O)—, —O—, —S—, —S(=O)—, —S(=O)$_2$—, —NH—, —N($CH_3$)—, or —N($CH_2CH_3$)—;

Z is H;

$C_1$-$C_8$ alkyl substituted with 0-3 $R^{12a}$;
$C_2$-$C_6$ alkenyl substituted with 0-3 $R^{12a}$;
$C_2$-$C_6$ alkynyl substituted with 0-3 $R^{12a}$;
$C_6$-$C_{10}$ aryl substituted with 0-4 $R^{12b}$;
$C_3$-$C_{10}$ carbocycle substituted with 0-4 $R^{12b}$; or
5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12a}$, at each occurrence, is independently selected from H, OH, Cl, F, $NR^{15}R^{16}$, $CF_3$, acetyl, $SCH_3$, S(=O)$CH_3$, S(=O)$_2CH_3$, methyl, ethyl, propyl, butyl, methoxy, ethoxy, propoxy, $C_1$-$C_2$ haloalkyl, and $C_1$-$C_2$ haloalkoxy;

phenyl substituted with 0-4 $R^{12b}$;
$C_3$-6 carbocycle substituted with 0-4 $R^{12b}$; or 5 to 6 membered heterocycle containing 1 to 4 heteroatoms selected from nitrogen, oxygen, and sulphur, wherein said 5 to 6 membered heterocycle is substituted with 0-3 $R^{12b}$;

$R^{12b}$, at each occurrence, is independently selected from H, OH, Cl, F, $NR^{15}R^{16}$, $CF_3$, acetyl, $SCH_3$, S(=O)$CH_3$, S(=O)$_2CH_3$, methyl, ethyl, propyl, butyl, methoxy, ethoxy, propoxy, $C_1$-$C_2$ haloalkyl, and $C_1$-$C_2$ haloalkoxy;

$R^{13}$, at each occurrence, is independently selected from H, OH, methyl, ethyl, propyl, butyl, methoxy, ethoxy, Cl, F, Br, CN, $NR^{15}R^{16}$, and $CF_3$;

$R^{14}$ is H, phenyl, benzyl, methyl, ethyl, propyl, or butyl;

$R^{15}$, at each occurrence, is independently selected from H, methyl, ethyl, propyl, and butyl; and $R^{16}$, at each occurrence, is independently selected from H, OH, methyl, ethyl, propyl, butyl, benzyl, and phenethyl.

$R^{18}$, at each occurrence, is independently selected from H, methyl, ethyl, propyl, butyl, phenyl, benzyl, and phenethyl;

$R^{19}$, at each occurrence, is independently selected from H, methyl, ethyl, propyl, and butyl; and $R^{20}$ is H, methyl, or ethyl.

[15] In another preferred embodiment the present invention provides a compound of Formula (Id) and (Ie) wherein:
L is —NHC(=O)—, —C(=O)NH—, or —OC(=O)NH—;
Ring C is selected from:

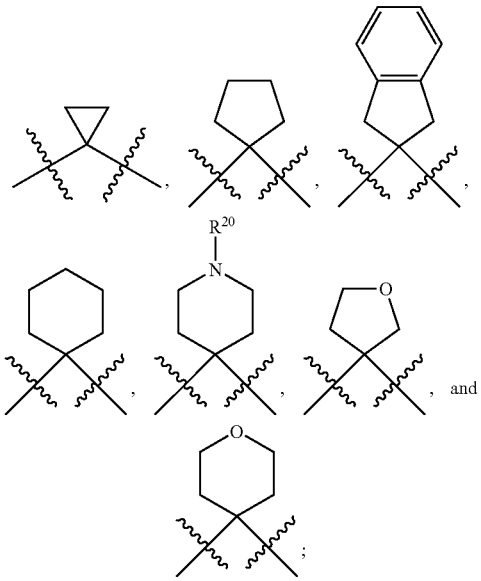

$R^3$ is —$CH_3$, —$CH_2CH_3$, —$CH_2CH_2CH_3$, —$CH_2CH_2CH_2CH_3$, —$CH_2CH_2CH(CH_3)_2$, —$CH_2(CH_3)_2$, —$CH(CH_3)CH_2CH_3$, —$CH_2CH(CH_3)_2$, —$CH_2C(CH_3)_3$, —$CF_3$, —$CH_2CF_3$, —$CH_2CH_2CF_3$, —$CH_2CH_2CH_2CF_3$, —$CH(OH)CH_2CH(CH_3)_2$, —$CH(OH)CH(CH_3)_2$, —$CH(NH_2)CH_2CH(CH_3)_2$, —$CH_2CH_2OCH_3$, —$CH_2OCH_2CH_3$, —$CF_2CH_2CH(CH_3)_2$, —$CH(NHCH_3)CH_2CH(CH_3)_2$, —$CH(NHSO_2CH_2CH_3)CH_2CH(CH_3)_2$, cyclohexyl-, cyclopentyl-, cyclopropyl-$CH_2$—, cyclobutyl-$CH_2$—, cyclopentyl-$CH_2$—, cyclohexyl-$CH_2$—, cyclopropyl-$CH_2CH_2$—, cyclobutyl-$CH_2CH_2$—, cyclopentyl- CH₂CH₂—, cyclohexyl-CH(OH)—, cyclohexyl-CH₂CH₂—, 1-NH₂-cyclopentyl, phenyl-CH₂—, (2-F-phenyl)CH₂—, (3-F-phenyl)CH₂—, (4-F-phenyl)CH₂—, (2-Cl-phenyl)CH₂—, (3-Cl-phenyl)CH₂—, (4-Cl-phenyl)CH₂—, (2,3-diF-phenyl)CH₂—, (2,4-diF-phenyl)CH₂—, (2,5-diF-phenyl)CH₂—, (2,6-diF-phenyl)CH₂—, (3,4-diF-phenyl)CH₂—, (3,5-diF-phenyl)CH₂—, (2,3-diCl-phenyl)CH₂—, (2,4-diCl-phenyl)CH₂—, (2,5-diCl-phenyl)CH₂—, (2,6-diCl-phenyl)CH₂—, (3,4-diCl-phenyl)CH₂—, (3,5-diCl-phenyl)CH₂—, (3-F-4-Cl-phenyl)CH₂—, (3-F-5-Cl-phenyl)CH₂—, (3-Cl-4-F-phenyl)CH₂—, phenyl-CH₂CH₂—, (2-F-phenyl)CH₂CH₂—, (3-F-phenyl)CH₂CH₂—, (4-F-phenyl)CH₂CH₂—, (2-Cl-phenyl)CH₂CH₂—, (3-Cl-phenyl)CH₂CH₂—, (4-Cl-phenyl)CH₂CH₂—, (2,3-diF-phenyl)CH₂CH₂—, (2,4-diF-phenyl)CH₂CH₂—, (2,5-diF-phenyl)CH₂CH₂—, (2,6-diF-phenyl)CH₂CH₂—, (3,4-diF-phenyl)CH₂CH₂—, (3,5-diF-phenyl)CH₂CH₂—, (2,3-diCl-phenyl)CH₂CH₂—, (2,4-diCl-phenyl)CH₂CH₂—, (2,5-diCl-phenyl)CH₂CH₂—, (2,6-diCl-phenyl)CH₂CH₂—, (3,4-diCl-phenyl)CH₂CH₂—, (3,5-diCl-phenyl)CH₂CH₂—, (3-F-4-Cl-phenyl)CH₂CH₂—, (3-F-5-Cl-phenyl)CH₂CH₂—, 4-piperidinyl-CH₂CH₂—, phenyl-CH₂CH₂CF₂—, phenyl-CH₂CH(OH)—, imidazolyl-CH₂CH(OH)—, or phenyl-CH₂OCH₂—;

W is a bond or —CH₂—;

X is a bond;

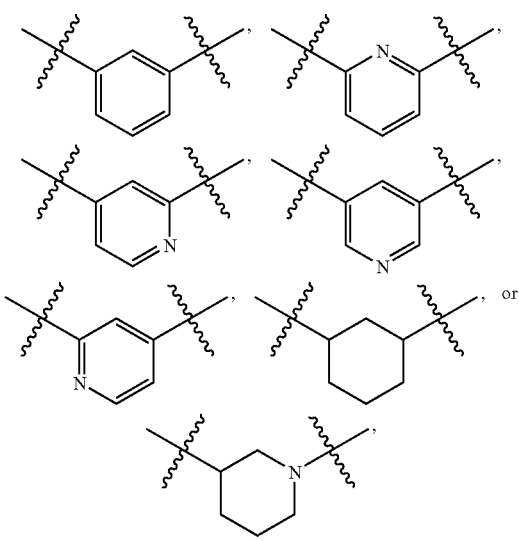

Y is a bond, —C(=O)—, —O—, —S—, —S(=O)—, —S(=O)₂—, —NH—, or —N(CH₃)—,

Z is methyl, ethyl, i-propyl, n-propyl, n-butyl, i-butyl, s-butyl, t-butyl, allyl, phenyl, 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF₃O-phenyl, 3-CF₃O-phenyl, 4-CF₃O-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, cyclopropyl, cyclobutyl, cyclopentyl, cyclohexyl, morpholino, N-piperinyl, phenyl-CH₂—, (2-F-phenyl)CH₂—, (3-F-phenyl)CH₂—, (4-F-phenyl)CH₂—, (2-Cl-phenyl)CH₂—, (3-Cl-phenyl)CH₂—, (4-Cl-phenyl)CH₂—, (2,3-diF-phenyl)CH₂—, (2,4-diF-phenyl)CH₂—, (2,5-diF-phenyl)CH₂—, (2,6-diF-phenyl)CH₂—, (3,4-diF-phenyl)CH₂—, (3,5-diF-phenyl)CH₂—, (2,3-diCl-phenyl)CH₂—, (2,4-diCl-phenyl)CH₂—, (2,5-diCl-phenyl)CH₂—, (2,6-diCl-phenyl)CH₂—, (3,4-diCl-phenyl)CH₂—, (3,5-diCl-phenyl)CH₂—, (3-F-4-Cl-phenyl)CH₂—, (3-F-5-Cl-phenyl)CH₂—, (3-Cl-4-F-phenyl)CH₂—, (2-MeO-phenyl)CH₂—, (3-MeO-phenyl)CH₂—, (4-MeO-phenyl)CH₂—, (2-Me-phenyl)CH₂—, (3-Me-phenyl)CH₂—, (4-Me-phenyl)CH₂—, (2-MeS-phenyl)CH₂—, (3-MeS-phenyl)CH₂—, 4-MeS-phenyl)CH₂—, (2-CF₃O-phenyl)CH₂—, (3-CF₃O-phenyl)CH₂—, (4-CF₃O-phenyl)CH₂—, (furanyl)CH₂—, (thienyl)CH₂—, (pyridyl)CH₂—, (2-Me-pyridyl)CH₂—, (3-Me-pyridyl)CH₂—, (4-Me-pyridyl)CH₂—, (1-imidazolyl)CH₂—, (oxazolyl)CH₂—, (isoxazolyl)CH₂—, (1-benzimidazolyl)CH₂—, (cyclopropyl)CH₂—, (cyclobutyl)CH₂—, (cyclopentyl)CH₂—, (cyclohexyl)CH₂—, (morpholino)CH₂—, (N-pipridinyl)CH₂—, phenyl-CH₂CH₂—, (phenyl)₂CHCH₂—, (2-F-phenyl)CH₂CH₂—, (3-F-phenyl)CH₂CH₂—, (4-F-phenyl)CH₂CH₂—, (2-Cl-phenyl)CH₂CH₂—, (3-Cl-phenyl)CH₂CH₂—, (4-Cl-phenyl)CH₂CH₂—, (2,3-diF-phenyl)CH₂CH₂—, (2,4-diF-phenyl)CH₂CH₂—, (2,5-diF-phenyl)CH₂CH₂—, (2,6-diF-phenyl)CH₂CH₂—, (3,4-diF-phenyl)CH₂CH₂—, (3,5-diF-phenyl)CH₂CH₂—, (2,3-diCl-phenyl)CH₂CH₂—, (2,4-diCl-phenyl)CH₂CH₂—, (2,5-diCl-phenyl)CH₂CH₂—, (2,6-diCl-phenyl)CH₂CH₂—, (3,4-diCl-phenyl)CH₂CH₂—, (3,5-diCl-phenyl)CH₂CH₂—, (3-F-4-Cl-phenyl)CH₂CH₂—, (3-F-5-Cl-phenyl)CH₂CH₂—, (3-Cl-4-F-phenyl)CH₂CH₂—, (2-MeO-phenyl)CH₂CH₂—, (3-MeO-phenyl)CH₂CH₂—, (4-MeO-phenyl)CH₂CH₂—, (2-Me-phenyl)CH₂CH₂—, (3-Me-phenyl)CH₂CH₂—, (4-Me-phenyl)CH₂CH₂—, (2-MeS-phenyl)CH₂CH₂—, (3-MeS-phenyl)CH₂CH₂—, (4-MeS-phenyl)CH₂CH₂—, (2-CF₃O-phenyl)CH₂CH₂—, (3-CF₃O-phenyl)CH₂CH₂—, (4-CF₃O-phenyl)CH₂CH₂—, (furanyl)CH₂CH₂—, (thienyl)CH₂CH₂—, (pyridyl)CH₂CH₂—, (2-Me-pyridyl)CH₂CH₂—, (3-Me-pyridyl)CH₂CH₂—, (4-Me-pyridyl)CH₂CH₂—, (imidazolyl)CH₂CH₂—, (oxazolyl)CH₂CH₂—, (isoxazolyl)CH₂CH₂—, (benzimidazolyl)CH₂CH₂—, (cyclopropyl)CH₂CH₂—, (cyclobutyl)CH₂CH₂—, (cyclopentyl)CH₂CH₂—, (cyclohexyl)CH₂CH₂—, (morpholino)CH₂CH₂—, or (N-pipridinyl)CH₂CH₂—;

R¹¹, at each occurrence, is independently selected from H, =O, methyl, ethyl, phenyl, benzyl, phenethyl, 4-F-phenyl, (4-F-phenyl)CH₂—, (4-F-phenyl)CH₂CH₂—, 3-F-phenyl, (3-F-phenyl)CH₂—, (3-F-phenyl)CH₂CH₂—, 2-F-phenyl, (2-F-phenyl)CH₂—, (2-F-phenyl)CH₂CH₂—, 4-Cl-phenyl, (4-Cl-phenyl)CH₂—, (4-Cl-phenyl)CH₂CH₂—, 3-Cl-phenyl, (3-Cl-phenyl)CH₂—, (3-Cl-phenyl)CH₂CH₂—, 4-CH₃-phenyl, (4-CH₃-phenyl)CH₂—, (4-CH₃-phenyl)CH₂CH₂—, 3-CH₃-phenyl, (3-CH₃-phenyl)CH₂—, (3-CH₃-phenyl)CH₂CH₂—, 4-CF₃-phenyl, (4-CF₃-phenyl)CH₂—, (4-CF₃-phenyl)CH₂CH₂—, cyclopentyl, pyrid-2-yl, pyrid-3-yl, or pyrid-4-yl; and R¹³, at each occurrence, is independently selected from H, F, Cl, OH, —CH₃, —CH₂CH₃, —OCH₃, or —CF₃.

[16] In another preferred embodiment the present invention provides a compound of Formula (If):

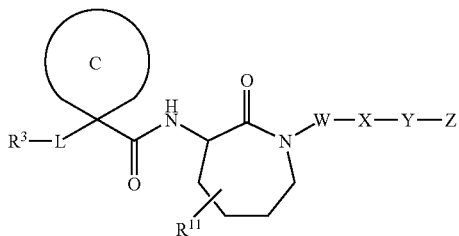

(If)

or a stereoisomer, pharmaceutically acceptable salt or prodrug thereof, wherein:

L is —NHC(=O)—, —C(=O)NH—, or —OC(=O)NH—;

$R^3$ is —$(CH_2)_n$—$R^4$,
—$(CH_2)_l$—S—$R^4$,
—$(CH_2)_l$—O—$R^4$, or
—$(CH_2)_l$—N($R^{7b}$)—$R^4$;

n is 0, 1 or 2;

l is 1 or 2;

$R^4$ is $C_1$-$C_8$ alkyl substituted with 0-3 $R^{4a}$,
$C_2$-$C_8$ alkenyl substituted with 0-3 $R^{4a}$,
$C_2$-$C_8$ alkynyl substituted with 0-3 $R^{4a}$,
$C_3$-$C_{10}$ carbocycle substituted with 0-3 $R^{4b}$,
$C_6$-$C_{10}$ aryl substituted with 0-3 $R^{4b}$, or
5 to 10 membered heterocycle containing 1 to 4 heteroatoms selected from nitrogen, oxygen, and sulphur, wherein said 5 to 10 membered heterocycle is substituted with 0-3 $R^{4b}$;

$R^{4a}$, at each occurrence, is independently selected from H, OH, F, Cl, Br, I, $NR^{15}R^{16}$, $CF_3$,
$C_3$-$C_{10}$ carbocycle substituted with 0-3 $R^{4b}$,
$C_6$-$C_{10}$ aryl substituted with 0-3 $R^{4b}$, and
5 to 10 membered heterocycle containing 1 to 4 heteroatoms selected from nitrogen, oxygen, and sulphur, wherein said 5 to 10 membered heterocycle is substituted with 0-3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
$C_1$-$C_6$ alkyl, $C_1$-$C_4$ alkoxy, $C_1$-$C_4$ haloalkyl,
$C_1$-$C_4$ haloalkoxy, and $C_1$-$C_4$ haloalkyl-S—;

$R^{7b}$ is H, methyl, or ethyl;

Ring C is a 3-8 membered carbocycle;
wherein said 3-8 membered carbocyclic moiety is saturated or partially saturated;
wherein said 3-8 membered carbocyclic moiety is substituted with 0-3 $R^{21}$;
optionally, the carbocycle contains a heteroatom selected from —O— and —N($R^{20}$)—;

$R^{21}$, at each occurrence, is independently selected from H, OH, Cl, F, Br, I, CN, $NO_2$, $CF_3$, acetyl, $SCH_3$, $S(=O)CH_3$, $S(=O)_2CH_3$, $NR^{15}R^{16}$, $OR^{14a}$, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, and $C_1$-$C_4$ haloalkyl-S—;

$R^{11}$ is selected from H, =O, $NR^{18}R^{19}$, $CF_3$;
$C_1$-$C_4$ alkyl optionally substituted with 0-1 $R^{11a}$;
phenyl substituted with 0-3 $R^{11b}$;
$C_3$-$C_6$ carbocycle substituted with 0-3 $R^{11b}$; and
5 to 7 membered heterocycle containing 1 to 4 heteroatoms selected from nitrogen, oxygen, and sulphur, wherein said 5 to 7 membered heterocycle is substituted with 0-3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, homopiperidinyl, and tetrazolyl;

$R^{11a}$, at each occurrence, is independently selected from H, $C_1$-$C_4$ alkyl, $OR^{14}$, F, Cl, =O, $NR^{15}R^{16}$, $CF_3$, or phenyl substituted with 0-3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$-$C_2$ haloalkyl, and $C_1$-$C_2$ haloalkoxy;

W is a bond, —$CH_2$—, —$CH_2CH_2$—;

X is a bond;
phenyl substituted with 0-2 $R^{Xb}$;
$C_3$-$C_6$ cycloalkyl substituted with 0-2 $R^{Xb}$; or
5 to 6 membered heterocycle substituted with 0-2 $R^{Xb}$;

$R^{Xb}$, at each occurrence, is independently selected from H, OH, Cl, F, $NR^{15}R^{16}$, $CF_3$, acetyl, $SCH_3$, $S(=O)CH_3$, $S(=O)_2CH_3$, $C_1$-$C_4$ alkyl, $C_1$-$C_3$ alkoxy, $C_1$-$C_2$ haloalkyl, and $C_1$-$C_2$ haloalkoxy;

Y is a bond, —C(=O)—, —O—, —S—, —S(=O)—, —S(=O)_2—, —N($R^{19}$)—, —C(=O)$NR^{19b}$—, —$NR^{19b}C$(=O)—, —$NR^{19b}S$(=O)_2—, —S(=O)_2$NR^{19b}$—, —$NR^{19b}S$(=O)—, —S(=O)$NR^{19b}$—, —C(=O)O—, or —OC(=O)—;

Z is H;
$C_1$-$C_8$ alkyl substituted with 0-3 $R^{12a}$;
$C_2$-$C_6$ alkenyl substituted with 0-3 $R^{12a}$;
$C_2$-$C_6$ alkynyl substituted with 0-3 $R^{12a}$;
$C_6$-$C_{10}$ aryl substituted with 0-4 $R^{12b}$;
$C_3$-$C_{10}$ carbocycle substituted with 0-4 $R^{12b}$; or
5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, $S(=O)CH_3$, $S(=O)_2CH_3$,
$C_1$-$C_6$ alkyl, $C_1$-$C_4$ alkoxy, $C_1$-$C_4$ haloalkyl,
$C_1$-$C_4$ haloalkoxy, $C_1$-$C_4$ haloalkyl-S—,
$C_6$-$C_{10}$ aryl substituted with 0-4 $R^{12b}$;
$C_3$-$C_{10}$ carbocycle substituted with 0-4 $R^{12b}$; and
5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
$C_1$-$C_6$ alkyl, $C_1$-$C_4$ alkoxy, $C_1$-$C_4$ haloalkyl,
$C_1$-$C_4$ haloalkoxy, and $C_1$-$C_4$ haloalkyl-S—;

$R^{14}$ is H, phenyl, benzyl, $C_1$-$C_6$ alkyl, $C_2$-$C_6$ alkoxyalkyl, or $C_3$-$C_6$ cycloalkyl;

$R^{14a}$ is H, phenyl, benzyl, or $C_1$-$C_4$ alkyl;

$R^{15}$, at each occurrence, is independently selected from H, $C_1$-$C_6$ alkyl, benzyl, phenethyl, ($C_1$-$C_6$ alkyl)-C(=O)—, and ($C_1$-$C_6$ alkyl)-S(=O)_2—;

$R^{16}$, at each occurrence, is independently selected from H, OH, $C_1$-$C_6$ alkyl, benzyl, phenethyl,
($C_1$-$C_4$ alkyl)-C(=O)—, and ($C_1$-$C_4$ alkyl)-S(=O)_2—;

$R^{18}$, at each occurrence, is independently selected from H, $C_1-C_6$ alkyl, phenyl, benzyl, phenethyl, ($C_1-C_6$ alkyl)-C(=O)—, and ($C_1-C_6$ alkyl)-S(=O)$_2$—;

$R^{19}$, at each occurrence, is independently selected from H, OH, methyl, ethyl, propyl, butyl, phenyl, benzyl, phenethyl; and $R^{20}$ is H or $C_1-C_4$ alkyl.

[17] In another preferred embodiment the present invention provides a compound of Formula (If) wherein:

L is —NHC(=O)—, —C(=O)NH—, or —OC(=O)NH—;

$R^3$ is —$R^4$, —$CH_2R^4$, —$CH_2CH_2R^4$, —$CH_2OR^4$, or —$CH_2CH_2OR^4$;

$R^4$ is $C_1-C_6$ alkyl substituted with 0-3 $R^{4a}$,
$C_2-C_6$ alkenyl substituted with 0-3 $R^{4a}$,
$C_2-C_6$ alkynyl substituted with 0-3 $R^{4a}$,
$C_3-C_6$ carbocycle substituted with 0-3 $R^{4b}$,
phenyl substituted with 0-3 $R^{4b}$, or
5 to 6 membered heterocycle containing 1 to 3 heteroatoms selected from nitrogen, oxygen, and sulphur, wherein said 5 to 6 membered heterocycle is substituted with 0-3 $R^{4b}$;

$R^{4a}$, at each occurrence, is independently selected from is H, OH, F, Cl, Br, I, $NR^{15}R^{16}$, $CF_3$,
$C_3-C_6$ carbocycle substituted with 0-3 $R^{4b}$,
phenyl substituted with 0-3 $R^{4b}$, or
5 to 6 membered heterocycle containing 1 to 3 heteroatoms selected from nitrogen, oxygen, and sulphur, wherein said 5 to 6 membered heterocycle is substituted with 0-3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
$C_1-C_6$ alkyl, $C_1-C_4$ alkoxy, $C_1-C_4$ haloalkyl,
$C_1-C_4$ haloalkoxy, and $C_1-C_4$ haloalkyl-S—;

Ring C is a 3-6 membered carbocycle;
wherein said 3-6 membered carbocyclic moiety is saturated or partially unsaturated;
wherein said 3-6 membered carbocyclic moiety is substituted with 0-2 $R^{21}$;
optionally, the carbocycle contains a heteroatom selected from —O— and —N($R^{20}$)—;

$R^{21}$, at each occurrence, is independently selected from H, OH, Cl, F, Br, I, CN, $NO_2$, $CF_3$, acetyl, $SCH_3$, methyl, ethyl, methoxy, ethoxy, allyl, —$OCF_3$, and —$SCF_3$;

$R^{11}$ is selected from H, =O, $NR^{18}R^{19}$, $CF_3$;
$C_1-C_4$ alkyl optionally substituted with 0-1 $R^{11a}$;
phenyl substituted with 0-3 $R^{11b}$;
$C_3-C_6$ carbocycle substituted with 0-3 $R^{11b}$; and
5 to 7 membered heterocycle containing 1 to 4 heteroatoms selected from nitrogen, oxygen, and sulphur, wherein said 5 to 7 membered heterocycle is substituted with 0-3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, homopiperidinyl, and tetrazolyl;

$R^{11a}$, at each occurrence, is independently selected from H, methyl, ethyl, propyl, butyl, methoxy, ethoxy, propoxy, phenoxy, F, Cl, =O, $NR^{15}R^{16}$, $CF_3$, or phenyl substituted with 0-3 $R^{11b}$;

$R^{11b}$, at each occurrence, is independently selected from H, OH, Cl, F, Br, I, $NR^{15}R^{16}$, $CF_3$, methyl, ethyl, propyl, butyl, methoxy, ethoxy, propoxy, $C_1-C_2$ haloalkyl, and $C_1-C_2$ haloalkoxy;

W is a bond, —$CH_2$—, —$CH_2CH_2$—;

X is a bond;
phenyl substituted with 0-1 $R^{Xb}$,
$C_3-C_6$ cycloalkyl substituted with 0-1 $R^{Xb}$; or
5 to 6 membered heterocycle substituted with 0-1 $R^{Xb}$;

$R^{Xb}$ is selected from H, OH, Cl, F, $NR^{15}R^{16}$, $CF_3$, acetyl, $SCH_3$, $S(=O)CH_3$, $S(=O)_2CH_3$, methyl, ethyl, propyl, methoxy, ethoxy, propoxy, and —$OCF_3$;

Y is a bond, —C(=O)—, —O—, —S—, —S(=O)—, —S(=O)$_2$—, —NH—, —N($CH_3$)—, or —N($CH_2CH_3$)—;

Z is H;
$C_1-C_8$ alkyl substituted with 0-3 $R^{12a}$;
$C_2-C_6$ alkenyl substituted with 0-3 $R^{12a}$;
$C_2-C_6$ alkynyl substituted with 0-3 $R^{12a}$;
$C_6-C_{10}$ aryl substituted with 0-4 $R^{12b}$;
$C_3-C_{10}$ carbocycle substituted with 0-4 $R^{12b}$; or
5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, $S(=O)CH_3$, $S(=O)_2CH_3$,
$C_1-C_6$ alkyl, $C_1-C_4$ alkoxy, $C_1-C_4$ haloalkyl,
$C_1-C_4$ haloalkoxy, $C_1-C_4$ haloalkyl-S—,
$C_6-C_{10}$ aryl substituted with 0-4 $R^{12b}$;
$C_3-C_{10}$ carbocycle substituted with 0-4 $R^{12b}$; or
5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
$C_1-C_6$ alkyl, $C_1-C_4$ alkoxy, $C_1-C_4$ haloalkyl,
$C_1-C_4$ haloalkoxy, and $C_1-C_4$ haloalkyl-S—;

$R^{14}$ is H, phenyl, benzyl, $C_1-C_4$ alkyl, or $C_2-C_4$ alkoxyalkyl;

$R^{15}$, at each occurrence, is independently selected from H, methyl, ethyl, propyl, butyl, benzyl, and phenethyl;

$R^{16}$, at each occurrence, is independently selected from H, OH, methyl, ethyl, propyl, butyl, benzyl, phenethyl, methyl-C(=O)—, ethyl-C(=O)—, methyl-S(=O)$_2$—, and ethyl-S(=O)$_2$—;

$R^{18}$, at each occurrence, is independently selected from H, methyl, ethyl, propyl, butyl, phenyl, benzyl, and phenethyl;

$R^{19}$, at each occurrence, is independently selected from H, methyl, ethyl, propyl, and butyl;

$R^{20}$ is H or $C_1-C_4$ alkyl.

[18] In another preferred embodiment the present invention provides a compound of Formula (If) wherein:

L is —NHC(=O)—, —C(=O)NH—, or —OC(=O)NH—;

$R^3$ is —$R^4$, —$CH_2R^4$, —$CH_2CH_2R^4$, —$CH_2OR^4$, or —$CH_2CH_2OR^4$;

$R^4$ is $C_1-C_6$ alkyl substituted with 0-3 $R^{4a}$,
$C_2-C_6$ alkenyl substituted with 0-3 $R^{4a}$, or
$C_2-C_6$ alkynyl substituted with 0-3 $R^{4a}$;

$R^{4a}$, at each occurrence, is independently selected from is H, OH, F, Cl, Br, I, $NR^{15}R^{16}$, $CF_3$,
$C_3-C_6$ carbocycle substituted with 0-3 $R^{4b}$,
phenyl substituted with 0-3 $R^{4b}$, or
5 to 6 membered heterocycle containing 1 to 3 heteroatoms selected from nitrogen, oxygen, and sulphur, wherein said 5 to 6 membered heterocycle is substituted with 0-3 $R^{4b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

Ring C is a 3-6 membered carbocycle selected from:

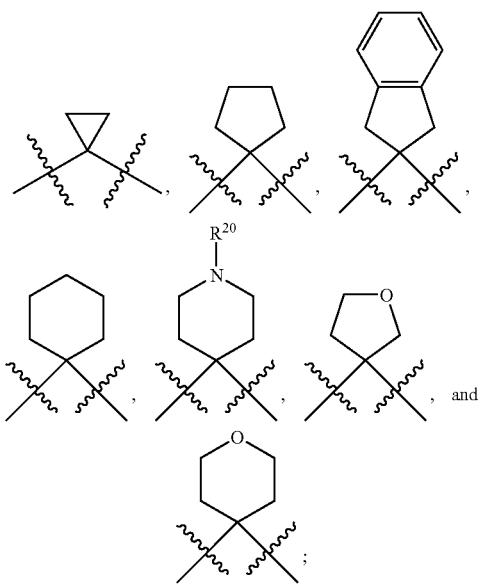

wherein said 3-6 membered carbocycle is substituted with 0-1 $R^{21}$;

$R^{21}$ is selected from H, OH, Cl, F, CN, $CF_3$, methyl, ethyl, methoxy, ethoxy, allyl, and —$OCF_3$;

$R^{11}$ is selected from
H, =O, $NR^{18}R^{19}$;
$C_1$-$C_4$ alkyl optionally substituted with 0-1 $R^{11a}$;
phenyl substituted with 0-3 $R^{11b}$;
5 to 7 membered heterocycle containing 1 to 4 heteroatoms selected from nitrogen, oxygen, and sulphur, wherein said 5 to 7 membered heterocycle is substituted with 0-3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, homopiperidinyl, and tetrazolyl;

$R^{11a}$, at each occurrence, is independently selected from H, methyl, ethyl, propyl, methoxy, ethoxy, propoxy, phenoxy, F, Cl, =O, $NR^{15}R^{16}$, $CF_3$, or phenyl substituted with 0-3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$-$C_2$ haloalkyl, and $C_1$-$C_2$ haloalkoxy;

W is a bond or —$CH_2$—;

X is a bond, phenyl, $C_3$-$C_6$ cycloalkyl or 5 to 6 membered heterocycle;

Y is a bond, —C(=O)—, —O—, —S—, —S(=O)—, —S(=O)$_2$—, —NH—, —N($CH_3$)—, or —N($CH_2CH_3$)—;

Z is H;
$C_1$-$C_8$ alkyl substituted with 0-3 $R^{12a}$;
$C_2$-$C_6$ alkenyl substituted with 0-3 $R^{12a}$;
$C_2$-$C_6$ alkynyl substituted with 0-3 $R^{12a}$;
$C_6$-$C_{10}$ aryl substituted with 0-4 $R^{12b}$;
$C_3$-$C_{10}$ carbocycle substituted with 0-4 $R^{12b}$; or
5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12a}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;
phenyl substituted with 0-4 $R^{12b}$;
$C_3$-6 carbocycle substituted with 0-4 $R^{12b}$; or
5 to 6 membered heterocycle containing 1 to 4 heteroatoms selected from nitrogen, oxygen, and sulphur, wherein said 5 to 6 membered heterocycle is substituted with 0-3 $R^{12b}$;

$R^{12b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;

$R^{14}$ is H, phenyl, benzyl, methyl, ethyl, propyl, or butyl;

$R^{15}$, at each occurrence, is independently selected from H, methyl, ethyl, propyl, and butyl; and $R^{16}$, at each occurrence, is independently selected from H, OH, methyl, ethyl, propyl, butyl, benzyl, and phenethyl.

$R^{18}$, at each occurrence, is independently selected from H, methyl, ethyl, propyl, butyl, phenyl, benzyl, and phenethyl;

$R^{19}$, at each occurrence, is independently selected from H, methyl, ethyl, propyl, and butyl; and $R^{20}$ is H, methyl, or ethyl.

[19] In another preferred embodiment the present invention provides a compound of Formula (If) wherein:

L is —NHC(=O)—, —C(=O)NH—, or —OC(=O)NH—;

Ring C is selected from:

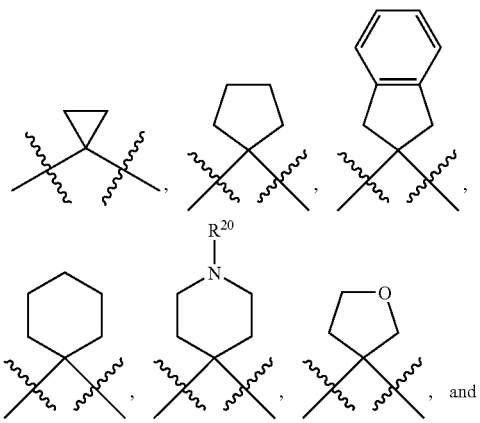

-continued

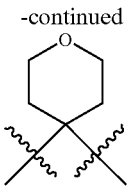

R³ is —CH₃, —CH₂CH₃, —CH₂CH₂CH₃, —CH₂CH₂CH₂CH₃, —CH₂CH₂CH(CH₃)₂, —CH₂(CH₃)₂, —CH(CH₃)CH₂CH₃, —CH₂CH(CH₃)₂, —CH₂C(CH₃)₃, —CF₃, —CH₂CF₃, —CH₂CH₂CF₃, —CH₂CH₂CH₂CF₃, —CH(OH)CH₂CH(CH₃)₂, —CH(OH)CH(CH₃)₂, —CH(NH₂)CH₂CH(CH₃)₂, —CH₂CH₂OCH₃, —CH₂OCH₂CH₃, —CF₂CH₂CH(CH₃)₂, —CH(NHCH₃)CH₂CH(CH₃)₂, —CH(NHSO₂CH₂CH₂CH₃)CH₂CH(CH₃)₂, cyclohexyl-, cyclopentyl-, cyclopropyl-CH₂—, cyclobutyl-CH₂—, cyclopentyl-CH₂—, cyclohexyl-CH₂—, cyclopropyl-CH₂CH₂—, cyclobutyl-CH₂CH₂—, cyclopentyl-CH₂CH₂—, cyclohexyl-CH(OH)—, cyclohexyl-CH₂CH₂—, 1-NH₂-cyclopentyl, phenyl-CH₂—, (2-F-phenyl)CH₂—, (3-F-phenyl)CH₂—, (4-F-phenyl)CH₂—, (2-Cl-phenyl)CH₂—, (3-Cl-phenyl)CH₂—, (4-Cl-phenyl)CH₂—, (2,3-diF-phenyl)CH₂—, (2,4-diF-phenyl)CH₂—, (2,5-diF-phenyl)CH₂—, (2,6-diF-phenyl)CH₂—, (3,4-diF-phenyl)CH₂—, (3,5-diF-phenyl)CH₂—, (2,3-diCl-phenyl)CH₂—, (2,4-diCl-phenyl)CH₂—, (2,5-diCl-phenyl)CH₂—, (2,6-diCl-phenyl)CH₂—, (3,4-diCl-phenyl)CH₂—, (3,5-diCl-phenyl)CH₂—, (3-F-4-Cl-phenyl)CH₂—, (3-F-5-Cl-phenyl)CH₂—, (3-Cl-4-F-phenyl)CH₂—, phenyl-CH₂CH₂—, (2-F-phenyl)CH₂CH₂—, (3-F-phenyl)CH₂CH₂—, (4-F-phenyl)CH₂CH₂—, (2-Cl-phenyl)CH₂CH₂—, (3-Cl-phenyl)CH₂CH₂—, (4-Cl-phenyl)CH₂CH₂—, (2,3-diF-phenyl)CH₂CH₂—, (2,4-diF-phenyl)CH₂CH₂—, (2,5-diF-phenyl)CH₂CH₂—, (2,6-diF-phenyl)CH₂CH₂—, (3,4-diF-phenyl)CH₂CH₂—, (3,5-diF-phenyl)CH₂CH₂—, (2,3-diCl-phenyl)CH₂CH₂—, (2,4-diCl-phenyl)CH₂CH₂—, (2,5-diCl-phenyl)CH₂CH₂—, (2,6-diCl-phenyl)CH₂CH₂—, (3,4-diCl-phenyl)CH₂CH₂—, (3,5-diCl-phenyl)CH₂CH₂—, (3-F-4-Cl-phenyl)CH₂CH₂—, (3-F-5-Cl-phenyl)CH₂CH₂—, 4-piperidinyl-CH₂CH₂—, phenyl-CH₂CH₂CF₂—, phenyl-CH₂CH(OH)—, imidazolyl-CH₂CH(OH)—, or phenyl-CH₂OCH₂—;

W is a bond or —CH₂—;

X is a bond;

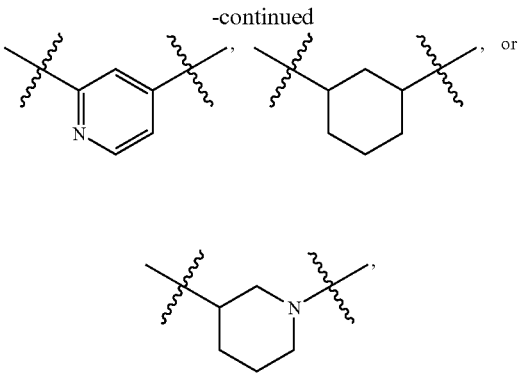

Y is a bond, —C(=O)—, —O—, —S—, —S(=O)—, —S(=O)₂—, —NH—, or —N(CH₃)—,

Z is methyl, ethyl, i-propyl, n-propyl, n-butyl, i-butyl, s-butyl, t-butyl, allyl, phenyl, 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF₃O-phenyl, 3-CF₃O-phenyl, 4-CF₃O-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, cyclopropyl, cyclobutyl, cyclopentyl, cyclohexyl, morpholino, N-piperinyl, phenyl-CH₂—, (2-F-phenyl)CH₂—, (3-F-phenyl)CH₂—, (4-F-phenyl)CH₂—, (2-Cl-phenyl)CH₂—, (3-Cl-phenyl)CH₂, (4-Cl-phenyl)CH₂—, (2,3-diF-phenyl)CH₂—, (2,4-diF-phenyl)CH₂—, (2,5-diF-phenyl)CH₂—, (2,6-diF-phenyl)CH₂—, (3,4-diF-phenyl)CH₂—, (3,5-diF-phenyl)CH₂—, (2,3-diCl-phenyl)CH₂—, (2,4-diCl-phenyl)CH₂—, (2,5-diCl-phenyl)CH₂—, (2,6-diCl-phenyl)CH₂—, (3,4-diCl-phenyl)CH₂—, (3,5-diCl-phenyl)CH₂—, (3-F-4-Cl-phenyl)CH₂—, (3-F-5-Cl-phenyl)CH₂—, (3-Cl-4-F-phenyl)CH₂—, (2-MeO-phenyl)CH₂—, (3-MeO-phenyl)CH₂—, (4-MeO-phenyl)CH₂—, (2-Me-phenyl)CH₂—, (3-Me-phenyl)CH₂—, (4-Me-phenyl)CH₂—, (2-MeS-phenyl)CH₂—, (3-MeS-phenyl)CH₂—, 4-MeS-phenyl)CH₂—, (2-CF₃O-phenyl)CH₂—, (3-CF₃O-phenyl)CH₂—, (4-CF₃O-phenyl)CH₂—, (furanyl)CH₂—, (thienyl)CH₂—, (pyridyl)CH₂—, (2-Me-pyridyl)CH₂—, (3-Me-pyridyl)CH₂—, (4-Me-pyridyl)CH₂—, (1-imidazolyl)CH₂—, (oxazolyl)CH₂—, (isoxazolyl)CH₂—, (1-benzimidazolyl)CH₂—, (cyclopropyl)CH₂—, (cyclobutyl)CH₂—, (cyclopentyl)CH₂—, (cyclohexyl)CH₂—, (morpholino)CH₂—, (N-pipridinyl)CH₂—, phenyl-CH₂CH₂—, (phenyl)₂CHCH₂—, (2-F-phenyl)CH₂CH₂—, (3-F-phenyl)CH₂CH₂—, (4-F-phenyl)CH₂CH₂—, (2-Cl-phenyl)CH₂CH₂—, (3-Cl-phenyl)CH₂CH₂—, (4-Cl-phenyl)CH₂CH₂—, (2,3-diF-phenyl)CH₂CH₂—, (2,4-diF-phenyl)CH₂CH₂—, (2,5-diF-phenyl)CH₂CH₂—, (2,6-diF-phenyl)CH₂CH₂—, (3,4-diF-phenyl)CH₂CH₂—, (3,5-diF-phenyl)CH₂CH₂—, (2,3-diCl-phenyl)CH₂CH₂—, (2,4-diCl-phenyl)CH₂CH₂—, (2,5-diCl-phenyl)CH₂CH₂—, (2,6-diCl-phenyl)CH₂CH₂—, (3,4-diCl-phenyl)CH₂CH₂—, (3,5-diCl-phenyl)CH₂CH₂—, (3-F-4-Cl-phenyl)CH₂CH₂—, (3-F-5-Cl-phenyl)CH₂CH₂—, (3-Cl-4-F-phenyl)CH₂CH₂—, (2-MeO-phenyl)CH₂CH₂—, (3-MeO-phenyl)CH₂CH₂—, (4-MeO-phenyl)CH₂CH₂—, (2-Me-phenyl)CH₂CH₂—, (3-Me-phenyl)CH₂CH₂—, (4-Me-phenyl)CH₂CH₂—, (2-MeS-phenyl)CH₂CH₂—, (3-MeS-phenyl)CH₂CH₂—, (4-MeS-phenyl)CH₂CH₂—, (2-CF₃O-phenyl)CH₂CH₂—, (3-CF₃O-phenyl)CH₂CH₂—, (4-CF₃O-phenyl)CH₂CH₂—, (furanyl)CH₂CH₂—, (thienyl)CH₂CH₂—, (pyridyl)CH₂CH₂—, (2-Me-pyridyl)CH₂CH₂—, (3-Me-pyridyl)CH₂CH₂—, (4-Me-pyridyl)CH₂CH₂—, (imidazolyl)CH₂CH₂—, (oxazolyl)CH₂CH₂—, (isoxazolyl)CH₂CH₂—, (benzimidazolyl)CH₂CH₂—, (cyclopropyl)CH₂CH₂—, (cyclobutyl)CH₂CH₂—, (cyclopentyl)CH₂CH₂—, (cyclohexyl)CH₂CH₂—, (morpholino)CH₂CH₂—, or (N-pipridinyl)CH₂CH₂—; and R¹¹, at each occurrence, is independently selected from H, =O, methyl, ethyl, phenyl, benzyl, phenethyl, 4-F-phenyl, (4-F-phenyl)CH₂—, (4-F-phenyl)CH₂CH₂—, 3-F-phenyl, (3-F-phenyl)CH₂—, (3-F-phenyl)CH₂CH₂—, 2-F-phenyl, (2-F-phenyl)CH₂—, (2-F-phenyl)CH₂CH₂—, 4-Cl-phenyl, (4-Cl-phenyl)CH₂—, (4-Cl-phenyl)CH₂CH₂—, 3-Cl-phenyl, (3-Cl-phenyl)CH₂—, (3-Cl-phenyl)CH₂CH₂—, 4-CH₃-phenyl, (4-CH₃-phenyl)CH₂—, (4-CH₃-phenyl)CH₂CH₂—, 3-CH₃-phenyl, (3-CH₃-phenyl)CH₂—, (3-CH₃-phenyl)CH₂CH₂—, 4-CF₃-phenyl, (4-CF₃-phenyl)CH₂—, (4-CF₃-phenyl)CH₂CH₂—, cyclopentyl, pyrid-2-yl, pyrid-3-yl, or pyrid-4-yl.

[20] In another preferred embodiment the present invention provides a compound of Formula (I) selected from:

{[N-(3-methylbutyl)carbamoyl]cyclopentyl}-N-(5-methyl-6-oxo(7H-dibenzo[d,f]azaperhydroepin-7-yl))carboxamide;

{[N-(3-methylbutyl)carbamoyl]cyclopentyl}-N-(1-methyl-2-oxo-5-phenyl((S)-3H-benzo[f]1,4-diazepin-3-yl))carboxamide;

[(N-butylcarbamoyl)cyclopentyl]-N-(1-methyl-2-oxo-5-phenyl((S)-3H-benzo[f]1,4-diazepin-3-yl))carboxamide;

2-(3,5-difluorophenyl)-N-{[N-(1-methyl-2-oxo-5-phenyl((S)-3H-benzo[f]1,4-diazepin-3-yl))carbamoyl]cyclohexyl}acetamide;

2-(3,5-difluorophenyl)-N-{[N-(1-methyl-2-oxo-5-phenyl((S)-3H-benzo[f]1,4-diazepin-3-yl))carbamoyl]cyclopentyl}acetamide;

2-(3,5-difluorophenyl)-N-{[N-(1-methyl-2-oxo-5-phenyl((S)-3H-benzo[f]1,4-diazepin-3-yl))carbamoyl]cyclopropyl}acetamide;

3-cyclopentyl-N-{[N-(1-methyl-2-oxo-5-phenyl((S)-3H-benzo[f]1,4-diazepin-3-yl))carbamoyl]cyclohexyl}propanamide;

2-(3,5-difluorophenyl)-N-{4-[N-(1-methyl-2-oxo-5-phenyl((S)-3H-benzo[f]1,4-diazepin-3-yl))carbamoyl](4-piperidyl)}acetamide;

phenyl 4-[2-(3,5-difluorophenyl)acetylamino]-4-[N-(1-methyl-2-oxo-5-phenyl((S)-3H-benzo[f]1,4-diazepin-3-yl))carbamoyl]piperidinecarboxylate;

4-methyl-N-{[N-(5-methyl-6-oxo(7H-dibenzo[d,f]azaperhydroepin-7-yl))carbamoyl]cyclopentyl}pentanamide;

N-{1-methyl-2-oxo-5-[4-(trifluoromethyl)phenyl](3H-benzo[f]1,4-diazepin-3-yl)}{[(phenylmethoxy)carbonylamino]cyclopentyl}carboxamide;

(2S)-N-{[N-(1-{[3-(4-fluorophenoxy)phenyl]methyl}-2-oxoazaperhydroepin-3-yl)carbamoyl]cyclopropyl}-2-hydroxy-4-methylpentanamide;

(2S)-N-{[N-(1-{[3-(4-fluorophenoxy)phenyl]methyl}-2-oxoazaperhydroepin-3-yl)carbamoyl]cyclopentyl)-2-hydroxy-3-methylbutanamide;

2,2-difluoro-N-[(N-{1-methyl-2-oxo-5-[4-(trifluoromethyl)phenyl](3H-benzo[f]1,4-diazepin-3-yl)}carbamoyl)cyclopentyl]-4-phenylbutanamide;

N-[(N-{1-methyl-2-oxo-5-[4-(trifluoromethyl)phenyl](3H-benzo[f]1,4-diazepin-3-yl)}carbamoyl)cyclopentyl]-3-(4-piperidyl)propanamide;

(2S)-2-hydroxy-4-methyl-N-[(N-{1-methyl-2-oxo-5-[4-(trifluoromethyl)phenyl](3H-benzo[f]1,4-diazepin-3-yl)}carbamoyl)cyclopentyl]pentanamide;

3-cyclopropyl-N-[(N-{1-methyl-2-oxo-5-[4-(trifluoromethyl)phenyl](3H-benzo[f]1,4-diazepin-3-yl)}carbamoyl)cyclopentyl]propanamide;

(2R)-2-hydroxy-3-imidazol-2-yl-N-[(N-{1-methyl-2-oxo-5-[4-(trifluoromethyl)phenyl](3H-benzo[f]1,4-diazepin-3-yl)}carbamoyl)cyclopentyl]propanamide;

2-ethoxy-N-[(N-{1-methyl-2-oxo-5-[4-(trifluoromethyl)phenyl](3H-benzo[f]1,4-diazepin-3-yl)}carbamoyl)cyclopentyl]acetamide;

3-cyclopentyl-N-[(N-{1-methyl-2-oxo-5-[4-(trifluoromethyl)phenyl](3H-benzo[f]1,4-diazepin-3-yl)}carbamoyl)cyclopentyl]propanamide;

(2S)-2-hydroxy-3-methyl-N-[(N-(1-methyl-2-oxo-5-[4-(trifluoromethyl)phenyl](3H-benzo[f]1,4-diazepin-3-yl)}carbamoyl)cyclopentyl]butanamide;

(2S)-2-cyclohexyl-2-hydroxy-N-[(N-{1-methyl-2-oxo-5-[4-(trifluoromethyl)phenyl](3H-benzo[f]1,4-diazepin-3-yl)}carbamoyl)cyclopentyl]acetamide;

(2R)-2-cyclohexyl-2-hydroxy-N-[(N-{1-methyl-2-oxo-5-[4-(trifluoromethyl)phenyl](3H-benzo[f]1,4-diazepin-3-yl)}carbamoyl)cyclopentyl]acetamide;

(2S)-2-amino-4-methyl-N-[(N-{1-methyl-2-oxo-5-[4-(trifluoromethyl)phenyl](3H-benzo[f]1,4-diazepin-3-yl)}carbamoyl)cyclopentyl]pentanamide;

[(cyclohexylcarbonylamino)cyclopentyl]-N-{1-methyl-2-oxo-5-[4-(trifluoromethyl)phenyl](3H-benzo[f]1,4-diazepin-3-yl)}carboxamide;

{[N-(3-methylbutyl)carbamoyl]cyclopentyl}-N-{1-methyl-2-oxo-5-[4-(trifluoromethyl)phenyl](3H-benzo[f]1,4-diazepin-3-yl)}carboxamide;

4-methyl-N-[(N-{1-methyl-2-oxo-5-[4-(trifluoromethyl)phenyl](3H-benzo[f]1,4-diazepin-3-yl)}carbamoyl)cyclopentyl]pentanamide;

(2S)-2-hydroxy-4-methyl-N-[(N-{1-methyl-2-oxo-5-(4-(trifluoromethyl)phenyl](3H-benzo[f]1,4-diazepin-3-yl)}carbamoyl)cyclopentyl]pentanamide;

3-methoxy-N-[(N-{1-methyl-2-oxo-5-[4-(trifluoromethyl)phenyl](3H-benzo[f]1,4-diazepin-3-yl)}carbamoyl)cyclopentyl]propanamide;

(2S)-2-hydroxy-N-[(N-{1-methyl-2-oxo-5-[4-(trifluoromethyl)phenyl](3H-benzo[f]1,4-diazepin-3-yl)}carbamoyl)cyclopentyl]-3-phenylpropanamide;
N-[(N-{1-methyl-2-oxo-5-[4-(trifluoromethyl)phenyl](3H-benzo[f]1,4-diazepin-3-yl)}carbamoyl)cyclopentyl]-2-(phenylmethoxy)acetamide;
(2S)-2-hydroxy-3-methyl-N-{[N-(5-methyl-6-oxo(7H-dibenzo[d,f]azaperhydroepin-7-yl))carbamoyl]cyclopentyl}butanamide;
(2S)-2-hydroxy-4-methyl-N-{[N-(5-methyl-6-oxo(7H-dibenzo[d,f]azaperhydroepin-7-yl))carbamoyl]cyclopentyl}pentanamide;
3-cyclopentyl-N-{[N-(5-methyl-6-oxo(7H-dibenzo[d,f]azaperhydroepin-7-yl))carbamoyl]cyclopentyl}propanamide;
(2S)-2-cyclohexyl-2-hydroxy-N-{[N-(5-methyl-6-oxo(7H-dibenzo[d,f]azaperhydroepin-7-yl))carbamoyl]cyclopentyl}acetamide;
3-cyclopropyl-N-{[N-(5-methyl-6-oxo(7H-dibenzo[d,f]azaperhydroepin-7-yl))carbamoyl]cyclopentyl}propanamide;
N-{[N-(1-butyl-5-cyclopentyl-2-oxo(3H-benzo[f]1,4-diazepin-3-yl))carbamoyl]cyclopentyl}-4-methylpentanamide;
N-{[N-(5-cyclopentyl-1-methyl-2-oxo(3H-benzo[f]1,4-diazepin-3-yl))carbamoyl]cyclopentyl}-4-methylpentanamide;
(2S)-2-hydroxy-3-methyl-N-({N-[2-oxo-1-benzyl(3H,4H,5H-benzo[f]azaperhydroepin-3-yl)]carbamoyl}cyclopentyl) butanamide;
(2S)-4-methyl-N-{[N-(5-methyl-6-oxo(7H-dibenzo[d,f]azaperhydroepin-7-yl))carbamoyl]cyclopentyl}-2-[(propylsulfonyl)amino]pentanamide;
(2S)-2-amino-4-methyl-N-{[N-(5-methyl-6-oxo(7H-dibenzo[d,f]azaperhydroepin-7-yl))carbamoyl]cyclopentyl}pentanamide;
2,2-difluoro-4-methyl-N-{[N-(5-methyl-6-oxo(7H-dibenzo[d,f]azaperhydroepin-7-yl))carbamoyl]cyclopentyl}pentanamide;
4-methyl-N-{[N-(6-oxo(5H,7H-dibenzo[d,f]azaperhydroepin-7-yl))carbamoyl]cyclopentyl}pentanamide;
N-({N-[5-(3,3-dimethyl-2-oxobutyl)-6-oxo(7H-dibenzo[d,f]azaperhydroepin-7-yl)]carbamoyl}cyclopentyl)-4-methylpentanamide;
4-methyl-N-[(N-{6-oxo-5-[(3-phenoxyphenyl)methyl](7H-dibenzo[d,f]azaperhydroepin-7-yl)}carbamoyl)cyclopentyl]pentanamide;
N-{[N-(5-butyl-6-oxo(7H-dibenzo[d,f]azaperhydroepin-7-yl))carbamoyl]cyclopentyl}-4-methylpentanamide;
4-methyl-N-({N-[6-oxo-5-benzyl(7H-dibenzo[d,f]azaperhydroepin-7-yl)]carbamoyl}cyclopentyl)pentanamide;
N-({N-[5-(tert-butyl)-1-methyl-2-oxo(3H-benzo[f]1,4-diazepin-3-yl)]carbamoyl}cyclopentyl)-4-methylpentanamide;
N-({N-[5-(tert-butyl)-1-butyl-2-oxo(3H-benzo[f]1,4-diazepin-3-yl)]carbamoyl}cyclopentyl)-4-methylpentanamide; and
N-({N-[5-butyl-2-oxo-1-(2-pyridylmethyl)(3H-benzo[f]1,4-diazepin-3-yl)]carbamoyl}cyclopentyl)-4-methylpentanamide.

In another embodiment the present invention provides for a method for the treatment of neurological disorders associated with β-amyloid production comprising administering to a host in need of such treatment a therapeutically effective amount of a compound of Formula (I):

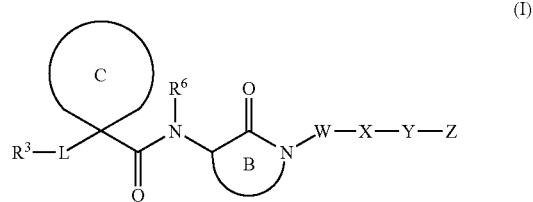

or a pharmaceutically acceptable salt or prodrug thereof.

It is understood that any and all embodiments of the present invention may be taken in conjunction with any other embodiment to describe additional even more preferred embodiments of the present invention.

In a second embodiment, the present invention provides a pharmaceutical composition comprising a compound of Formula (I) and a pharmaceutically acceptable carrier.

In a third embodiment, the present invention provides a method for the treatment of neurological disorders associated with β-amyloid production comprising administering to a host in need of such treatment a therapeutically effective amount of a compound of Formula (I).

In a preferred embodiment the neurological disorder associated with β-amyloid production is Alzheimer's Disease.

In a fourth embodiment, the present invention provides a method for inhibiting γ-secretase activity for the treatment of a physiological disorder associated with inhibiting γ-secretase activity comprising administering to a host in need of such inhibition a therapeutically effective amount of a compound of Formula (I) that inhibits γ-secretase activity.

Thus, the present invention provides a method for inhibiting γ-secretase activity comprising administering to a host in need of such inhibition a therapeutically effective amount of a compound of Formula (I) that inhibits γ-secretase activity.

In a preferred embodiment the physiological disorder associated with inhibiting γ-secretase activity is Alzheimer's Disease.

In a fifth embodiment, the present invention provides a compound of Formula (I) for use in therapy.

In a preferred embodiment the present invention provides a compound of Formula (I) for use in therapy of Alzheimer's Disease.

In a sixth embodiment, the present invention provides for the use of a compound of Formula (I) for the manufacture of a medicament for the treatment of Alzheimer's Disease.

It is understood that any and all embodiments of the present invention may be taken in conjunction with any other embodiment to describe additional even more preferred embodiments of the present invention.

DEFINITIONS

As used herein, the term "Aβ" denotes the protein designated Aβ, β-amyloid peptide, and sometimes β/A4, in the art. Aβ is an approximately 4.2 kilodalton (kD) protein of about 39 to 43 amino acids found in amyloid plaques, the walls of meningeal and parenchymal arterioles, small arteries, capillaries, and sometimes, venules. The isolation and sequence data for the first 28 amino acids are described in U.S. Pat. No. 4,666,829. The 43 amino acid sequence is:

```
1
Asp   Ala   Glu   Phe   Arg   His   Asp   Ser   Gly   Tyr

11
Glu   Val   His   His   Gln   Lys   Leu   Val   Phe   Phe

21
Ala   Glu   Asp   Val   Gly   Ser   Asn   Lys   Gly   Ala

31
Ile   Ile   Gly   Leu   Met   Val   Gly   Gly   Val   Val

41
Ile   Ala   Thr
```

The term "APP", as used herein, refers to the protein known in the art as β amyloid precursor protein. This protein is the precursor for Aβ and through the activity of "secretase" enzymes, as used herein, it is processed into Aβ. Differing secretase enzymes, known in the art, have been designated β secretase, generating the N-terminus of Aβ, α secretase cleaving around the 16/17 peptide bond in Aβ, and "γ secretases", as used herein, generating C-terminal Aβ fragments ending at position 38, 39, 40, 42, and 43 or generating C-terminal extended precursors which are subsequently truncated to the above polypeptides.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g., $R^{5b}$) occurs more than one time in any constituent or formula for a compound, its definition at each occurrence is independent of its definition at every other occurrence. Thus, for example, if a group is shown to be substituted with 0-2 $R^{5b}$, then said group may optionally be substituted with up to two $R^{5b}$ groups and $R^{5b}$ at each occurrence is selected independently from the definition of $R^{5b}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms; for example, "$C_1$-$C_6$ alkyl" denotes alkyl having 1, 2, 3, 4, 5, or 6 carbon atoms. Examples of alkyl include, but are not limited to, methyl, ethyl, n-propyl, i-propyl, n-butyl, i-butyl, sec-butyl, t-butyl, pentyl, and hexyl. Preferred "alkyl" group, unless otherwise specified, is "$C_1$-$C_4$ alkyl". Additionally, unless otherwise specified, "propyl" denotes n-propyl or i-propyl; "butyl" denotes n-butyl, i-butyl, sec-butyl, or t-butyl.

As used herein, "alkenyl" or "alkenylene" is intended to include hydrocarbon chains of either a straight or branched configuration and one or more unsaturated carbon-carbon bonds which may occur in any stable point along the chain. Examples of "$C_2$-$C_6$ alkenyl" include, but are not limited to, ethenyl, 1-propenyl, 2-propenyl, 1-butenyl, 2-butenyl, 3-butenyl, 3-methyl-2-butenyl, 2-pentenyl, 3-pentenyl, hexenyl, and the like.

As used herein, "alkynyl" or "alkynylene" is intended to include hydrocarbon chains of either a straight or branched configuration and one or more carbon-carbon triple bonds which may occur in any stable point along the chain, such as ethynyl, 1-propynyl, 2-propynyl, 1-butynyl, 2-butynyl, 3-butynyl, and the like.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy. Similarly, "alkylthio" or "thioalkoxy" is represents an alkyl group as defined above with the indicated number of carbon atoms attached through a sulphur bridge.

"Halo" or "halogen" as used herein refers to fluoro, chloro, bromo, and iodo. Unless otherwise specified, preferred halo is fluoro and chloro. "Counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example –$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, 2,2-difluoroethyl, heptafluoropropyl, and heptachloropropyl. "Haloalkoxy" is intended to mean a haloalkyl group as defined above with the indicated number of carbon atoms attached through an oxygen bridge; for example trifluoromethoxy, pentafluoroethoxy, 2,2,2-trifluoroethoxy, and the like. "Halothioalkoxy" is intended to mean a haloalkyl group as defined above with the indicated number of carbon atoms attached through a sulphur bridge.

"Cycloalkyl" is intended to include saturated ring groups, having the specified number of carbon atoms. For example, "$C_3$-$C_6$ cycloalkyl" denotes such as cyclopropyl, cyclobutyl, cyclopentyl, or cyclohexyl.

As used herein, "carbocycle" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred "carbocycle" are cyclopropyl, cyclobutyl, cyclopentyl, and cyclohexyl.

As used herein, the term "heterocycle" or "heterocyclic ring" is intended to mean a stable 5- to 7-membered monocyclic or bicyclic or 7- to 14-membered bicyclic heterocyclic ring which is saturated partially unsaturated or unsaturated (aromatic), and which consists of carbon atoms and 1, 2, 3 or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, but are not limited to, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, tetrazolyl; more preferred 5 to 6 membered heterocycles include, but are not limited to, pyridinyl, pyrimidinyl, triazinyl, furanyl, thienyl, thiazolyl, piperazinyl, piperidinyl, pyrazolyl, imidazolyl, and tetrazolyl. Also included are fused ring and spiro compounds containing, for example, the above heterocycles.

As used herein, the term "aryl", "$C_6$-$C_{10}$ aryl" or aromatic residue, is intended to mean an aromatic moiety containing the specified number of carbon atoms; for example phenyl, pyridinyl or naphthyl. Preferred "aryl" is phenyl. Unless otherwise specified, "aryl" may be unsubstituted or substituted with 0 to 3 groups selected from H, methyl, ethyl, propyl, butyl, methoxy, ethoxy, propoxy, butoxy, amino, hydroxy, Cl, F, Br, I, $CF_3$, $SCH_3$, $S(O)CH_3$, $SO_2CH_3$, —$N(CH_3)_2$, $N(CH_3)H$, CN, $NO_2$, $OCF_3$, $C(=O)CH_3$, $CO_2H$, $CO_2CH_3$, or $C_1$-$C_4$ haloalkyl.

The phrase "additional lactam carbons", as used herein, is intended to denote the number of optional carbon atoms in the lactam ring B of Formula (I). Formula (I"):

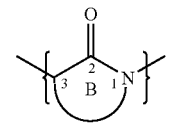

(I")

represents the lactam ring B of Formula (I). Additional lactam carbons are carbons in lactam ring B other than the carbons numbered 2 and 3 in the backbone of the formula. The additional lactam carbons may be optionally replaced by a heteroatom selected from oxygen, nitrogen and sulfur. Lactam ring B contains 1, 2, 3, 4, 5, 6 or 7 optional carbons, wherein one optional carbon may optionally be replaced by a heteroatom, such that the total number of members of lactam ring B, including atoms numbered 1, 2 and 3 in the backbone, does not exceed 10. It is preferred that the total number of atoms of lactam ring B is 6, 7 or 8; it is more preferred that the total number of atoms of lactam ring B is seven. It is further understood that lactam ring B may optionally be unsaturated or partially unsaturated (i.e. two adjacent atoms in the ring form a double bond) wherein the backbone of lactam ring B may contain one, two or three double bonds. Examples of lactam ring B include:

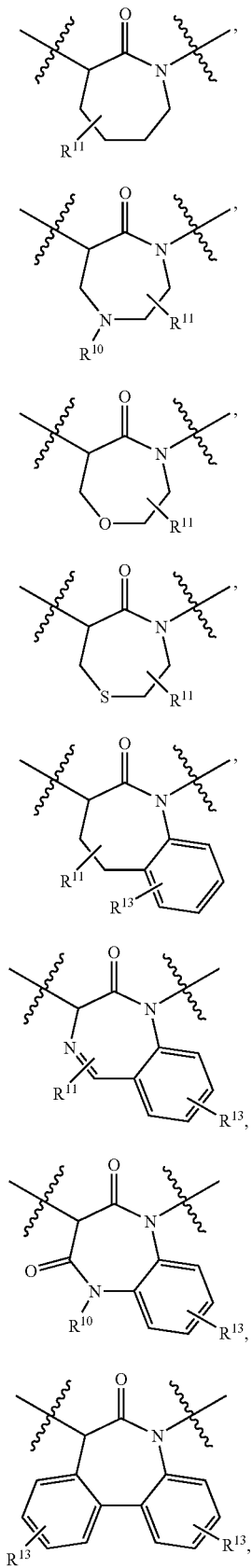
but are not intended to limit the invention. Preferred examples of lactam ring B are B1, B2, B5, B6, B8, B9, B13, and B16; more preferred examples of lactam ring B are B1, B6, B8, B9, and B13. Preferred examples of substituent $R^{10}$ or $R^{11}$ on lactam B are methyl, ethyl, phenyl, 4-fluorophenyl, 4-chlorophenyl, 4-trifluoromethylphenyl, (4-fluorophenyl) methyl, (4-chlorophenyl) methyl, (4-trifluoromethylphenyl) methyl, and 2-, 3-, and 4-pyridinyl. Preferred examples of $R^{13}$ on lactam B are F, Cl, OH, methyl, ethyl, methoxy, and trifluoromethyl.

The compounds herein described may have asymmetric centers. One enantiomer of a compound of Formula (I) may display superior biological activity over the opposite enantiomer. For example carbon 3 of lactam ring B Formula (I") may exist in either an S or R configuration. Thus, an R or S configuration at carbon 3 in Formula (I") is considered part of the invention. An example of such configuration includes,

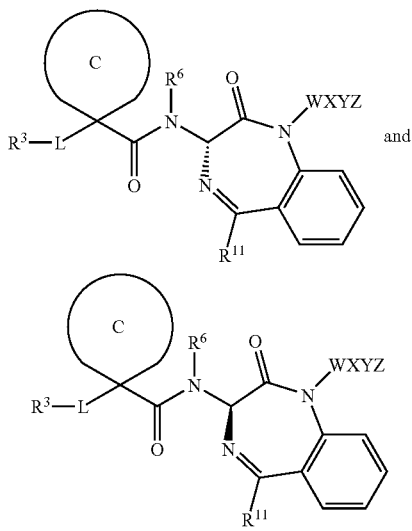

but is not intended to be limited to this example of ring B. When required, separation of the racemic material can be achieved by methods known in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like.

"Stable compound" and "stable structure" are meant to indicate a compound that is sufficiently robust to survive isolation to a useful degree of purity from a reaction mixture, and formulation into an efficacious therapeutic agent.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and which are suitable for the transformations being effected. Also, in the description of the synthetic methods described below, it is to be understood that all proposed reaction conditions, including choice of solvent, reaction atmosphere, reaction temperature, duration of the experiment and work-up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

In a preferred method of synthesis, the compounds of Formula (I) of the present invention can be prepared from carboxylic acid 1 and amine 2 using amide bond syntheses known in the art, including methods commonly used in peptide syntheses, such as HATU, TBTU, BOP, EDC, CDI, and DCC-mediated couplings, as illustrated in Scheme 1. Depending on the structure of the final product, it is appreciated by those skilled in the art that protecting groups or precursor functionality convertible to the desired groups may be desirable. Protecting groups and their use in synthesis are described in Green and Wuts, *Protective Groups in Organic Synthesis*, (Wiley 1991).

Scheme 1

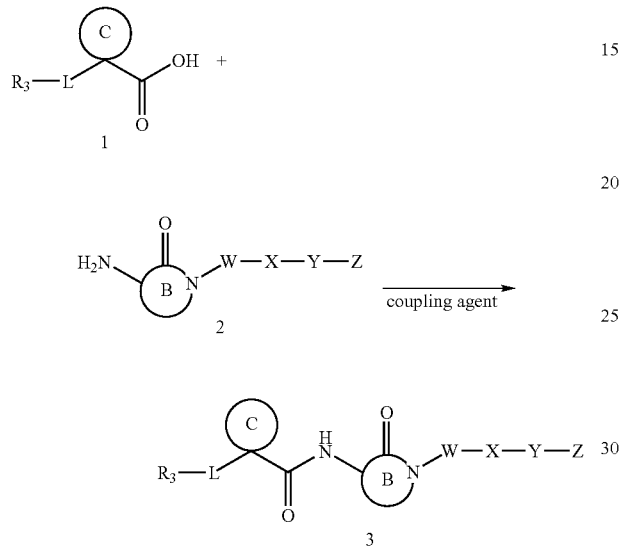

Additionally, the syntheses of a representative malonamide and a representative acetamide of Formula (I) are illustrated in Scheme 2 and Scheme 3, respectively. As will be readily apparent to those of ordinary skill in the art, the synthetic procedure illustrated in Scheme 2 and 3, and the reaction conditions described below can be modified by selecting the appropriate starting materials and reagents to allow the preparation of other compounds of the present invention.

Scheme 2

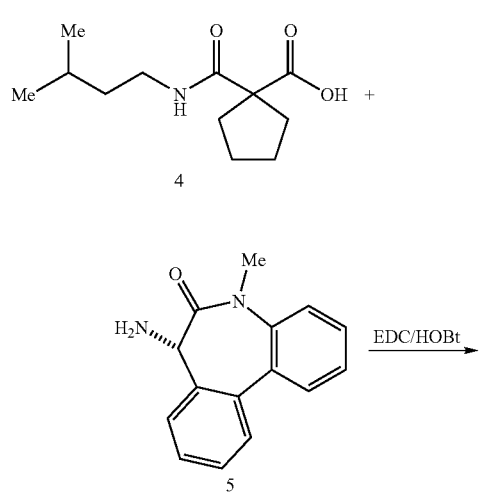

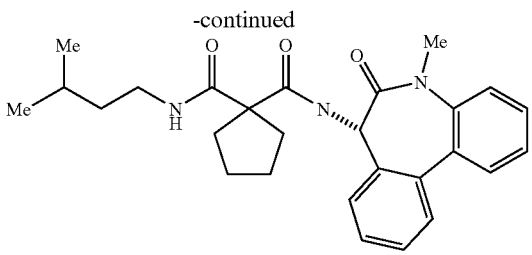

Scheme 3

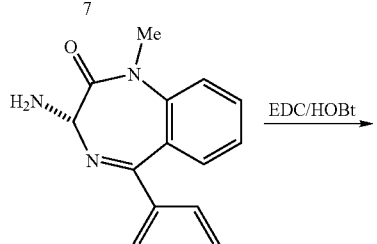

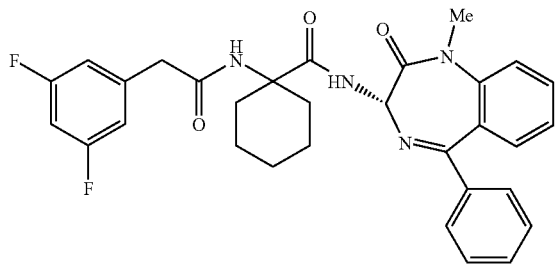

Methods for the synthesis of lactams useful as intermediates in the synthesis of compounds of the present invention, including amino bisbenzodiazepine 5 and amino benzodiazepine 8, are known in the art and are disclosed in a number of references including PCT publication number WO 98/28268, WO 99/66934, and WO00/07995, which are hereby incorporated by reference. Additional references include Bock, et. al., J. Org. Chem., 1987, 52, 3232-3239; Sherrill et. al., J. Org. Chem., 1995, 60, 730-734; Walsh, D. A., Synthesis, September 1980, p. 677; and Brown, at. al., Tetrahedron Letters, 1971, 8, 667-670.

Cyclic carboxylic acid intermediates, such as 4, are useful for the synthesis of the current invention, and may be synthesized by a number of ways well known in the art. One of the preferred syntheses of the compounds of this invention is shown in Scheme 4. Typically a convergent route is employed, which joins the acid 11 and the amine together to afford the key intermediate 12 using standard bond-forming procedures (Synthesis 1989, 37-38). The desired carboxylic acid 4 may be prepared from the known malonate ester 10

(e.g. Chung, S. K. Korean J. Med. Chem. 1995, 5, 94-111) via a three-step protocol as shown in Scheme 4.

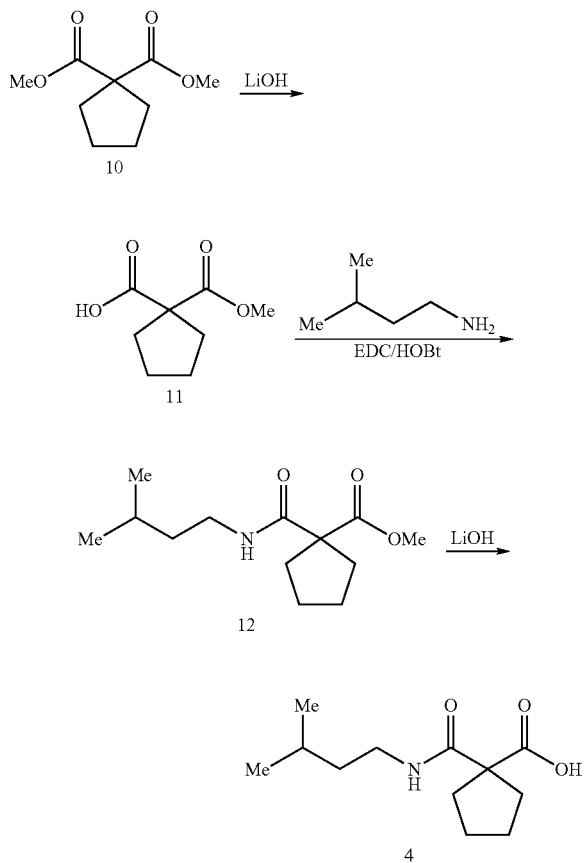

One of the preferred syntheses of cyclic amino acids, such as 7 which is useful in the preparation of compounds of Formula (I), is outlined in Scheme 5. As illustrated for the synthesis of carboxylic acid 7, the desired intermediate ester 18 is prepared by the initial coupling reaction of acid 14 and amine 13 under standard conditions using EDC and HOBt. Both the acids and the amines employed as starting materials in this invention are either commercially available or can be prepared from commercially available materials using conventional procedures and reagents. As apparent to those of ordinary skill in the art, the synthetic procedure illustrated in Scheme 5 and the reaction conditions described will allow the preparation of many other analogs of 7 by selecting the appropriate starting materials and reagents.

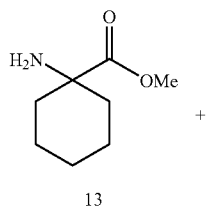

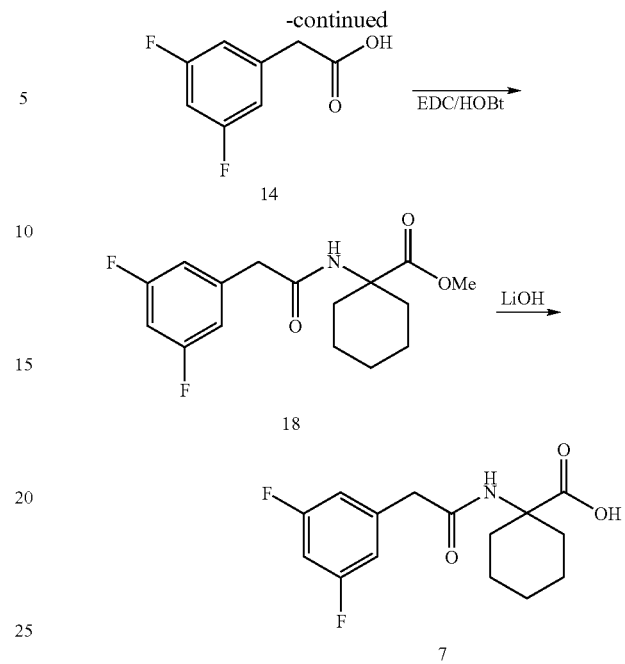

Methods for the synthesis of lactams useful as intermediates in the synthesis of compounds of the present invention are known in the art and are disclosed in a number of references including PCT publication number WO 98/28268, WO 99/66934, and WO00/07995, which are hereby incorporated by reference. Additional references include Bock, et. al., J. Org. Chem., 1987, 52, 3232-3239; Sherrill et. al., J. Org. Chem., 1995, 60, 730-734; Walsh, D. A., Synthesis, September 1980, p. 677; and Brown, at. al., Tetrahedron Letters, 1971, 8, 667-670.

One of the preferred syntheses of the lactam intermediates, such as 23, is outlined in Scheme 6.

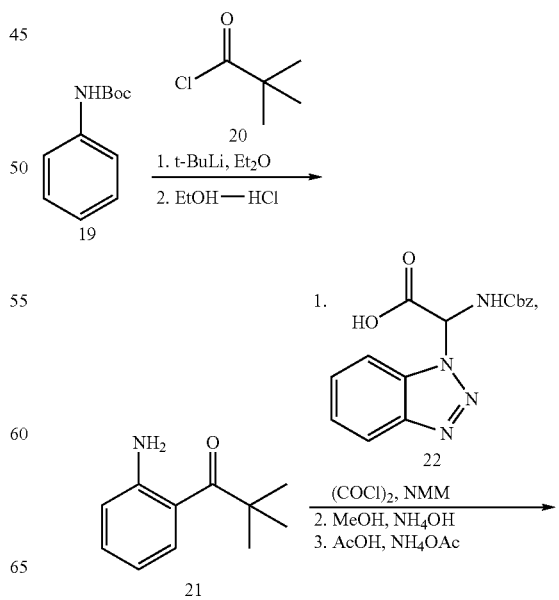

-continued

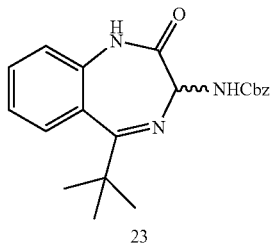

23 a) Preparation of 21

To a suspension of 19 (30.0 g, 155 mmol) in dry Et$_2$O (300 mL) under N$_2$ at −70° C. was added t-BuLi (205 mL, 1.7 M in pentane) and stirred for 4 h between −20° C. and −10° C. The reaction was cooled to −70° C. and transferred via canula to a round bottom containing 20 (23.0 mL, 186 mmol) in dry Et$_2$O (150 mL) under N$_2$ at −70° C. The reaction was stirred while warming to rt for 14 h and quenched with 20% citric acid. The resulting layers were separated and the organic layer was washed with sat. NaHCO$_3$, brine, dried over Na$_2$SO$_4$, filtered and concentrated to give a yellow oil. The oil was dissolved in EtOH-HCl (200 mL) and stirred overnight. The solvent was removed in vacuo at 70° C. and the resulting oil triturated with Et$_2$O. The resultant solid was filtered and washed with Et$_2$O to afford 21 HCl (23.9 g, 64%) as a orange solid: $^1$H NMR (500 MHz, CD$_3$OD) δ 8.10 (d, 1 H), 7.66 (t, 1 H), 7.56 (t, 1 H), 7.51 (d, 1 H), 1.41 (s, 9 H); ESI MS m/z=178 [C$_{11}$H$_{15}$NO+H]$^+$.

The orange solid was dissolved in 1N NaOH and EtOAC and the layers were separated. The organic layer was washed with brine, dried over Na$_2$SO$_4$, filtered and concentrated to afford 21 (21 g, 99%) as a yellow oil: $^1$H NMR (500 MHz, CD$_3$OD) δ 7.70 (d, 1 H), 7.16 (t, 1 H), 6.78 (d, 1 H), 6.59 (t, 1 H), 1.38 (s, 9 H).

b) Preparation of Example 23

To a solution of 22 (5.5 g, 17.0 mmol) in dry THF (50 mL) at 0° C. was added oxalyl chloride (1.47 mL, 17.0 mmol) and DMF (0.2 mL) and stirred for 1.25 h. A solution of 21 (3.3 g, 15.4 mmol) and N-methylmorpholine (4.7 mL, 42.4 mmol) in dry THF (20 mL) was added to the reaction dropwise and the reaction was stirred at rt for 1.5 h. The reaction was filtered and MeOH (100 mL) and NH$_4$OH (50 mL) was added to the filtrate and the reaction was sealed. After 45 min, the reaction was concentrated to half its volume and added dropwise to a cooled solution (15° C.) of ammonium acetate (5.75 g) in acetic acid (120 ml). The reaction was stirred over night at rt, dissolved in Et$_2$O (100 mL), made basic with 6 N NaOH, and cooled in ice while stirring for 1 h. The resulting solid was filtered, washed with H$_2$O and Et$_2$O, and dried in a vacuum oven at 30° C. to afford 23 (3.5 g, 63%) as a white solid: $^1$H NMR (500 MHz, CD$_3$OD) δ 7.78-7.16 (m, 10 H), 5.12 (s, 2 H), 1.27 (s, 9 H).

Abbreviations used in the description of the chemistry and in the examples that follow are:

Ac acetyl or acetate aq aqueous

Bn benzyl

Boc t-butyloxycarbonyl

Cbz benzyloxycarbonyl

DIEA N,N'-diisopropylethylamine

DMAP 4-dimethylaminopyridine

DME ethylene glycol dimethyl ether

DMF N,N'-dimethylformamide

DMSO dimethylsulfoxide or methyl sulfoxide

EDC.HCl 1-(3-dimethylaminopropyl)-3-ethylcarbodiimide

HOBT 1-hydroxybenzotriazole

HPLC high performance liquid chromatography

LiHMDS lithium hexamethyldisilazide

MeCN acetonitrile

MS mass spectrometry satd saturated rt or RT room temperature

TFA trifluoroacetic acid

THF tetrahydrofuran

TLC thin layer chromatography

EXAMPLES

The examples provided are intended to assist in a further understanding of the invention. Particular materials employed, species and conditions are intended to be further illustrate of the invention and not limit the reasonable scope thereof.

Compounds of the present invention are generally purified by HPLC using conditions known to one skilled in the art. However, unless otherwise indicated, the following conditions are generally applicable. HPLC Condition A: reverse-phase HPLC can be carried out using a Vydac C-18 column with gradient elution from 10% to 100% buffer B in buffer A (buffer A: water containing 0.1% trifluoroacetic acid, buffer B: 10% water, 90% acetonitrile containing 0.1% trifluoroacetic acid). Alternatively: HPLC Condition B: reverse-phase HPLC can be carried out using a Vydac C-18 column with gradient elution from 10% to 90% acetonitrile in water.

Example 1

{[N-(3-methylbutyl)carbamoyl]cyclopentyl}-N-(5-methyl-6-oxo(7H-dibenzo[d,f]azaperhydroepin-7-yl))carboxamide.

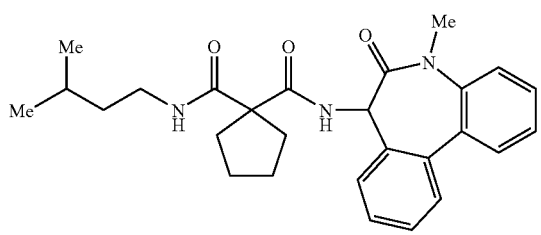

(a) Methyl 1-[N-(3-methylbutyl)carbamoyl]cyclopentanecarboxylate

To 1-(methoxycarbonyl)cyclopentanecarboxylic acid (630 mg, 3.7 mmol) in CH$_2$Cl$_2$/DMF (5:1, 37 mL) at 0° C. was added HOBT (730 mg, 4.8 mmol) and EDC (920 mg, 4.8 mmol). The mixture was stirred for 10 min then 3-methylbutylamine (640 mg, 7.4 mmol) was added and stirring was continued for 1 h. The solution was poured into water and the layers separated. The aqueous layer was extracted with methylene chloride and the combined extracts were washed with water, 1N HCl, sat'd NaHCO$_3$, dried over magnesium sulfate, and concentrated to a glassy solid (800 mg, 90%). MS [M+H]$^+$ 243.

(b) Methyl 1-[N-(3-methylbutyl)carbamoyl]cyclopentanecarboxylic acid

To a solution of methyl 1-[N-(3-methylbutyl)carbamoyl]cyclopentanecarboxylate (820 mg, 3.4 mmol) in 25 mL of THF cooled to 0° C. was added dropwise a solution of lithium hydroxide monohydrate (260 mg, 6.12 mmol) in 5.0 mL of water. The reaction mixture was stirred at rt for 16 h. THF was removed under reduced pressure to give a yellow oil which was diluted with 10 mL of 1N HCl. The aqueous phase was extracted with CH$_2$Cl$_2$ (8×15 mL), and the extracts were combined, dried over Na$_2$SO$_4$, and concentrated to afford 700 mg (90%) of methyl 1-[N-(3-methylbutyl)carbamoyl]-cyclopentanecarboxylic acid as a white solid. MS [M+H]$^+$ 228.

(c) {[N-(3-methylbutyl)carbamoyl]cyclopentyl}-N-(5-methyl-6-oxo(7H-dibenzo[d,f]azaperhydroepin-7-yl))carboxamide To 1-[N-(3-methylbutyl)carbamoyl]cyclopentane carboxylic acid (38 mg, 0.16 mmol) in CH$_2$Cl$_2$/DMF (5:1, 15 mL) at 0° C. was added HOBT (28 mg, 0.18 mmol) and EDC (34 mg, 0.18 mmol). The mixture was stirred for 10 min then 7-amino-5-methyl-7H-dibenzoazaperhydroepin-6-one (40 mg, 0.16 mmol) (obtained as the first eluting peak of a racemic mixture on a CHIRALCEL OD column with 20% iPrOH/Hexane with diethylamine) was added and stirring was continued for 1 h. The solution was poured into water and the layers separated. The aqueous layer was extracted with methylene chloride and the combined extracts were washed with water, 1N HCl, sat'd NaHCO$_3$, dried over magnesium sulfate, and concentrated to a glassy solid (67 mg, 94%). $^1$H NMR (300 MHz, CD$_3$OD) δ 7.20-7.80 (m, 9H), 6.25 (m, 1H), 5.25 (d, 1H), 3.38 (s, 3H), 3.27 (m, 1H), 2.58-2.05 (m, 5H), 1.80-1.25 (m, 8H), 0.95, (m, 6H). MS [M+H]$^+$ 448.

Example 2

{[N-(3-Methylbutyl)carbamoyl]cyclopentyl}-N-(1-methyl-2-oxo-5-phenyl((S)-3H-benzo[f]1,4-diazepin-3-yl))carboxamide

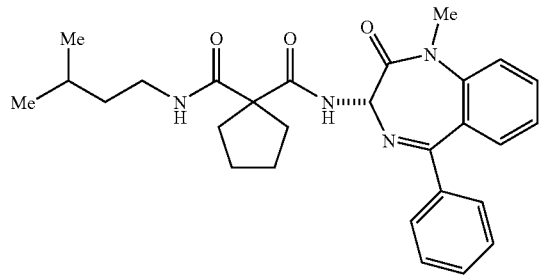

The title compound was prepared in a manner similar to that described for Example 1. The product was obtained as a solid. MS [M+H]$^+$ 475.

Example 3

[(N-Butylcarbamoyl)cyclopentyl]-N-(1-methyl-2-oxo-5-phenyl((S)-3H-benzo[f]1,4-diazepin-3-yl))carboxamide

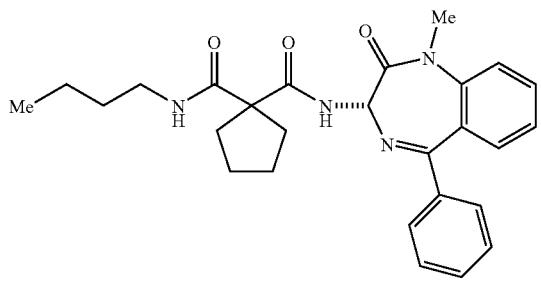

The title compound was prepared in a manner similar to that described for Example 1. The product was obtained as a solid. MS [M+H]$^+$ 461.

Example 4

2-(3,5-Difluorophenyl)-N-{[N-(1-methyl-2-oxo-5-phenyl((S)-3H-benzo[f]1,4-diazepin-3-yl))carbamoyl]cyclohexyl}-acetamide

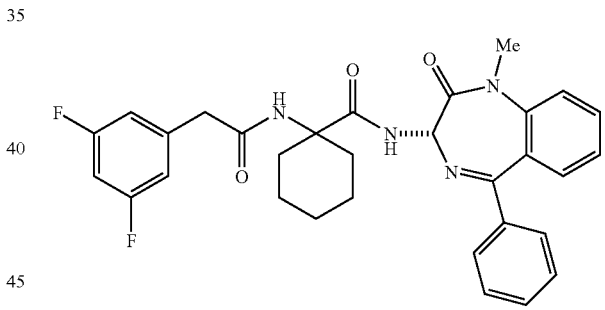

(a) {[(tert-Butoxy)carbonylamino]cyclohexyl}-N-(1-methyl-2-oxo-5-phenyl((S)-3H-benzo[f]1,4-diazepin-3-yl))carboxamide Diisopropylethylamine (2.5 mL, 15.0 mmol) and HATU (2.85 g, 7.5 mmol) were added to a solution of 1-[(tert-butoxy)carbonylamino]cyclohexanecarboxylic acid (1.75 g, 7.2 mmol) in CH$_2$Cl$_2$ (10 mL) at 0° C. and stirred for 10 min. (S)-3-amino-1-methyl-5-phenyl-3H-benzoazepin-2-one (3.0 g, 6.0 mmol) was then added. The solution was allowed to warm to room temperature and stirred overnight. The reaction was quenched with water. The organic layer was separated and washed with a saturated solution of NaHCO$_3$, 20% citric acid, brine, dried over Na$_2$SO$_4$, filtered and concentrated to afford a white solid (2.98 g, 99%). This compound underwent no further purification: $^1$H NMR (500 MHz, CD$_3$OD) δ 7.33-7.13 (m, 9 H), 5.35 (s, 1 H), 3.48 (s, 3 H), 2.21-1.29 (m, 10 H), 1.50, (s, 9 H).

(b) (Aminocyclohexyl)-N-(1-methyl-2-oxo-5-phenyl((S)-3H-benzo[f]1,4-diazepin-3-yl))carboxamide A saturated solution of HCl in EtOAc (50 mL) was added to a solution of {[(tert-butoxy)carbonylamino]cyclohexyl}-(S)-3-N-(1-methyl-2-oxo-5-phenyl(3H-benzoazepin-3-yl))carboxamide (2.9 g, 5.9 mmol) in EtOAc (75 mL) and stirred at room temperature overnight. The reaction was quenched with 1N NaOH (100 mL). The organic layer was separated, and the aqueous layer was extracted with EtOAc. The organic layers were combined, washed with brine, dried over $Na_2SO_4$, filtered and concentrated to give a white solid (1.76 g, 77%). mp 106-110° C.; $^1$H NMR (500 MHz, $CD_3OD$) δ 7.33-7.13 (m, 9 H), 5.32 (s, 1 H), 3.48 (s, 3 H), 1.98-1.25 (m, 10 H); CI MS m/z=391 $[C_{23}H_{26}N_4O_2+H]^+$; HPLC 100%, $t_r$=9.17 min. (HPLC Conditions A).

(c) 2-(3,5-Difluorophenyl)-N-{[N-(1-methyl-2-oxo-5-phenyl((S)-3H-benzo[f]1,4-diazepin-3-yl))carbamoyl]-cyclohexyl}acetamide Diisopropylethylamine (0.87 ml, 5.15 mmol) and HATU (979 mg, 2.58 mmol) were added to a solution of 2-(3,5-difluorophenyl)acetic acid (426 mg, 2.47 mmol) in $CH_2Cl_2$ (40 mL) at 0° C. and stirred for 5 min. (Aminocyclohexyl)-(S)-3-N-(1-methyl-2-oxo-5-phenyl(3H-benzoazepin-3-yl))carboxamide (800 mg, 2.06 mmol) was then added, and the solution was allowed to warm to room temperature and stirred overnight. The reaction was quenched with water. The organic layer was separated and washed with a saturated solution of $NaHCO_3$, 20% citric acid, brine, dried over $Na_2SO_4$, filtered and concentrated to give a white solid. Further purification by flash column chromatography afforded the title compound (659 mg, 60%) as a white solid: mp 126-129° C.; $^1$H NMR (500 MHz, $CD_3OD$) δ 7.72-7.32 (m, 9 H), 6.97 (d, 2 H), 6.80 (t, 1 H), 5.31 (s, 1 H), 3.70 (s, 2 H), 3.48 (s, 3 H), 2.24-1.30 (m 10 H); API MS m/z=545 $[C_{31}H_{30}F_2N_4O_3+H]^+$; HPLC 99.5%, $t_r$=22.26 min. (HPLC Conditions A).

Example 5

2-(3,5-Difluorophenyl)-N-{[N-(1-methyl-2-oxo-5-phenyl((S)-3H-benzo[f]1,4-diazepin-3-yl))carbamoyl]cyclopentyl}-acetamide

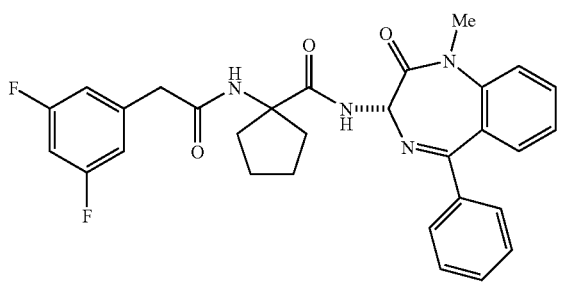

The title compound was prepared in a manner similar to that described for Example 4. The product was obtained as a solid. mp 112-117° C.; $^1$H NMR (500 MHz, $CD_3OD$) δ 7.72-7.31(m, 9 H), 6.96 (d, 2 H), 6.81 (t, 1 H) 5.33 (s, 1 H), 3.63 (s, 2 H), 3.47 (s, 3 H), 2.41-1.72 (m, 8 H); API MS m/z=531 $[C_{30}H_{28}F_2N_4O_3+H]^+$; HPLC 99.4%, $t_r$=21.23 min. (HPLC Conditions A).

Example 6

2-(3,5-Difluorophenyl)-N-{[N-(1-methyl-2-oxo-5-phenyl((S)-3H-benzo[f]1,4-diazepin-3-yl))carbamoyl]cyclopropyl}-acetamide

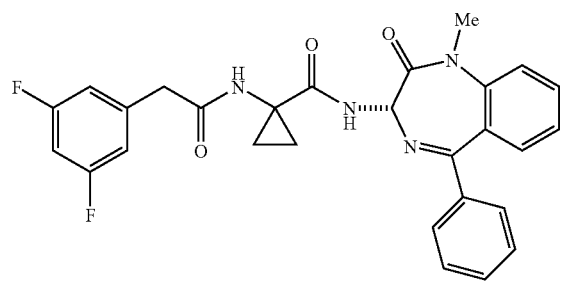

The title compound was prepared in a manner similar to that described for Example 4. The product was obtained as a solid. mp 212-214° C.; $^1$H NMR (500 MHz, $CD_3OD$) δ 7.71-7.30 (m, 9 H), 6.98 (d, 2 H), 6.81 (t, 1 H), 5.28 (s, 1 H), 3.65 (s, 2 H), 3.48 (s, 3 H), 1.48 (m, 2 H), 1.08 (m, 2H); API MS m/z=503 $[C_{28}H_{24}F_2N_4O_3+H]^+$; HPLC 97.7%, $t_r$=19.48 min. (HPLC Conditions A).

Example 7

3-Cyclopentyl-N-{[N-(1-methyl-2-oxo-5-phenyl((S)-3H-benzo[f]1,4-diazepin-3-yl))carbamoyl]cyclohexyl}propanamide

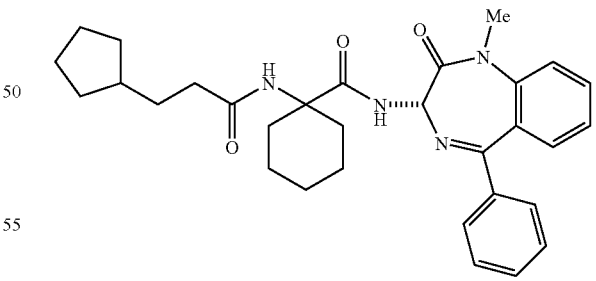

The title compound was prepared in a manner similar to that described for Example 4. The product was obtained as a solid. mp 88-103° C.; $^1$H NMR (500 MHz, $CD_3OD$) δ 7.71-7.30 (m, 9 H), 5.28 (d, 1 H), 3.51 (d, 3 H), 2.39-0.82 (m, 23 H); CI MS m/z=516 $[C_{31}H_{38}N_4O_3+H]^+$; HPLC 96.5%, $t_r$=14.79 min. (HPLC Conditions A).

Example 8

2-(3,5-Difluorophenyl)-N-{4-[N-(1-methyl-2-oxo-5-phenyl((S)-3H-benzo[f]1,4-diazepin-3-yl))carbamoyl](4-piperidyl)}acetamide

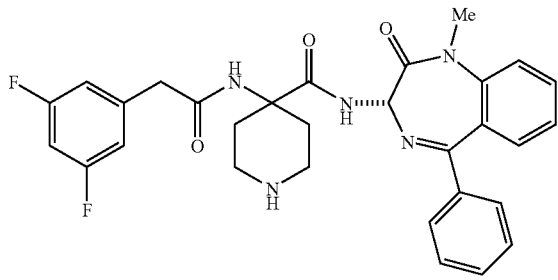

The title compound was prepared in a manner similar to that described for Example 4. The product was obtained as an oil. $^1$H NMR (300 MHz, CD$_3$OD) δ 7.15-7.60 (m, 10H), 6.05-6.80 (m, 3H), 5.40 (d, 1H), 3.60 (s, 2H), 3.40 (s, 3H), 2.90 (m, 2H), 2.60 (m, 2H), 2.05, (m, 4H). MS [M+H]$^+$ 546.

Example 9

Phenyl 4-[2-(3,5-difluorophenyl)acetylamino]-4-[N-(1-methyl-2-oxo-5-phenyl((S)-3H-benzo[f]1,4-diazepin-3-yl))carbamoyl]piperidine carboxylate

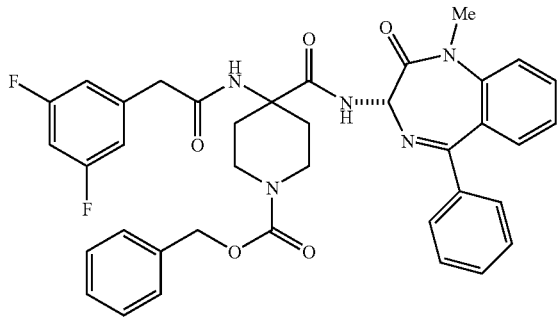

The title compound was prepared in a manner similar to that described for Example 4. The product was obtained as an oil. $^1$H NMR (300 MHz, CD$_3$OD) δ 7.20-7.40 (m, 15H), 6.45-6.80 (m, 3H), 5.40 (d, 1H), 5.15 (s, 2H), 4.85 (s, 3H), 3.85 (m, 1H), 3.60 (s, 2H), 3.40 (s, 3H), 2.20, (m, 4H). MS [M+H]$^+$ 680.

Example 10

4-Methyl-N-{[N-(5-methyl-6-oxo(7H-dibenzo[d,f]azaperhydroepin-7-yl))carbamoyl]cyclopentyl}pentanamide

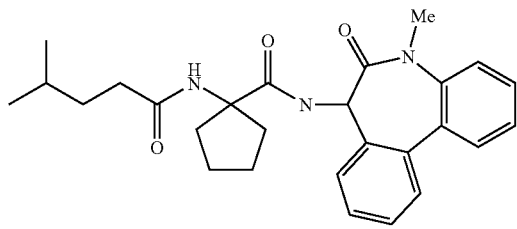

The title compound was prepared in a manner similar to that described for Example 4. This compound was made from the amino bisbenzazepine obtained as the first eluting peak of a racemic mixture on a CHIRALCEL OD column with 20% iPrOH/Hexane with diethylamine. The product was obtained as an oil. $^1$H NMR (300 MHz, CD$_3$OD) δ 7.20-7.60 (m, 8H), 6.59 (s, 1H), 5.20 (d, 1H), 3.40 (s, 3H), 2.40-1.60 (m, 13H), 0.9, (d, 6H). MS [M+H$^+$ 448.

Example 11

N-{1-Methyl-2-oxo-5-[4-(trifluoromethyl)phenyl](3H-benzo[f]1,4-diazepin-3-yl)}{[(phenylmethoxy)carbonylamino]-cyclopentyl}carboxamide

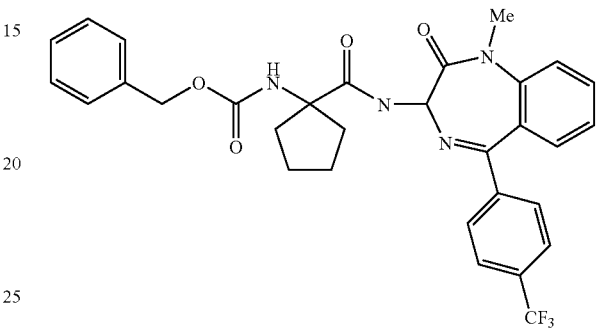

The title compound was prepared in a manner similar to that described for Example 4. This compound was made from the corresponding amino benzodiazepine that, as the CBz protected form, was the first eluting peak of the racemic mixture on a CHIRALCEL AD column using acetonitrile. The product was obtained as an oil. $^1$H NMR (300 MHz, CD$_3$OD) δ 7.20-7.40 (m, 13H), 5.2 (s, 2H), 5.60 (m, 1H), 5.40 (d, 1H), 5.15 (s, 2H), 3.45 (s, 3H), 2.40 (m, 2H), 2.05-1.80 (m, 6H). MS [M+H]$^+$ 579.

Example 12

(2S)-N-{[N-(1-{[3-(4-Fluorophenoxy)phenyl]methyl}-2-oxoazaperhydroepin-3-yl)carbamoyl]cyclopropyl}-2-hydroxy-4-methylpentanamide

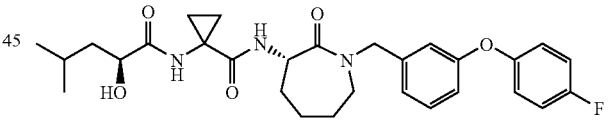

The title compound was prepared in a manner similar to that described for Example 4. The product was obtained as an oil. $^1$H NMR (300 MHz, CD$_3$OD) δ 7.00-6.70 (m, 8H), 4.45 (m, 5H), 4.15 (m, 1H), 3.10-3.40 (m, 2H), 2.00-1.00 (m, 12H), 0.90, (m, 6H). MS [M+H]$^+$ 526.

Example 13

(2S)-N-{[N-(1-{[3-(4-Fluorophenoxy)phenyl]methyl}-2-oxoazaperhydroepin-3-yl)carbamoyl]cyclopentyl}-2-hydroxy-3-methylbutanamide

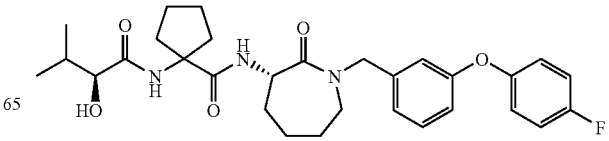

The title compound was prepared in a manner similar to that described for Example 4. The product was obtained as an oil. $^1$H NMR (300 MHz, CD$_3$OD) δ 7.20-6.80 (m, 8H), 4.60 (m, 3H), 4.00 (d, 1H), 3.5 (m, 1H), 3.20 (m, 1H), 2.40-1.05 (m, 17H), 1.00 (d, 3H), 0.90 (d, 3H). MS [M+H]$^+$ 540.

Example 14

2,2-Difluoro-N-[(N-{1-methyl-2-oxo-5-[4-(trifluoromethyl)phenyl](3H-benzo[f]1,4-diazepin-3-yl)}carbamoyl)cyclopentyl]-4-phenylbutanamide

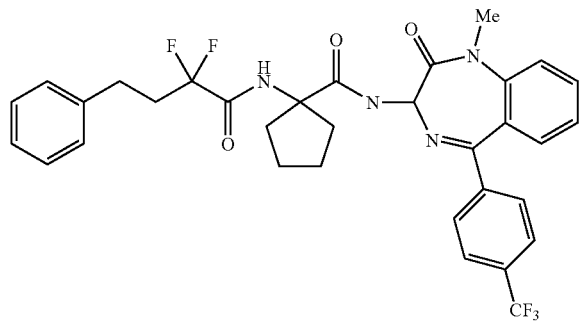

The title compound was prepared in a manner similar to that described for Example 4 using the amino benzodiazepine employed in Example 1. The product was obtained as an oil. $^1$H NMR (300 MHz, CD$_3$OD) δ 7.90-7.00 (m, 13H), 5.45 (d, 1H), 3.45 (s, 3H), 2.80 (m, 2H), 2.60-2.20 (m, 6H), 1.80-1.90 (m, 8H). MS [M+H]$^+$ 627.

Example 15

N-[(N-{1-Methyl-2-oxo-5-[4-(trifluoromethyl)phenyl](3H-benzo[f]1,4-diazepin-3-yl)}carbamoyl)cyclopentyl]-3-(4-piperidyl)propanamide

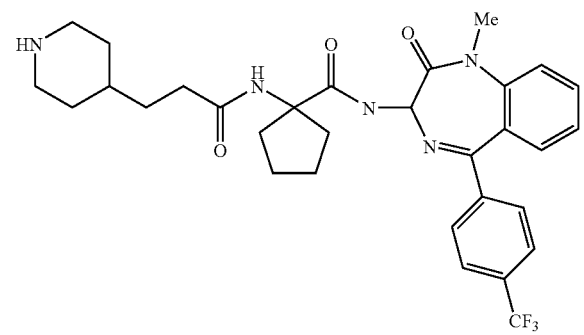

The title compound was prepared in a manner similar to that described for Example 4 using the amino benzodiazepine employed in Example 1. The product was obtained as an oil. $^1$H NMR (300 MHz, CD$_3$OD) δ 8.00-7.20 (m, 9H), 6.10 (s, 1H), 5.40 (d, 1H), 5.15 (s, 2H), 3.60 (m, 1H), 3.40 (s, 3H), 3.15 (m, 1H), 2.60-1.20 (m, 14H). MS [M+H]$^+$ 584.

Example 16

(2S)-2-Hydroxy-4-methyl-N-[(N-{1-methyl-2-oxo-5-[4-(trifluoromethyl)phenyl](3H-benzo[f]1,4-diazepin-3-yl)}carbamoyl)cyclopentyl]pentanamide

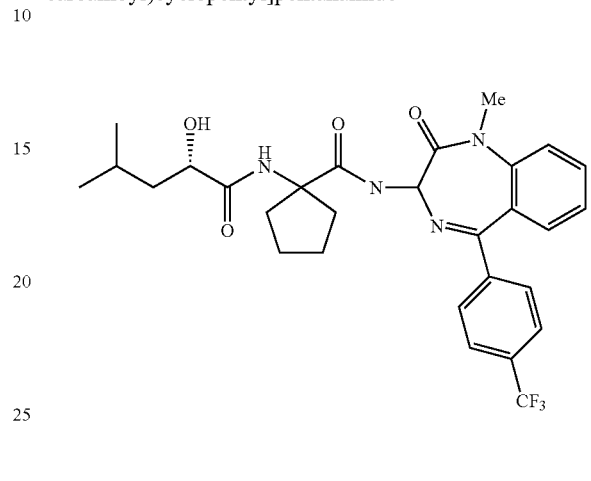

The title compound was prepared in a manner similar to that described for Example 4 using the amino benzodiazepine employed in Example 1. The product was obtained as an oil. MS [M+H]$^+$ 559.

Example 17

3-Cyclopropyl-N-[(N-{1-methyl-2-oxo-5-[4-(trifluoromethyl)phenyl](3H-benzo[f]1,4-diazepin-3-yl)}carbamoyl)cyclopentyl]propanamide

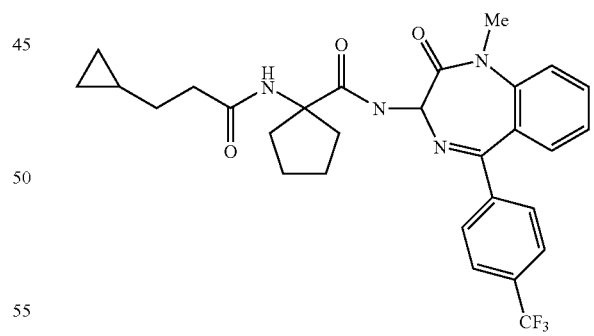

The title compound was prepared in a manner similar to that described for Example 4 using the amino benzodiazepine employed in Example 1. The product was obtained as an oil. $^1$H NMR (300 MHz, CD$_3$OD) δ 7.60-7.20 (m, 8H), 5.40 (m, 1H), 3.45 (s, 3H), 2.70 (s, 2H), 2.40 (m, 4H), 2.05-1.09 (m, 14H), 0.4 (m, 1H), 0.00 (m, 1H). MS [M+H]$^+$ 541.

Example 18

(Aminocyclopentyl)-N-{1-methyl-2-oxo-5-[4-(trifluoromethyl)phenyl](3H-benzo[f]1,4-diazepin-3-yl)}carboxamide

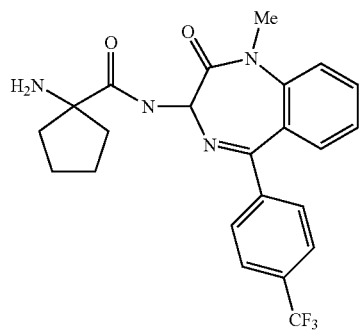

The title compound was prepared in a manner similar to that described for Example 4. This compound was made from the BZD amine that, as a CBz protected form, was the first peak of the racemic mixture on the CHIRALCEL AD column with acetonitrile. The product was obtained as an oil. $^1$H NMR (300 MHz, CD$_3$OD) δ 7.20-7.80 (m, 8H), 5.45 (m, 1H), 3.45 (s, 3H), 2.20 (m, 3H), 2.00-1.60 (m, 5H). MS [M+H]$^+$ 445.

Example 19

{[(Aminocyclopentyl)carbonylamino]cyclopentyl}-N-((S) 1-methyl-2-oxo-5-phenyl(3H-benzo[f]1,4-diazepin-3-yl)) carboxamide

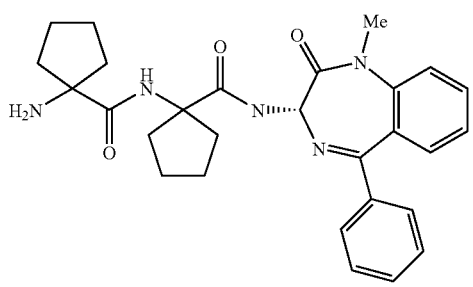

The title compound was prepared in a manner similar to that described for Example 4. The product was obtained as an oil. $^1$H NMR (300 MHz, CD$_3$OD) δ 7.20-7.60 (m, 9H); 5.45 (d, 1H), 3.45 (s, 3H), 2.80-2.00 (m, 8H), 1.90-1.50 (m, 8H). MS [M+H]$^+$ 445.

Example 20

(2R)-2-Hydroxy-3-imidazol-2-yl-N-[(N-{1-methyl-2-oxo-5-[4-(trifluoromethyl)phenyl](3H-benzo[f]1,4-diazepin-3-yl)}carbamoyl)cyclopentyl]propanamide

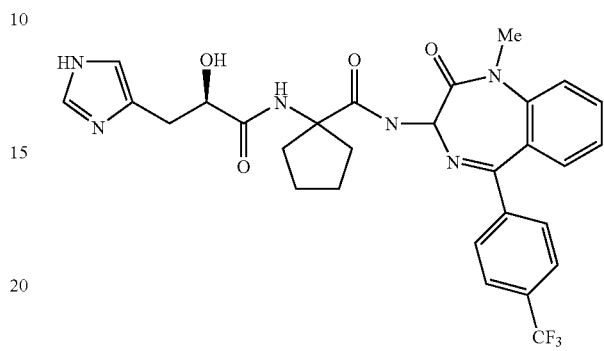

The title compound was prepared in a manner similar to that described for Example 4 using the amino benzodiazepine employed in Example 1. The product was obtained as an oil. $^1$H-NMR(CDCl$_3$) 9.16 (d, 1H), 7.69-7.52 (m, 5H), 7.33 (d, 1H), 7.24-7.15 (m, 3H), 5.45 (d, 1H), 3.42 (s, 3H), 2.24-2.14 (m, 3H), 2.11-1.84 (m, 1H), 1.83-1.72 (m, 4H), 1.66-1.56 (m, 2H); MS [M+H]$^+$ 583.

Example 21

2-Ethoxy-N-[(N-{1-methyl-2-oxo-5-[4-(trifluoromethyl)phenyl](3H-benzo[f]1,4-diazepin-3-yl)}carbamoyl)cyclopentyl]acetamide

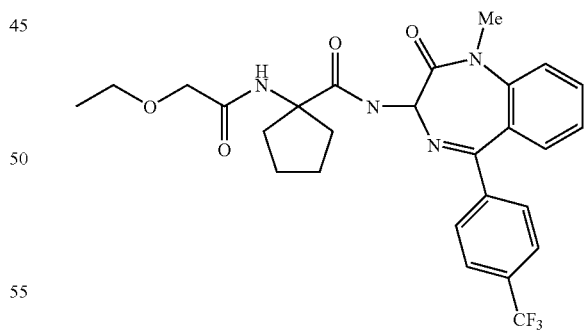

The title compound was prepared in a manner similar to that described for Example 4 using the amino benzodiazepine employed in Example 1. The product was obtained as an oil. $^1$H-NMR(CDCl$_3$) 8.17 (d, 1H), 7.76-7.60 (m, 5H), 7.40 (d, 1H), 7.32-7.23 (m, 1H), 6.99 (s, 1H), 5.52 (d, 1H), 4.01 (d, 2H), 3.67-3.60 (q, 2H), 3.48 (s, 3H), 2.48-2.40 (m, 2H), 2.14-2.08 (m, 2H), 1.89-1.83 (m, 3H), 1.64 (s, 2H), 1.29 (s, 3H); MS [M+H]$^+$ 531.

Example 22

3-Cyclopentyl-N-[(N-{1-methyl-2-oxo-5-[4-(trifluoromethyl)phenyl](3H-benzo[f]1,4-diazepin-3-yl)}carbamoyl)cyclopentyl]propanamide

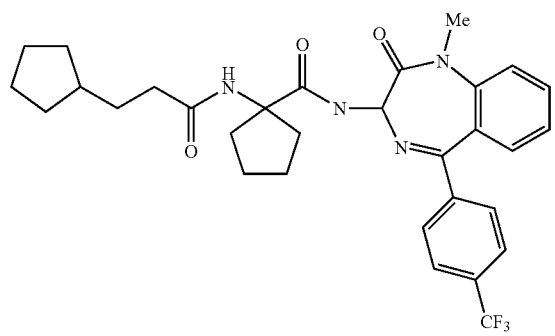

The title compound was prepared in a manner similar to that described for Example 4 using the amino benzodiazepine employed in Example 1. The product was obtained as an oil. $^1$H-NMR(CDCl$_3$) 8.00 (d, 1H), 7.68-7.51 (m, 5H), 7.32 (d, 1H), 7.23-7.17 (m, 2H), 5.85 (s, 1H), 5.41 (d, 1H), 3.39 (s, 3H), 2.42-2.22 (m, 2H), 2.20 (t, 2H), 2.10-1.90 (m, 2H), 1.76-1.44 (m, 13H), 1.10-1.0 (m, 2H); MS [M+H]$^+$ 569.

Example 23

(2S)-2-Hydroxy-3-methyl-N-[(N-{1-methyl-2-oxo-5-[4-(trifluoromethyl)phenyl](3H-benzo[f]1,4-diazepin-3-yl)}carbamoyl)cyclopentyl]butanamide

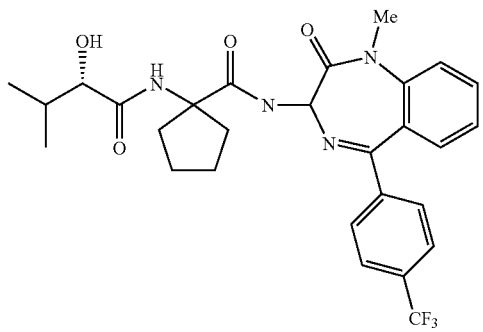

The title compound was prepared in a manner similar to that described for Example 4 using the amino benzodiazepine employed in Example 1. The product was obtained as an oil. $^1$H-NMR(CDCl$_3$) 8.50 (d, 1H), 7.76-7.61 (m, 4H), 7.41 (d, 1H), 7.32-7.28 (m, 1H), 7.03 (s, 1H), 5.53-5.51 (m, 1H), 4.06 (d, 1H), 3.48 (s, 3H), 2.57-2.35 (m, 2H), 2.30-2.10 (m, 2H), 2.09-1.90 (m, 1H), 1.80-1.70 (m, 5H), 1.05 (d, 3H), 0.94 (d, 3H); MS [M+H]$^+$ 545.

Example 24

(2S)-2-Cyclohexyl-2-hydroxy-N-[(N-{1-methyl-2-oxo-5-[4-(trifluoromethyl)phenyl](3H-benzo[f]1,4-diazepin-3-yl)}carbamoyl)cyclopentyl]acetamide

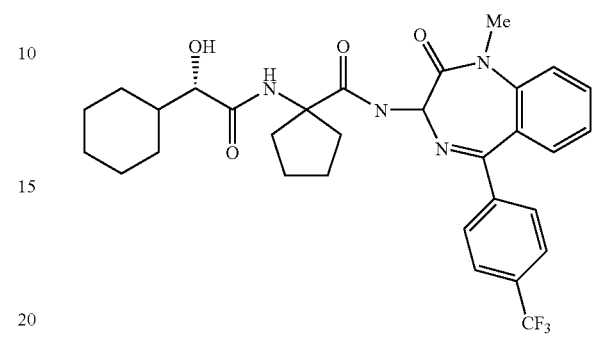

The title compound was prepared in a manner similar to that described for Example 4 using the amino benzodiazepine employed in Example 1. The product was obtained as an oil. $^1$H-NMR(CDCl$_3$) 8.04 (d, 1H), 7.67-7.51 (m, 4H), 7.31 (d, 1H), 7.23-7.18 (m, 1H), 7.02 (s, 1H), 5.42 (d, 1H), 3.94 (m, 1H), 3.78 (s, 3H), 2.42-2.25 (m, 2H), 2.18-1.90 (m, 2H), 1.80-1.65 (m, 9H), 1.30-1.00 (m, 6H); MS [M+H]+ 585.

Example 25

(2R)-2-Cyclohexyl-2-hydroxy-N-[(N-{1-methyl-2-oxo-5-[4-(trifluoromethyl)phenyl](3H-benzo[f]1,4-diazepin-3-yl)}carbamoyl)cyclopentyl]acetamide

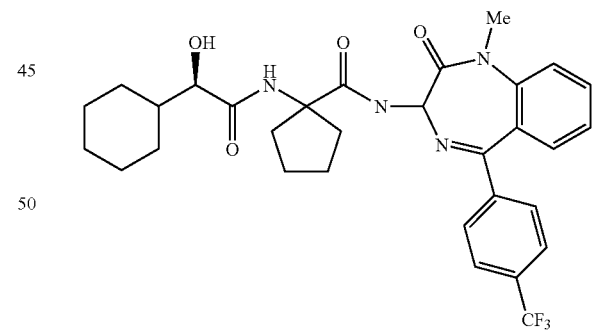

The title compound was prepared in a manner similar to that described for Example 4 using the amino benzodiazepine employed in Example 1. The product was obtained as an oil. $^1$H-NMR(CDCl$_3$) 8.17 (d, 1H), 7.67-7.52 (m, 4H), 7.32 (d, 1H), 7.23-7.15 (m, 1H), 6.89 (s, 1H), 5.45 (d, 1H), 3.92 (d, 1H), 3.39 (s, 3H), 2.45-2.25 (m, 2H), 2.10-1.95 (m, 2H), 1.80-1.50 (m, 10H), 1.25-1.00 (m, 6H); MS [M+H]$^+$ 585.

Example 26

(2S)-2-Amino-4-methyl-N-[(N-{1-methyl-2-oxo-5-[4-(trifluoromethyl)phenyl](3H-benzo[f]1,4-diazepin-3-yl)}carbamoyl)cyclopentyl]pentanamide

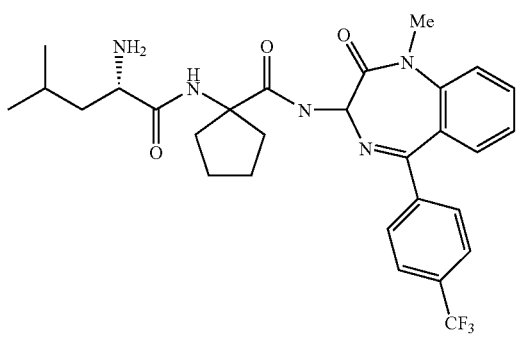

The title compound was prepared in a manner similar to that described for Example 4 using the amino benzodiazepine employed in Example 1. The product was obtained as an oil. $^1$H-NMR(CDCl$_3$) 8.95 (s, 1H), 7.79-7.63 (m, 5H), 7.40-7.30 (m, 2H), 5.46 (s, 1H), 4.20 (d, 2H), 4.0-3.90 (m, 1H), 3.51 (s, 3H), 2.40-2.20 (m, 2H), 2.10 2.00 (m, 2H), 1.90-1.70 (m, 4H), 1.40-1.20 (m, 2H), 1.10-1.00 (m, 3H), 1.00-0.90 (m, 3H); MS [M+H]$^+$ 559.

Example 27

[(Cyclohexylcarbonylamino)cyclopentyl]-N-{1-methyl-2-oxo-5-[4-(trifluoromethyl)phenyl](3H-benzo[f]1,4-diazepin-3-yl)}carboxamide

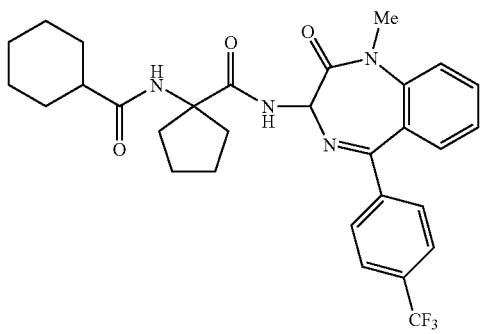

The title compound was prepared in a manner similar to that described for Example 4 using the amino benzodiazepine employed in Example 1. The product was obtained as an oil. $^1$H-NMR(CDCl$_3$) 8.10 (d, 1H), 7.75-7.62 (m, 3H), 7.42-7.39 (m, 3H), 7.30-7.20 (m, 1H), 6.11 (s, 1H), 5.47 (d, 1H), 3.46 (s, 3H), 2.50-2.45 (m, 2H), 2.30-2.10 (m, 1H), 2.09-1.75 (m, 9H), 1.70-1.60 (m, 1H), 1.50-1.40 (m, 2H), 1.39-1.20 (m, 3H); MS [M+H]$^+$ 555.

Example 29

{[N-(3-Methylbutyl)carbamoyl]cyclopentyl}-N-{1-methyl-2-oxo-5-[4-(trifluoromethyl)phenyl](3H-benzo[f]1,4-diazepin-3-yl)}carboxamide

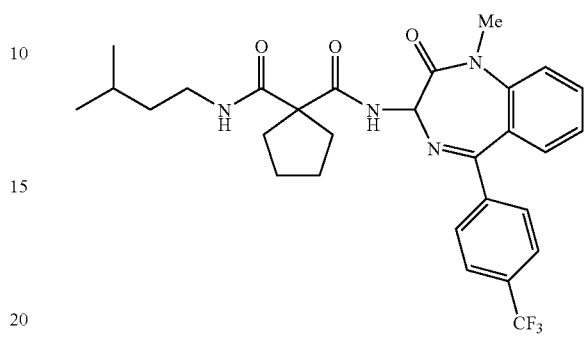

The title compound was prepared in a manner similar to that described for Example 4 using the amino benzodiazepine employed in Example 1. The product was obtained as an oil. $^1$H NMR (300 MHz CDCl$_3$) 7.78-7.60 (m, 5H), 7.48-7.22 (m, 3H), 5.47 (d, 1H), 3.49 (s, 3H), 3.30 (m, 2H), 2.38-2.22 (m, 4H), 1.84-1.38 (m, 7H), 0.90 (d, 6H). MS [M+H]$^+$ 543.

Example 30

4-Methyl-N-[(N-{1-methyl-2-oxo-5-[4-(trifluoromethyl)phenyl](3H-benzo[f]1,4-diazepin-3-yl)}carbamoyl)cyclopentyl]pentanamide

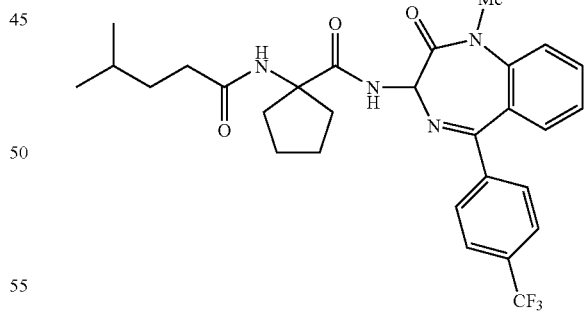

The title compound was prepared in a manner similar to that described for Example 4 using the amino benzodiazepine employed in Example 1. The product was obtained as an oil. $^1$H NMR (300 MHz CDCl$_3$) 7.78-7.56 (m, 5H), 7.42-7.20 (m, 3H), 5.46 (d, 1H), 3.44(s, 3H), 2.48-2.20 (m, 4H), 2.05 (m, 2H), 1.80 (m, 4H), 1.58 (m, 3H), 0.88 (d, 6H). MS [M+H]$^+$ 543.

Example 31

(2S)-2-Hydroxy-4-methyl-N-[(N-{1-methyl-2-oxo-5-[4-(trifluoromethyl)phenyl](3H-benzo[f]1,4-diazepin-3-yl)}carbamoyl)cyclopentyl]pentanamide

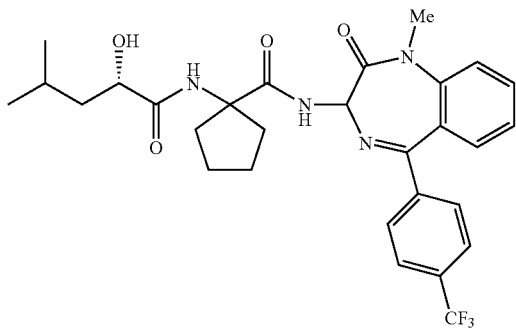

The title compound was prepared in a manner similar to that described for Example 4 using the amino benzodiazepine employed in Example 1. The product was obtained as an oil. $^1$H NMR (300 MHz CDCl$_3$) 7.78-7.58 (m, 5H), 7.43-7.20 (m, 3H), 5.49 (d, 1H), 4.17 (m, 1H), 3.45 (s, 3H), 2.40 (m, 2H), 2.10 (m, 2H), 1.92-1.50 (m, 8H), 0.92 (m, 6H). MS [M+H]$^+$ 559.

Example 32

3-Methoxy-N-[(N-{1-methyl-2-oxo-5-[4-(trifluoromethyl)phenyl](3H-benzo[f]1,4-diazepin-3-yl)}carbamoyl)cyclopentyl]propanamide

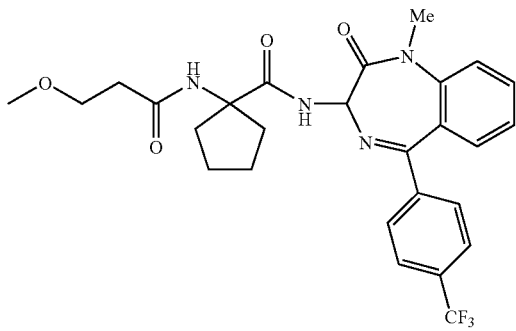

The title compound was prepared in a manner similar to that described for Example 4 using the amino benzodiazepine employed in Example 1. The product was obtained as an oil. $^1$H NMR (300 MHz CDCl$_3$) 7.78-7.56 (m, 5H), 7.40-7.20 (m, 3H), 5.51 (d, 1H), 3.72 (m, 2H), 3.44 (s, 3H), 3.39 (s, 3H), 2.58-2.30 (m, 4H), 2.02 (m, 2H), 1.88 (m, 4H). MS [M+H]$^+$ 531.

Example 33

(2S)-2-Hydroxy-N-[(N-{1-methyl-2-oxo-5-[4-(trifluoromethyl)phenyl](3H-benzo[f]1,4-diazepin-3-yl)}carbamoyl)cyclopentyl]-3-phenylpropanamide

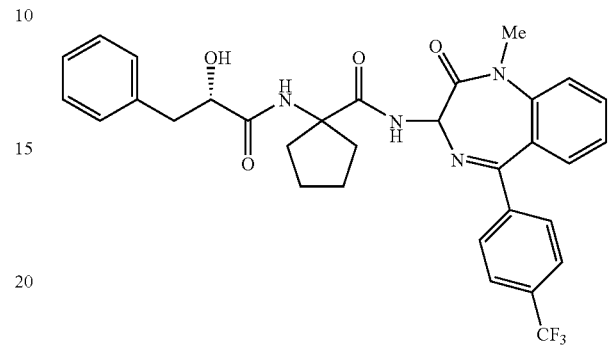

The title compound was prepared in a manner similar to that described for Example 4 using the amino benzodiazepine employed in Example 1. The product was obtained as an oil. $^1$H NMR (300 MHz CDCl$_3$) 7.72-7.57 (m, 5H), 7.40-7.20 (m, 3H), 5.48 (d, 1H), 4.37 (m, 1H), 3.42 (s, 3H), 3.20 (q, 1H), 2.97 (q, 1H), 2.38 (m, 2H), 1.96 (m, 2H), 1.80-1.52 (m, 4H). MS [M+H]$^+$ 593.

Example 34

N-[(N-{1-Methyl-2-oxo-5-[4-(trifluoromethyl)phenyl](3H-benzo[f]1,4-diazepin-3-yl)}carbamoyl)cyclopentyl]-2-(phenylmethoxy)acetamide

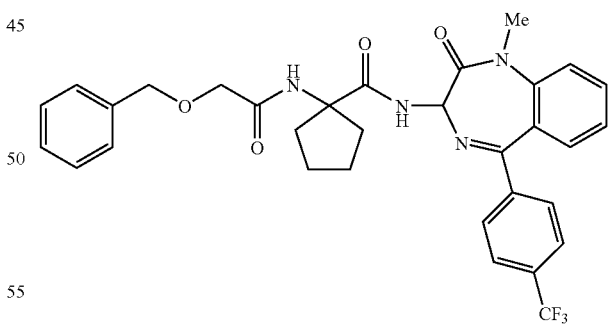

The title compound was prepared in a manner similar to that described for Example 4 using the amino benzodiazepine employed in Example 1. The product was obtained as an oil. $^1$H NMR (300 MHz CDCl$_3$) 7.74-7.55 (m, 5H), 7.40-7.20 (m, 3H), 5.48 (d, 1H), 4.61 (q, 2H), 4.12 (q, 2H), 3.44 (s, 3H), 2.42 (m, 2H), 2.05 (m, 2H), 1.80 (m, 4H). MS [M+H]$^+$ 593.

Example 35

(2S)-2-Hydroxy-3-methyl-N-{[N-(5-methyl-6-oxo(7H-dibenzo[d,f]azaperhydroepin-7-yl))carbamoyl]cyclopentyl}-butanamide

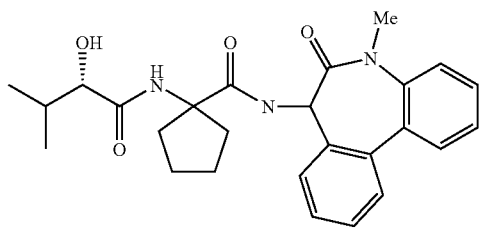

The title compound was prepared in a manner similar to that described for Example 4 using the amino bisbenzazepine employed in Example 10. The product was obtained as an oil. $^1$H NMR (300 MHz CDCl$_3$) 7.64-7.35 (m, 8H), 5.25 (d, 1H), 4.06 (d, 1H), 3.35 (s, 3H), 2.42-2.05 (m, 6H), 1.80 (m, 4H), 1.05 (d, 3H), 0.95 (d, 3H). MS [M+H]$^+$ 450.

Example 36

(2S)-2-Hydroxy-4-methyl-N-{[N-(5-methyl-6-oxo(7H-dibenzo[d,f]azaperhydroepin-7-yl))carbamoyl]cyclopentyl}pentanamide

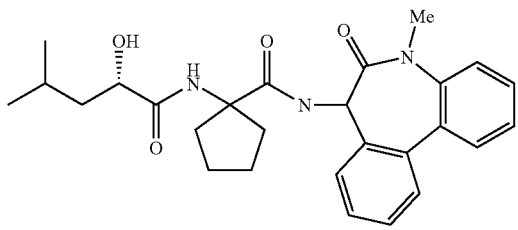

The title compound was prepared in a manner similar to that described for Example 4 using the amino bisbenzazepine employed in Example 10. The product was obtained as an oil. $^1$H NMR (300 MHz CDCl$_3$) 7.64-7.32 (m, 8H), 5.24 (d, 1H), 4.20 (q, 1H), 3.34 (s, 3H), 2.38 (m, 2H), 2.20-1.60 (m, 9H), 0.97 (m, 6H). MS [M+H]$^+$ 464.

Example 37

3-Cyclopentyl-N-{[N-(5-methyl-6-oxo(7H-dibenzo[d,f]azaperhydroepin-7-yl))carbamoyl]cyclopentyl}propanamide

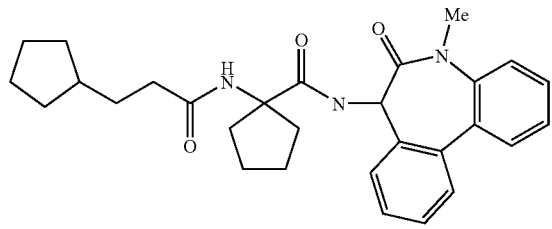

The title compound was prepared in a manner similar to that described for Example 4 using the amino bisbenzazepine employed in Example 10. The product was obtained as an oil. $^1$H NMR (300 MHz CDCl$_3$) 7.64-7.35 (m, 8H), 5.25 (d, 1H), 3.36 (s, 3H), 2.42-1.45 (m, 21H). MS [M+H]$^+$ 474.

Example 38

(2S)-2-Cyclohexyl-2-hydroxy-N-{[N-(5-methyl-6-oxo(7H-dibenzo[d,f]azaperhydroepin-7-yl))carbamoyl]cyclopentyl}-acetamide

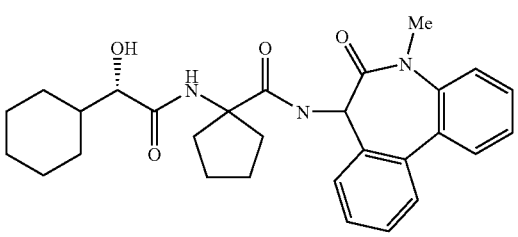

The title compound was prepared in a manner similar to that described for Example 4 using the amino bisbenzazepine employed in Example 10. The product was obtained as an oil. $^1$H NMR (300 MHz CDCl$_3$) 7.62-7.36 (m, 8H), 5.24 (d, 1H), 3.98 (d, 1H), 3.33 (s, 3H), 2.42-1.04 (m, 19H). MS [M+H]$^+$ 490.

Example 39

3-Cyclopropyl-N-{[N-((S)-5-methyl-6-oxo(7H-dibenzo[d,f]azaperhydroepin-7-yl))carbamoyl]cyclopentyl}-propanamide

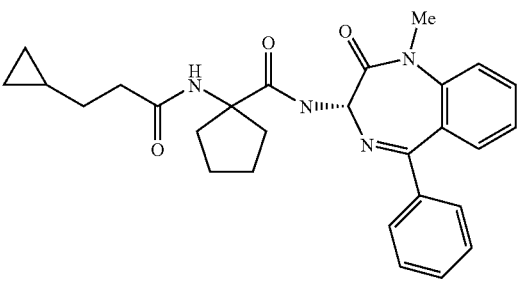

The title compound was prepared in a manner similar to that described for Example 4. The product was obtained as an oil. $^1$H NMR (300 MHz CDCl$_3$) 7.56-7.24 (m, 8H), 5.16 (d, 1H), 3.27 (s, 3H), 2.38-2.15 (m, 4H), 2.10-1.82 (m, 2H), 1.78-1.42 (m, 6H), 0.64 (m, 1H), 0.36 (m, 2H), 0.02 (m, 2H). MS [M+H]$^+$ 446.

Example 40

N-{[N-(1-Butyl-5-cyclopentyl-2-oxo(3H-benzo[f]1,4-diazepin-3-yl))carbamoyl]cyclopentyl}-4-methylpentanamide

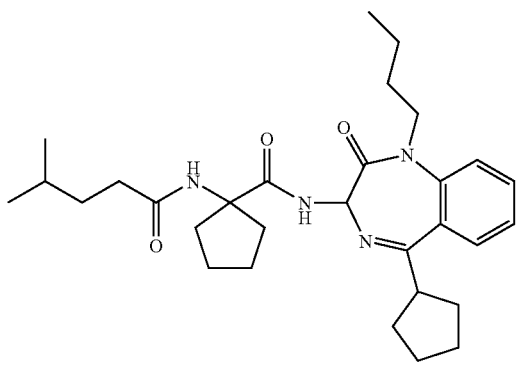

The amino benzodiazepine core was made in a manner similar to that described in the Scheme 6. The title compound was prepared in a manner similar to that described for Example 4. The product was obtained as an oil. $^1$H NMR (300 MHz CDCl$_3$) 7.60-7.22 (m, 4H), 5.25 (d, 1H), 4.36 (m, 1H), 3.56 (m, 1H), 3.31 (m, 1H), 2.40-0.78 (m, 34H). MS [M+H]$^+$ 509.

Example 41

N-{[N-(5-Cyclopentyl-1-methyl-2-oxo(3H-benzo[f]1,4-diazepin-3-yl))carbamoyl]cyclopentyl}-4-methylpentanamide

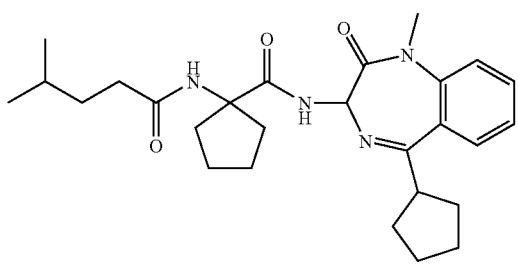

The amino benzodiazepine core was made in a manner similar to that described in the Scheme 6. The title compound was prepared in a manner similar to that described for Example 4. The product was obtained as an oil. $^1$H NMR (300 MHz CDCl$_3$) 7.58-7.20 (m, 4H), 5.30 (d, 1H), 3.38 (s, 3H), 3.30 (m, 1H), 2.40-1.20 (m, 21H), 0.89 (d, 6H). MS [M+H]$^+$ 467.

Example 42

(2S)-2-Hydroxy-3-methyl-N-({N-[2-oxo-1-benzyl(3H,4H,5H-benzo[f]azaperhydroepin-3-yl)]carbamoyl}cyclopentyl)butanamide

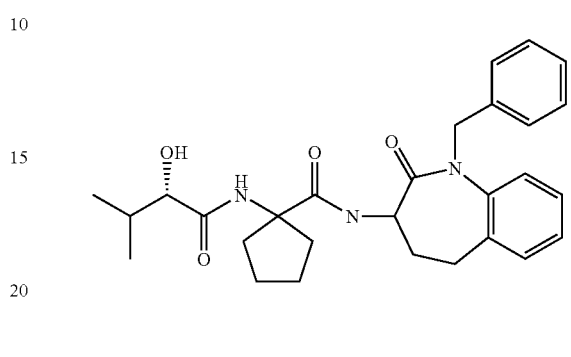

The amino benzoazepine core was made in a manner similar to that described in J. Med. Chem. 1999, 42, 2621. The title compound was prepared in a manner similar to that described for Example 4. The product was obtained as an oil. $^1$H NMR (300 MHz CDCl$_3$) 7.34-7.10 (m, 9H), 5.16 (m, 1H), 4.76 (m, 1H), 4.42 (m, 1H), 3.94 (m, 1H), 2.64-1.64 (m, 13H), 1.00-0.86 (m, 6H). MS [M+H]$^+$ 478.

Example 43

(2S)-4-Methyl-N-{[N-(5-methyl-6-oxo(7H-dibenzo[d,f]azaperhydroepin-7-yl))carbamoyl]cyclopentyl}-2-[(propylsulfonyl)amino]pentanamide

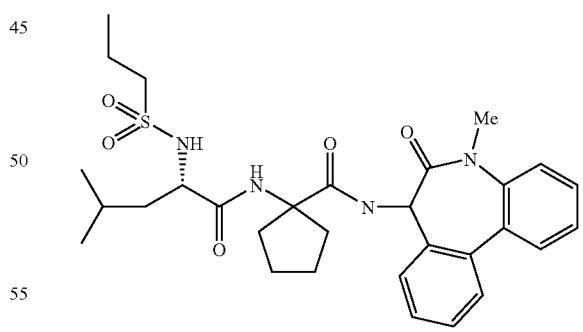

The title compound was prepared in a manner similar to that described for Example 4 using the amino bisbenzazepine employed in Example 10. The product was obtained as an oil. $^1$H NMR (300 MHz CDCl$_3$) 7.62-7.32 (m, 8H), 5.40 (d, 1H), 5.24 (d, 1H), 4.02 (m, 1H), 3.34 (s, 3H), 2.98 (m, 2H), 2.42-1.58 (m, 13H), 0.94-0.85 (m, 9H). MS [M+H]$^+$ 569.

Example 44

(2S)-2-Amino-4-methyl-N-{[N-(5-methyl-6-oxo(7H-dibenzo[d,f]azaperhydroepin-7-yl))carbamoyl]cyclopentyl}pentanamide

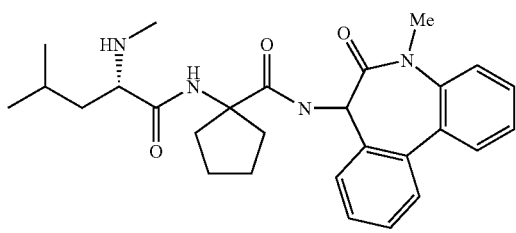

The title compound was prepared in a manner similar to that described for Example 4 using the amino bisbenzazepine employed in Example 10. The product was obtained as an oil. $^1$H NMR (300 MHz CDCl$_3$) 7.60-7.30 (m, 8H), 5.22 (d, 1H), 3.32 (s, 3H), 3.08 (m, 1H), 2.48 (s, 3H), 2.46-1.45 (m, 11H), 0.98-0.92 (q, 6H). MS [M+H]$^+$ 477.

Example 45

2,2-Difluoro-4-methyl-N-([N-(5-methyl-6-oxo(7H-dibenzo[d,f]azaperhydroepin-7-yl))carbamoyl]cyclopentyl)-pentanamide

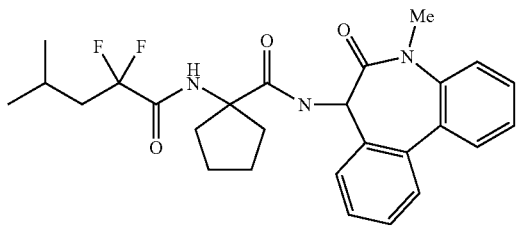

The title compound was prepared in a manner similar to that described for Example 4 using the amino bisbenzazepine employed in Example 10. The product was obtained as an oil. $^1$H NMR (300 MHz CDCl$_3$) 7.62-7.30 (m, 8H), 5.23 (d, 1H), 3.34 (s, 3H), 2.42-1.80 (m, 11H), 1.00 (d, 6H). MS [M+H]$^+$ 484.

Example 56

4-Methyl-N-{(N-(6-oxo(5H,7H-dibenzo[d,f]azaperhydroepin-7-yl))carbamoyl]cyclopentyl}pentanamide

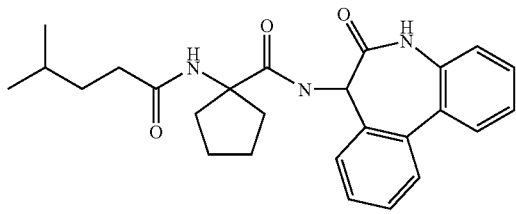

The title compound was prepared in a manner similar to that described for Example 4. The product was obtained as an oil. $^1$H NMR (300 MHz, CD$_3$OD): δ 7.91 (d, J=6.7 Hz, 1 H), 7.63 (m, 1 H), 7.51-7.28 (m, 7 H), 7.08 (d, J=7.0 Hz, 1 H), 5.84 (s, 1 H), 5.25 (d, J=6.7 Hz, 1 H), 2.41-0.89 (m, 19 H); ESI MS m/z=434 [C$_{26}$H$_{31}$N$_3$O$_3$+H]$^+$.

Example 57

N-({N-[5-(3,3-Dimethyl-2-oxobutyl)-6-oxo(7H-dibenzo[d,f]azaperhydroepin-7-yl)]carbamoyl}cyclopentyl)-4-methylpentanamide

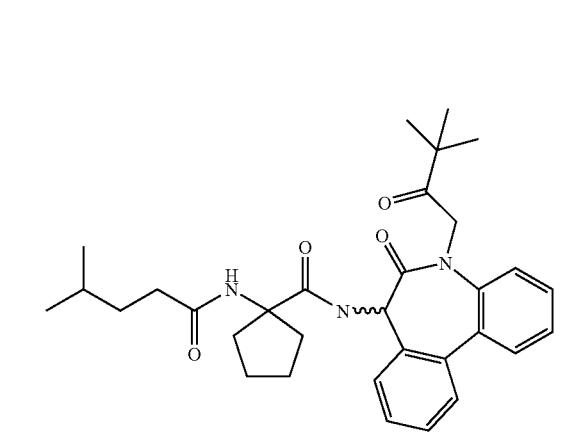

To a solution of 4-methyl-N-{[N-(6-oxo(5H,7H-dibenzo[d,f]azaperhydroepin-7-yl))carbamoyl]cyclopentyl}pentanamide (540 mg, 1.3 mmol), in DMF (25 mL) was added K$_2$CO$_3$ (0.52 g, 3.7 mmol) and bromopinacolone (0.45 g, 2.5 mmol), and the solution was allowed to stir for 40 h at room temperature. The contents of the flask were partitioned between EtOAc and a 5% LiCl solution (150 mL each), the organic phase washed with 5% LiCl (2×50 mL), dried over anhydrous Na$_2$SO$_4$ and concentrated to yield a white solid. This was further purified by column chromatography [silica gel, EtOAc/hexanes (35:65)] to yield the title compound (340 mg, 51%) as a white solid. The title compound were separated by chiral HPLC using the following conditions: Column, Chiralpak AD column (5 cm×50 cm); Eluent, 96:4 Hexanes/2-Propanol; Flow rate, 100 mL/min; Monitoring wavelength, 220 nm.

Enantiomer A: 158 mg: mp 126-130° C.; $^1$H NMR (300 MHz, CDCl$_3$) δ 7.89 (d, J=6.7 Hz, 1 H), 7.62-7.13 (m, 8 H), 5.82 (s, 1 H), 5.35 (d, J=7.4 Hz, 1 H), 4.62 (q$_{ab}$, J=14.1 Hz, 2 H), 2.47-1.59 (m, 13 H), 1.22 (s, 9 H), 0.92 (d, J=5.8 Hz, 6 H); IR (KBr) 3410, 2958, 2475, 1724, 1663 cm$^{-1}$; ESI MS m/z=532 [C$_{32}$H$_{41}$N$_3$O$_4$+H]$^+$; HPLC 97.8%, t$_r$=24.83 min. (HPLC Conditions A).

Enantiomer B: 165 mg; mp 126-130° C.; $^1$H NMR (300 MHz, CDCl$_3$) δ 7.89 (d, J=6.7 Hz, 1 H), 7.62-7.13 (m, 8 H), 5.82 (s, 1 H), 5.35 (d, J=7.4 Hz, 1 H), 4.62 (q$_{ab}$, J=14.1 Hz, 2 H), 2.47-1.59 (m, 13 H), 1.22 (s, 9 H), 0.92 (d, J=5.8 Hz, 6 H); IR (KBr) 3410, 2958, 2475, 1724, 1663 cm$^{-1}$; ESI MS m/z=532 [C$_{32}$H$_{41}$N$_3$O$_4$+H]$^+$; HPLC 97.8%, t$_r$=24.83 min. (HPLC Conditions A).

Example 58

4-Methyl-N-[(N-{6-oxo-5-[(3-phenoxyphenyl)methyl](7H-dibenzo[d,f]azaperhydroepin-7-yl)}carbamoyl)cyclopentyl]pentanamide

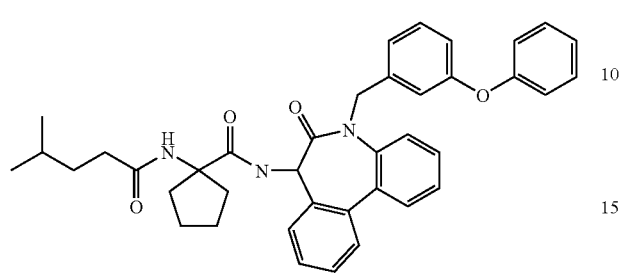

The title compound was prepared in a manner similar to that described for Example 57. The product was obtained as a white solid: mp 94-100° C.; $^1$H NMR (500 MHz, CDCl$_3$) δ 7.99 (d, J=6.9 Hz, 1 H), 7.58-6.43 (m, 17 H), 5.82 (s, 1 H), 5.39 (d, J=7.4 Hz, 1 H), 5.12 (q$_{ab}$, J=14.5 Hz, 2 H), 2.47-1.57 (m, 13 H), 0.82 (d, J=6.1 Hz, 6 H); IR (KBr) 3332, 2955, 1660, 1584, 1487 cm$^{-1}$; ESI MS m/z=616 [C$_{39}$H$_{41}$N$_3$O$_4$+H]$^+$; HPLC 99.4%, t$_r$=19.54 min. (HPLC Conditions A).

Example 59

N-{[N-(5-Butyl-6-oxo(7H-dibenzo[d,f]azaperhydroepin-7-yl))carbamoyl]cyclopentyl}-4-methylpentanamide

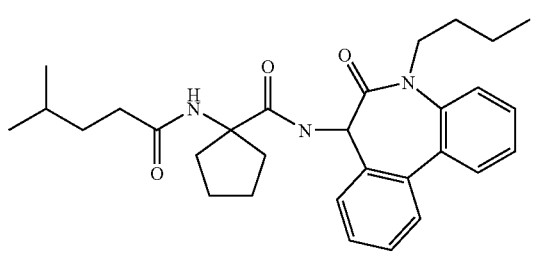

The title compound was prepared in a manner similar to that described for Example 57. The product was obtained as a white solid. The enantiomers were separated by chiral HPLC using the following conditions: Column, Chiralcel OD column (5 cm×50 cm); Eluent, 95:5 Hexanes/2-Propanol; Flow rate, 100 mL/min; Monitoring wavelength, 270 nm.

Enantiomer A: 197 mg: mp 123-126° C.; $^1$H NMR (500 MHz, CDCl$_3$) δ 7.99 (d, J=7.0 Hz, 1 H), 7.58-6.43 (m, 8 H), 5.91 (s, 1 H), 5.26 (d, J=7.4 Hz, 1 H), 4.29 (m, 2 H), 3.52 (m, 2 H), 2.43-1.19 (m, 15 H), 0.95 (d, J=6.1 Hz, 6 H), 0.62 (m, 3 H); IR (KBr) 3325, 2957, 2871, 1655, 1498 cm$^{-1}$; ESI MS m/z=490 [C$_{30}$H$_{39}$N$_3$O$_3$+H]$^+$; HPLC 100%, t$_r$=20.25 min. (HPLC Conditions A).

Enantiomer B: 167 mg: mp 110-115° C.; $^1$H NMR (500 MHz, CDCl$_3$) δ 7.99 (d, J=7.0 Hz, 1 H), 7.58-6.43 (m, 8 H), 5.91 (s, 1 H), 5.26 (d, J=7.4 Hz, 1 H), 4.29 (m, 2 H), 3.52 (m, 2 H), 2.43-1.19 (m, 15 H), 0.95 (d, J=6.1 Hz, 6 H), 0.62 (m, 3 H); IR (KBr) 3325, 2957, 2871, 1655, 1498 cm$^{-1}$; ESI MS m/z=490 [C$_{30}$H$_{39}$N$_3$O$_3$+H]$^+$; HPLC 100%, t$_r$=20.26 min. (HPLC Conditions A).

Example 60

4-Methyl-N-({N-[6-oxo-5-benzyl(7H-dibenzo[d,f]azaperhydroepin-7-yl)]carbamoyl}cyclopentyl)pentanamide

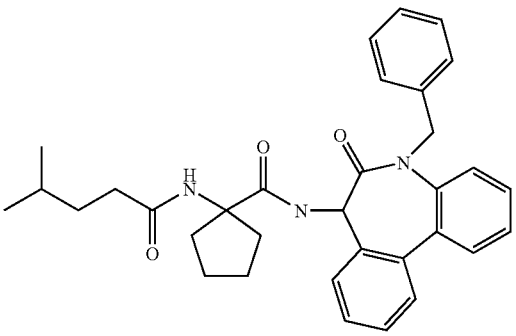

The title compound was prepared in a manner similar to that described for Example 57. The product was obtained as a white solid: mp 103-106° C.; $^1$H NMR (500 MHz, CDCl$_3$) δ 8.01 (d, J=6.8 Hz, 1 H), 7.52-7.25 (m, 8 H), 7.05 (m, 3 H), 6.78 (m, 2 H), 5.84 (s, 1 H), 5.36 (d, J=7.4 Hz, 1 H), 5.04 (q$_{ab}$, J=14.7 Hz, 2 H), 2.41-1.26 (m, 13 H), 0.91 (d, J=5.8 Hz, 6 H); IR (KBr) 3325, 2956, 1655, 1498, 1396 cm$^{-1}$; ESI MS m/z=524 [C$_{33}$H$_{37}$N$_3$O$_3$+H]$^+$; HPLC 100%, t$_r$=27.04 min. (HPLC Conditions A).

Example 61

N-({N-[5-(tert-Butyl)-1-methyl-2-oxo(3H-benzo[f]1,4-diazepin-3-yl)]carbamoyl}cyclopentyl)-4-methylpentanamide

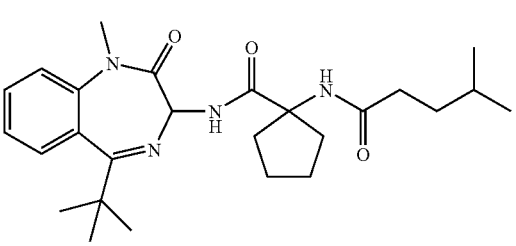

Scheme 7

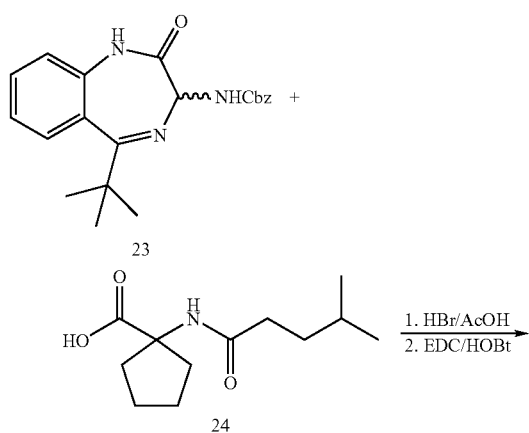

-continued

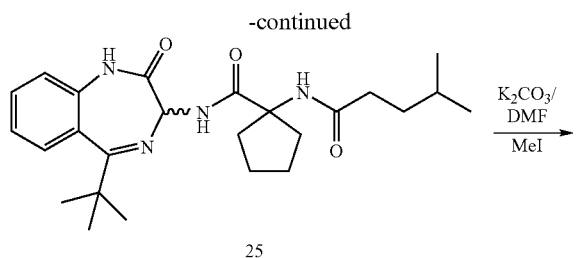

25

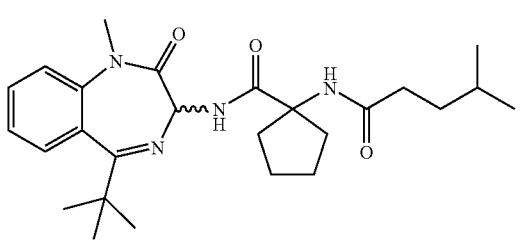

Example 61 c) Preparation of 25

To a stirred solution of 23 (see Scheme 6) (1.0 equiv) in CH$_2$Cl$_2$ (0.1 M) was added a 30% solution of HBr in acetic acid (16 equiv). The mixture was stirred for 14 h. The reaction mixture was concentrated in vacuo and dissolved in EtOAc and water and separated. The aqueous layer was made basic using 6 N NaOH and was extracted with CH$_2$Cl$_2$. The organic extracts were washed with brine, dried over Na$_2$SO$_4$, filtered and concentrated. The resulting solid was dissolved in CH$_2$Cl$_2$ and added to a stirring solution of the acid 24 (1.2 equiv), EDC-HCl (1.5 equiv), HOBt (1.5 equiv), and DIPEA (5.0 equiv) in CH$_2$Cl$_2$ (0.15 M). The reaction was stirred overnight, quenched with water, washed with 20% citric acid (3×), sat NaHCO$_3$ (2×), brine, dried over Na$_2$SO$_4$, filtered and concentrated. Crude material was recrystallized from EtOAc and Et$_2$O to give 25 (4.4 g, 95%) as a white powder: $^1$H NMR (500 MHz, CDCl$_3$) δ 7.71-6.98 (m, 6 H), 5.87 (S, 1 H), 5.29 (d, 1 H), 2.38 (m, 2 H), 2.21 (t, 2 H) 2.01 (m, 2 H), 1.52 (m, 7 H), 1.23 (s, 9 H), 0.88 (d, 6 H).

d) Preparation of Example 61

To a suspension of 25 (1 equiv) and freshly powderedqj K$_2$CO$_3$ (3.0 equiv) in DMF (0.05 M) was added methyl iodide (1.5 equiv). The mixture was stirred (5 h). To the reaction was added EtOAc and water and the layers separated. The organic layer was washed with 5% LiCl (2×), brine, dried over Na$_2$SO$_4$, filtered and concentrated. The resulting material was dissolved in Et$_2$O and concentrated in vacuo providing N-({N-[5-(tert-butyl)-1-methyl-2-oxo(3H-benzo[f]1,4-diazepin-3-yl)]carbamoyl}-cyclopentyl)-4-methylpentanamide (60 mg, 66%) as a white powder: mp 175-178° C.; $^1$H NMR (500 MHz, CDCl$_3$) δ 7.71-7.17 (m, 5 H), 5.89 (s, 1 H), 5.23 (d, 1 H), 3.34 (s, 3 H), 2.41-2.29 (m, 3 H), 2.21 (m, 2 H), 2.04 (m, 3 H), 1.80 (m, 4 H), 1.60 (m, 1 H), 1.18 (s, 9 H), 0.90 (d, 6 H); ESI MS m/z=455 [C$_{26}$H$_{38}$N$_4$O$_3$+H]$^+$; IR (KBr)=3324, 2958, 1677, 1508, 1366, 1197 cm$^{-1}$; HPLC 96.8%, t$_r$=15.75 min. (HPLC Conditions A).

Example 62

N-({N-[5-(tert-Butyl)-1-butyl-2-oxo(3H-benzo[f]1,4-diazepin-3-yl)]carbamoyl}cyclopentyl)-4-methylpentanamide

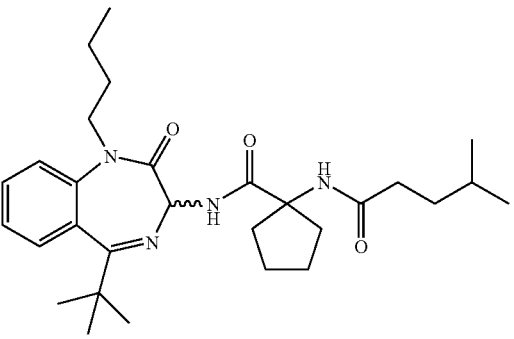

The title compound was prepared in a manner similar to that described for Example 62. The product was obtained as a white powder (450 mg, 70%): mp 175-177° C.; $^1$H NMR (500 MHz, CDCl$_3$) δ 7.71-7.13 (m, 5 H), 5.89 (s, 1 H), 5.20 (d, 1 H), 4.36 (m, 1 H), 3.50 (m, 1 H), 2.32 (m, 3 H) 2.20 (m, 2 H), 2.02 (m, 3 H), 1.80 (m, 4 H), 1.57 (m, 1 H), 1.35 (m, 2 H) 1.26 (s, 9 H), 1.21 (m, 2 H), 0.89 (d, 6 H), 0.83 (t, 3 H); ESI MS m/z=497 [C$_{29}$H$_{44}$N$_4$O$_3$+H]$^+$; IR (KBr)=3321, 2959, 2363, 1676, 1508, 1365 cm$^{-1}$; HPLC 95.4%, t$_r$=19.69 min. (HPLC Conditions A).

Example 63

N-({N-[5-Butyl-2-oxo-1-(2-pyridylmethyl)(3H-benzo[f]1,4-diazepin-3-yl)]carbamoyl}cyclopentyl)-4-methylpentanamide

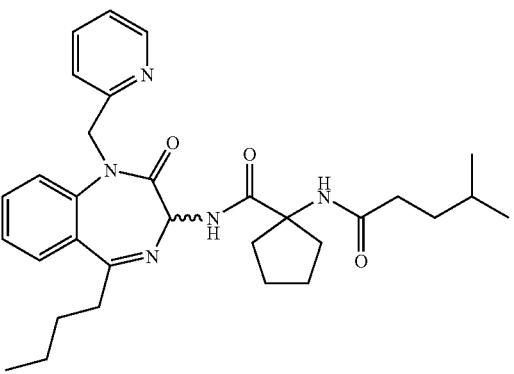

The title compound was prepared in a manner similar to that described for Example 62. The product was obtained as a white powder: mp 63-67° C.; $^1$H NMR (CDCl$_3$) δ 8.46-7.11 (m, 8 H), 5.89 (s, 1 H), 5.40 (d, J=6.87 Hz, 1 H), 5.28 (d, J=15.77 Hz, 1 H), 5.12 (d, J=15.82 Hz, 1 H), 2.74 (m, 2 H), 2.43-0.77 (m, 27 H); ESI MS m/z=532 [C$_{31}$H$_{41}$N$_5$O$_3$+H]$^+$; IR (KBr) 3310 (br.), 1670 cm$^{-1}$; HPLC>95 % t$_r$=17.07 min. (HPLC Conditions A). Anal. Calcd for [C$_{31}$H$_{41}$N$_5$O$_3$.0.5H$_2$O]: C, 68.86; H, 7.83; N, 12.95. Found: C, 68.73; H, 7.86; N, 12.79.

Tables 1-4 below provide representative Examples of compounds of Formula (I) of the present invention.

TABLE 1

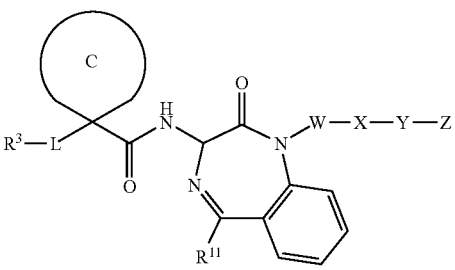

| Ex # | R³ | L | C | —WXYZ | R¹¹ |
|---|---|---|---|---|---|
| 2 | 3-Me-butyl | NHC(=O) | cyclopentyl | Me | phenyl |
| 3 | n-butyl | NHC(=O) | cyclopentyl | Me | phenyl |
| 4 | 3,5-diF-benzyl | C(=O)NH | cyclohexyl | Me | phenyl |
| 5 | 3,5-diF-benzyl | C(=O)NH | cyclopentyl | Me | phenyl |
| 6 | 3,5-diF-benzyl | C(=O)NH | cyclopropyl | Me | phenyl |
| 7 | cyclopentyl ethyl | C(=O)NH | cyclohexyl | Me | phenyl |
| 8 | 3,5-diF-benzyl | C(=O)NH | 4-piperidyl | Me | phenyl |
| 9 | 3,5-diF-benzyl | C(=O)NH | N-benzyloxy-carbonyl-4-piperidyl | Me | phenyl |
| 11 | benzyl | O—C(=O)NH | cyclopentyl | Me | 4-$CF_3$-phenyl |
| 14 | 3-phenyl-1,1-diF-propyl | C(=O)NH | cyclopentyl | Me | 4-$CF_3$-phenyl |
| 15 | 2-(4-piperidyl)ethyl | C(=O)NH | cyclopentyl | Me | 4-$CF_3$-phenyl |
| 16 | 1-hydroxy-3-Me-butyl | C(=O)NH | cyclopentyl | Me | 4-$CF_3$-phenyl |
| 17 | 2-cyclopropyl-ethyl | C(=O)NH | cyclopentyl | Me | 4-$CF_3$-phenyl |
| 19 | 1-amino cyclopentyl | C(=O)NH | cyclopentyl | Me | phenyl |
| 20 | 1-hydxoxy-2-imidazol-2-yl-ethyl | C(=O)NH | cyclopentyl | Me | 4-$CF_3$-phenyl |
| 21 | ethyoxy-methyl | C(=O)NH | cyclopentyl | Me | 4-$CF_3$-phenyl |
| 22 | 2-cyclopentyl-ethyl | C(=O)NH | cyclopentyl | Me | 4-$CF_3$-phenyl |
| 23 | 1-hydxoxy-2-Me-propyl | C(=O)NH | cyclopentyl | Me | 4-$CF_3$-phenyl |
| 24* | 1-hydroxy-1-cyclohexyl-methyl | C(=O)NH | cyclopentyl | Me | 4-$CF_3$-phenyl |
| 25* | 1-hydroxy-1-cyclohexyl-methyl | C(=O)NH | cyclopentyl | Me | 4-$CF_3$-phenyl |
| 26 | 1-$NH_2$-3-Me-butyl | C(=O)NH | cyclopentyl | Me | 4-$CF_3$-phenyl |
| 27 | cyclohexyl | C(=O)NH | cyclopentyl | Me | 4-$CF_3$-phenyl |
| 29 | 3-Me-butyl | NHC(=O) | cyclopentyl | Me | 4-$CF_3$-phenyl |
| 30 | 3-Me-butyl | C(=O)NH | cyclopentyl | Me | 4-$CF_3$-phenyl |
| 31 | 1-hydroxy-3-Me-butyl | C(=O)NH | cyclopentyl | Me | 4-$CF_3$-phenyl |
| 32 | 2-methoxy-ethyl | C(=O)NH | cyclopentyl | Me | 4-$CF_3$-phenyl |
| 33 | 1-hydroxy-2-phenyl-ethyl | C(=O)NH | cyclopentyl | Me | 4-$CF_3$-phenyl |
| 34 | benzyloxy-methyl | C(=O)NH | cyclopentyl | Me | 4-$CF_3$-phenyl |
| 39 | 2-cyclopropyl-ethyl | C(=O)NH | cyclopentyl | Me | phenyl |
| 40 | 3-Me-butyl | C(=O)NH | cyclopentyl | n-butyl | cyclopentyl |
| 41 | 3-Me-butyl | C(=O)NH | cyclopentyl | Me | cyclopentyl |
| 61 | 3-Me-butyl | C(=O)NN | cyclopentyl | Me | t-butyl |
| 62 | 3-Me-butyl | C(=O)NH | cyclopentyl | n-butyl | t-butyl |
| 63 | 3-Me-butyl | C(=O)NH | cyclopentyl | 2-pyridyl-methyl | n-butyl |

*stereoisomers

TABLE 2

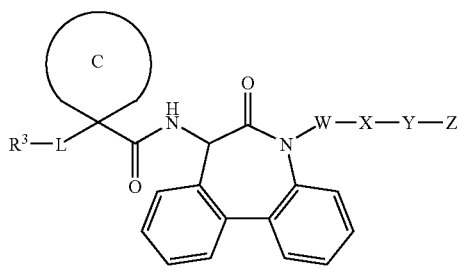

| Ex. # | R³ | L | C | Z-Y-X-W- |
|---|---|---|---|---|
| 1 | 3-Me-butyl | NHC(=O) | cyclopentyl | Me |
| 10 | 3-Me-butyl | C(=O)NH | cyclopentyl | Me |
| 35 | 1-hydroxy-2-Me-propyl | C(=O)NH | cyclopentyl | Me |
| 36 | 1-hydroxy-3-Me-butyl | C(=O)NH | cyclopentyl | Me |
| 37 | 2-cyclopentyl-ethyl | C(=O)NH | cyclopentyl | Me |
| 38 | 1-hydroxy-1-cyclohexyl-methyl | C(=O)NH | cyclopentyl | Me |
| 43 | 1-(propyl-sulfamide)-3-Me-butyl | C(=O)NH | cyclopentyl | Me |
| 44 | 1-(N-Me-amino)-3-Me-butyl | C(=O)NH | cyclopentyl | Me |
| 45 | 1,1-diF-3-Me-butyl | C(=O)NH | cyclopentyl | Me |
| 56 | 3-Me-butyl | C(=O)NH | cyclopentyl | H |
| 57 | 3-Me-butyl | C(=O)NH | cyclopentyl | 3,3-dimethyl-2-oxobutyl |
| 58 | 3-Me-butyl | C(=O)NH | cyclopentyl | 3-phenoxy-benzyl |
| 59 | 3-Me-butyl | C(=O)NH | cyclopentyl | n-butyl |
| 60 | 3-Me-butyl | C(=O)NH | cyclopentyl | benzyl |

TABLE 3

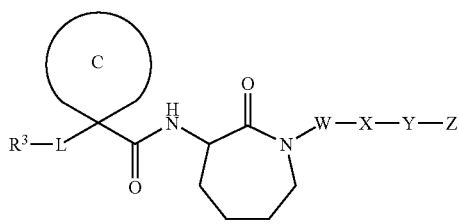

| Ex. # | R³ | L | C | Z-Y-X-W- |
|---|---|---|---|---|
| 12 | 1-hydroxy-3-Me-butyl | C(=O)NH | cyclopropyl | 3-(4-F-phenoxy)-benzyl |
| 13 | 1-hydroxy-3-Me-propyl | C(=O)NN | cyclopentyl | 3-(4-F-phenoxy)-benzyl |

TABLE 4

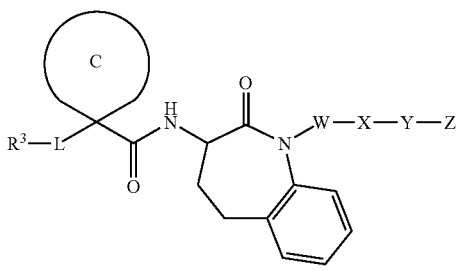

| Ex. # | R³ | L | C | Z-Y-X-W- |
|---|---|---|---|---|
| 42 | 1-hydroxy-2-Me-propyl | C(=O)NH | cyclopentyl | benzyl |

Utility

Aβ production has been implicated in the pathology of Alzheimer's Disease (AD). The compounds of the present invention have utility for the prevention and treatment of AD by inhibiting Aβ production. Methods of treatment target formation of Aβ production through the enzymes involved in the proteolytic processing of β amyloid precursor protein. Compounds that inhibit β or γ secretase activity, either directly or indirectly, control the production of Aβ. Such inhibition of β or γ secretases reduces production of Aβ, and is expected to reduce or prevent the neurological disorders associated with Aβ protein, such as Alzheimer's Disease.

Cellular screening methods for inhibitors of Aβ production, testing methods for the in vivo suppression of Aβ production, and assays for the detection of secretase activity are known in the art and have been disclosed in numerous publications, including J. Med. Chem. 1999, 42, 3889-3898, PCT publication number WO 98/22493, EPO publication number 0652009, U.S. Pat. No. 5,703,129 and U.S. Pat. No. 5,593,846; all hereby incorporated by reference.

The compounds of the present invention have utility for the prevention and treatment of disorders involving Aβ production, such as cerebrovascular disorders.

Compounds of Formula (I) are expected to possess γ-secretase inhibitory activity. The γ-secretase inhibitory activity of the compound of the present invention is demonstrated using assays for such activity, for example, using the assay described below. Compounds of the present invention have been shown to inhibit the activity of γ-secretase, as determined by the Aβ immunoprecipitation assay.

Compounds provided by this invention should also be useful as a standard and reagent in determining the ability of a potential pharmaceutical to inhibit Aβ production. These would be provided in commercial kits comprising a compound of this invention.

As used herein "µg" denotes microgram, "mg" denotes milligram, "g" denotes gram, "µL" denotes microliter, "mL" denotes milliliter, "L" denotes liter, "nM" denotes nanomolar, "µM" denotes micromolar, "mM" denotes millimolar, "M" denotes molar, "nm" denotes nanometer, "SDS" denotes sodium dodecyl sulfate, and "DMSO" denotes dimethyl sulfoxide, and "EDTA" denotes ethylenediaminetetraacetic acid.

A compound is considered to be active if it has an $IC_{50}$ or $K_i$ value of less than about 100 µM for the inhibition of Aβ production. Preferably the $IC_{50}$ or $K_i$ value is less than about 10 µM; more preferably the $IC_{50}$ or $K_i$ value is less than about 0.1 µM. The present invention has been shown to inhibit Aβ protein production with an $IC_{50}$ or $K_i$ value of less than 100 µM.

β Amyloid Precursor Protein Accumulation Assay

A novel assay to evaluate the accumulation of Aβ protein was developed to detect potential inhibitors of secretase. The assay uses the N 9 cell line, characterized for expression of exogenous APP by immunoblotting and immunoprecipitation.

The effect of test compounds on the accumulation of Aβ in the conditioned medium is tested by immunoprecipitation. Briefly, N 9 cells are grown to confluency in 6-well plates and washed twice with 1×Hank's buffered salt solution. The cells are starved in methionine/cysteine deficient media for 30 min, followed by replacement with fresh deficient media containing 150 uCi S35 Translabel (Amersham). Test compounds dissolved in DMSO (final concentration 1%) are added together with the addition of radiolabel. The cells are incubated for 4 h at 37° C. in a tissue culture incubator.

At the end of the incubation period, the conditioned medium is harvested and pre-cleared by the addition of 5 µl normal mouse serum and 50 µl of protein A Sepharose (Pharmacia), mixed by end-over-end rotation for 30 minutes at 4° C., followed by a brief centrifugation in a microfuge. The supernatant is then harvested and transferred to fresh tubes containing 5 ug of a monoclonal antibody (clone 1101.1; directed against an internal peptide sequence in Aβ) and 50 µl protein A Sepharose. After incubation overnight at 4° C., the samples are washed three times with high salt washing buffer (50 mM Tris, pH 7.5, 500 mM NaCl, 5 mM EDTA, 0.5% Nonidet P-40), three times with low salt wash buffer (50 mM Tris, pH 7.5, 150 mM NaCl, 5 mM EDTA, 0.5% Nonidet P-40), and three times with 10 mM Tris, pH 7.5. The pellet after the last wash is resuspended in SDS sample buffer (Laemmli, 1970) and boiled for 3 minutes. The supernatant is then fractionated on either 10-20% Tris/Tricine SDS gels or on 16.5% Tris/Tricine SDS gels. The gels are dried and exposed to X-ray film or analyzed by phosphorimaging. The resulting image is analyzed for the presence of Aβ polypeptides. The steady-state level of Aβ in the presence of a test compound is compared to wells treated with DMSO (1%) alone. A typical test compound blocks Aβ accumulation in the conditioned medium, and is therefore considered active, with an $IC_{50}$ less than 100 µM.

C-Terminus β Amyloid Precursor Protein Accumulation Assay

The effect of a test compound on the accumulation of C-terminal fragments is determined by immunoprecipitation of APP and fragments thereof from cell lysates. N 9 cells are metabolically labeled as above in the presence or absence of test compounds. At the end of the incubation period, the conditioned medium are harvested and cells lysed in RIPA buffer (10 mM Tris, pH 8.0 containing 1% Triton X-100, 1% deoxycholate, 0.1% SDS, 150 mM NaCl, 0.125% $NaN_3$). Again, lysates are precleared with 5 ul normal rabbit serum/50 ul protein A Sepharose, followed by the addition of BC-1 antiserum (15 µl;) and 50 µl protein A Sepharose for 16 hours at 4° C. The immunoprecipitates are washed as above, bound proteins eluted by boiling in SDS sample buffer and fractionated by Tris/Tricine SDS-PAGE. After exposure to X-ray film or phosphorimager, the resulting images are analyzed for the presence of C-terminal APP fragments. The steady-state level of C-terminal APP fragments is compared to wells treated with DMSO (1%) alone. A typical test compound stimulates C-terminal fragment accumulation in the cell lysates, and is therefore considered active, with an $IC_{50}$ less than 100 µM.

Aβ-Immunoprecipitation Assay

This immunoprecipitation assay is specific for γ-secretase (i.e., proteolytic activity required to generate the C-terminal end of Aβ either by direct cleavage or generating a C-terminal extended species which is subsequently further proteolyzed). N 9 cells are pulse labeled in the presence of a reported γ-secretase inhibitor (MDL 28170) for 1 h, followed by washing to remove radiolabel and MDL 28170. The media is replaced and test compounds are added. The cells are chased for increasing periods of times and Aβ is isolated from the conditioned medium and C-terminal fragments from cell lysates (see above). The test compound is characterized whether a stabilization of C-terminal fragments is observed and whether Aβ is generated from these accumulated precursor. A typical test compound prevents the generation of Aβ out of accumulated C-terminal fragments and is considered active with an $IC_{50}$ less than 100 µM.

Dosage and Formulation

The compound of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compound of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed to prevent or treat neurological disorders related to β-amyloid production or accumulation, such as Alzheimer's disease and Down's Syndrome.

The compound of this invention can be administered by any means that produces contact of the active agent with the agent's site of action in the body of a host, such as a human or a mammal. The compound can be administered by any conventional means available for use in conjunction with pharmaceuticals, either as individual therapeutic agents or in a combination of therapeutic agents. The compound can be administered alone, but generally administered with a pharmaceutical carrier selected on the basis of the chosen route of administration and standard pharmaceutical practice.

The dosage regimen for the compound of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

Advantageously, the compounds of the present invention may be administered in a single daily dose, or the total daily-dosage may be administered in divided doses of two, three, or four times daily.

The compound for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittent throughout the dosage regimen.

In the methods of the present invention, the compound herein described in detail can form the active ingredient, and is typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or β-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compound of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compound of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

What is claimed is:

1. A process of preparing a compound of Formula (I),

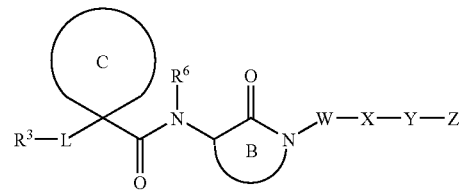

(I)

or a stereoisomer, or a pharmaceutically acceptable salt thereof, comprising an amide bond synthesis coupling a carboxylic acid 1 and an amine 2 including amide coupling methods comprising HATU, TBTU, BOP, EDC, CDI, and DCC-mediated couplings:

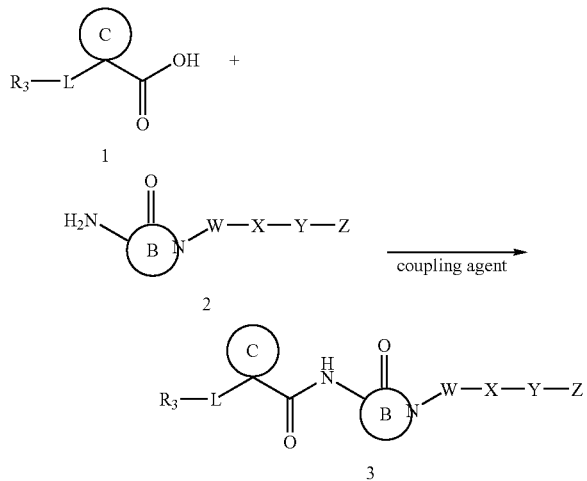

wherein the product, 3, comprises Formula (I)

wherein:

L is $-NR^{26}C(=O)-$, $-C(=O)NR^{26}-$, $-NR^{26}C(=O)O-$, $-OC(=O)NR^{26}$, or $-NR^{26}C(=O)NR^{26}-$;

$R^3$ is —$(CR^7R^{7a})_n$—$R^4$,
—$(CR^7R^{7a})_l$—S—$(CR^7R^{7a})_m$—$R^4$,
—$(CR^7R^{7a})_l$—O—$(CR^7R^{7a})_m$—$R^4$,
—$(CR^7R^{7a})_l$—$N(R^{7b})$—$(CR^7R^{7a})_m$—$R^4$,
—$(CR^7R^{7a})_l$—S(=O)—$(CR^7R^{7a})_m$—$R^4$,
—$(CR^7R^{7a})_l$—$S(=O)_2$—$(CR^7R^{7a})_m$—$R^4$,
—$(CR^7R^{7a})_l$—C(=O)—$(CR^7R^{7a})_m$—$R^4$,
—$(CR^7R^{7a})_l$—$N(R^{7b})C(=O)$—$(CR^7R^{7a})_m$—$R^4$,
—$(CR^7R^{7a})_l$—$C(=O)N(R^{7b})$—$(CR^7R^{7a})_m$—$R^4$,
—$(CR^7R^{7a})_l$—$N(R^{7b})S(=O)_2$—$(CR^7R^{7a})_m$—$R^4$, or
—$(CR^7R^{7a})_l$—$S(=O)_2N(R^{7b})$—$(CR^7R^{7a})_m$—$R^4$;

n is 0, 1, 2, or 3;
m is 0, 1, 2, or 3;
l is 1, 2, or 3;
Ring C is a 3 to 8 membered carbocycle,
  wherein the carbocycle is saturated or partially saturated;
  optionally, the carbocycle contains a heteroatom selected from —O—, —S—, —S(=O)—, —$S(=O)_2$—, and —$N(R^{20})$—; and
  wherein the carbocycle is substituted with 0-4 $R^{21}$;
$R^4$ is H, OH, $OR^{14a}$,
  $C_1$-$C_8$ alkyl substituted with 0-3 $R^{4a}$,
  $C_2$-$C_8$ alkenyl substituted with 0-3 $R^{4a}$,
  $C_2$-$C_8$ alkynyl substituted with 0-3 $R^{4a}$,
  $C_3$-$C_{10}$ carbocycle substituted with 0-3 $R^{4b}$,
  aryl substituted with 0-3 $R^{4b}$, or
  5 to 10 membered heterocycle containing 1 to 4 heteroatoms selected from nitrogen, oxygen, and sulphur, wherein said 5 to 10 membered heterocycle is substituted with 0-3 $R^{4b}$;
$R^{4a}$, at each occurrence, is independently selected from H, OH, F, Cl, Br, I, $NR^{15}R^{16}$, $CF_3$,
  $C_3$-$C_{10}$ carbocycle substituted with 0-3 $R^{4b}$,
  aryl substituted with 0-3 $R^{4b}$, and
  5 to 10 membered heterocycle containing 1 to 4 heteroatoms selected from nitrogen, oxygen, and sulphur, wherein said 5 to 10 membered heterocycle is substituted with 0-3 $R^{4b}$;
$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;
$R^6$ is H;
  $C_1$-$C_6$ alkyl substituted with 0-3 $R^{6a}$;
  $C_3$-$C_{10}$ carbocycle substituted with 0-3 $R^{6b}$; or
  aryl substituted with 0-3 $R^{6b}$;
$R^{6a}$, at each occurrence, is independently selected from H, $C_1$-$C_6$ alkyl, $OR^{14}$, Cl, F, Br, I, =O, CN, $NO_2$, $NR^{15}R^{16}$, aryl and $CF_3$;
$R^{6b}$, at each occurrence, is independently selected from H, OH, Cl, F, Br, I, CN, $NO_2$, $NR^{15}R^{16}$, $CF_3$, $C_1$-$C_6$ alkyl, $C_1$-$C_4$ alkoxy, $C_1$-$C_4$ haloalkyl, and $C_1$-$C_4$ haloalkoxy;
$R^7$, at each occurrence, is independently selected from H, OH, Cl, F, Br, I, CN, $NO_2$, $CF_3$, $C_1$-$C_4$ alkyl, phenyl substituted with 0-5 $R^{7c}$;
$R^{7a}$, at each occurrence, is independently selected from H, Cl, F, Br, I, CN, $CF_3$, and $C_1$-$C_4$ alkyl;
$R^{7b}$ is independently selected from H and $C_1$-$C_4$ alkyl;
$R^{7c}$, at each occurrence, is independently selected from H, OH, Cl, F, Br, I, CN, $CF_3$, $C_1$-$C_4$ alkoxy, and $C_1$-$C_4$ alkyl;

B is

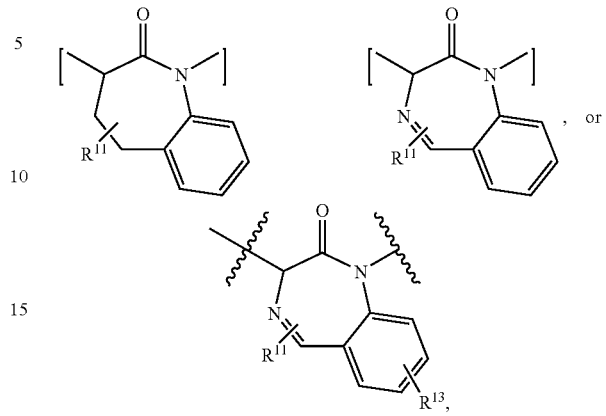

$R^{11}$, at each occurrence, is independently selected from H, $C_1$-$C_4$ alkoxy, Cl, F, Br, I, =O, CN, $NO_2$, $NR^{18}R^{19}$, $C(=O)R^{17}$, $C(=O)OR^{17}$, $C(=O)NR^{18}R^{19}$, $S(=O)_2NR^{18}R^{19}$, $CF_3$;
  $C_1$-$C_6$ alkyl optionally substituted with 0-3 $R^{11a}$;
  aryl substituted with 0-3 $R^{11b}$;
  $C_3$-$C_{10}$ carbocycle substituted with 0-3 $R^{11b}$; and
  5 to 10 membered heterocycle containing 1 to 4 heteroatoms selected from nitrogen, oxygen, and sulphur, wherein said 5 to 10 membered heterocycle is substituted with 0-3 $R^{11b}$;
$R^{11a}$, at each occurrence, is independently selected from H, $C_1$-$C_6$ alkyl, $OR^{14}$, Cl, F, Br, I, =O, CN, $NO_2$, $NR^{15}R^{16}$, $CF_3$;
  phenyl substituted with 0-3 $R^{11b}$;
  $C_3$-$C_6$ cycloalkyl substituted with 0-3 $R^{11b}$; and
  5 to 6 membered heterocycle containing 1 to 3 heteroatoms selected from nitrogen, oxygen, and sulphur, wherein said 5 to 6 membered heterocycle is substituted with 0-3 $R^{11b}$;
$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
  $C_1$-$C_6$ alkyl, $C_1$-$C_4$ alkoxy, $C_1$-$C_4$ haloalkyl,
  $C_1$-$C_4$ haloalkoxy, and $C_1$-$C_4$ haloalkyl-S—;
additionally, two $R^{11}$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0-3 $R^{13}$;
additionally, two $R^{11}$ substituents on the same or adjacent carbon atoms may be combined to form a $C_3$-$C_6$ carbocycle substituted with 0-3 $R^{13}$;
additionally, two $R^{11}$ substituents on adjacent atoms may be combined to form a benzo fused radical; wherein said benzo fused radical is substituted with 0-4 $R^{13}$;
W is —$(CR^8R^{8a})_p$—;
p is 0, 1, 2, 3, or 4;
$R^8$ and $R^{8a}$, at each occurrence, are independently selected from H, F, $C_1$-$C_4$ alkyl, $C_2$-$C_4$ alkenyl, $C_2$-$C_4$ alkynyl and $C_3$-$C_8$ cycloalkyl;
X is a bond;
  aryl substituted with 0-3 $R^{Xb}$;
  $C_3$-$C_{10}$ carbocycle substituted with 0-3 $R^{Xb}$; or
  5 to 10 membered heterocycle substituted with 0-2 $R^{Xb}$;

$R^{Xb}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$-C$_6$ alkyl, C$_1$-C$_4$ alkoxy, C$_1$-C$_4$ haloalkyl, C$_1$-C$_4$ haloalkoxy, and C$_1$-C$_4$ halothioalkoxy;

Y is a bond or —(CR$^9$R$^{9a}$)$_t$—V—(CR$^9$R$^{9a}$)$_u$—;

t is 0, 1, 2, or 3;

u is 0, 1, 2, or 3;

R$^9$ and R$^{9a}$, at each occurrence, are independently selected from H, F, C$_1$-C$_6$ alkyl and C$_3$-C$_8$ cycloalkyl;

V is a bond, —C(=O)—, —O—, —S—, —S(=O)—, —S(=O)$_2$—, —N(R$^{19}$)—, —C(=O)NR$^{19b}$—, —NR$^{19b}$C(=O)—, —NR$^{19b}$S(=O)$_2$—, —S(=O)$_2$NR$^{19b}$—, —NR$^{19b}$S(=O)—, —S(=O)NR$^{19b}$—, —C(=O)O—, or —OC(=O)—;

Z is H;
- C$_1$-C$_8$ alkyl substituted with 1-3 R$^{12}$;
- C$_2$-C$_4$ alkenyl substituted with 1-3 R$^{12}$;
- C$_2$-C$_4$ alkynyl substituted with 1-3 R$^{12}$;
- C$_1$-C$_8$ alkyl substituted with 0-3 R$^{12a}$;
- C$_2$-C$_4$ alkenyl substituted with 0-3 R$^{12a}$;
- C$_2$-C$_4$ alkynyl substituted with 0-3 R$^{12a}$;
- aryl substituted with 0-4 R$^{12b}$;
- C$_3$-C$_{10}$ carbocycle substituted with 0-4 R$^{12b}$; or
- 5 to 10 membered heterocycle containing 1 to 4 heteroatoms selected from nitrogen, oxygen, and sulphur, wherein said 5 to 10 membered heterocycle is substituted with 0-3 R$^{12b}$;

R$^{12}$, at each occurrence, is independently selected from aryl substituted with 0-4 R$^{12b}$;
- C$_3$-C$_{10}$ carbocycle substituted with 0-4 R$^{12b}$; and
- 5 to 10 membered heterocycle containing 1 to 4 heteroatoms selected from nitrogen, oxygen, and sulphur, wherein said 5 to 10 membered heterocycle is substituted with 0-3 R$^{12b}$;

R$^{12a}$, at each occurrence, is independently selected from H, OH, Cl, F, Br, I, CN, NO$_2$, NR$^{15}$R$^{16}$, —C(=O)NR$^{15}$R$^{16}$, CF$_3$, acetyl, SCH$_3$, S(=O)CH$_3$, S(=O)$_2$CH$_3$, C$_1$-C$_6$ alkyl, C$_1$-C$_4$ alkoxy, C$_1$-C$_4$ haloalkyl, C$_1$-C$_4$ haloalkoxy, and C$_1$-C$_4$ haloalkyl-S—;

R$^{12b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$-C$_6$ alkyl, C$_1$-C$_4$ alkoxy, C$_1$-C$_4$ haloalkyl, C$_1$-C$_4$ haloalkoxy, and C$_1$-C$_4$ haloalkyl-S—;

R$^{13}$, at each occurrence, is independently selected from H, OH, C$_1$-C$_6$ alkyl, C$_1$-C$_4$ alkoxy, Cl, F, Br, I, CN, NO$_2$, NR$^{15}$R$^{16}$, and CF$_3$;

R$^{14}$ is H, phenyl substituted with 0-4 R$^{14b}$, benzyl substituted with 0-4 R$^{14b}$, C$_1$-C$_6$ alkyl, C$_2$-C$_6$ alkoxyalkyl, or C$_3$-C$_6$ cycloalkyl;

R$^{14a}$ is H, C$_6$-C$_{10}$ aryl, benzyl, heterocycle, or C$_1$-C$_4$ alkyl;

R$^{14b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$-C$_6$ alkyl, C$_1$-C$_4$ alkoxy, C$_1$-C$_4$ haloalkyl, C$_1$-C$_4$ haloalkoxy, and C$_1$-C$_4$ haloalkyl-S—;

R$^{15}$, at each occurrence, is independently selected from H, C$_1$-C$_6$ alkyl, aryl-(C$_1$-C$_6$ alkyl)- wherein the aryl is substituted with 0-4 R$^{15b}$, (C$_1$-C$_6$ alkyl)-C(=O)—, and (C$_1$-C$_6$ alkyl)-S(=O)$_2$—;

R$^{15b}$, at each occurrence, is independently selected from H, OH, Cl, F, Br, I, CN, NO$_2$, CF$_3$, acetyl, SCH$_3$, S(=O)CH$_3$, S(=O)$_2$CH$_3$, C$_1$-C$_6$ alkyl, C$_1$-C$_4$ alkoxy, C$_1$-C$_4$ haloalkyl, C$_1$-C$_4$ haloalkoxy, and C$_1$-C$_4$ haloalkyl-S—;

R$^{16}$, at each occurrence, is independently selected from H, C$_1$-C$_6$ alkyl, benzyl, phenethyl, (C$_1$-C$_6$ alkyl)-C(=O)—, and (C$_1$-C$_6$ alkyl)-S(=O)$_2$—;

R$^{17}$ is H, C$_1$-C$_6$ alkyl, C$_2$-C$_6$ alkoxyalkyl, aryl substituted by 0-4 R$^{17a}$, or —CH$_2$-aryl substituted by 0-4 R$^{17a}$;

R$^{17a}$ is H, methyl, ethyl, propyl, butyl, methoxy, ethoxy, propoxy, butoxy, —OH, F, Cl, Br, I, CF$_3$, OCF$_3$, SCH$_3$, S(O)CH$_3$, SO$_2$CH$_3$, —NH$_2$, —N(CH$_3$)$_2$, or C$_1$-C$_4$ haloalkyl;

R$^{18}$, at each occurrence, is independently selected from H, C$_1$-C$_6$ alkyl, phenyl, benzyl, phenethyl, (C$_1$-C$_6$ alkyl)-C(=O)—, and (C$_1$-C$_6$ alkyl)-S(=O)$_2$—;

R$^{19}$, at each occurrence, is independently selected from H, OH, C$_1$-C$_6$ alkyl, phenyl, benzyl, phenethyl, (C$_1$-C$_6$ alkyl)-C(=O)—, and (C$_1$-C$_6$ alkyl)-S(=O)$_2$—;

R$^{20}$ is H, C(=O)R$^{17}$, C(=O)OR$^{17}$, C(=O)NR$^{18}$R$^{19}$, S(=O)$_2$NR$^{18}$R$^{19}$, S(=O)$_2$R$^{17}$;
- C$_1$-C$_6$ alkyl optionally substituted with 0-2 R$^{20a}$;
- aryl substituted with 0-4 R$^{20b}$;
- C$_3$-C$_{10}$ carbocycle substituted with 0-3 R$^{20b}$; or
- 5 to 10 membered heterocycle containing 1 to 4 heteroatoms selected from nitrogen, oxygen, and sulphur, wherein said 5 to 10 membered heterocycle is substituted with 0-3 R$^{20b}$;

R$^{20a}$, at each occurrence, is independently selected from H, C$_1$-C$_6$ alkyl, OR$^{14}$, F, =O, CN, NO$_2$, NR$^{15}$R$^{16}$, CF$_3$, aryl substituted with 0-4 R$^{20b}$, and heterocycle substituted with 0-4 R$^{20b}$;

R$^{20b}$, at each occurrence, is independently selected from H, OH, C$_1$-C$_6$ alkyl, C$_1$-C$_4$ alkoxy, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$-C$_6$ alkyl, C$_1$-C$_4$ alkoxy, C$_1$-C$_4$ haloalkyl, C$_1$-C$_4$ haloalkoxy, and C$_1$-C$_4$ haloalkyl-S—;

R$^{21}$, at each occurrence, is independently selected from H, C$_1$-C$_4$ alkoxy, Cl, F, Br, I, =O, CN, NO$_2$, NR$^{18}$R$^{19}$, C(=O)R$^{17}$, C(=O)OR$^{17}$, C(=O)NR$^{18}$R$^{19}$, S(=O)$_2$NR$^{18}$R$^{19}$, CF$_3$;
- C$_1$-C$_6$ alkyl optionally substituted with 0-3 R$^{21a}$;
- aryl substituted with 0-3 R$^{21b}$;
- C$_3$-C$_{10}$ carbocycle substituted with 0-3 R$^{21b}$; and
- 5 to 10 membered heterocycle containing 1 to 4 heteroatoms selected from nitrogen, oxygen, and sulphur, wherein said 5 to 10 membered heterocycle is substituted with 0-3 R$^{21b}$;

R$^{21a}$, at each occurrence, is independently selected from H, C$_1$-C$_6$ alkyl, OR$^{14}$, Cl, F, Br, I, =O, CN, NO$_2$, NR$^{15}$R$^{16}$, CF$_3$;
- phenyl substituted with 0-3 R$^{21b}$;
- C$_3$-C$_6$ cycloalkyl substituted with 0-3 R$^{21b}$; and
- 5 to 6 membered heterocycle containing 1 to 3 heteroatoms selected from nitrogen, oxygen, and sulphur, wherein said 5 to 6 membered heterocycle is substituted with 0-3 R$^{21b}$;

R$^{21b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$-C$_6$ alkyl, C$_1$-C$_4$ alkoxy, C$_1$-C$_4$ haloalkyl, C$_1$-C$_4$ haloalkoxy, and C$_1$-C$_4$ haloalkyl-S—;

additionally, two R$^{21}$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0-3 $R^{23}$;

additionally, two $R^{21}$ substituents on the same or adjacent carbon atoms may be combined to form a $C_3$-$C_6$ carbocycle substituted with 0-3 $R^{23}$;

additionally, two $R^{21}$ substituents on adjacent atoms may be combined to form a benzo fused radical; wherein said benzo fused radical is substituted with 0-4 $R^{23}$;

$R^{23}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, and $CF_3$;

$R^{26}$ is H;
$C_1$-$C_6$ alkyl substituted with 0-3 $R^{26a}$;
$C_3$-$C_{10}$ carbocycle substituted with 0-3 $R^{26b}$; or
aryl substituted with 0-3 $R^{26b}$;

$R^{26a}$, at each occurrence, is independently selected from H, $C_1$-$C_6$ alkyl, $OR^{14}$, Cl, F, Br, I, =O, CN, $NO_2$, $NR^{15}R^{16}$, aryl and $CF_3$; and $R^{26b}$, at each occurrence, is independently selected from H, OH, Cl, F, Br, I, CN, $NO_2$, $NR^{15}R^{16}$, $CF_3$, $C_1$-$C_6$ alkyl, $C_1$-$C_4$ alkoxy, $C_1$-$C_4$ haloalkyl, and $C_1$-$C_4$ haloalkoxy.

2. A process according to claim 1 for preparing a compound of Formula I or a stereoisomer, or a pharmaceutically acceptable salt thereof, wherein:

L is —$NR^{26}C$(=O)—, —C(=O)$NR^{26}$—, or —OC(=O)$NR^{26}$—;

$R^3$ is —(CHR$^7$)$_n$—$R^4$,
—(CHR$^7$)$_l$—N—(CR$^7$R$^{7a}$)$_m$—$R^4$, or
—(CHR$^7$)$_l$—O—(CR$^7$R$^{7a}$)$_m$—$R^4$;

n is 0, 1 or 2;
m is 0, 1 or 2;
l is 1;

Ring C is a 3 to 8 membered carbocycle substituted with 0-4 $R^{21}$;
optionally, the carbocycle contains a heteroatom selected from —O— and —N($R^{20}$)—;

$R^4$ is H, OH, $OR^{14a}$,
$C_1$-$C_6$ alkyl substituted with 0-3 $R^{4a}$,
$C_2$-$C_6$ alkenyl substituted with 0-2 $R^{4a}$,
$C_2$-$C_6$ alkynyl substituted with 0-1 $R^{4a}$,
$C_3$-$C_6$ carbocycle substituted with 0-3 $R^{4b}$,
aryl substituted with 0-3 $R^{4b}$, or
5 to 6 membered heterocycle containing 1 to 4 heteroatoms selected from nitrogen, oxygen, and sulphur, wherein said 5 to 6 membered heterocycle is substituted with 0-3 $R^{4b}$;

$R^{4a}$, at each occurrence, is independently selected from H, OH, F, Cl, Br, I, $NR^{15}R^{16}$, $CF_3$,
$C_3$-$C_6$ carbocycle substituted with 0-3 $R^{4b}$,
phenyl substituted with 0-3 $R^{4b}$, and
5 to 6 membered heterocycle containing 1 to 4 heteroatoms selected from nitrogen, oxygen, and sulphur, wherein said 5 to 6 membered heterocycle is substituted with 0-3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$-$C_4$ alkyl, $C_1$-$C_3$ alkoxy, $C_1$-$C_2$ haloalkyl, and $C_1$-$C_2$ haloalkoxy;

$R^6$ is H;

$R^7$, at each occurrence, is independently selected from H, OH, F, $CF_3$, methyl, and ethyl;

Ring B is

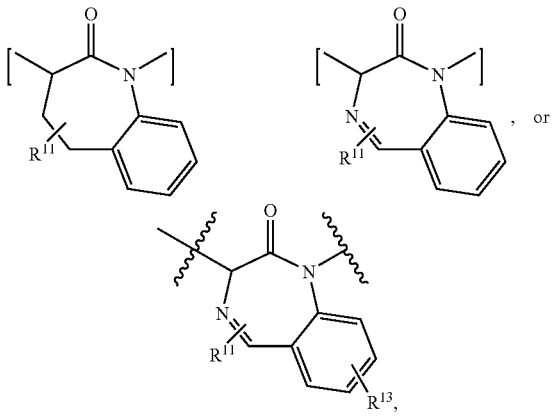

$R^{11}$, at each occurrence, is independently selected from H, $C_1$-$C_4$ alkoxy, Cl, F, Br, I, =O, CN, $NO_2$, $NR^{18}R^{19}$, C(=O)$R^{17}$, C(=O)$OR^{17}$, C(=O)$NR^{18}R^{19}$, S(=O)$_2NR^{18}R^{19}$, $CF_3$;

$C_1$-$C_6$ alkyl optionally substituted with 0-3 $R^{11a}$;
aryl substituted with 0-3 $R^{11b}$;
$C_3$-$C_{10}$ carbocycle substituted with 0-3 $R^{11b}$; and
5 to 10 membered heterocycle containing 1 to 4 heteroatoms selected from nitrogen, oxygen, and sulphur, wherein said 5 to 10 membered heterocycle is substituted with 0-3 $R^{11b}$;

$R^{11a}$, at each occurrence, is independently selected from H, $C_1$-$C_6$ alkyl, $OR^{14}$, Cl, F, Br, I, =O, CN, $NO_2$, $NR^{15}R^{16}$, $CF_3$, or phenyl substituted with 0-3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$-$C_6$ alkyl, $C_1$-$C_4$ alkoxy, $C_1$-$C_4$ haloalkyl, and $C_1$-$C_4$ haloalkoxy;

additionally, two $R^{11}$ substituents on adjacent atoms may be combined to form a benzo fused radical; wherein said benzo fused radical is substituted with 0-2 $R^{13}$;

additionally, two $R^{11}$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0-2 $R^{13}$;

additionally, two $R^{11}$ substituents on the same or adjacent carbon atoms may be combined to form a $C_3$-$C_6$ carbocycle substituted with 0-2 $R^{13}$;

W is a bond, —$CH_2$—, —CH($CH_3$)—, —$CH_2CH_2$— or —CH($CH_3$)$CH_2$—;

X is a bond;
phenyl substituted with 0-2 $R^{Xb}$;
$C_3$-$C_6$ cycloalkyl substituted with 0-2 $R^{Xb}$; or
5 to 6 membered heterocycle substituted with 0-2 $R^{Xb}$;

$R^{Xb}$, at each occurrence, is independently selected from H, OH, Cl, F, $NR^{15}R^{16}$, $CF_3$, acetyl, $SCH_3$, S(=O)$CH_3$, S(=O)$_2CH_3$, $C_1$-$C_4$ alkyl, $C_1$-$C_3$ alkoxy, $C_1$-$C_2$ haloalkyl, and $C_1$-$C_2$ haloalkoxy;

Y is a bond, —$CH_2$—V—, —V—, or —V—$CH_2$—;

V is a bond, —C(=O)—, —O—, —S—, —S(=O)—, —S(=O)$_2$—, —NH—, —N($CH_3$)—, or —N($CH_2CH_3$)—, Z is H; $C_1$-$C_6$ alkyl; $C_2$-$C_4$ alkenyl; $C_2$-$C_4$ alkynyl;
$C_1$-$C_3$ alkyl substituted with 1-2 $R^{12}$;
$C_2$-$C_3$ alkenyl substituted with 1-2 $R^{12}$;
$C_2$-$C_3$ alkynyl substituted with 1-2 $R^{12}$;
aryl substituted with 0-4 $R^{12b}$;
$C_3$-$C_6$ carbocycle substituted with 0-3 $R^{12b}$; or
5 to 10 membered heterocycle substituted with 0-3 $R^{12b}$;
$R^{12}$, at each occurrence, is independently selected from
aryl substituted with 0-4 $R^{12b}$;
$C_3$-$C_{10}$ carbocycle substituted with 0-4 $R^{12b}$; and
5 to 10 membered heterocycle containing 1 to 4 heteroatoms selected from nitrogen, oxygen, and sulphur, wherein said 5 to 10 membered heterocycle is substituted with 0-3 $R^{12b}$;
$R^{12b}$, at each occurrence, is independently selected from
H, OH, Cl, F, Br, I, CN, $NO_2$, $NR^{15}R^{16}$, $CF_3$, acetyl, $SCH_3$, $S(=O)CH_3$, $S(=O)_2CH_3$,
$C_1$-$C_6$ alkyl, $C_1$-$C_4$ alkoxy, $C_1$-$C_4$ haloalkyl,
$C_1$-$C_4$ haloalkoxy, and $C_1$-$C_4$ haloalkyl-S—;
$R^{13}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, and $CF_3$;
$R^{14}$ is H, phenyl, benzyl, $C_1$-$C_4$ alkyl, or $C_2$-$C_4$ alkoxyalkyl;
$R^{14a}$ is H, phenyl, benzyl, or $C_1$-$C_4$ alkyl;
$R^1$-5 at each occurrence, is independently selected from
H, $C_1$-$C_4$ alkyl, benzyl, phenethyl, ($C_1$-$C_4$ alkyl)-C(=O)—, and ($C_1$-$C_4$ alkyl)-S(=O)$_2$—;
$R^{16}$, at each occurrence, is independently selected from H, OH, $C_1$-$C_4$ alkyl, benzyl, phenethyl,
($C_1$-$C_4$ alkyl)-C(=O)—, and ($C_1$-$C_4$ alkyl)-S(=O)$_2$—;
$R^{17}$ is H, methyl, ethyl, propyl, butyl, methoxymethyl, ethoxymethyl, methoxyethyl, ethoxyethyl, phenyl substituted by 0-3 $R^{17a}$, or
—$CH_2$-phenyl substituted by 0-3 $R^{17a}$;
$R^{17a}$ is H, methyl, methoxy, —OH, F, Cl, $CF_3$, or $OCF_3$;
$R^{18}$, at each occurrence, is independently selected from H, methyl, ethyl, propyl, butyl, phenyl, benzyl, and phenethyl;
$R^{19}$, at each occurrence, is independently selected from H, methyl, and ethyl;
$R^{20}$ is H or C(=O)$OR^{17}$;
$R^{26}$ is Hr methyl, or ethyl.

3. A process for preparing a compound of Formula I or a stereolsomer, or a pharmaceutically acceptable salt thereof, according to claim 2, wherein:
Ring C is selected from:

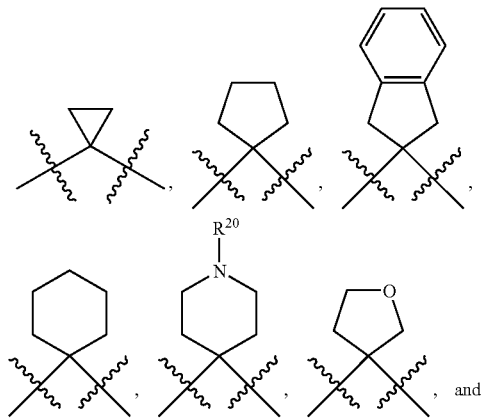

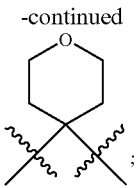

wherein Ring C is substituted with 0-2 $R^{21}$; and
Ring B is selected from:

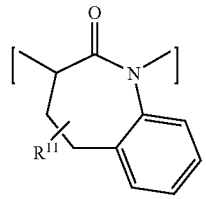 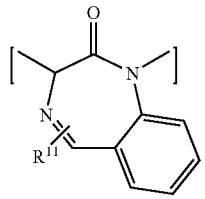

4. A process for preparing a compound of Formula I or a stereolsomer, or a pharmaceutically acceptable salt thereof, claim 3, wherein:
L is —NHC(=O)—, —C(=O)NH—, or —OC(=O)NH—;
$R^3$ is $R^4$, —$CH_2OR^4$, or —$CH_2CH_2OR^4$;
$R^4$ is $C_1$-$C_6$ alkyl substituted with 0-3 $R^{4a}$,
$C_2$-$C_6$ alkenyl substituted with 0-1 $R^{4a}$, or
$C_2$-$C_6$ alkynyl substituted with 0-1 $R^{4a}$;
$R^{4a}$, at each occurrence, is independently selected from H, OH, F, $NR^{15}R^{16}$, $CF_3$,
$C_3$-$C_6$ carbocycle substituted with 0-3 $R^{4b}$,
phenyl substituted with 0-3 $R^{4b}$, and
5 to 6 membered heterocycle containing 1 to 4 heteroatoms selected from nitrogen, oxygen, and sulphur, wherein said 5 to 6 membered heterocycle is substituted with 0-3 $R^{4b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;
$R^{4b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;
W is a bond, —$CH_2$—, —$CH(CH_3)$—, —$CH_2CH_2$— or —$CH(CH_3)CH_2$—;
X is a bond, phenyl, $C_3$-$C_6$ cycloalkyl, or 5 to 6 membered heterocycle;
Y is a bond, —C(=O)—, —O—, —S—, —S(=O)—, —$S(=O)_2$—, —NH—, —$N(CH_3)$—, or —$N(CH_2CH_3)$—,
Z is H; $C_1$-$C_6$ alkyl, $C_2$-$C_4$ alkenyl, $C_2$-$C_4$ alkynyl,
$C_1$-$C_3$ alkyl substituted with 1-2 $R^{12}$;
$C_2$-$C_3$ alkenyl substituted with 1-2 $R^{12}$;
$C_2$-$C_3$ alkynyl substituted with 1-2 $R^{12}$;
aryl substituted with 0-4 $R^{12b}$;
$C_3$-$C_6$ carbocycle substituted with 0-3 $R^{12b}$; or
5 to 6 membered heterocycle containing 1 to 4 heteroatoms selected from nitrogen, oxygen, and sulphur, wherein said 5 to 6 membered heterocycle is substituted with 0-3 $R^{12b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{12}$, at each occurrence, is independently selected from aryl substituted with 0-4 $R^{12b}$;

$C_3$-$C_6$ carbocycle substituted with 0-3 $R^{12b}$; and 5 to 10 membered heterocycle containing 1 to 4 heteroatoms selected from nitrogen, oxygen, and sulphur, wherein said 5 to 10 membered heterocycle is substituted with 0-3 $R^{12b}$;

wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{12b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;

$R^{13}$, at each occurrence, is independently selected from H, OH, methyl, ethyl, propyl, butyl, methoxy, ethoxy, Cl, F, Br, CN, $NR^{15}R^{16}$, and $CF_3$;

$R^{14}$ is H, phenyl, benzyl, methyl, ethyl, propyl, or butyl;

$R^{15}$, at each occurrence, is independently selected from H, methyl, ethyl, propyl, and butyl;

$R^{16}$, at each occurrence, is independently selected from H, OH, methyl, ethyl, propyl, butyl, benzyl, phenethyl, methyl-C(=O)—, ethyl-C(=O)—, methyl-S(=O)$_2$—, ethyl-S(=O)$_2$—, and propyl-S(=O)$_2$—;

$R^{18}$, at each occurrence, is independently selected from H, methyl, ethyl, propyl, butyl, phenyl, benzyl, and phenethyl;

$R^{19}$, at each occurrence, is independently selected from H, methyl, and ethyl;

$R^{20}$ is H.

5. A process of preparing a compound of Formula (I):

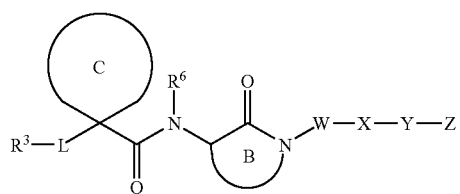

(I)

or a stereoisomer, pharmaceutically acceptable salt thereof, comprising an amide bond synthesis coupling a carboxylic acid 1 and an amine 2 including methods comprising HATU, TBTU, BOB, EDC, CDI, and DCC-mediated amide couplings,

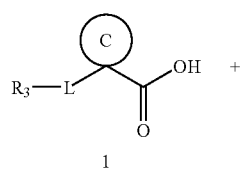

1

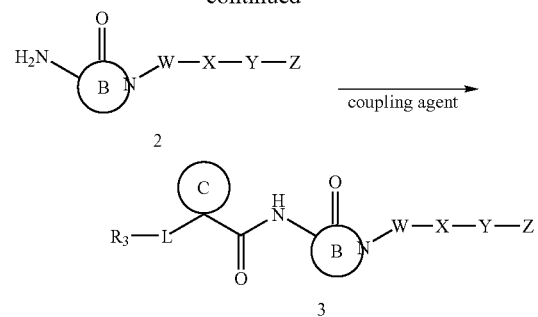

wherein the reaction product 3 comprises Formula (I)

L is —$NR^{26}C(=O)$—, —$C(=O)NR^{26}$—, —$NR^{26}C(=O)O$—, —$OC(=O)NR^{26}$, or —$NR^{26}C(=O)NR^{26}$—;

$R^3$ is —$(CR^7R^{7a})_n$—$R^4$,
—$(CR^7R^{7a})_l$—S—$R^4$,
—$(CR^7R^{7a})_l$—O—$R^4$;
—$(CR^7R^{7a})_l$—$N(R^{7b})$—$R^4$,
—$(CR^7R^{7a})_l$—S(=O)—$R^4$, or
—$(CR^7R^{7a})_l$—S(=O)$_2$—$R^4$, n is 0, 1 or 2;

l is 1 or 2;

$R^4$ is H,
$C_1$-$C_8$ alkyl substituted with 0-3 $R^{4a}$,
$C_2$-$C_8$ alkenyl substituted with 0-3 $R^{4a}$,
$C_2$-$C_8$ alkynyl substituted with 0-3 $R^{4a}$,
$C_3$-$C_{10}$ carbocycle substituted with 0-3 $R^{4b}$,
aryl substituted with 0-3 $R^{4b}$, or
5 to 10 membered heterocycle containing 1 to 4 heteroatoms selected from nitrogen, oxygen, and sulphur, wherein said 5 to 10 membered heterocycle is substituted with 0-3 $R^{4b}$;

$R^{4a}$, at each occurrence, is independently selected from H, OH, F, Cl, Br, I, $NR^{15}R^{16}$, $CF_3$,
$C_3$-$C_{10}$ carbocycle substituted with 0-3 $R^{4b}$,
aryl substituted with 0-3 $R^{4b}$, and
5 to 10 membered heterocycle containing 1 to 4 heteroatoms selected from nitrogen, oxygen, and sulphur, wherein said 5 to 10 membered heterocycle is substituted with 0-3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
$C_1$-$C_6$ alkyl, $C_1$-$C_4$ alkoxy, $C_1$-$C_4$ haloalkyl,
$C_1$-$C_4$ haloalkoxy, and $C_1$-$C_4$ haloalkyl-S—;

Ring C is a 3-8 membered carbocycle;
wherein said 3-8 membered carbocycle is saturated or partially unsaturated;
wherein said 3-8 membered carbocycle is substituted with 0-4 $R^{21}$; and
optionally, the carbocycle contains a heteroatom selected from —O— and —$N(R^{20})$—;

additionally, two $R^{21}$ substituents on adjacent atoms may be combined to form a benzo fused radical; wherein said benzo fused radical is substituted with 0-4 $R^{23}$;

additionally, two $R^{21}$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0-3 $R^{23}$;

additionally, two $R^{21}$ substituents on the same or adjacent carbon atoms may be combined to form a $C_3$-$C_6$ carbocycle substituted with 0-3 $R^{23}$;

$R^{21}$, at each occurrence, is independently selected from H, OH, Cl, F, Br, I, CN, $NO_2$, $CF_3$, acetyl, $SCH_3$, $S(=O)CH_3$, $S(=O)_2CH_3$, $NR^{15}R^{16}$, $OR^{14a}$, $C_1$-$C_4$ alkyl, $C_2$-$C_6$ alkenyl, alkynyl, $C_1$-$C_4$ alkoxy, $C_1$-$C_4$ haloalkyl, $C_1$-$C_4$ haloalkoxy, and $C_1$-$C_4$ haloalkyl-S—, $C_3$-$C_6$ carbocycle, phenyl, and a 5 to 6 membered heterocycle containing 1 to 4 heteroatoms selected from nitrogen, oxygen, and sulphur;

$R^6$ is H, methyl, or ethyl;

$R^7$, at each occurrence, is independently H or $C_1$-$C_4$ alkyl;

$R^{7a}$, at each occurrence, is independently H or $C_1$-$C_4$ alkyl;

$R^{7b}$ is H or $C_1$-$C_4$ alkyl;

Ring B is:

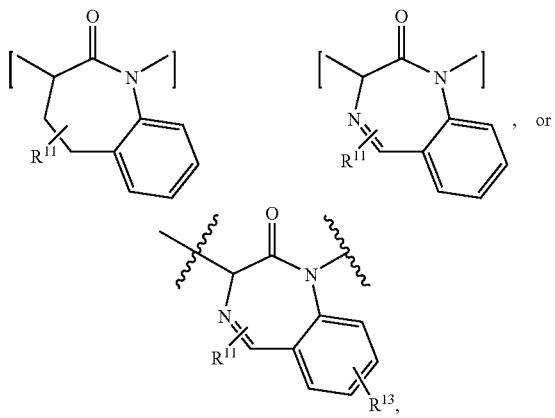

$R^{11}$, at each occurrence, is independently selected from H, $C_1$-$C_4$ alkoxy, Cl, F, Br, I, =O, CN, $NO_2$, $NR^{18}R^{19}$, $C(=O)R^{17}$, $C(=O)OR^{17}$, $C(=O)NR^{18}R^{19}$, $S(=O)_2NR^{18}R^{19}$, $CF_3$;

$C_1$-$C_6$ alkyl optionally substituted with 0-3 $R^{11a}$;

aryl substituted with 0-3 $R^{11b}$;

$C_3$-$C_{10}$ carbocycle substituted with 0-3 $R^{11b}$; and 5 to 10 membered heterocycle containing 1 to 4 heteroatoms selected from nitrogen, oxygen, and sulphur, wherein said 5 to 10 membered heterocycle is substituted with 0-3 $R^{11b}$;

$R^{11a}$, at each occurrence, is independently selected from H, $C_1$-$C_6$ alkyl, $OR^{14}$, Cl, F, Br, I, =O, CN, $NO_2$, $NR^{15}R^{16}$, $CF_3$;

phenyl substituted with 0-3 $R^{11b}$;

$C_3$-$C_6$ cycloalkyl substituted with 0-3 $R^{11b}$; and 5 to 6 membered heterocycle containing 1 to 4 heteroatoms selected from nitrogen, oxygen, and sulphur, wherein said 5 to 6 membered heterocycle is substituted with 0-3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

W is a bond or —$(CH_2)_p$—;

p is 1 or 2;

X is a bond;

phenyl substituted with 0-2 $R^{Xb}$;

$C_3$-$C_6$ carbocycle substituted with 0-2 $R^{Xb}$; or 5 to 6 membered heterocycle substituted with 0-2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_4$ alkyl, $C_1$-$C_3$ alkoxy, $C_1$-$C_3$ haloalkyl, $C_1$-$C_3$ haloalkoxy, and $C_1$-$C_3$ halothioalkoxy;

Y is a bond, —C(=O)—, —O—, —S—, —S(=O)—, —S(=O)_2—, —N(R^{19})—, —C(=O)NR^{19b}—, —NR^{19b}C(=O)—, —NR^{19b}S(=O)_2—, —S(=O)_2NR^{19b}—, —NR^{19b}S(=O)—, —S(=O)NR^{19b}—, —C(=O)O—, or —OC(=O)—;

Z is H;

$C_1$-$C_8$ alkyl substituted with 0-3 $R^{12a}$;

$C_2$-$C_6$ alkenyl substituted with 0-3 $R^{12a}$;

$C_2$-$C_6$ alkynyl substituted with 0-3 $R^{12a}$;

aryl substituted with 0-4 $R^{12b}$;

$C_3$-$C_{10}$ carbocycle substituted with 0-4 $R^{12b}$; or 5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12a}$, at each occurrence, is independently selected from H, OH, Cl, F, Br, I, CN, $NO_2$, $NR^{15}R^{16}$, —C(=O)NR^{15}R^{16}, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, $C_1$-$C_4$ haloalkyl-S—, aryl substituted with 0-4 $R^{12b}$;

$C_3$-$C_{10}$ carbocycle substituted with 0-4 $R^{12b}$; and 5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

$R^{13}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, and $CF_3$;

$R^{14}$ is H, phenyl, benzyl, $C_1$-$C_6$ alkyl, $C_2$-$C_6$ alkoxyalkyl, or $C_3$-$C_6$ cycloalkyl;

$R^{14a}$ is H, phenyl, benzyl, or $C_1$-$C_4$ alkyl;

$R^{15}$, at each occurrence, is independently selected from H, $C_1$-$C_6$ alkyl, benzyl, phenethyl, ($C_1$-$C_6$ alkyl)-C(=O)—, and ($C_1$-$C_6$ alkyl)-S(=O)_2—;

$R^{16}$, at each occurrence, is independently selected from H, OH, $C_1$-$C_6$ alkyl, benzyl, phenethyl, ($C_1$-$C_6$ alkyl)-C(=O)—, and ($C_1$-$C_6$ alkyl)-S(=O)_2—;

$R^{17}$ is H, $C_1$-$C_6$ alkyl, $C_2$-$C_6$ alkoxyalkyl, aryl substituted by 0-4 $R^{17a}$, or —$CH_2$-aryl substituted by 0-4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(O)CH_3$, $SO_2CH_3$, —$NH_2$, —$N(CH_3)_2$, or $C_1$-$C_4$ haloalkyl;

$R^{18}$, at each occurrence, is independently selected from H, $C_1$-$C_6$ alkyl, phenyl, benzyl, phenethyl, ($C_1$-$C_6$ alkyl)-C(=O)—, and ($C_1$-$C_6$ alkyl)-S(=O)_2—;

$R^{19}$, at each occurrence, is independently selected from H, OH, methyl, ethyl, propyl, butyl, phenyl, benzyl, and phenethyl;

$R^{19b}$, at each occurrence, is independently is H or $C_1$-$C_4$ alkyl;

$R^{20}$ is H, $C_1$-$C_4$ alkyl, or $C(=O)OR^{17}$;

$R^{23}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, and $CF_3$; and $R^{26}$ is H or $C_1$-$C_4$ alkyl.

6. A process according to claim 5 for preparing a compound of Formula (Ia)

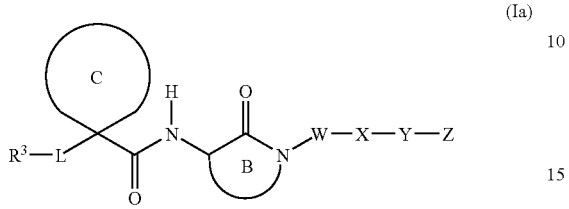

or a stereoisomer, pharmaceutically acceptable salt, wherein:

L is —$NR^{26}C(=O)$—, —$C(=O)NR^{26}$—, —$NR^{26}C(=O)O$—, —$OC(=O)NR^{26}$, or —$NR^{26}C(=O)NR^{26}$—;

$R^3$ is —$(CHR^7)_n$—$R^4$,
—$(CHR^7)_l$—S—$R^4$,
—$(CHR^7)_l$—O—$R^4$;
—$(CR^7R^{7a})_l$—$N(R^{7b})$—$R^4$,
—$(CR^7R^{7a})_l$—$S(=O)$—$R^4$, or
—$(CR^7R^{7a})_l$—$S(=O)_2$—$R^4$;

n is 0, 1 or 2;

l is 1 or 2;

$R^4$ is H,
$C_1$-$C_8$ alkyl substituted with 0-3 $R^{4a}$,
$C_2$-$C_8$ alkenyl substituted with 0-3 $R^{4a}$,
$C_2$-$C_8$ alkynyl substituted with 0-3 $R^{4a}$,
$C_3$-$C_{10}$ carbocycle substituted with 0-3 $R^{4b}$,
aryl substituted with 0-3 $R^b$, or
5 to 10 membered heterocycle containing 1 to 4 heteroatoms selected from nitrogen, oxygen, and sulphur, wherein said 5 to 10 membered heterocycle is substituted with 0-3 $R^{4b}$;

$R^{4a}$, at each occurrence, is independently selected from H, OH, F, Cl, Br, I, $NR^{15}R^{16}$, $CF_3$,
$C_3$-$C_{10}$ carbocycle substituted with 0-3 $R^{4b}$,
aryl substituted with 0-3 $R^{4b}$, and
5 to 10 membered heterocycle containing 1 to 4 heteroatoms selected from nitrogen, oxygen, and sulphur, wherein said 5 to 10 membered heterocycle is substituted with 0-3 $R^{4b}$;

$R^{4b}$, at each occurrence, is independently selected from H, OR, Cl, F, Br, I, CN, $NO_2$, $NR^{15}R^{16}$, $CF_3$, acetyl, $SCH_3$, $S(=O)CH_3$, $S(=O)_2CH_3$,
$C_1$-$C_6$ alkyl, $C_1$-$C_4$ alkoxy, $C_1$-$C_4$ haloalkyl,
$C_1$-$C_4$ haloalkoxy, and $C_1$-$C_4$ haloalkyl-S—;

Ring C is a 3-8 membered carbocycle;
wherein said 3-8 membered carbocycle is saturated or partially unsaturated;
wherein said 3-8 membered carbocycle is substituted with 0-4 $R^{21}$;
optionally, the carbocycle contains a heteroatom selected from —O—, and —$N(R^{20})$—;
additionally, two $R^{21}$ substituents on adjacent atoms may be combined to form a benzo fused radical; wherein said benzo fused radical is substituted with 0-4 $R^{23}$;
additionally, two $R^{21}$ substituents on the same or adjacent carbon atoms may be combined to form a $C_3$-$C_6$ carbocycle substituted with 0-3 $R^{23}$;

$R^{21}$, at each occurrence, is independently selected from H, OH, Cl, F, Br, I, CN, $NO_2$, $CF_3$, acetyl, $SCH_3$, $S(=O)CH_3$, $S(=O)_2CH_3$, $NR^{15}R^{16}$, $OR^{14a}$, $C_1$-$C_4$ alkyl, $C_2$-$C_6$ alkenyl, alkynyl, $C_1$-$C_4$ alkoxy $C_1$-$C_4$ haloalkyl, $C_1$-$C_4$ haloalkoxy, and $C_1$-$C_4$ haloalkyl-S—,
$C_3$-$C_6$ carbocycle, phenyl, and a
5 to 6 membered heterocycle containing 1 to 4 heteroatoms selected from nitrogen, oxygen, and sulphur;

$R^7$, at each occurrence, is independently H, methyl, or ethyl;

$R^{7b}$ is H, methyl, or ethyl;

Ring B is selected from:

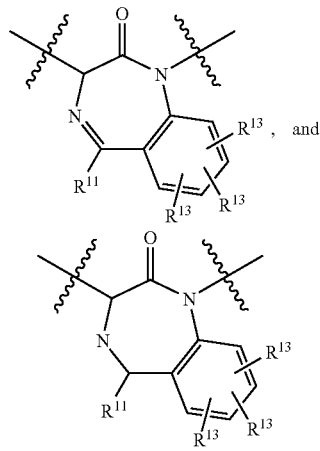

$R^{11}$, at each occurrence, is independently selected from H, $C_1$-$C_4$ alkoxy, Cl, F, Br, I, =O, CN, $NO_2$, $NR^{18}R^{19}$, $C(=O)R^{17}$, $C(=O)OR^{17}$, $C(=O)NR^{18}R^{19}$, $S(=O)_2NR^{18}R^{19}$, $CF_3$;
$C_1$-$C_6$ alkyl optionally substituted with 0-3 $R^{11a}$;
aryl substituted with 0-3 $R^{11b}$;
$C_3$-$C_{10}$ carbocycle substituted with 0-3 $R^{11b}$; and
5 to 10 membered heterocycle containing 1 to 4 heteroatoms selected from nitrogen, oxygen, and sulphur, wherein said 5 to 10 membered heterocycle is substituted with 0-3 $R^{11b}$;

$R^{11a}$, at each occurrence, is independently selected from H, $C_1$-$C_6$ alkyl, $OR^{14}$, Cl, F, Br, I, =O, CN, $NO_2$, $NR^{15}R^{16}$, $CF_3$;
phenyl substituted with 0-3 $R^{11b}$;
$C_3$-$C_6$ cycloalkyl substituted with 0-3 $R^{11b}$; and
5 to 6 membered heterocycle containing 1 to 4 heteroatoms selected from nitrogen, oxygen, and sulphur, wherein said 5 to 6 membered heterocycle is substituted with 0-3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
$C_1$-$C_6$ alkyl, $C_1$-$C_4$ alkoxy, $C_1$-$C_4$ haloalkyl,
$C_1$-$C_4$ haloalkoxy, and $C_1$-$C_4$ haloalkyl-S—;

W is a bond or —$(CH_2)_p$—;

p is 1 or 2;

X is a bond;
phenyl substituted with 0-2 $R^{Xb}$;
$C_3$-$C_6$ carbocycle substituted with 0-2 $R^{Xb}$; or
5 to 6 membered heterocycle substituted with 0-2 $R^{Xb}$;

$R^{Xb}$, at each occurrence, is independently selected from H, OH, Cl, F, Br, I, CN, $NO_2$, $NR^{15}R^{16}$, $CF_3$, acetyl, SCH$_3$, S(=O)CH$_3$, S(=O)$_2$OH$_3$, C$_1$-C$_4$ alkyl, C$_1$-C$_3$ alkoxy, C$_1$-C$_3$ haloalkyl, C$_1$-C$_3$ haloalkoxy, and C$_1$-C$_3$ halothioalkoxy;

Y is a bond, —C(=O)—, —O—, —S—, —S(=O)—, —S(=O)$_2$—, —N(R$^{19}$)—, —C(=O)NR$^{19b}$—, —NR$^{19b}$C(=O)—, —NR$^{19b}$S(=O)$_2$—, —S(=O)$_2$NR$^{19b}$—, —NR$^{19b}$S(=O)—, —S(=O)NR$^{19b}$—, —C(=O)O—, or —OC(=O)—;

Z is H;
C$_1$-C$_8$ alkyl substituted with 0-3 R$^{12a}$,
C$_2$-C$_6$ alkenyl substituted with 0-3 R$^{12a}$;
C$_2$-C$_6$ alkynyl substituted with 0-3 R$^{12a}$;
aryl substituted with 0-4 R$^{12b}$;
C$_3$-C$_{10}$ carbocycle substituted with 0-4 R$^{12b}$; or
5 to 10 membered heterocycle containing 1 to 4 heteroatoms selected from nitrogen, oxygen, and sulphur, wherein said 5 to 10 membered heterocycle is substituted with 0-3 R$^{12b}$;

R$^{12a}$, at each occurrence, is independently selected from H, OH, Cl, F, Br, I, CN, NO$_2$, NR$^{15}$R$^{16}$, —C(=O)NR$^{15}$R$^{16}$, CF$_3$, acetyl, SCH$_3$, S(=O)CH$_3$, S(=O)$_2$CH$_3$,
C$_1$-C$_6$ alkyl, C$_1$-C$_4$ alkoxy, C$_1$-C$_4$ haloalkyl,
C$_1$-C$_4$ haloalkoxy, C$_1$-C$_4$ haloalkyl-S—,
aryl substituted with 0-4 R$^{12b}$;
C$_3$-C$_{10}$ carbocycle substituted with 0-4 R$^{12b}$; and
5 to 10 membered heterocycle containing 1 to 4 heteroatoms selected from nitrogen, oxygen, and sulphur, wherein said 5 to 10 membered heterocycle is substituted with 0-3 R$^{12b}$;

R$^{12b}$, at each occurrence, is independently selected from H, OH, Cl, F, Br, I, CN, NO$_2$, NR$^{15}$R$^{16}$, CF$_3$, acetyl, SCH$_3$, S(=O)CR$_3$, S(=O)$_2$CH$_3$,
C$_1$-C$_6$ alkyl, C$_1$-C$_4$ alkoxy, C$_1$-C$_4$ haloalkyl,
C$_1$-C$_4$ haloalkoxy, and C$_1$-C$_4$ haloalkyl-S—;

R$^{13}$, at each occurrence, is independently selected from H, OH, C$_1$-C$_6$ alkyl, C$_1$-C$_4$ alkoxy, Cl, F, Br, r, CN, NO$_2$, NR$^{15}$R$^{16}$, and CF$_3$;

R$^{14}$ is H, phenyl, benzyl, C$_1$-C$_6$ alkyl, C$_2$-C$_6$ alkoxyalkyl, or C$_3$-C$_6$ cycloalkyl;

R$^{14a}$ is H, phenyl, benzyl, or C$_1$-C$_4$ alkyl;

R$^{15}$, at each occurrence, is independently selected from H, C$_1$-C$_6$ alkyl, benzyl, phenethyl, (C$_1$-C$_6$ alkyl)-C(=O)—, and (C$_1$-C$_6$ alkyl)-S(=O)$_2$—;

R$^{16}$, at each occurrence, is independently selected from H, OH, C$_1$-C$_6$ alkyl, benzyl, phenethyl,
(C$_1$-C$_6$ alkyl)-C(=O)—, and (C$_1$-C$_6$ alkyl)-S(=O)$_2$—;

R$^{17}$ is H, C$_1$-C$_6$ alkyl, C$_2$-C$_6$ alkoxyalkyl,
aryl substituted by 0-4 R$^{17a}$, or
—CH$_2$-aryl substituted by 0-4 R$^{17a}$;

R$^{17a}$ is H, methyl, ethyl, propyl, butyl, methoxy, ethoxy, propoxy, butoxy, —OH, F, Cl, Br, I, CF$_3$, OCF$_3$, SCH$_3$, S(O)CH$_3$, SO$_2$CH$_3$, —NH$_2$, —N(CH$_3$)$_2$, or C$_1$-C$_4$ haloalkyl;

R$^{18}$, at each occurrence, is independently selected from H, C$_1$-C$_6$ alkyl, phenyl, benzyl, phenethyl,
(C$_1$-C$_6$ alkyl)-C(=O)—, and (C$_1$-C$_6$ alkyl)-S(=O)$_2$—;

R$^{19}$, at each occurrence, is independently selected from H, OH, methyl, ethyl, propyl, butyl, phenyl, benzyl, phenethyl;

R$^{20}$ is H, C$_1$-C$_4$ alkyl, or C(=O)OR$^{17}$;

R$^{23}$, at each occurrence, is independently selected from H, OH, C$_1$-C$_6$ alkyl, C$_1$-C$_4$ alkoxy, Cl, F, Br, I, CN, NO$_2$, NR$^{15}$R$^{16}$, and CF$_3$; and R$^{26}$ is H or C$_1$-C$_4$ alkyl.

7. A process according to claim 1 for preparing a compound of Formula (Id) or Formula (Ie),

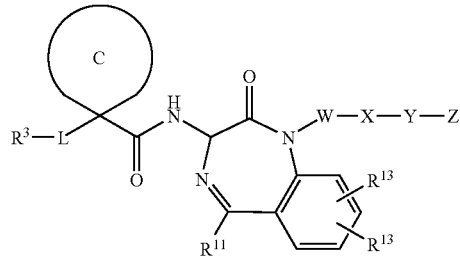

(Id)

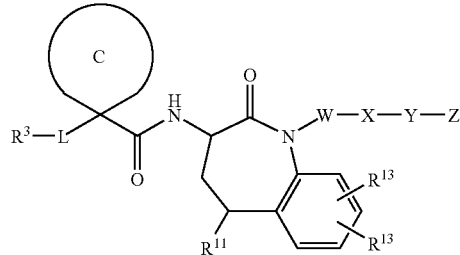

(Ie)

or a stereoisomer, pharmaceutically acceptable salt thereof, comprising an amide bond synthesis coupling a carboxylic acid 1 and an amine 2 including coupling methods comprising HATU, TBTU, BOP, EDC, CDI, and DCC-mediated couplings, wherein the amine 2 is selected from an amino benzo-1,4-diazepine and an amino benzoazepine, wherein:
L is —NHC(=O)—, —C(=O)NH—, or —OC(=O)NH—;
R$^3$ is —(CH$_2$)$_n$—R$^4$,
—(CH$_2$)$_l$—S—R$^4$,
—(CH$_2$)$_l$—O—R$^4$, or
—(CH$_2$)$_l$—N(R$^{7b}$)—R$^4$;

n is 0, 1 or 2;
l is 1 or 2;

R$^4$ is C$_1$-C$_8$ alkyl substituted with 0-3 R$^{4a}$,
C$_2$-C$_8$ alkenyl substituted with 0-3 R$^{4a}$,
C$_2$-C$_8$ alkynyl substituted with 0-3 R$^{4a}$,
C$_3$-C$_{10}$ carbocycle substituted with 0-3 R$^{4b}$,
aryl substituted with 0-3 R$^{4b}$, or
5 to 10 membered heterocycle containing 1 to 4 heteroatoms selected from nitrogen, oxygen, and sulphur, wherein said 5 to 10 membered heterocycle is substituted with 0-3 R$^{4b}$;

R$^{4a}$, at each occurrence, is independently selected from H, OH, F, Cl, Br, I, NR$^{15}$R$^{16}$, CF$_3$,
C$_3$-C$_{10}$ carbocycle substituted with 0-3 R$^{4b}$,
aryl substituted with 0-3 R$^{4b}$, and
5 to 10 membered heterocycle containing 1 to 4 heteroatoms selected from nitrogen, oxygen, and sulphur, wherein said 5 to 10 membered heterocycle is substituted with 0-3 R$^{4b}$;

R$^{4b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$,
C$_1$-C$_6$ alkyl, C$_1$-C$_4$ alkoxy, C$_1$-C$_4$ haloalkyl,
C$_1$-C$_4$ haloalkoxy, and C$_1$-C$_4$ haloalkyl-S—;

R$^{7b}$ is H, methyl, or ethyl;

Ring C is a 3-8 membered carbocycle;
wherein said 3-8 membered carbocyclic moiety is saturated or partially saturated;
wherein said 3-8 membered carbocyclic moiety is substituted with 0-3 $R^{21}$;
optionally, the carbocycle contains a heteroatom selected from —O— and —N($R^{20}$)—;

$R^{21}$, at each occurrence, is independently selected from H, OH, Cl, F, Br, I, CN, $NO_2$, $CF_3$, acetyl, $SCH_3$, S(=O)$CH_3$, S(=O)$_2CH_3$, $NR^{15}R^{16}$, $OR^{14a}$, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, and $C_1$-$C_4$ haloalkyl-S—;

$R^{11}$, at each occurrence, is independently selected from H, =O, $NR^{18}R^{19}$, $CF_3$;
$C_1$-$C_4$ alkyl optionally substituted with 0-1 $R^{11a}$;
phenyl substituted with 0-3 $R^{11b}$;
$C_3$-$C_6$ carbocycle substituted with 0-3 $R^{11b}$; and
5 to 7 membered heterocycle containing 1 to 4 heteroatoms selected from nitrogen, oxygen, and sulphur, wherein said 5 to 7 membered heterocycle is substituted with 0-3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, homopiperidinyl, and tetrazolyl;

$R^{11a}$, at each occurrence, is independently-selected from H, $C_1$-$C_4$ alkyl, $OR^{14}$, F, Cl, =O, $NR^{15}R^{16}$, $CF_3$, or phenyl substituted with 0-3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$-$C_2$ haloalkyl, and $C_1$-$C_2$ haloalkoxy;

W is a bond, —$CH_2$—, —$CH_2CH_2$—;
X is a bond;
phenyl substituted with 0-2 $R^{Xb}$;
$C_3$-$C_6$ cycloalkyl substituted with 0-2 $R^{Xb}$; or
5 to 6 membered heterocycle substituted with 0-2 $R^{Xb}$;

$R^{Xb}$, at each occurrence, is independently selected from H, OH, Cl, F, $NR^{15}R^{16}$, $CF_3$, acetyl, $SCH_3$, S(=O)$CH_3$, S(=O)$_2CH_3$, $C_1$-$C_4$ alkyl, $C_1$-$C_3$ alkoxy, $C_1$-$C_2$ haloalkyl, and $C_1$-$C_2$ haloalkoxy;

Y is a bond, —C(=O)—, —O—, —S—, —S(—O)—, —S(=O)$_2$—, —N($R^{19}$)—, —C(=O)$NR^{19b}$—, —$NR^{19b}$C(=O)—, —$NR^{19b}$S(O)$_2$—, —S(=O)$_2$ $NR^{19b}$—, —$NR^{19b}$S(=O)—, —S(=O)$NR^{19b}$—, —C(=O)O—, or —OC(=O)—;

Z is H;
$C_1$-$C_8$ alkyl substituted with 0-3 $R^{12a}$;
$C_2$-$C_6$ alkenyl substituted with 0-3 $R^{12a}$;
$C_2$-$C_6$ alkynyl substituted with 0-3 $R^{12a}$;
aryl substituted with 0-4 $R^{12b}$;
$C_3$-$C_{10}$ carbocycle substituted with 0-4 $R^{12b}$; or
5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, S(=O)$CH_3$, S(=O)$_2CH_3$,
$C_1$-$C_6$ alkyl, $C_1$-$C_4$ alkoxy, $C_1$-$C_4$ haloalkyl, $C_1$-$C_4$ haloalkoxy, $C_1$-$C_4$ haloalkyl-S—,
aryl substituted with 0-4 $R^{12b}$;
$C_3$-$C_{10}$ carbocycle substituted with 0-4 $R^{12b}$; and
5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$,
$C_1$-$C_6$ alkyl, $C_1$-$C_4$ alkoxy, $C_1$-$C_4$ haloalkyl,
$C_1$-$C_4$ haloalkoxy, and $C_1$-$C_4$ haloalkyl-S—;

$R^{13}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, and $CF_3$;

$R^{14}$ is H, phenyl, benzyl, $C_1$-$C_6$ alkyl, $C_2$-$C_6$ alkoxyalkyl, or $C_3$-$C_6$ cycloalkyl;

$R^{14a}$ is H, phenyl, benzyl, or $C_1$-$C_4$ alkyl;

$R^{15}$, at each occurrence, is independently selected from H, $C_1$-$C_6$ alkyl, benzyl, phenethyl, ($C_1$-$C_6$ alkyl)-C(=O)—, and ($C_1$-$C_6$ alkyl)-S(O)$_2$—;

$R^{16}$, at each occurrence, is independently selected from H, OH, $C_1$-$C_6$ alkyl, benzyl, phenethyl, ($C_1$-$C_4$ alkyl)-C(=O)—, and ($C_1$-$C_4$ alkyl)-S(=O)$_2$—;

$R^{18}$, at each occurrence, is independently selected from H, $C_1$-$C_6$ alkyl, phenyl, benzyl, phenethyl, ($C_1$-$C_6$ alkyl)-C(=O)—, and ($C_1$-$C_6$ alkyl)-S(=O)$_2$—;

$R^{19}$, at each occurrence, is independently selected from H, OH, methyl, ethyl, propyl, butyl, phenyl, benzyl, phenethyl; and $R^{20}$ is H or $C_1$-$C_4$ alkyl.

8. A process according to claim 7 for preparing a compound of Formula (Id) or Formula (Ie), wherein:

L is —NHC(=O)—, —C(=O)NH—, or —OC(=O)NH—;

$R^3$ is —$R^4$, —$CH_2R^4$, —$CH_2CH_2R^4$, —$CH_2OR^4$, or —$CH_2CH_2OR^4$;

$R^4$ is $C_1$-$C_6$ alkyl substituted with 0-3 $R^{4a}$,
$C_2$-$C_6$ alkenyl substituted with 0-3 $R^{4a}$,
$C_2$-$C_6$ alkynyl substituted with 0-3 $R^{4a}$,
$C_3$-$C_6$ carbocycle substituted with 0-3 $R^{4b}$,
phenyl substituted with 0-3 $R^{4b}$, or
5 to 6 membered heterocycle containing 1 to 3 heteroatoms selected from nitrogen, oxygen, and sulphur, wherein said to 6 membered heterocycle is substituted with 0-3 $R^{4b}$;

$R^{4a}$, at each occurrence, is independently selected from is H, OH, F, Cl, Br, I, $NR^{15}R^{16}$, $CF_3$,
$C_3$-$C_6$ carbocycle substituted with 0-3 $R^{4b}$,
phenyl substituted with 0-3 $R^{4b}$, or
5 to 6 membered heterocycle containing 1 to 3 heteroatoms selected from nitrogen, oxygen, and sulphur, wherein said 5 to 6 membered heterocycle is substituted with 0-3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$,
$C_1$-$C_6$ alkyl, $C_1$-$C_4$ alkoxy, $C_1$-$C_4$ haloalkyl,
$C_1$-$C_4$ haloalkoxy, and $C_1$-$C_4$ haloalkyl-S—;

Ring C is a 3-6 membered carbocycle;
wherein said 3-6 membered carbocyclic moiety is saturated or partially unsaturated;
wherein said 3-6 membered carbocyclic moiety is substituted with 0-2 $R^{21}$;
optionally, the carbocycle contains a heteroatom selected from —O— and —N($R^{20}$)—;

$R^{21}$, at each occurrence, is independently selected from H, OH, Cl, F, Br, I, CN, $NO_2$, $CF_3$, acetyl, $SCH_3$, methyl, ethyl, methoxy, ethoxy, allyl, —$OCF_3$, and —$SCF_3$;

$R^{11}$, at each occurrence, is independently selected from H, =O, $NR^{18}R^{19}$, $CF_3$;
  $C_1$-$C_4$ alkyl optionally substituted with 0-1 $R^{11a}$;
  phenyl substituted with 0-3 $R^{11b}$;
  $C_3$-$C_6$ carbocycle substituted with 0-3 $R^{11b}$; and
  5 to 7 membered heterocycle containing 1 to 4 heteroatoms selected from nitrogen, oxygen, and sulphur, wherein said 5 to 7 membered heterocycle is substituted with 0-3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, homopiperidinyl, and tetrazolyl;
$R^{11a}$, at each occurrence, is independently selected from H, methyl, ethyl, propyl, butyl, methoxy, ethoxy, propoxy, phenoxy, F, Cl, =O, $NR^{15}R^{16}$, $CF_3$, or phenyl substituted with 0-3 $R^{11b}$;
$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$-$C_2$ haloalkyl, and $C_1$-$C_2$ haloalkoxy;
W is a bond, —$CH_2$—, —$CH_2CH_2$—;
X is a bond;
  phenyl substituted with 0-1 $R^{Xb}$;
  $C_3$-$C_6$ cycloalkyl substituted with 0-1 $R^{Xb}$; or
  5 to 6 membered heterocycle substituted with 0-1 $R^{Xb}$;
$R^{Xb}$ is selected from H, OH, Cl, F, $NR^{15}R^{16}$, $CF_3$, acetyl, $SCH_3$, $S(=O)CH_3$, $S(=O)_2CH_3$, methyl, ethyl, propyl, methoxy, ethoxy, propoxy, and —$OCF_3$;
Y is a bond, —C(=O)—, —O—, —S—, —S(=O)—, —S(=O)_2—, —NH—, —N(CH_3)—, or —N(CH_2CH_3)—;
Z is H;
  $C_1$-$C_8$ alkyl substituted with 0-3 $R^{12a}$;
  $C_2$-$C_6$ alkenyl substituted with 0-3 $R^{12a}$;
  $C_2$-$C_6$ alkynyl substituted with 0-3 $R^{12a}$;
  aryl substituted with 0-4 $R^{12b}$;
  $C_3$-$C_{10}$ carbocycle substituted with 0-4 $R^{12b}$; or
  5 to 10 membered heterocycle containing 1 to 4 heteroatoms selected from nitrogen, oxygen, and sulphur, wherein said 5 to 10 membered heterocycle is substituted with 0-3 $R^{12b}$;
$R^{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, $S(=O)CH_3$, $S(=O)_2CH_3$,
  $C_1$-$C_6$ alkyl, $C_1$-$C_4$ alkoxy, $C_1$-$C_4$ haloalkyl, $C_1$-$C_4$ haloalkoxy, $C_1$-$C_4$ haloalkyl-S—,
  aryl substituted with 0-4 $R^{12b}$;
  $C_3$-$C_{10}$ carbocycle substituted with 0-4 $R^{12b}$; or
  5 to 10 membered heterocycle containing 1 to 4 heteroatoms selected from nitrogen, oxygen, and sulphur, wherein said 5 to 10 membered heterocycle is substituted with 0-3 $R^{12b}$;
$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
  $C_1$-$C_6$ alkyl, $C_1$-$C_4$ alkoxy, $C_1$-$C_4$ haloalkyl,
  $C_1$-$C_4$ haloalkoxy, and $C_1$-$C_4$ haloalkyl-S—;
$R^{13}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, and $CF_3$;
$R^{14}$ is H, phenyl, benzyl, $C_1$-$C_4$ alkyl, or $C_2$-$C_4$ alkoxyalkyl;
$R^{15}$, at each occurrence, is independently selected from H, methyl, ethyl, propyl, butyl, benzyl, and phenethyl;

$R^{16}$, at each occurrence, is independently selected from H, OH, methyl, ethyl, propyl, butyl, benzyl, phenethyl, methyl-C(=O)—, ethyl-C(=O)—, methyl-S(=O)_2—, and ethyl-S(=O)_2—;
$R^{18}$, at each occurrence, is independently selected from H, methyl, ethyl, propyl, butyl, phenyl, benzyl, and phenethyl;
$R^{19}$, at each occurrence, is independently selected from H, methyl, ethyl, propyl, and butyl;
$R^{20}$ is H or $C_1$-$C_4$ alkyl.

9. A process according to claim 7 for preparing a compound of Formula (Id) or Formula (Ie), wherein:
L is —NHC(=O)—, —C(=O)NH—, or —OC(=O)NH—;
$R^3$ is —$R^4$, —$CH_2R^4$, —$CH_2CH_2R^4$, —$CH_2OR^4$, or —$CH_2CH_2OR^4$;
$R^4$ is $C_1$-$C_6$ alkyl substituted with 0-3 $R^{4a}$,
  $C_2$-$C_6$ alkenyl substituted with 0-3 $R^{4a}$, or
  $C_2$-$C_6$ alkynyl substituted with 0-3 $R^{4a}$;
$R^{4a}$, at each occurrence, is independently selected from is H, OH, F, Cl, Br, I, $NR^{15}R^{16}$, $CF_3$,
  $C_3$-$C_6$ carbocycle substituted with 0-3 $R^{4b}$,
  phenyl substituted with 0-3 $R^{4b}$, or
  5 to 6 membered heterocycle containing 1 to 3 heteroatoms selected from nitrogen, oxygen, and sulphur, wherein said 5 to 6 membered heterocycle is substituted with 0-3 $R^{4b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;
$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
  $C_1$-$C_6$ alkyl, $C_1$-$C_4$ alkoxy, $C_1$-$C_4$ haloalkyl,
  $C_1$-$C_4$ haloalkoxy, and $C_1$-$C_4$ haloalkyl-S—;
Ring C is a 3-6 membered carbocycle selected from:

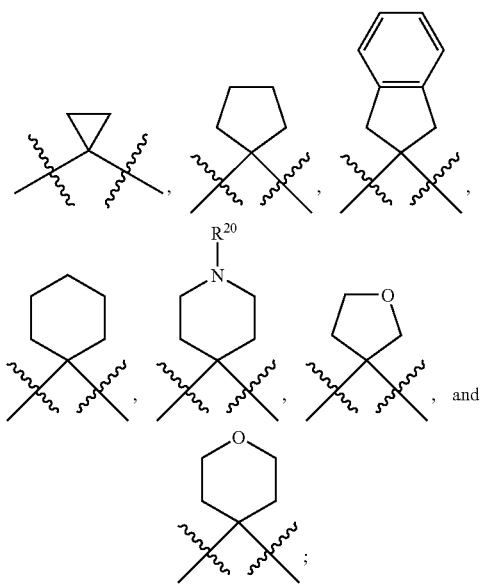

wherein said 3-6 membered carbocycle is substituted with 0-1 $R^{21}$;

R²¹ is selected from H, OH, Cl, F, CN, CF$_3$, methyl, ethyl, methoxy, ethoxy, allyl, and —OCF$_3$;

R¹¹, at each occurrence, is independently selected from H, =O, NR¹⁸R¹⁹;
C$_1$-C$_4$ alkyl optionally substituted with 0-1 R¹¹ᵃ;
phenyl substituted with 0-3 R¹¹ᵇ;
5 to 7 membered heterocycle containing 1 to 4 heteroatoms selected from nitrogen, oxygen, and sulphur, wherein said 5 to 7 membered heterocycle is substituted with 0-3 R¹¹ᵇ; wherein said 5 to 7 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, homopiperidinyl, and tetrazolyl;

R¹¹ᵃ, at each occurrence, is independently selected from H, methyl, ethyl, propyl, methoxy, ethoxy, propoxy, phenoxy, F, Cl, =O, NR¹⁵R¹⁶, CF$_3$, or phenyl substituted with 0-3 R¹¹ᵇ;

R¹¹ᵇ, at each occurrence, is independently selected from H, OH, Cl, F, NR¹⁵R¹⁶, CF$_3$, methyl, ethyl, propyl, butyl, methoxy, ethoxy, propoxy, C$_1$-C$_2$ haloalkyl, and C$_1$-C$_2$ haloalkoxy;

W is a bond or —CH$_2$—;

X is a bond, phenyl, C$_3$-C$_6$ cycloalkyl or 5 to 6 membered heterocycle;

Y is a bond, —C(=O)—, —O—, —S—, —S(=O)—, —S(=O)$_2$—, —NH—, —N(CH$_3$)—, or —N(CH$_2$CH$_3$)—;

Z is H;
C$_1$-C$_8$ alkyl substituted with 0-3 R¹²ᵃ;
C$_2$-C$_6$ alkenyl substituted with 0-3 R¹²ᵃ;
C$_2$-C$_6$ alkynyl substituted with 0-3 R¹²ᵃ;
aryl substituted with 0-4 R¹²ᵇ;
C$_3$-C$_{10}$ carbocycle substituted with 0-4 R¹²ᵇ; or
5 to 10 membered heterocycle containing 1 to 4 heteroatoms selected from nitrogen, oxygen, and sulphur, wherein said 5 to 10 membered heterocycle is substituted with 0-3 R¹²ᵇ;

R¹²ᵃ, at each occurrence, is independently selected from H, OH, Cl, F, NR¹⁵R¹⁶, CF$_3$, acetyl, SCH$_3$, S(=O)CH$_3$, S(=O)$_2$CH$_3$, methyl, ethyl, propyl, butyl, methoxy, ethoxy, propoxy, C$_1$-C$_2$ haloalkyl, and C$_1$-C$_2$ haloalkoxy;
phenyl substituted with 0-4 R¹²ᵇ;
C$_3$-6 carbocycle substituted with 0-4 R¹²ᵇ; or
5 to 6 membered heterocycle containing 1 to 4 heteroatoms selected from nitrogen, oxygen, and sulphur, wherein said 5 to 6 membered heterocycle is substituted with 0-3 R¹²ᵇ;

R¹²ᵇ, at each occurrence, is independently selected from H, OH, Cl, F, NR¹⁵R¹⁶, CF$_3$, acetyl, SCH$_3$, S(=O)CH$_3$, S(=O)$_2$CH$_3$, methyl, ethyl, propyl, butyl, methoxy, ethoxy, propoxy, C$_1$-C$_2$ haloalkyl, and C$_1$-C$_2$ haloalkoxy;

R¹³, at each occurrence, is independently selected from H, OH, methyl, ethyl, propyl, butyl, methoxy, ethoxy, Cl, F, Br, CN, NR¹⁵R¹⁶, and CF$_3$;

R¹⁴ is H, phenyl, benzyl, methyl, ethyl, propyl, or butyl;

R¹⁵, at each occurrence, is independently selected from H, methyl, ethyl, propyl, and butyl; and R¹⁶, at each occurrence, is independently selected from H, OH, methyl, ethyl, propyl, butyl, benzyl, and phenethyl, R¹⁸, at each occurrence, is independently selected from H, methyl, ethyl, propyl, butyl, phenyl, benzyl, and phenethyl;

R¹⁹, at each occurrence, is independently selected from H, methyl, ethyl, propyl, and butyl; and R²⁰ is H, methyl, or ethyl.

10. A process according to claim 9 for preparing a compound of Formula (Id) or Formula (Ie), wherein:

L is —NHC(=O)—, —C(=O)NH—, or —OC(=O)NH—;

Ring C is selected from:

R³ is —CH$_3$, —CH$_2$CH$_3$, —CH$_2$CH$_2$CH$_3$, —CH$_2$CH$_2$CH$_2$CH$_3$, —CH$_2$CH$_2$CH(CH$_3$)$_2$, —CH$_2$(CH$_3$)$_2$, —CH(CH$_3$)CH$_2$CH$_3$, —CH$_2$CH(CH$_3$)$_2$, —CH$_2$C(CH$_3$)$_3$, —CF$_3$, —CH$_2$CF$_3$, —CH$_2$CH$_2$CF$_3$, —CH$_2$CH$_2$CH$_2$CF$_3$, —CH(OH)CH$_2$CH(CH$_3$)$_2$, —CH(OH)CH(CH$_3$)$_2$, —CH(NH$_2$)CH$_2$CH(CH$_3$)$_2$, —CH$_2$CH$_2$OCH$_3$, —CH$_2$OCH$_2$CH$_3$, —CF$_2$CH$_2$CH(CH$_3$)$_2$, —CH(NHCH$_3$)CH$_2$CH(CH$_3$)$_2$, —CH(NHSO$_2$CH$_2$CH$_2$CH$_3$)CH$_2$CH(CH$_3$)$_2$, cyclohexyl-, cyclopentyl-, cyclopropyl-CH$_2$—, cyclobutyl-CH$_2$—, cyclopentyl-CH$_2$—, cyclohexyl-CH$_2$—, cyclopropyl-CH$_2$CH$_2$—, cyclobutyl-CH$_2$CH$_2$—, cyclopentyl-CH$_2$CH$_2$—, cyclohexyl-CH(OH)—, cyclohexyl-CH$_2$CH$_2$—, 1-NH$_2$-cyclopentyl, phenyl-CH$_2$—, (2-F-phenyl)CH$_2$—, (3-F-phenyl)CH$_2$—, (4-F-phenyl)CH$_2$—, (2-Cl-phenyl)CH$_2$—, (3-Cl-phenyl)CH$_2$—, (4-Cl-phenyl)CH$_2$—, (2,3-diF-phenyl)CH$_2$—, (2,4-diF-phenyl)CH$_2$—, (2,5-diF-phenyl)CH$_2$—, (2,6-diF-phenyl)CH$_2$—, (3,4-diF-phenyl)CH$_2$—, (3,5-diF-phenyl)CH$_2$—, (2,3-diCl-phenyl)CH$_2$—, (2,4-diCl-phenyl)CH$_2$—, (2,5-diCl-phenyl)CH$_2$—, (2,6-diCl-phenyl)CH$_2$—, (3,4-diCl-phenyl)CH$_2$—, (3,5-diCl-phenyl)CH$_2$—, (3-F-4-Cl-phenyl)CH$_2$—, (3-F-5-Cl-phenyl)CH$_2$—, (3-Cl-4-F-phenyl)CH$_2$—, phenyl-CH$_2$CH$_2$—, (2-F-phenyl)CH$_2$CH$_2$—, (3-F-phenyl)CH$_2$CH$_2$—, (4-F-phenyl)CH$_2$CH$_2$—, (2-Cl-phenyl)CH$_2$CH$_2$—, (3-Cl-phenyl)CH$_2$CH$_2$—, (4-Cl-phenyl)CH$_2$CH$_2$—, (2,3-diF-phenyl)CH$_2$CH$_2$—, (2,4-diF-phenyl)CH$_2$CH$_2$—, (2,5-diF-phenyl)CH$_2$CH$_2$—, (2,6-diF-phenyl)CH$_2$CH$_2$—, (3,4-diF-phenyl)CH$_2$CH$_2$—, (3,5-diF-phenyl)CH$_2$CH$_2$—, (2,3-diCl-phenyl)CH$_2$CH$_2$—, (2,4-diCl-phenyl)CH$_2$CH$_2$—, (2,5-diCl-phenyl)CH$_2$CH$_2$—, (2,6-diCl-phenyl)CH$_2$CH$_2$—, (3,4-diCl-phenyl)CH$_2$CH$_2$—, (3,5-diCl-phenyl)CH$_2$CH$_2$—, (3-F-4-Cl-phenyl)CH$_2$CH$_2$—, (3-F-5-Cl-phenyl)CH$_2$CH$_2$—, 4-piperidinyl-CH$_2$CH$_2$—, phenyl-CH$_2$CH$_2$CF$_2$—, phenyl-CH$_2$CH(OH)—, imidazolyl-CH$_2$CH(OR)—, or phenyl-CH$_2$OCH$_2$—;

W is a bond or —CH$_2$—;

X is a bond;

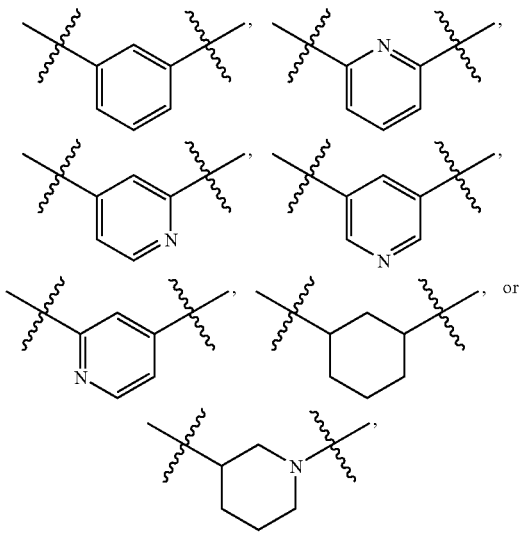

Y is a bond, —C(=O)—, —O—, —S—, —S(=O)—, —S(=O)$_2$—, —NH—, or —N(CH$_3$)—,

Z is methyl, ethyl, i-propyl, n-propyl, n-butyl, i-butyl, s-butyl, t-butyl, allyl, phenyl, 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF$_3$O-phenyl, 3-CF$_3$O-phenyl, 4-CF$_3$O-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, cyclopropyl, cyclobutyl, cyclopentyl, cyclohexyl, morpholino, N-piperinyl, phenyl-CH$_2$—, (2-F-phenyl)CH$_2$—, (3-F-phenyl)CH$_2$—, (4-F-phenyl)CH$_2$—, (2-Cl-phenyl)CH$_2$—, (3-Cl-phenyl)CH$_2$, (4-Cl-phenyl)CH$_2$—, (2,3-diF-phenyl)CH$_2$—, (2,4-diF-phenyl)CH$_2$—, (2,5-diF-phenyl)CH$_2$—, (2,6-diF-phenyl)CH$_2$—, (3,4-diF-phenyl)CH$_2$—, (3,5-diF-phenyl)CH$_2$—, (2,3-diCl-phenyl)CH$_2$—, (2,4-diCl-phenyl)CH$_2$—, (2,5-diCl-phenyl)CH$_2$—, (2,6-diCl-phenyl)CH$_2$—, (3,4-diCl-phenyl)CH$_2$—, (3,5-diCl-phenyl)CH$_2$—, (3-F-4-Cl-phenyl)CH$_2$—, (3-F-5-Cl-phenyl)CH$_2$—, (3-Cl-4-F-phenyl)CH$_2$—, (2-MeO-phenyl)CH$_2$—, (3-MeO-phenyl)CH$_2$—, (4-MeO-phenyl)CH$_2$—, (2-Me-phenyl)CH$_2$—, (3-Me-phenyl)CH$_2$—, (4-Me-phenyl)CH$_2$—, (2-MeS-phenyl)CH$_2$—, (3-MeS-phenyl)CH$_2$—, 4-MeS-phenyl)CH$_2$—, (2-CF$_3$O-phenyl)CH$_2$—, (3-CF$_3$O-phenyl)CH$_2$—, (4-CF$_3$O-phenyl)CH$_2$—, (furanyl)CH$_2$—, (thienyl)CH$_2$—, (pyridyl)CH$_2$—, (2-Me-pyridyl)CH$_2$—, (3-Me-pyridyl)CH$_2$—, (4-Me-pyridyl)CH$_2$—, (1-imidazolyl)CH$_2$—, (oxazolyl)CH$_2$—, (isoxazolyl)CH$_2$—, (1-benzimidazolyl)CH$_2$—, (cyclopropyl)CH$_2$—, (cyclobutyl)CH$_2$—, (cyclopentyl)CH$_2$—, (cyclohexyl)CH$_2$—, (morpholino)CH$_2$—, (N-pipridinyl)CH$_2$—, phenyl-CH$_2$CH$_2$—, (phenyl)$_2$CHCH$_2$—, (2-F-phenyl)CH$_2$CH$_2$—, (3-F-phenyl)CH$_2$CH$_2$—, (4-F-phenyl)CH$_2$CH$_2$—, (2-Cl-phenyl)CH$_2$CH$_2$—, (3-Cl-phenyl)CH$_2$CH$_2$—, (4-Cl-phenyl)CH$_2$CH$_2$—, (2,3-diF-phenyl)CH$_2$CH$_2$—, (2,4-diF-phenyl)CH$_2$CH$_2$—, (2,5-diF-phenyl)CH$_2$CH$_2$—, (2,6-diF-phenyl)CH$_2$CH$_2$—, (3,4-diF-phenyl)CH$_2$CH$_2$—, (3,5-diF-phenyl)CH$_2$CH$_2$—, (2,3-diCl-phenyl)CH$_2$CH$_2$—, (2,4-diCl-phenyl)CH$_2$CH$_2$—, (2,5-diCl-phenyl)CH$_2$CH$_2$—, (2,6-diCl-phenyl)CH$_2$CH$_2$—, (3,4-diCl-phenyl)CH$_2$CH$_2$—, (3,5-diCl-phenyl)CH$_2$CH$_2$—, (3-F-4-Cl-phenyl)CH$_2$CH$_2$—, (3-F-5-Cl-phenyl)CH$_2$CH$_2$—, (3-Cl-4-F-phenyl)CH$_2$CH$_2$—, (2-MeO-phenyl)CH$_2$CH$_2$—, (3-MeO-phenyl)CH$_2$CH$_2$—, (4-MeO-phenyl)CH$_2$CH$_2$—, (2-Me-phenyl)CH$_2$CH$_2$—, (3-Me-phenyl)CH$_2$CH$_2$—, (4-Me-phenyl)CH$_2$CH$_2$—, (2-MeS-phenyl)CH$_2$CH$_2$—, (3-MeS-phenyl)CH$_2$CH$_2$—, (4-MeS-phenyl)CH$_2$CH$_2$—, (2-CF$_3$O-phenyl)CH$_2$CH$_2$—, (3-CF$_3$O-phenyl)CH$_2$CH$_2$—, (4-CF$_3$O-phenyl)CH$_2$CH$_2$—, (furanyl)CH$_2$CH$_2$—, (thienyl)CH$_2$CH$_2$—, (pyridyl)CH$_2$CH$_2$—, (2-Me-pyridyl)CH$_2$CH$_2$—, (3-Me-pyridyl)CH$_2$CH$_2$—, (4-Me-pyridyl)CH$_2$CH$_2$—, (imidazolyl)CH$_2$CH$_2$—, (oxazolyl)CH$_2$CH$_2$—, (isoxazolyl)CH$_2$CH$_2$—, (benzimidazolyl)CH$_2$CH$_2$—, (cyclopropyl)CH$_2$CH$_2$—, (cyclobutyl)CH$_2$CH$_2$—, (cyclopentyl)CH$_2$CH$_2$—, (cyclohexyl)CH$_2$CH$_2$—, (morpholino)CH$_2$CH$_2$—, or (N-pipridinyl)CH$_2$CH$_2$—;

R$^{11}$, at each occurrence, is independently selected from H, =O, methyl, ethyl, phenyl, benzyl, phenethyl, 4-F-phenyl, (4-F-phenyl)CH$_2$—, (4-F-phenyl)CH$_2$CH$_2$—, 3-F-phenyl, (3-F-phenyl)CH$_2$—, (3-F-phenyl)CH$_2$CH$_2$—, 2-F-phenyl, (2-F-phenyl)CH$_2$—, (2-F-phenyl)CH$_2$CH$_2$—, 4-Cl-phenyl, (4-Cl-phenyl)CH$_2$—, (4-Cl-phenyl)CH$_2$CH$_2$—, 3-Cl-phenyl, (3-Cl-phenyl)CH$_2$—, (3-Cl-phenyl)CH$_2$CH$_2$—, 4-CH$_3$-phenyl, (4-CH$_3$-phenyl)CH$_2$—, (4-CH$_3$-phenyl)CH$_2$CH$_2$—, 3-CH$_3$-phenyl, (3-CH$_3$-phenyl)CH$_2$—, (3-CH$_3$-phenyl)CH$_2$CH$_2$—, 4-CF$_3$-phenyl, (4-CF$_3$-phenyl)CH$_2$—, (4-CF$_3$-phenyl)CH$_2$CH$_2$—, cyclopentyl, pyrid-2-yl, pyrid-3-yl, or pyrid-4-yl; and R$^{13}$, at each occurrence, is independently selected from H, F, Cl, OH, —CH$_3$, —CH$_2$CH$_3$, —OCH$_3$, or —CF$_3$.

11. A process according to claim 1 for preparing a compound selected from:

{[N-(3-methylbutyl)carbamoyl]cyclopentyl}-N-(5-methyl-6-oxo(7H-dibenzo[d,f]azaperhydroepin-7-yl))carboxamide;

{[N-(3-methylbutyl)carbamoyl]cyclopentyl}-N-(1-methyl-2-oxo-5-phenyl((S)-3H-benzo[f]1,4-diazepin-3-yl))carboxamide;

[(N-butylcarbamoyl)cyclopentyl]-N-(1-methyl-2-oxo-5-phenyl((S)-3H-benzo[f]1,4-diazepin-3-yl))carboxamide;

2-(3,5-difluorophenyl)-N-{[N-(1-methyl-2-oxo-5-phenyl((S)-3H-benzo[f]1,4-diazepin-3-yl))carbamoyl]cyclohexyl}acetamide;

2-(3,5-difluorophenyl)-N-{[N-(1-methyl-2-oxo-5-phenyl((S)-3H-benzo[f]1,4-diazepin-3-yl))carbamoyl]cyclopentyl}acetamide;

2-(3,5-difluorophenyl)-N-{[N-(1-methyl-2-oxo-5-phenyl((S)-3H-benzo[f]1,4-diazepin-3-yl))carbamoyl]cyclopropyl}acetamide;

3-cyclopentyl-N-{[N-(1-methyl-2-oxo-5-phenyl((S)-3H-benzo[f]1,4-diazepin-3-yl))carbamoyl]cyclohexyl}propanamide;

2-(3,5-difluorophenyl)-N-{4-[N-(1-methyl-2-oxo-5-phenyl((S)-3H-benzo[f]1,4-diazepin-3-yl))carbamoyl](4-piperidyl)}acetamide;

phenyl 4-[2-(3,5-difluorophenyl)acetylamino]-4-[N-(1-methyl-2-oxo-5-phenyl((S)-3H-benzo[f]1,4-diazepin-3-yl))carbamoyl]piperidinecarboxylate;

4-methyl-N-{[N-(5-methyl-6-oxo(7H-dibenzo[d,f]azaperhydroepin-7-yl))carbamoyl]cyclopentyl}pentanamide;

N-{1-methyl-2-oxo-5-[4-(trifluoromethyl)phenyl](3H-benzo[f]1,4-diazepin-3-yl)}{[(phenylmethoxy)carbonylamino]cyclopentyl}carboxamide;

(2S)-N-{[(N-(1-{[3-(4-fluorophenoxy)phenyl]methyl}-2-oxoazaperhydroepin-3-yl)carbamoyl]cyclopropyl}-2-hydroxy-4-methylpentanamide;

(2S)-N-{[N-(1-{[3-(4-fluorophenoxy)phenyl]methyl}-2-oxoazaperhydroepin-3-yl)carbamoyl]cyclopentyl}-2-hydroxy-3-methylbutanamide;

2,2-difluoro-N-[(N-{1-methyl-2-oxo-5-[4-(trifluoromethyl)phenyl](3H-benzo[f]1,4-diazepin-3-yl)}carbamoyl)cyclopentyl]-4-phenylbutanamide;

N-[(N-{1-methyl-2-oxo-5-[4-(trifluoromethyl)phenyl](3H-benzo[f]1,4-diazepin-3-yl)}carbamoyl)cyclopentyl]-3-(4-piperidyl)propanamide;

(2S)-2-hydroxy-4-methyl-N-[(N-{1-methyl-2-oxo-5-[4-(trifluoromethyl)phenyl](3H-benzo[f]1,4-diazepin-3-yl)}carbamoyl)cyclopentyl]pentanamide;

3-cyclopropyl-N-[(N-{1-methyl-2-oxo-5-[4-(trifluoromethyl)phenyl](3H-benzo[f]1,4-diazepin-3-yl)}carbamoyl)cyclopentyl]propanamide;

(2R)-2-hydroxy-3-imidazol-2-yl-N-[(N-{1-methyl-2-oxo-5-[4-(trifluoromethyl)phenyl](3H-benzo[f]1,4-diazepin-3-yl)}carbamoyl)cyclopentyl]propanamide;

2-ethoxy-N-[(N-{1-methyl-2-oxo-5-[4-(trifluoromethyl)phenyl](3H-benzo[f]1,4-diazepin-3-yl)}carbamoyl)cyclopentyl]acetamide;

3-cyclopentyl-N-[(N-{1-methyl-2-oxo-S-[4-(trifluoromethyl)phenyl](3H-benzo[f]1,4-diazepin-3-yl)}carbamoyl)cyclopentyl]propanamide;

(2S)-2-hydroxy-3-methyl-N-[(N-{1-methyl-2-oxo-5-[4-(trifluoromethyl)phenyl](3H-benzo[f]1,4-diazepin-3-yl)}carbamoyl)cyclopentyl]butanamide;

(2S)-2-cyclohexyl-2-hydroxy-N-[(N-{1-methyl-2-oxo-5-[4-(trifluoromethyl)phenyl](3H-benzo[f]1,4-diazepin-3-yl)}carbamoyl)cyclopentyl]acetamide;

(2R)-2-cyclohexyl-2-hydroxy-N-[(N-{1-methyl-2-oxo-5-[4-(trifluoromethyl)phenyl](3H-benzo[f]1,4-diazepin-3-yl)}carbamoyl)cyclopentyl]acetamide;

(2S)-2-amino-4-methyl-N-[(N-{1-methyl-2-oxo-5-[4-(trifluoromethyl)phenyl](3H-benzo[f]1,4-diazepin-3-yl)}carbamoyl)cyclopentyl]pentanamide;

[(cyclohexylcarbonylamino)cyclopentyl]-N-{1-methyl-2-oxo-5-[4-(trifluoromethyl)phenyl](3H-benzo[f]1,4-diazepin-3-yl)}carboxamide;

{[N-(3-methylbutyl)carbamoyl]cyclopentyl}-N-{1-methyl-2-oxo-5-[4-(trifluoromethyl)phenyl](3H-benzo[f]1,4-diazepin-3-yl)}carboxamide;

4-methyl-N-[(N-{1-methyl-2-oxo-5-[4-(trifluoromethyl)phenyl](3H-benzo[f]1,4-diazepin-3-yl)}carbamoyl)cyclopentyl]pentanamide;

(2S)-2-hydroxy-4-methyl-N-[(N-{1-methyl-2-oxo-5-[4-(trifluoromethyl)phenyl](3H-benzo[f]1,4-diazepin-3-yl)}carbamoyl)cyclopentyl]pentanamide;

3-methoxy-N-[(N-{1-methyl-2-oxo-5-[4-(trifluoromethyl)phenyl](3H-benzo[f]1,4-diazepin-3-yl)}carbamoyl)cyclopentyl]propanamide;

(2S)-2-hydroxy-N-[(N-{1-methyl-2-oxo-5-[4-(trifluoromethyl)phenyl](3H-benzo[f]1,4-diazepin-3-yl)}carbamoyl)cyclopentyl]-3-phenylpropanamide;

N-[(N-{1-methyl-2-oxo-5-[4-(trifluoromethyl)phenyl](3H-benzo[f]1,4-diazepin-3-yl)}carbamoyl)cyclopentyl]-2-(phenylmethoxy)acetamide;

N-{[N-(1-butyl-5-cyclopentyl-2-oxo(3H-benzo[f]1,4-diazepin-3-yl))carbamoyl]cyclopentyl}-4-methylpentanamide;

N-{[N-(5-cyclopentyl-1-methyl-2-oxo(3H-benzo[f]1,4-diazepin-3-yl))carbamoyl]cyclopentyl}-4-methylpentanamide;

(2S)-2-hydroxy-3-methyl-N-({N-[2-oxo-1-benzyl(3H,4H,5H-benzo[f]azaperhydroepin-3-yl)]carbamoyl}cyclopentyl)butanamide;

N-({N-[5-(tert-butyl)-1-methyl-2-oxo(3H-benzo[f]1,4-diazepin-3-yl)]carbamoyl}cyclopentyl)-4-methylpentanamide;

N-({N-[5-(tert-butyl)-1-butyl-2-oxo(3H-benzo[f]1,4-diazepin-3-yl)]carbamoyl}cyclopentyl)-4-methylpentanamide; and N-({N-[5-butyl-2-oxo-1-(2-pyridylmethyl)(3H-benzo[f]1,4-diazepin-3-yl)]carbamoyl}cyclopentyl)-4-methylpentanamide.

12. A process of preparing a pharmaceutical composition comprising combining a compound made by the process according to claim 1, and a pharmaceutically acceptable carrier.

13. A process for synthesis of 2-(3,5-Difluorophenyl)-N-{[N(1-methyl-2-oxo-5-phenyl ((S)-3H-benzo[f]1,4-diazepin-3-yl))carbamoyl]cyclohexyl}-acetamide (Compound 9), comprising the steps of:

(i) preparing an carboxylic intermediate 7 by combining an ester intermediate 18 by coupling an acid 14 and an amine 13 under standard conditions using EDC and HOBt, and producing an intermediate 18 using a reducing agent in accordance with the following scheme:

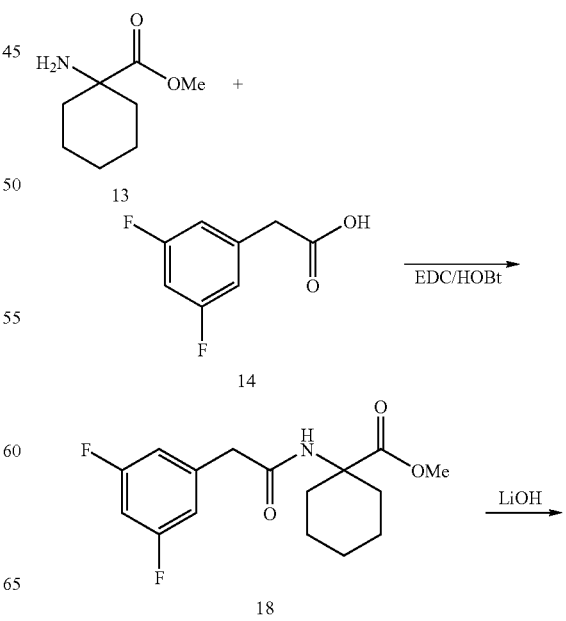

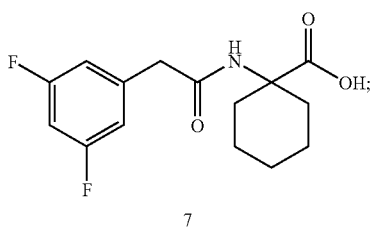

(ii) coupling the intermediate 7 and 8 in order to prepare said compound 9:

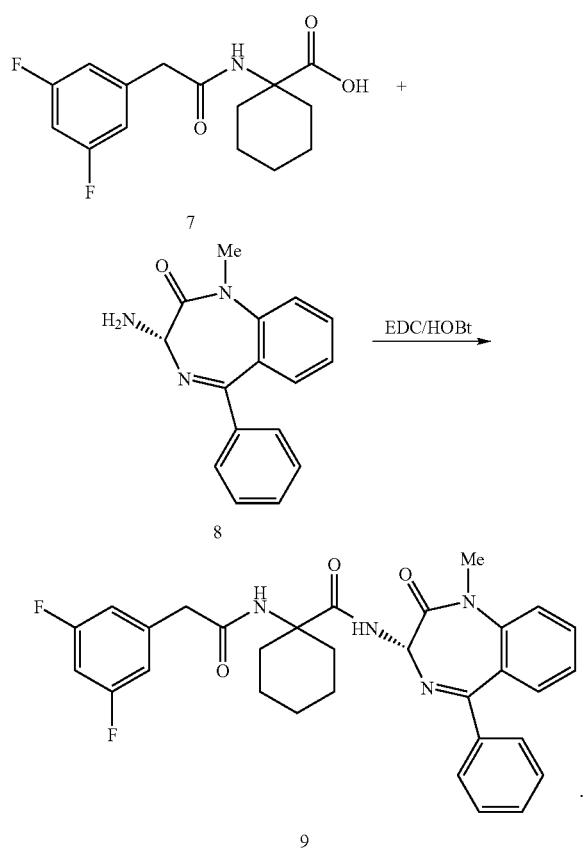

14. The process for producing 2-(3,5-Difluorophenyl)-N-{[N-(1-methyl-2-oxo-5-phenyl((S)-3H-benzo[f]1,4-diazepin-3-yl))carbamoyl]cyclohexyl}-acetamide

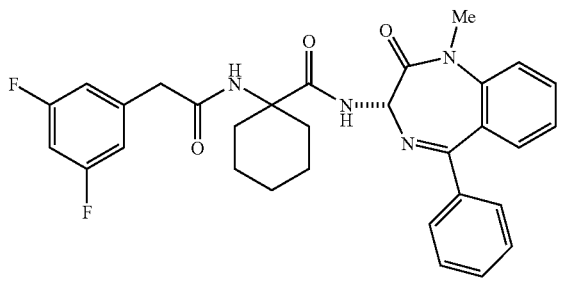

according to claim 13, wherein:

(a) the intermediate {[(tert-Butoxy)carbonylamino]cyclohexyl}-N-(1-methyl-2-oxo-5-phenyl((S)-3H-benzo[f]1,4-diazepin-3-yl))carboxamide is produced by:

(i) adding in approximately equimolar ratio, diisopropylethylamine and HATU to a solution of 1[(tertbutoxy)carbonylamino]cyclohexanecarboxylic acid (1.75 g, 7.2 mmol) in $CH_2Cl_2$ (10 mL) at 0° C. and stirred for 10 min.;

(ii) adding (S)-3-amino-1-methyl-5-phenyl-3H-benzoazepin-2-one (3.0 g, 6.0 mmol), and allowing the solution to warm to room temperature while stirring overnight; and (iii) quenching the reaction with water; separating the organic layer, filtering, and drying a residue to afford a white solid;

(b) the intermediate (aminocyclohexyl)-N-(1-methyl-2-oxo-5-phenyl((S)-3H-benzo[f]1,4-diazepin-3-yl))carboxamide is produced by:

(i) adding a saturated solution of HCl in EtOAc (organic layer) to a solution of the intermediate compound of (a) and stirring at room temperature overnight;

(ii) quenching the reaction with 1N NaOH; separating the organic layer, and repeatedly extract the aqueous layer with EtOAc;

(iii) combining, filtering, and drying the organic layers to a white solid; and (c) the desired compound, 2-(3,5-Difluorophenyl)-N-{[N-(1-methyl-2-oxo-5-phenyl((S)-3H-benzo[f]1,4-diazepin-3-yl))carbamoyl]-cyclohexyl}acetamide, is prepared by (i) adding diisopropylethylamine and HATU to a solution of 2-(3,5-difluorophenyl)acetic acid in $CH_2Cl_2$ at 0° C. and stirring for 5 min.;

(ii) adding (aminocyclohexyl)-(S)-3-N-(1-methyl-2-oxo-5-phenyl(3H-benzoazepin-3-yl))carboxamide and allowing the solution to warm to room temperature, stirring overnight; and (iii) quenching the reaction with water and separating, washing and drying the organic layer to a white solid, and characterized by $^1$H NMR (500 MHz, $CD_3OD$) δ 7.72-7.32 (m, 9 H), 6.97 (d, 2 H), 6.80 (t, 1 H), 5.31 (s, 1 H), 3.70 (s, 2 H), 3.48 (s, 3 H), 2.24-1.30 (m 10 H).

15. A process for preparing 2-(3,5-Difluorophenyl)-N-{[N-(1-methyl-2-oxo-5-phenyl((S)-3H-benzo[f]1,4-diazepin-3-yl))carbamoyl]cyclopentyl}-acetamide, as a solid,

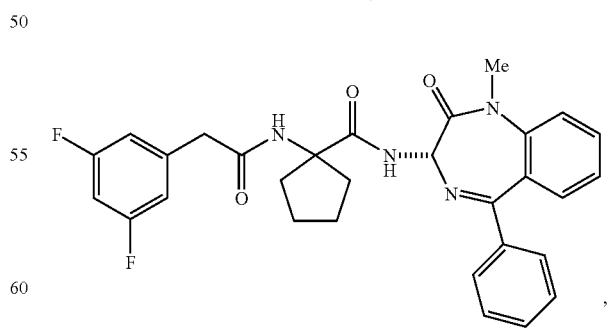

comprising method steps similar to that described in claim 14, and characterized by $^1$H NMR (500 MHz, $CD_3OD$) δ 7.72-7.31 (m, 9 H), 6.96 (d, 2 H), 6.81 (t, 1 H) 5.33 (s, 1 H), 3.63 (s, 2 H), 3.47 (s, 3 H), 2.41-1.72 (m, 8 H).

16. A process for preparing 2-(3,5-Difluorophenyl)-N-{[N-(1-methyl-2-oxo-5-phenyl((S)-3H-benzo[f]1,4-diazepin-3-yl))carbamoyl]cyclopropyl}-acetamide

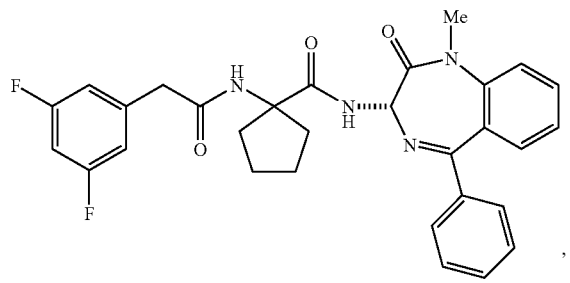

as a solid, comprises method steps similar to that described in claim 14, and characterized by $^1$H NMR (500 MHz, CD$_3$OD) δ 7.71-7.30 (m, 9 H), 6.98 (d, 2 H), 6.81 (t, 1 H), 5.28 (s, 1 H), 3.65 (s, 2 H), 3.48 (s, 3 H), 1.48 (m, 2 H), 1.08 (m, 2 H).

17. A process of preparing a pharmaceutical composition comprising combining a compound made by the process according to claim 13, and a pharmaceutically acceptable carrier.

18. A process of preparing a pharmaceutical composition comprising combining a compound made by the process according to claim 14, and a pharmaceutically acceptable carrier.

19. A process of preparing a pharmaceutical composition comprising combining made by the process a compound according to claim 15, and a pharmaceutically acceptable carrier.

20. A process of preparing a pharmaceutical composition comprising combining a compound made by the process according to claim 16, and a pharmaceutically acceptable carrier.

* * * * *

UNITED STATES PATENT AND TRADEMARK OFFICE
CERTIFICATE OF CORRECTION

PATENT NO. : 7,276,496 B2 Page 1 of 1
APPLICATION NO. : 11/327721
DATED : October 2, 2007
INVENTOR(S) : Richard E. Olson and Michael G. Yang It is certified that error appears in the above-identified patent and that said Letters Patent is hereby corrected as shown below:

In the Title

Delete the word "Protection" and insert the word --Production--

Signed and Sealed this

Twenty-ninth Day of April, 2008

JON W. DUDAS
*Director of the United States Patent and Trademark Office*

UNITED STATES PATENT AND TRADEMARK OFFICE
CERTIFICATE OF CORRECTION

PATENT NO. : 7,276,496 B2  Page 1 of 1
APPLICATION NO. : 11/327721
DATED : October 2, 2007
INVENTOR(S) : Richard E. Olson and Michael G. Yang It is certified that error appears in the above-identified patent and that said Letters Patent is hereby corrected as shown below:

In the Title Item [54] and Column 1, line 2

Delete the word "Protection" and insert the word --Production--

This certificate supersedes the Certificate of Correction issued April 29, 2008.

Signed and Sealed this

Twentieth Day of May, 2008

JON W. DUDAS
*Director of the United States Patent and Trademark Office*